(12) United States Patent
Hamon et al.

(10) Patent No.: US 9,023,656 B2
(45) Date of Patent: May 5, 2015

(54) REACTIVE MASS LABELS

(75) Inventors: Christian Hamon, Kriftel (DE); Josef Schwarz, Frankfurt am Main (DE); Wolfgang Becker, Eppstein (DE); Stefan Kienle, Frankfurt am Main (DE); Karsten Kuhn, Hofheim am Taunus (DE); Juergen Schaefer, Lauterbach (DE)

(73) Assignee: Electrophoretics Limited, Cobham Surrey (GB)

( * ) Notice: Subject to any disclaimer, the term of this patent is extended or adjusted under 35 U.S.C. 154(b) by 948 days.

(21) Appl. No.: 11/996,910

(22) PCT Filed: Jul. 26, 2006

(86) PCT No.: PCT/GB2006/002787
§ 371 (c)(1), (2), (4) Date: Mar. 30, 2010

(87) PCT Pub. No.: WO2007/012849
PCT Pub. Date: Feb. 1, 2007

(65) Prior Publication Data
US 2010/0178710 A1   Jul. 15, 2010

(30) Foreign Application Priority Data
Jul. 26, 2005  (GB) .................................. 0515323.4

(51) Int. Cl.
*G01N 33/68* (2006.01)
*C07D 401/12* (2006.01)
(Continued)

(52) U.S. Cl.
CPC .......... *C07D 403/12* (2013.01); *G01N 2458/00* (2013.01); *Y10T 436/24* (2015.01);
(Continued)

(58) Field of Classification Search
CPC .................................................. G01N 2458/00
See application file for complete search history.

(56) References Cited

U.S. PATENT DOCUMENTS 2,856,405 A   10/1958   Biel
(Continued)

FOREIGN PATENT DOCUMENTS

EP   1267170 A1   12/2002
(Continued)

OTHER PUBLICATIONS

Takeda, S. et al. "Site-specific conjugation of oligonucleotides to the C-terminus of recombinant protein by expressed protein ligation," Bioorganic & Medicinal Chemistry Letters 14 (2004) 2407-2410.*
(Continued)

*Primary Examiner* — Yelena G Gakh
*Assistant Examiner* — Michelle Adams
(74) *Attorney, Agent, or Firm* — Arent Fox LLP

(57) ABSTRACT

A mass label for labelling and detecting a biological molecule by mass spectroscopy, which label comprises the following structure: X-L-M wherein X is a mass marker moiety comprising the following group: formula (I), wherein the cyclic unit is aromatic or aliphatic and comprises from 0-3 double bonds independently between any two adjacent atoms; each Z is independently N, N($R^1$), C($R^1$), CO, CO($R^1$), C($R^1$)$_2$, O or S; X is N, C or C($R^1$); each $R^1$ is independently H, a substituted or unsubstituted straight or branched $C_1$-$C_6$ alkyl group, a substituted or unsubstituted aliphatic cyclic group, a substituted or unsubstituted aromatic group or a substituted or unsubstituted heterocyclic group; and y is an integer from 0-10, L is a cleavable linker comprising an amide bond and M is a mass normalization moiety.

(I)

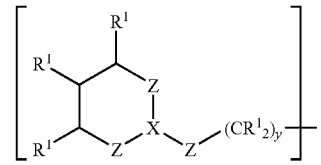

48 Claims, 47 Drawing Sheets

(51) Int. Cl.
- C07D 239/04 (2006.01)
- C07D 403/12 (2006.01)
- C07D 207/404 (2006.01)
- C07K 5/078 (2006.01)

(52) U.S. Cl.
CPC .......... C07D207/404 (2013.01); C07D 401/12 (2013.01); C07K 5/06139 (2013.01); G01N 33/6848 (2013.01)

(56) References Cited

U.S. PATENT DOCUMENTS

| | | | |
|---|---|---|---|
| 6,509,335 | B1 | 1/2003 | Berryman et al. |
| 6,855,726 | B1 * | 2/2005 | Dudley et al. .................. 514/312 |
| 2005/0037423 | A1 | 2/2005 | Lerchen et al. |

FOREIGN PATENT DOCUMENTS

| | | |
|---|---|---|
| FR | 2.036.922 | 12/1970 |
| WO | WO 89/10919 A1 | 11/1989 |
| WO | 9504160 A1 | 2/1995 |
| WO | WO 97/22619 A2 * | 6/1997 |
| WO | 9727325 A2 | 7/1997 |
| WO | 9727331 A2 | 7/1997 |
| WO | 9826095 A1 | 6/1998 |
| WO | 9831830 A1 | 7/1998 |
| WO | 9832876 A1 | 7/1998 |
| WO | 0002893 A1 | 1/2000 |
| WO | 0002895 A1 | 1/2000 |
| WO | 0020870 A1 | 4/2000 |
| WO | WO 01/68664 A2 | 9/2001 |
| WO | WO 02/10140 A2 | 2/2002 |
| WO | WO 02/055496 A1 | 7/2002 |
| WO | WO 03/025576 A2 | 3/2003 |
| WO | WO 03/040093 A2 | 5/2003 |
| WO | WO 03/056342 A2 | 7/2003 |
| WO | WO 2004/005255 A1 | 1/2004 |
| WO | WO 2004/064972 A2 | 8/2004 |
| WO | WO 2004/086050 A2 * | 10/2004 |
| WO | WO-2004/086050 A2 * | 10/2004 |
| WO | WO 2005/037828 A1 | 4/2005 |
| WO | WO 2005/057207 A1 | 6/2005 |
| WO | WO 2006/052378 A1 | 5/2006 |

OTHER PUBLICATIONS

Yoo, J.-S. et al. "Synthesis and Antimicrobial Evaluation of 3-(Substituted) Pyrrolidine Cephalosporins," Yakhak Hoeji vol. 43, No. 3, 306-315 (1999).*
Sauter, F. et al., ARPMAS; Arch.Pharm., vol. 310, 1977, pp. 680-682, Weinheim, Germany, Database Beilstein 1977, XP-002413515.
Dofek, Vrba: Experientia, vol. 15, 1959, p. 120, Database Beilstein 1959, XP-002413514.
Davioud-Carvet, Elisabeth et al., J. Med. Chem., vol. 24, 2001, pp. 4268-4276, Database Beilstein 2001, XP-002413518.
Terauchi, Yoshiaki et al., J. Pharm. Sci., vol. 79, No. 5, 1990, pp. 432-436, Database Beilstein 1990, XP-002413517.
Schulze, W. et al., Pharmazie, vol. 30, 1975, pp. 498-506, Database Beilstein 1975, XP-002413516.
Chillemi, R. et al., "Nicaeensin, A New Amidinoureido Compound From the Red Alga *Schottera nicaeensis*", Journal of Natural Products, Sep.-Oct. 1990, vol. 53, No. 5, pp. 1220-1224.
International Search Report dated Jan. 24, 2007 (Seven (7) pages).
German Search Report dated Dec. 12, 2005 (Four (4) pages).
Gygi, S.P., et al., "Quantitative analysis of complex protein mixtures using isotope-coded affinity tags", Nature America Inc., Nature Biotechnology, vol. 17, Oct. 1999, pp. 994-999.
Maskos, U. et al., "Oligonucleotide hybridisations on glass supports: a novel linker for oligonucleotide synthesis and hybridisation properties of oligonucleotides synthesised in situ", Nucleic Acids Research, vol. 20, No. 7, Mar. 1992, pp. 1679-1684.

Lloyd-Williams, P. et al., "Convergent Solid-Phase Peptide Synthesis", Tetrahedron, vol. 49, No. 48, 1993, pp. 11065-11133.
Geahlen, R.L. et al., "A General Method for Preparation of Peptides Biotinylated at the Carboxy Terminus", Analytical Biochemistry, vol. 202, 1992, pp. 68-70.
Sawutz, D.G. et al., "Synthesis and Molecular Characterization of a Biotinylated Analog of [Lys]Bradykinin", Peptides, vol. 12, 1991, pp. 1019-1024.
Natarajan, S. et al., "Site-Specific Biotinylation; A Novel Approach and its Application to Endothelin-1 Analogs and PTH-Analog", Int. J. Peptide Protein Res., vol. 40, 1992, pp. 567-574.
Bian, N., et al., "Detection Via Laser Desorption and Mass Spectrometry of Multiplex Electrophore-labeled Albumin", Rapid Communications in Mass Spectrometry, vol. 11, 1997, pp. 1781-1784.
Abdel-Baky, S., et al., "Gas Chromatography/Electron Capture Negative-Ion Mass Spectrometry at the Zeptomole Level", American Chemical Society, Analytical Chemistry, vol. 63, 1991, pp. 2986-2989.
Roth, K.D.W., et al., "Charge Derivatization of Peptides for Analysis by Mass Spectrometry", Mass Spectrometry Reviews, vol. 17, 1998, pp. 255-274.
Schlosser, A., et al., "Five-membered ring formation in unimolecular reactions of peptides: a key structural element controlling low-energy collision-induced dissociation of peptides", Journal of Mass Spectrometry, vol. 35, Oct. 6, 2000, pp. 1382-1390.
Schwartz, B.L. et al., "Some Proline Substituent Effects in the Tandem Mass Spectrum of Protonated Pentaalanine", Bioligical Mass Spectrometry, vol. 21, 1992, pp. 92-96.
Wysocki, V.H., et al., "Mobile and localized protons: a framework for understanding peptide dissociation", John Wiley & Sons, Ltd., Journal of Mass Spectrometry, vol. 35, 2000, pp. 1399-1406.
Wilm, M., et al., "Parent Ion Scans of Unseparated Peptide Mixtures", Analytical Chemistry, vol. 68, No. 3, Feb. 1, 1996, pp. 527-533.
Shevchenko, A. et al., "Rapid 'de Novo' Peptide Sequencing by a Combination of Nanoelectrospray, Isotropic Labeling and a Quadrupole/Time-of-gflight Mass Spectrometer", Rapid Communications in Mass Spectrometry, vol. 11, 1997, pp. 1015-1024.
Iyer, V.R., et al., "The Transcriptional Program in the Response of Human Fibrblasts to Serum", Science, vol. 283, No. 83, Jan. 1, 1999, pp. 83-87.
Gerard, C., "Purification of Glycoproteins", Methods in Enzymology, vol. 182, 1990, pp. 529-539.
Bayer, E.A. et al., "Biocytin Hyrdazide—A Selective Label for Sialic Acids, Galactose, and Other Sugars in Glycoconjugates Using Avidin-Biotin Technology", Analytical Biochemistry, vol. 170, 1988, pp. 271-281.
Means, G.E., "Reductive Alkylation of Amino Groups", Methods in Enzymology, vol. 47, 1977, pp. 469-478.
Rayment, I., "Reductive Alkylation of Lysine Residues to Alter Crystallization Properties of Proteins", Methods in Enzymology, vol. 276, 1997, pp. 171-179.
Holmes, C.F.B., "A new method for the selective isolation of phosphoserine-containing peptides", Federation of European Biochemical Societies Letters, vol. 215, No. 1, May 1987, pp. 21-24.
Fadden, P. et al., "Quatitative and Selective Fluorophore Labeling of Phosphoserine on Peptides and Proteins: Characterization at the Attomole Level by Capillary Electrophoresis and Laser-Induced Fluorescence", Analytical Biochemistry, vol. 225, 1995, pp. 81-88.
Oda, Y. et al., "Enrichment analysis of phosphorylated proteins as a tool for probing the phosphoproteome", Nature Biotechnology, vol. 19, Apr. 2001, pp. 379-382.
Frackelton, A.R. et al., "Generation of Monoclonal Antibodies against Phosphotyrosine and Their Use for Affinity Purification of Phosphotyrosine-Containing Proteins", Methods in Enzymology, vol. 201, 1991, pp. 79-92.
Posewitz, M.C. et al., "Immobolized Gallium(III) Affinity Chromatography of Phosphopeptides", Analytical Chemistry, vol. 71, No. 14, Jul. 15, 1999, pp. 2883-2892.

* cited by examiner

TMT fragment: 126 Da 127 Da

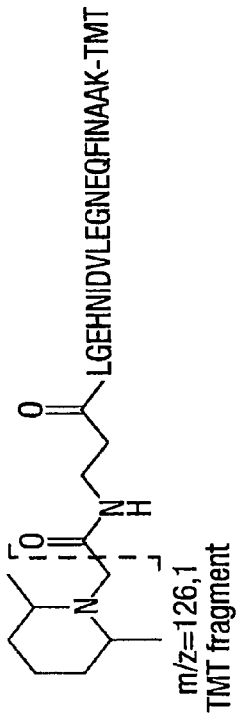
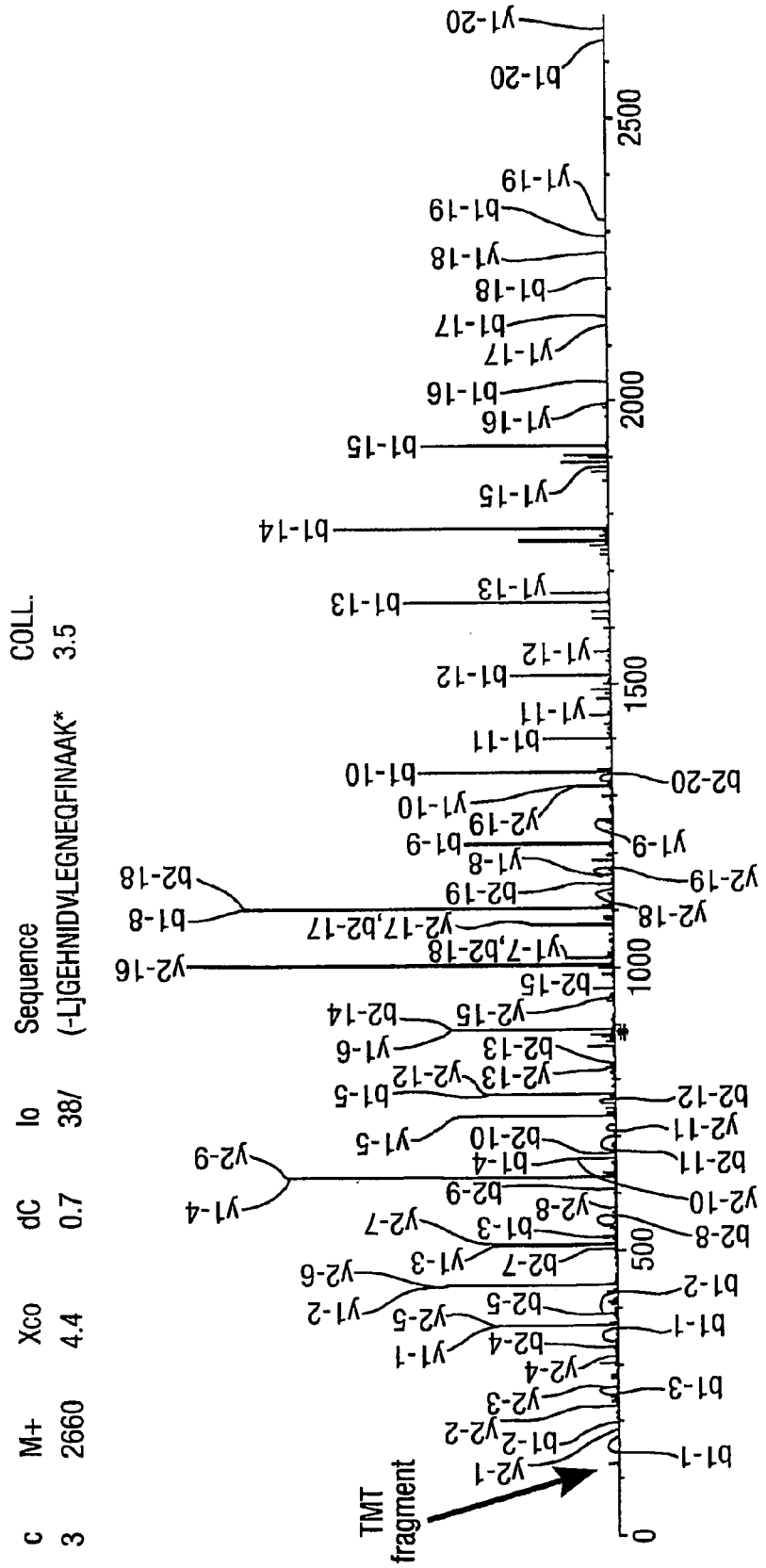
Fig.9(cont).

Fig.11(Cont).
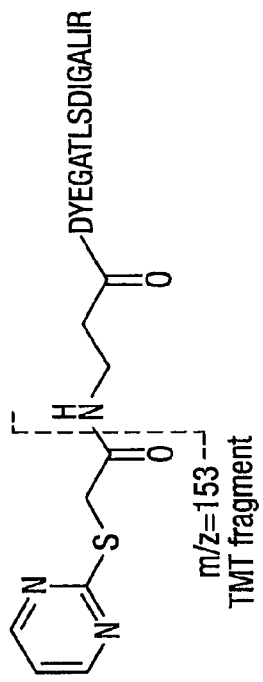
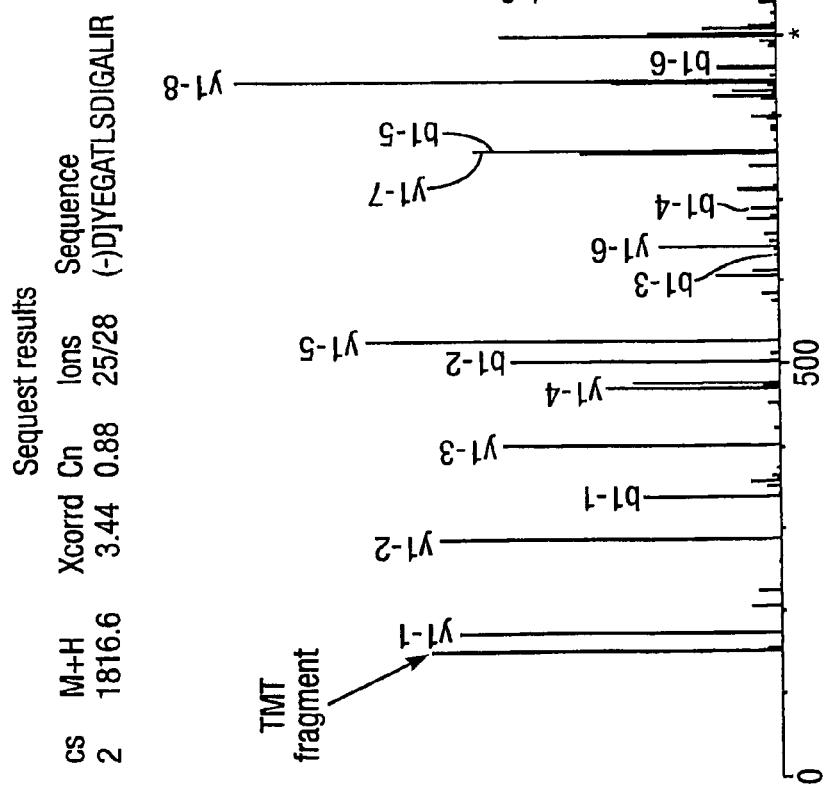

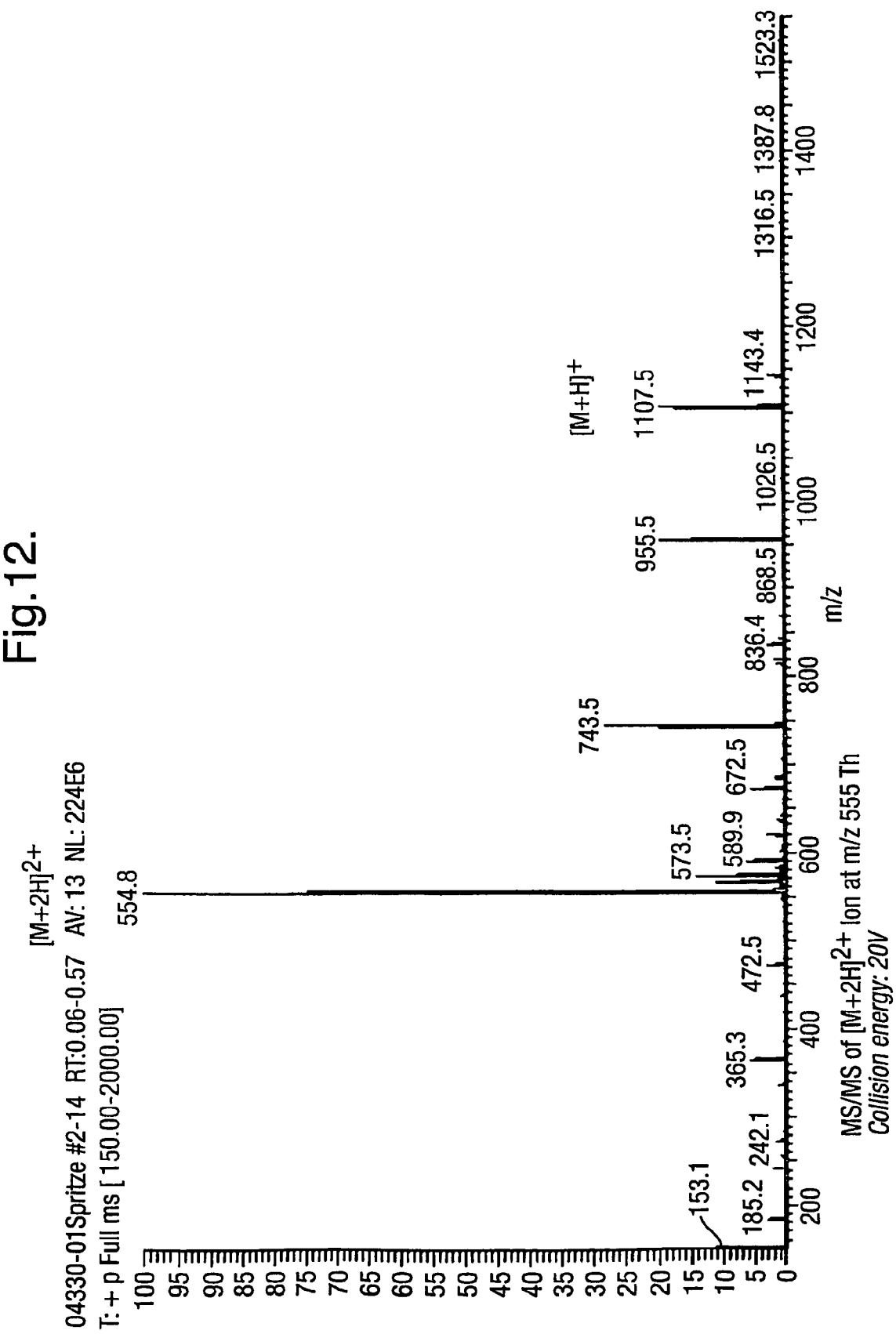

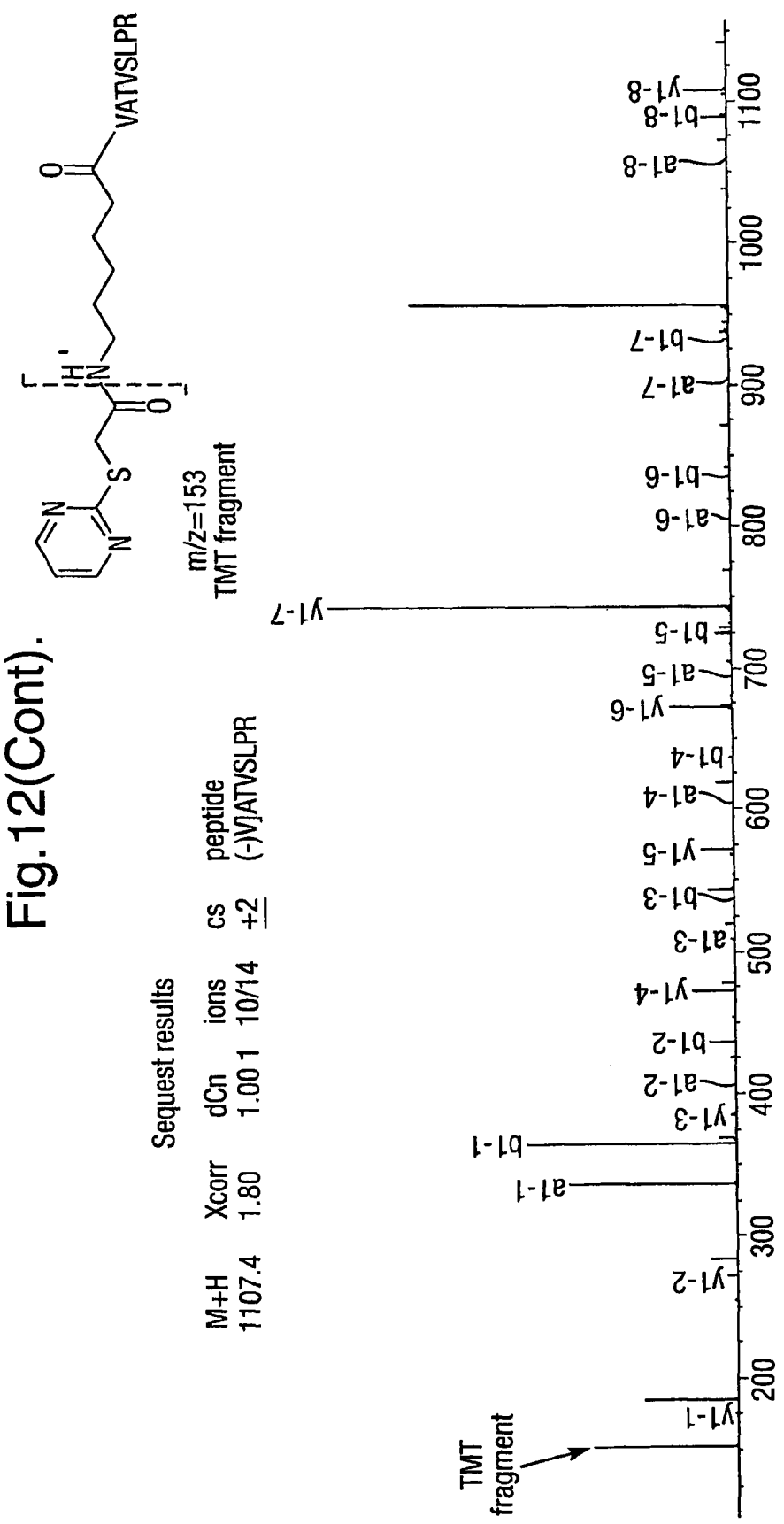

Fig.20(Cont).
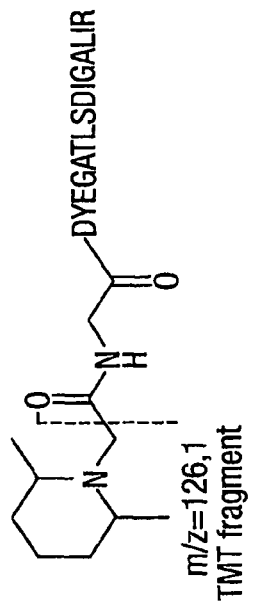
m/z=126,1
TMT fragment
peptide
D]YEGATLSDIGALIR
Sequest results
Xcorr  dCn   ions    cs
3.49   0.83  25/28   +2
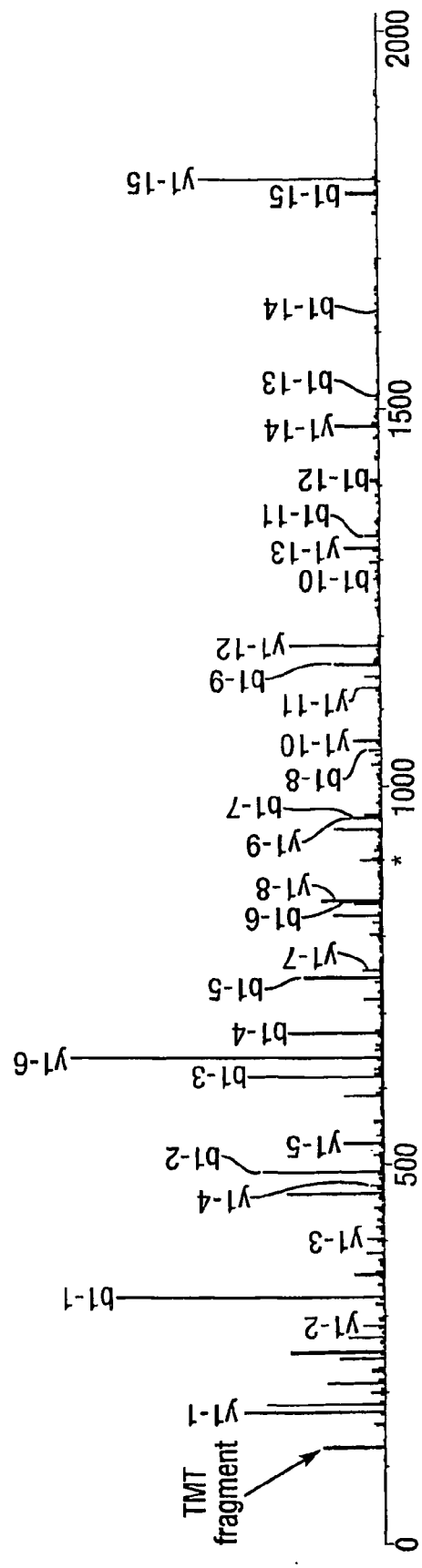

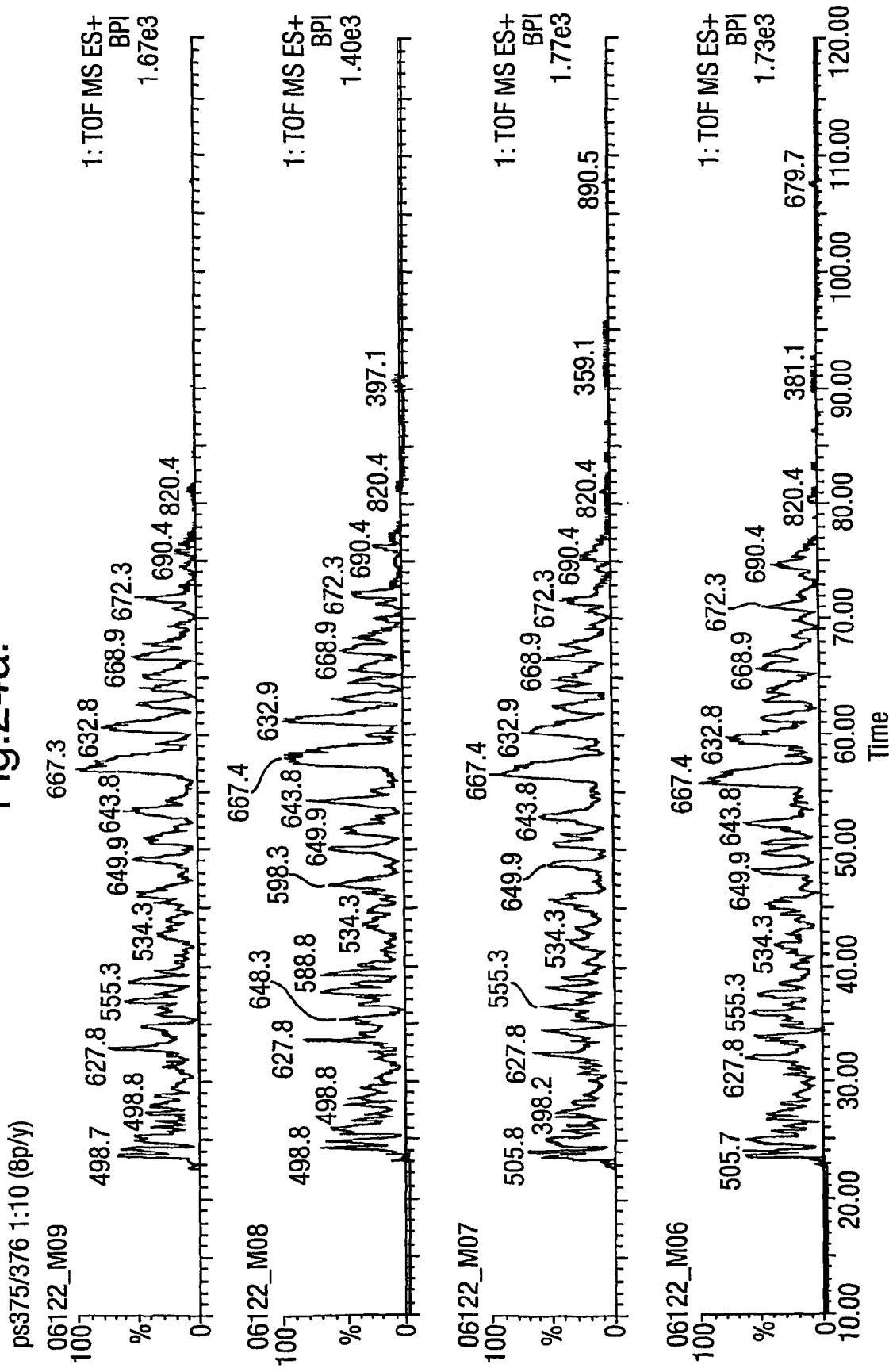

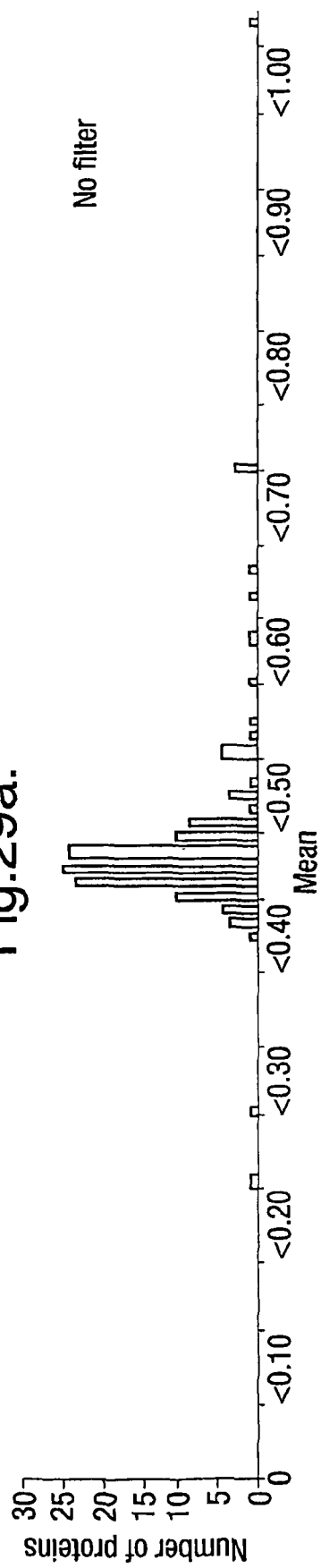
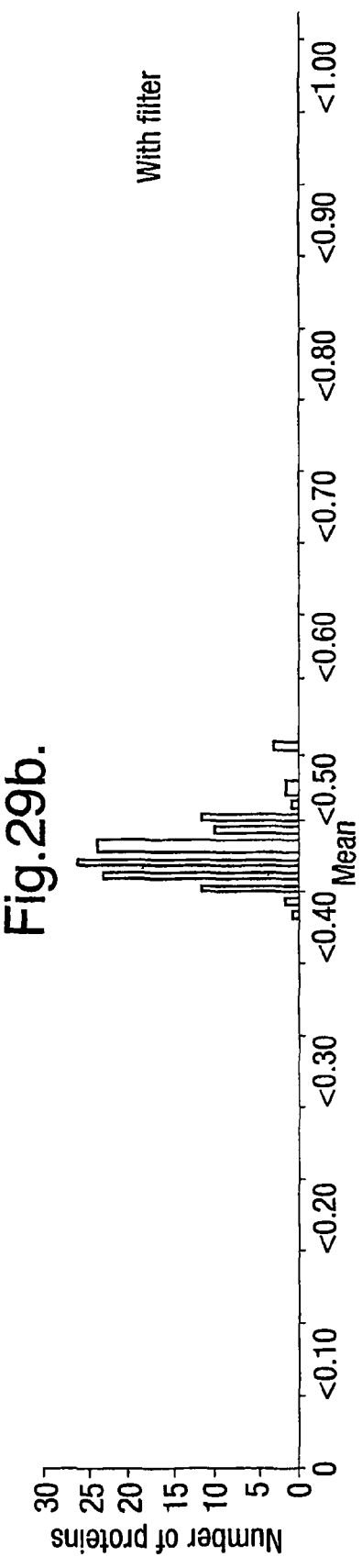

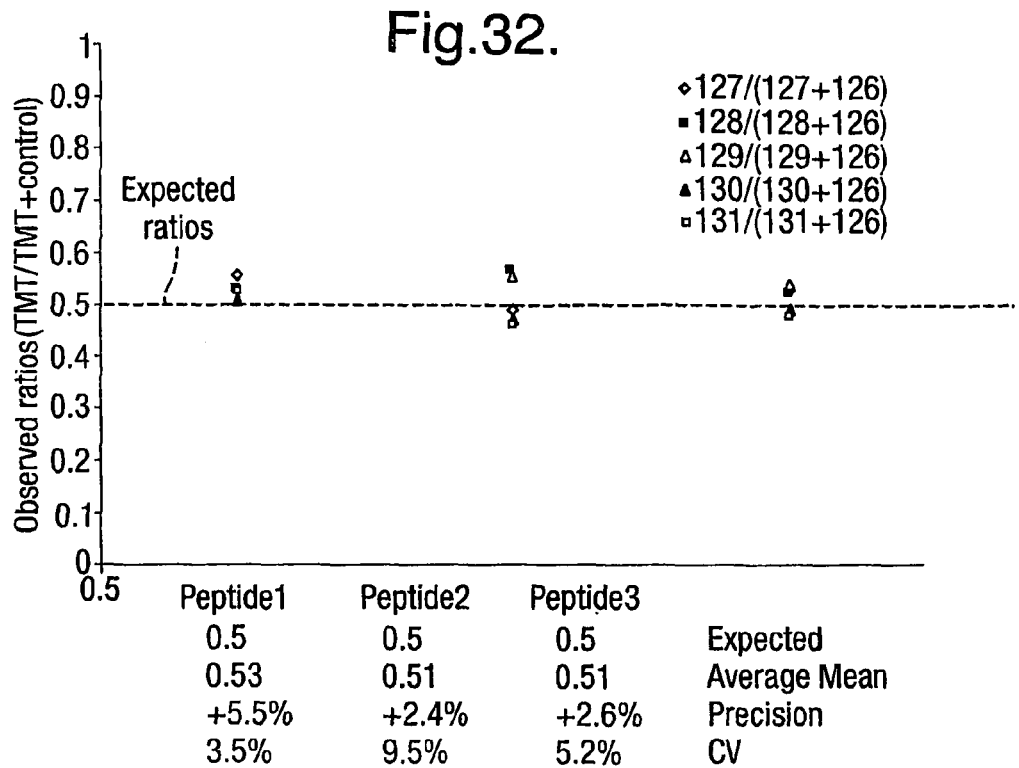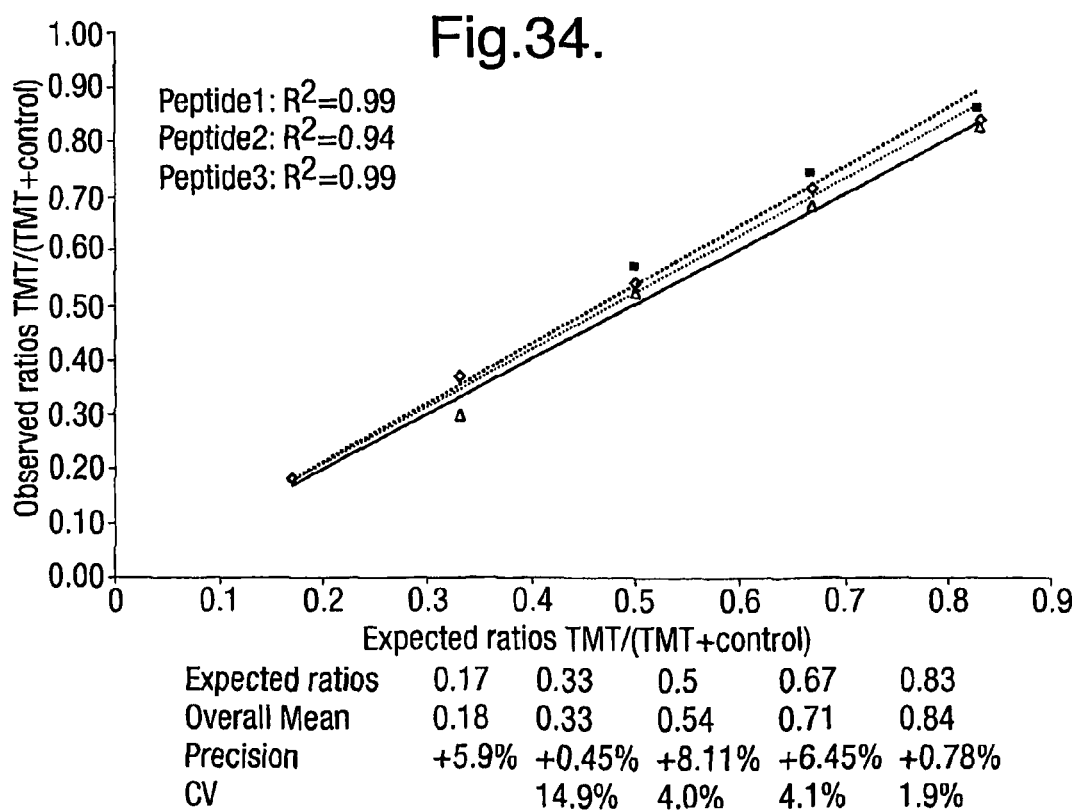

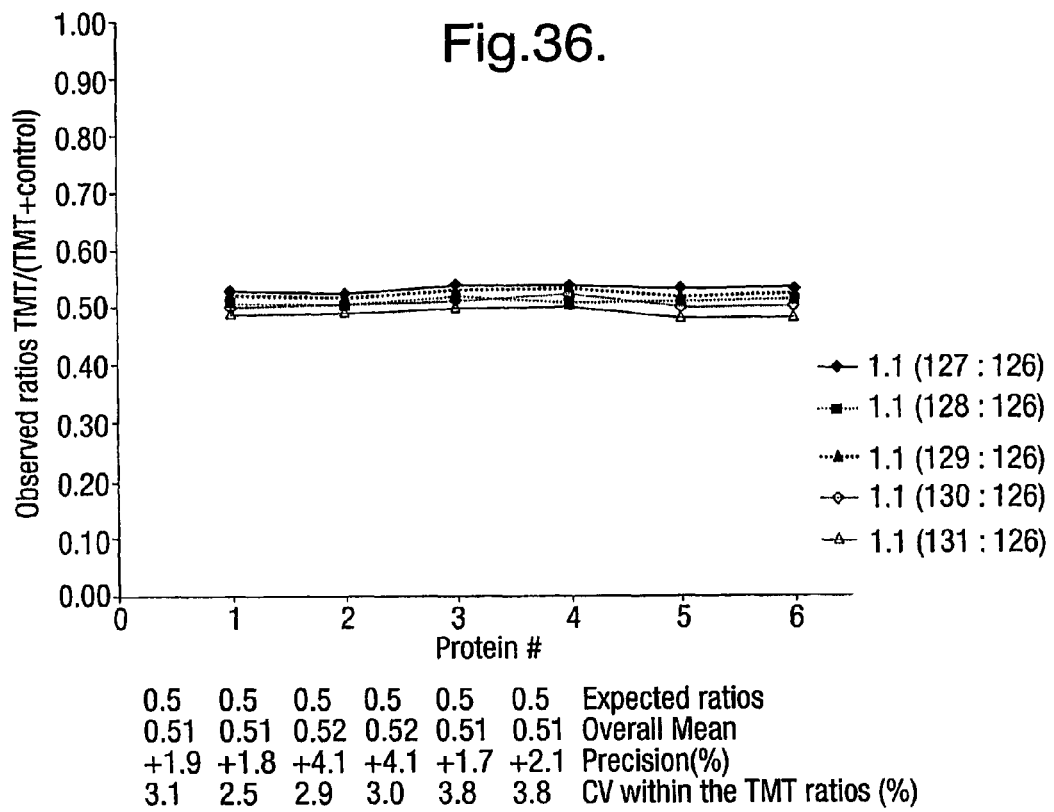
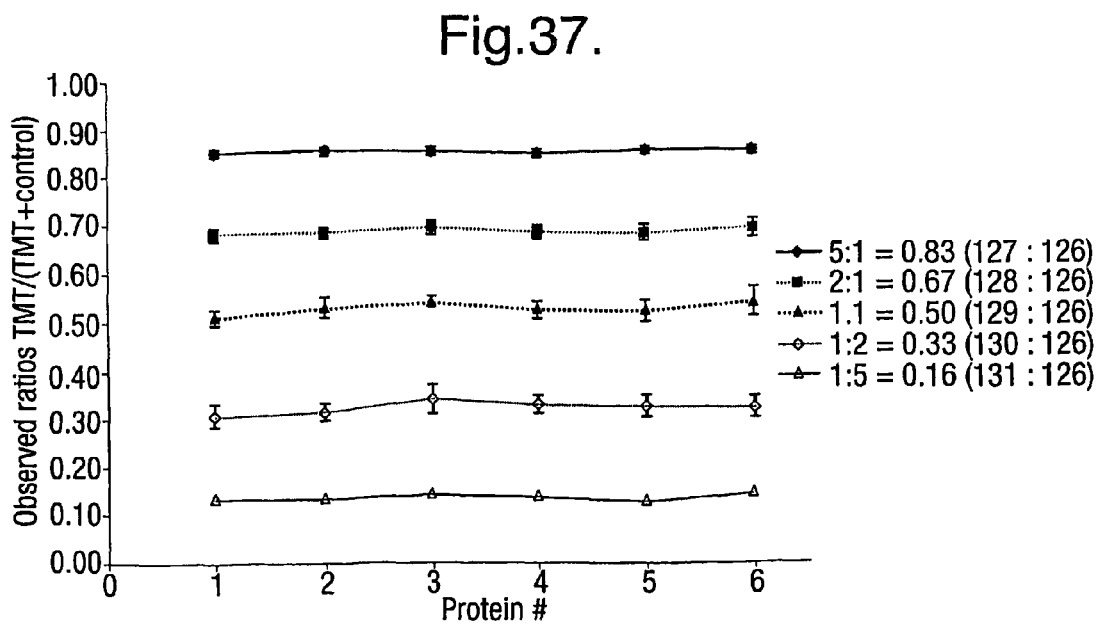

REACTIVE MASS LABELS

This invention relates to useful compounds for labelling molecules of interest, particularly biomolecules such as peptides and proteins. Specifically this invention relates to labelling of analytes for detection by mass spectrometry and associated methods of analysing mass labelled analytes by mass spectrometry. Relative quantitation of the biomolecules is particularly facilitated by the invention.

Various methods of labelling molecules of interest are known in the art, including radioactive atoms, fluorescent dyes, luminescent reagents, electron capture reagents and light absorbing dyes. Each of these labelling systems has features which make it suitable for certain applications and not others. For reasons of safety, interest in non-radioactive labelling systems lead to the widespread commercial development of fluorescent labelling schemes particularly for genetic analysis. Fluorescent labelling schemes permit the labelling of a relatively small number of molecules simultaneously, typically 4 labels can be used simultaneously and possibly up to eight. However the costs of the detection apparatus and the difficulties of analysing the resultant signals limit the number of labels that can be used simultaneously, in a fluorescence detection scheme.

More recently there has been development in the area of mass spectrometry as a method of detecting labels that are cleavably attached to their associated molecule of interest. In many molecular biology applications one needs to be able to perform separations of the molecules of interest prior to analysis. These are generally liquid phase separations. Mass spectrometry in recent years has developed a number of interfaces for liquid phase separations which make mass spectrometry particularly effective as a detection system for these kinds of applications. Until recently Liquid Chromatography Mass Spectrometry was used to detect analyte ions or their fragment ions directly, however for many applications such as nucleic acid analysis, the structure of the analyte can be determined from indirect labelling. This is advantageous particularly with respect to the use of mass spectrometry because complex biomolecules such as DNA have complex mass spectra and are detected with relatively poor sensitivity. Indirect detection means that an associated label molecule can be used to identify the original analyte, where the label is designed for sensitive detection and a simple mass spectrum. Simple mass spectra mean that multiple labels can be used to analyse multiple analytes simultaneously.

PCT/GB98/00127 describes arrays of nucleic acid probes covalently attached to cleavable labels that are detectable by mass spectrometry which identify the sequence of the covalently linked nucleic acid probe. The labelled probes of this application have the structure Nu-L-M where Nu is a nucleic acid covalently linked to L, a cleavable linker, covalently linked to M, a mass label. Preferred cleavable linkers in this application cleave within the ion source of the mass spectrometer. Preferred mass labels are substituted poly-aryl ethers. This application discloses a variety of ionisation methods and analysis by quadrupole mass analysers, TOF analysers and magnetic sector instruments as specific methods of analysing mass labels by mass spectrometry.

PCT/GB94/01675 disclose ligands, and specifically nucleic acids, cleavably linked to mass tag molecules. Preferred cleavable linkers are photo-cleavable. This application discloses Matrix Assisted Laser Desorption Ionisation (MALDI) Time of Flight (TOF) mass spectrometry as a specific method of analysing mass labels by mass spectrometry.

PCT/US97/22639 discloses releasable non-volatile mass-label molecules. In preferred embodiments these labels comprise polymers, typically biopolymers which are cleavably attached to a reactive group or ligand, i.e. a probe. Preferred cleavable linkers appear to be chemically or enzymatically cleavable. This application discloses MALDI TOF mass spectrometry as a specific method of analysing mass labels by mass spectrometry.

PCT/US97/01070, PCT/US97/01046, and PCT/US97/01304 disclose ligands, and specifically nucleic acids, cleavably linked to mass tag molecules. Preferred cleavable linkers appear to be chemically or photo-cleavable. These applications disclose a variety of ionisation methods and analysis by quadrupole mass analysers, TOF analysers and magnetic sector instruments as specific methods of analysing mass labels by mass spectrometry.

None of these prior art applications mention the use of tandem or serial mass analysis for use in analysing mass labels.

Gygi et al. (Nature Biotechnology 17: 994-999, "Quantitative analysis of complex protein mixtures using isotope-coded affinity tags" 1999) disclose the use of 'isotope encoded affinity tags' for the capture of peptides from proteins, to allow protein expression analysis. In this article, the authors describe the use of a biotin linker, which is reactive to thiols, for the capture peptides with cysteine in them. A sample of protein from one source is reacted with the biotin linker and cleaved with an endopeptidase. The biotinylated cysteine-containing peptides can then be isolated on avidinated beads for subsequent analysis by mass spectrometry. Two samples can be compared quantitatively by labelling one sample with the biotin linker and labelling the second sample with a deuterated form of the biotin linker. Each peptide in the samples is then represented as a pair of peaks in the mass spectrum. Integration of the peaks in the mass spectrum corresponding to each tag indicate the relative expression levels of the peptide linked to the tags.

Applied Biosystems have marketed so-called iTRAQ reagents, amine-modifying labelling reagents for multiplexed protein quantitation. Generally, a plurality of isobaric reagents are provided for labelling a number of samples. For example, for a set of four isobaric reagents, four samples can be multiplexed. However, it is still desirable to improve on the performance of these reagents. Typically the reagents are used in an LC/MS/MS method.

PCT/GB01/01122 discloses a set of two or more mass labels, each label in the set comprising a mass marker moiety attached via a cleavable linker to a mass normalisation moiety, the mass marker moiety being fragmentation resistant. The aggregate mass of each label in the set may be the same or different and the mass of the mass marker moiety of each label in the set may be the same or different. In any group of labels within the set having a mass marker moiety of a common mass each label has an aggregate mass different from all other labels in that group, and in any group of labels within the set having a common aggregate mass each label has a mass marker moiety having a mass different from that of all other mass marker moieties in that group, such that all of the mass labels in the set are distinguishable from each other by mass spectrometry. This application also discloses an array of mass labels, comprising two or more sets of mass labels as defined above. The aggregate mass of each of the mass labels in any one set is different from the aggregate mass of each of the mass labels in every other set in the array. This application further discloses methods of analysis comprising detecting an analyte by identifying by mass spectrometry a mass label or a combination of mass labels unique to the analyte. This application discloses a vast number of different specific mass labels. Preferred mass labels have the structure M-L-X, where M is the mass normalization group, L is the cleavable linker and X is the mass marker moiety. The nature of M and X is not particularly limited. Preferred mass normalization groups are benzyl groups optionally substituted with one or more F atoms. The preferred linker is an amide bond. The preferred mass marker moiety is a pyridyl group optionally substituted with one or more F atoms.

PCT/GB02/04240 discloses a set of two or more mass labels, each label in the set comprising a mass marker moiety attached via at least one amide bond to a mass normalisation moiety. The mass marker moiety comprises an amino acid and the mass normalisation moiety comprises an amino acid. As for PCT/GB01/01122 the aggregate mass of each label in the set may be the same or different and the mass of the mass marker moiety of each label in the set may be the same or different such that all of the mass labels in the set are distinguishable from each other by mass spectrometry. As for PCT/GB01/01122 this application also discloses an array of mass labels and a method of analysis. This application is specifically directed to the analysis of peptides and mass labels with mass normalisation moieties and mass marker moieties comprising at least one amino acid.

Whilst the mass labels and methods of analysis disclosed in PCT/GB01/01122 and PCT/GB02/04240 are by and large successful, there is still a requirement to provide improved mass labels and methods of detecting an analyte by identifying by mass spectrometry a mass label. In particular, whilst these new mass labels and methods of analysis allow multiple samples to be analysed simultaneously and quantitatively without significantly increasing the complexity of the mass spectrum there is still a requirement to provide improved mass labels which can be easily identified in a mass spectrometer and allow sensitive quantification. It is also desirable to provide improved mass labels which can easily reacted with an analyte to be identified and allow easy removal of excess mass labels prior to analysis in a mass spectrometer.

Accordingly, it is an aim of the present invention to solve the problems of the prior art in this field and provide improved mass labels that can be clearly identified in a mass spectrum with improved quantification. It is also an aim of the present invention to provide improved mass labels which can be easily reacted with analytes and easily separated from mass labels which are attached to the analyte to be identified prior to analysis in a mass spectrometer.

It is also an aim of the present invention to provide improved methods of analysing biological molecules which exploit the labels of this invention to maximise sensitivity of such methods, particularly for the analysis of peptides.

In a first aspect the invention provides a mass label for labelling and detecting a biological molecule by mass spectrometry, which label comprises the following structure:

X-L-M wherein X is a mass marker moiety comprising the following group:

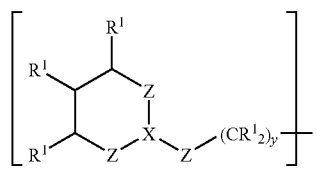

wherein the cyclic unit is aromatic or aliphatic and comprises from 0-3 double bonds independently between any two adjacent atoms; each Z is independently N, N($R^1$), C($R^1$), CO, CO($R^1$) (i.e. —O—C($R^1$)— or —C($R^1$)—O—), C($R^1$)$_2$, O or S; X is N, C or C($R^1$); each $R^1$ is independently H, a substituted or unsubstituted straight or branched $C_1$-$C_6$ alkyl group, a substituted or unsubstituted aliphatic cyclic group, a substituted or unsubstituted aromatic group or a substituted or unsubstituted heterocyclic group; and y is an integer from 0-10, L is a cleavable linker comprising an amide bond and M is a mass normalization moiety.

The term mass label used in the present context is intended to refer to a moiety suitable to label an analyte for determination. The term label is synonymous with the term tag.

The term mass marker moiety used in the present context is intended to refer to a moiety that is to be detected by mass spectrometry.

The term mass normalisation moiety used in the present context is intended to refer to a moiety that is not necessarily to be detected by mass spectrometry, but is present to ensure that a mass label has a desired aggregate mass. The mass normalisation moiety is not particularly limited structurally, but merely serves to vary the overall mass of the mass label.

In the above general formula, when Z is C($R^1$)$_2$, each $R^1$ on the carbon atom may be the same or different (i.e. each $R^1$ is independent). Thus the C($R^1$)$_2$ group includes groups such as CH($R^1$), wherein one $R^1$ is H and the other $R^1$ is another group selected from the above definition of $R^1$.

In the above general formula, the bond between X and the non-cyclic Z may be single bond or a double bond depending upon the selected X and Z groups in this position. For example, when X is N or C($R^1$) the bond from X to the non-cyclic Z must be a single bond. When X is C, the bond from X to the non-cyclic Z may be a single bond or a double bond depending upon the selected non-cyclic Z group and cyclic Z groups. When the non-cyclic Z group is N or C($R^1$) the bond from non-cyclic Z to X is a single bond or if y is 0 may be a double bond depending on the selected X group and the group to which the non-cyclic Z is attached. When the non-cyclic Z is N($R^1$), CO($R^1$), CO, C($R^1$)$_2$, O or S the bond to X must be a single bond. The person skilled in the art may easily select suitable X, Z and (C$R^1{}_2$)$_y$ groups with the correct valencies (single or double bond links) according to the above formula.

The present invention also provides a mass label as defined above, for labelling and detecting a biological molecule by mass spectrometry, which label comprises the following structure:

X-L-M wherein X is a mass marker moiety comprising the following group:

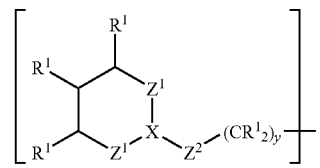

wherein the cyclic unit is aromatic or aliphatic and comprises from 0-3 double bonds independently between any two adjacent atoms; each $Z^1$ and $Z^2$ is independently N, N($R^1$), C($R^1$), CO, CO($R^1$) (i.e. —O—C($R^1$)— or —C($R^1$)—O—), C($R^1$)$_2$, O or S; X is N, C or C($R^1$); wherein at least one of $Z^1$ and X is N; each $R^1$ is independently H, a substituted or unsubstituted straight or branched $C_1$-$C_6$ alkyl group, a substituted or unsubstituted aliphatic cyclic group, a substituted or unsubstituted aromatic group or a substituted or unsubstituted heterocyclic group; and y is an integer from 0-10, L is a cleavable linker comprising an amide bond and M is a mass normalization moiety.

The present invention also provides a mass label as defined above, for labelling and detecting a biological molecule by mass spectrometry, which label comprises the following structure:

X-L-M wherein X is a mass marker moiety comprising the following group:

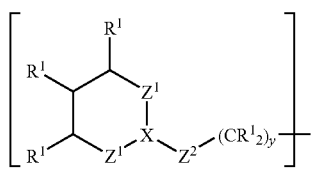

wherein the cyclic unit is aromatic or aliphatic and comprises from 0-3 double bonds independently between any two adjacent atoms; each $Z^1$ is independently N, $N(R^1)$, $C(R^1)$, CO, $CO(R^1)$ (i.e. —O—$C(R^1)$— or —$C(R^1)$—O—), $C(R^1)_2$, O or S; $Z^2$ is N, $N(R^2)$, $C(R^1)$, CO, $CO(R^1)$ (i.e. —O—C$(R^1)$— or —$C(R^1)$—O—), $C(R^1)_2$ or S; X is N, C or $C(R^1)$; each $R^1$ is independently H, a substituted or unsubstituted straight or branched $C_1$-$C_6$ alkyl group, a substituted or unsubstituted aliphatic cyclic group, a substituted or unsubstituted aromatic group or a substituted or unsubstituted heterocyclic group; $R^2$ is a substituted or unsubstituted straight or branched $C_1$-$C_6$ alkyl group, a substituted or unsubstituted aliphatic cyclic group, a substituted or unsubstituted aromatic group or a substituted or unsubstituted heterocyclic group and y is an integer from 0-10, L is a cleavable linker comprising an amide bond and M is a mass normalization moiety.

The present invention also provides a mass label as defined above, for labelling and detecting a biological molecule by mass spectrometry, which label comprises the following structure:

X-L-M wherein X is a mass marker moiety comprising the following group:

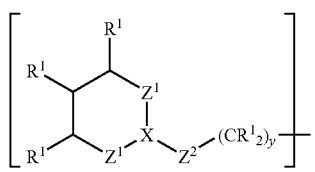

wherein the cyclic unit is aromatic or aliphatic and comprises from 0-3 double bonds independently between any two adjacent atoms; each $Z^1$ is independently N, $N(R^1)$, $C(R^1)$, CO, $CO(R^1)$ (i.e. —O—$C(R^1)$— or —$C(R^1)$—O—), $C(R^1)_2$, O or S; $Z^2$ is N, $N(R^1)$, $C(R^1)$, CO, $CO(R^1)$ (i.e. —O—C$(R^1)$— or —$C(R^1)$—O—), $C(H)R^3$, $C(R^1)(R^2)$, O or S; X is N, C or $C(R^1)$; each $R^1$ is independently H, a substituted or unsubstituted straight or branched $C_1$-$C_6$ alkyl group, a substituted or unsubstituted aliphatic cyclic group, a substituted or unsubstituted aromatic group or a substituted or unsubstituted heterocyclic group; $R^2$ is a substituted or unsubstituted straight or branched $C_1$-C6 alkyl, a substituted or unsubstituted aliphatic cyclic group, a substituted or unsubstituted aromatic group or a substituted or unsubstituted heterocyclic group; $R^3$ is H, a substituted or unsubstituted straight or branched $C_1$-$C_6$ alkyl group, a substituted or unsubstituted aliphatic cyclic group or a substituted or unsubstituted heterocyclic group; y is an integer from 0-10; and L is a cleavable linker comprising an amide bond and M is a mass normalization moiety.

The present invention also provides a mass label as defined above, for labelling and detecting a biological molecule by mass spectrometry, which label comprises the following structure:

wherein X is a mass marker moiety comprising the following group:

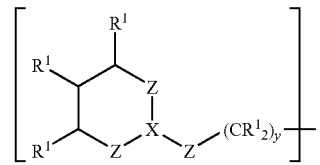

wherein the cyclic unit is aromatic or aliphatic and comprises from 0-3 double bonds independently between any two adjacent atoms; each Z is independently N, $N(R^1)$, $C(R^1)$, CO, $CO(R^1)$ (i.e. —O—$C(R^1)$— or —$C(R^1)$—O—), $C(R^1)_2$, O or S; X is N, C or $C(R^1)$; each $R^1$ is independently H, a substituted or unsubstituted straight or branched $C_1$-$C_6$ alkyl group, a substituted or unsubstituted aliphatic cyclic group, a substituted or unsubstituted aromatic group or a substituted or unsubstituted heterocyclic group; and y is an integer from 0-10, L is a cleavable linker comprising an amide bond and M is a mass normalization moiety, wherein when y is 3 or 4 and the amide bond in L is adjacent to $(CR^1_2)_y$ then at least one of $R^1$ in $(CR^1_2)_y$ is selected from a substituted or unsubstituted straight or branched $C_1$-$C_6$ alkyl group, a substituted or unsubstituted aliphatic cyclic group, a substituted or unsubstituted aromatic group or a substituted or unsubstituted heterocyclic group.

In a preferred embodiment the mass label of the present invention as defined in any one or more of the formulae above, does not include one or more of the following formulae or compounds:

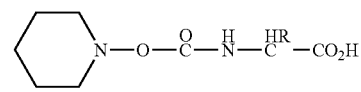

wherein the $CHRCO_2H$ group is a naturally occurring amino acid;

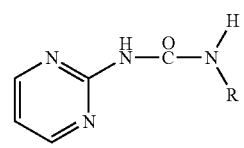

wherein R is a $C_1$-$C_4$ alkyl group, a $C_2$-$C_3$ alkenyl group, a radical cycloalkyl group having up to 6 C atoms, or a phenyl or naphthyl group optionally substituted by one or more halogens or one or more lower alkyl groups;

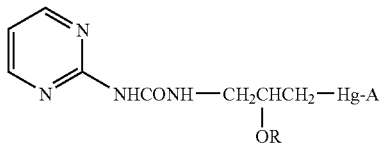

wherein R is H or a lower alkyl group and A is acyloxy, halogen, hydroxyl, a residue of an acidic nitrogen compound from which a hydrogen has been displaced so that the nitrogen from which the hydrogen has been removed is bonded directly to the mercury atom, or an S—R' group in which R' is a monocarboxy substituted lower alkyl group, a polycarboxy substituted lower alkyl group, a monocarboxy substituted aromatic group, a polycarboxy substituted aromatic group, a lower monohydric alcohol group and a lower polyhydric alcohol group and salts thereof, as well as intermediate compounds useful in the production thereof;

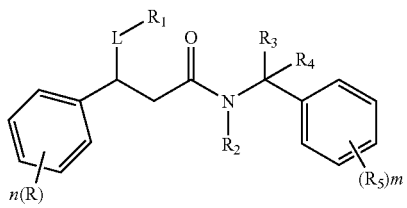

wherein R represents halogen, $C_1$-$C_4$ alkyl, cyano, $C_1$-$C_4$ alkoxy, trifluoromethyl or trifluoromethoxy; $R_1$ represents piperidyl, 1,2,3,6-tetrahydro-4-pyridinyl, pyridyl or pyrrolidinyl, $R_2$ represents hydrogen of $C_1$-$C_4$ alkyl, $R_3$ and $R_4$ independently represent hydrogen, $C_1$-$C_4$ alkyl or $R_3$ together with $R_4$ represents $C_3$-$C_7$ cycloalkyl, $R_5$ represents trifluoromethyl, $S(O)_q C_1$-$C_4$ alkyl, $C_1$-$C_4$ alkyl, $C_1$-$C_4$ alkoxy, trifluoromethoxy, halogen or cyano, L is a single or double bond, n is an integer from 1 to 3, m is zero or an integer from 1 to 3 and q is zero or an integer from 1 to 2;

N-(3,5-Bis-trifluoromethyl-benzyl)-3-(4-fluoro-phenyl)-N-methyl-3-piperidin-4-yl-propionamide;

N-(3,5-Dichloro-benzyl)-3-(4-fluoro-phenyl)-N-methyl-3-piperidin-4-yl-propionamide;

N-[1-(3,5-Dichloro-phenyl)-ethyl]-3-(4-fluoro-phenyl)-N-methyl-3-piperidin-4-yl-propionamide;

N-[1-(3,5-Dichloro-phenyl)-ethyl]-3-(4-fluoro-phenyl)-N-methyl-3-[1-(2-methoxyethyl)-piperidin-4-yl]-propionamide;

N-(3,5-Dichloro-benzyl)-3-(4-fluoro-phenyl)-3-(4-fluoro-piperidin-4-yl)-N-methylpropionamide;

N-{[3,5-bis(trifluoromethyl)phenyl]methyl}-3-(4-fluorophenyl)-N-methyl-3-{1-[2-(methyloxy)ethyl]-4-piperidinyl}propionamide-N-{-1-[3,5-bis(trifluoromethyl)phenyl]ethyl}-3-(4-fluorophenyl)-N-methyl-3-(4-piperidinyl)propionamide;

N-{1-[3,5-bis(trifluoromethyl)phenyl]-1-methylethyl}-3-(4-fluorophenyl)-3-(4-piperidinyl)propionamide;

N-{[3-bromo-4-(methyloxy)phenyl]methyl}-3-(4-fluorophenyl)-N-methyl-3-(4-piperidinyl)propionamide;

N-[(3,5-dimethylphenyl)methyl]-3-(4-fluorophenyl)-N-methyl-3-(4-piperidinyl)propionamide;

N-[(3,4-dibromophenyl)methyl]-3-(4-fluorophenyl)-N-methyl-3-(4-piperidinyl)propionamide;

N-[(3-fluoro-2-methylphenyl)methyl]-3-(4-fluorophenyl)-N-methyl-3-(4-piperidinyl)propionamide;

N-{[2-chloro-3-(trifluoromethyl)phenyl]methyl}-3-(4-fluorophenyl)-N-methyl-3-(4-piperidinyl)propionamide;

N-{-1-[3,5-bis(trifluoromethyl)phenyl]ethyl}-3-(4-fluorophenyl)-3-(4-fluoro-4-piperidinyl)-N-methylpropionamide;

N-[(3,5-dibromophenyl)methyl]-3-(4-fluorophenyl)-3-(4-fluoro-4-piperidinyl)-N-methylpropionamide;

N-{-1-[3,5-bis(trifluoromethyl)phenyl]ethyl}-3-(2,4-dichlorophenyl)-3-(4-fluoro-4-piperidinyl)-N-methylpropionamide;

N-[(3,5-bis(trifluoromethyl)phenyl]ethyl]-3-(4-fluoro-2-methylphenyl)-3-(4-fluoro-4-piperidinyl)-N-methylpropionamide;

N-[(3,5-dibromophenyl)methyl]-3-(4-fluoro-2-methylphenyl)-3-(4-fluoro-4-piperidinyl)-N-methylpropionamide;

N-[(3,5-dibromophenyl)methyl]-3-(3,4-dichlorophenyl)-3-(4-fluoro-4-piperidinyl)-N-methylpropionamide;

N-{[3,5-bis(trifluoromethyl)phenyl]methyl}-3-(4-fluorophenyl)-3-(4-fluorok-4-piperidinyl)-N-methylpropionamide;

3-(4-chlorophenyl)-N-[(3,5-dibromophenyl)methyl]-3-(4-fluoro-4-piperidinyl)-N-methylpropionamide;

N-{[3,5-bis(trifluoromethyl)phenyl]methyl}-3-(4-fluorophenyl)-N-methyl-3-(3-piperidinylidene)propionamide;

N-[(3,5-dibromophenyl)methyl]-3-(4-fluorophenyl)-N-methyl-3-(4-piperidinylidene)propionamide;

N-{[3,5-bis(trifluoromethyl)phenyl]methyl}-3-(4-fluoro-2-methylphenyl)-N-methyl-3-(1,2,3,6-tetrahydro-4-pyridinyl)propionamide;

N-{(1R)-1-[3,5-bis(trifluoromethyl)phenyl]ethyl}-3-(4-fluoro-2-methylphenyl)-N-methyl-3-(1,2,3,6-tetrahydro-4-pyridinyl)propionamide;

N-{[3,5-bis(trifluoromethyl)phenyl]methyl}-3-(4-fluorophenyl)-N-methyl-3-(3-pyrrolidinyl)propionamide;

N-{[3,5-bis(trifluoromethyl)phenyl]methyl}-3-(4-fluorophenyl)-3-(3-fluoro-3-piperidinyl)-N-methylpropionamide;

N-{-1-[3,5-bis(trifluoromethyl)phenyl]ethyl}-3-(4-fluorophenyl)-N-methyl-3-(2-morpholinyl)propionamide;

N-{[3,5-bis(trifluoromethyl)phenyl]methyl}-3-(4-fluorophenyl)-N-methyl-3-(3-piperidinyl)propionamide;

N-{(3,5-bis(trifluoromethyl)phenyl]methyl}-3-(4-fluorophenyl)-N-methyl-3-(4-pyridinyl)propionamide;

and enantiomers, diastereoisomers, pharmaceutically acceptable salts (e.g hydrochloride) and solvates thereof; and N{(1R)-1-[3,5-bis(trifluoromethyl)phenyl]ethyl}-3-(4-fluorophenyl)-N-methyl-3-(4-piperidinyl)propionamide(diastereoisomer 1);

N{(1S)-1-[3,5-bis(trifluoromethyl)phenyl]ethyl}-3-(4-fluorophenyl)-N-methyl-3-(4-piperidinyl)propionamide(diastereoisomer 2);

N{(1R)-1-[3,5-bis(trifluoromethyl)phenyl]ethyl}-3-(4-fluorophenyl)-3-(4-fluoro-4-piperidinyl)-N-methylpropionamide(diastereoisomer 1);

N-[(3,5-dibromophenyl)methyl]-3-(4-fluorophenyl)-3-(4-fluoro-4-piperidinyl)-N-methylpropionamide (enantiomer 2);

N-{[3,5-bis(trifluoromethyl)phenyl]methyl}-3-(4-fluorophenyl)-3-(3-fluoro-3-piperidinyl)-N-methylpropionamide (diastereoisomer A);

and pharmaceutically acceptable salts (e.g hydrochloride) and solvates thereof;

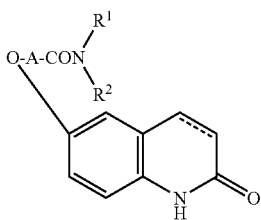

wherein A represents a lower alkylene group, $R^1$ represents a substituted or unsubstituted cycloalkyl-lower alkyl group, a cycloalkyl group, a tetrahydropyranyl-lower alkyl group, a lower alkylenedioxy-substituted lower alkyl group, a substituted phenyl-lower alkyl group or a lower alkyl-substituted piperidinyl-lower alkyl group, $R^2$ represents a substituted or unsubstituted 5- or 6-membered, saturated or unsaturated heterocyclic-lower alkyl group, a tetrahydropyranylthio-lower alkyl group, a pyridylthio-lower alkyl group, a lower alkylene-dioxy-substituted lower alkyl group or a substituted or unsubstituted lower alkyl group, and the carbon-to-carbon bond between the 3-position and the 4-position of the carbostyril skeleton represents either a single or a double bond;

4-(4-chloro-benzoylamino)-N-{-4-[4-(2,4-dimethoxy-phenyl)-piperidin-1-yl]-butyl}-benzamide;
4-(4-chloro-benzoylamino)-N-{4-[4-(2-ethoxy-4-methyl-phenyl)-piperidin-1-yl]-butyl}-benzamide;
4-(4-chloro-benzoylamino)-N-{4-[4-(2-ethoxy-4-ethyl-phenyl)-piperidin-1-yl]-butyl}-benzamide;
4-(4-chloro-benzoylamino)-N-{4-[4-(4-ethyl-2-methoxy-phenyl)-piperidin-1-yl]-butyl}-benzamide;
4-(4-chloro-benzoylamino)-N-{4-[4-(4-isopropyl-2-methoxy-phenyl)-piperidin-1-yl]-butyl}-benzamide;
4-(4-chloro-benzoylamino)-N-{4-[4-(2-ethoxy-4-isopropyl-phenyl)-piperidin-1-yl]-butyl}-benzamide;
4'-Trifluoromethyl-biphenyl-4-carboxylic acid (4-{4-[2,5-dimethyl-4-(pyridine-2-ylmethoxyl)-phenyl]-piperidin-1-yl}-butyl)-amide;
4-(4-chloro-benzoylamino)-N-[4-(4-benzo[1,3]dioxol-5-yl-piperidin-1-yl]-butyl}-benzamide;
4-(4-chloro-benzoylamino)-N-[4-(4-naphthalen-2-yl-piperidin-1-yl]-butyl}-benzamide;
4-(4-chloro-benzoylamino)-N-{-4-[4-(5,6,7,8-tetrahydro-naphthalen-2-yl)-piperidin-1-yl]-butyl}-benzamide;
4-(4-chloro-benzoylamino)-N-{4-[4-(4-naphthalen-1-yl-piperidin-1-yl]-butyl}-benzamide;
4-(4-chloro-benzoylamino)-N-{4-[4-(2-trifluoroethoxy-4-methyl-phenyl)-piperidin-1-yl]-butyl}-benzamide;
4'-Trifluoromethyl-biphenyl-4-carboxylic acid {4-[4-(2-methylsulfanyl-phenyl)-piperidin-1-yl]-butyl}-amide;
4'-Trifluoromethyl-biphenyl-4-carboxylic acid{4-[4-(1-methyl-1H-indol-3-yl)-piperidin-1-yl]-butyl}-amide;
4'-Trifluoromethyl-biphenyl-4-carboxylic acid{4-[4-(1H-indol-3-yl)-piperidin-1-yl]-butyl}-amide;
4'-Trifluoromethyl-biphenyl-4-carboxylic acid [4-(4-benzo[b]thiophen-3-yl-piperidin-1-yl)-butyl]-amide;
4-(4-chloro-benzoylamino)-N-{4-[4-(2,4-dimethoxy-phenyl)-piperazin-1-yl]-butyl}-benzamide;
4-(4-Chloro-benzoylamino)-N-{4-[4-(2,4-dimethoxy-phenyl)-[1,4]diazocan-1-yl]-butyl}-benzamide;
4'-Trifluoromethyl-biphenyl-4-carboxylic acid{4-[4-(2-ethoxyl-4-methyl-phenylamino)-piperidin-1-yl]-butyl}-amide;
4'-Trifluoromethyl-biphenyl-4-carboxylic acid (4-{4-[benzenesulfonyl-(2-ethoxy-4-methyl-phenyl)-amino]-piperidin-1-yl}-butyl)-amide;
4'-Trifluoromethyl-biphenyl-4-carboxylic acid {4-[4-(naphtalen-1-yloxy)-piperidin-1-yl]-butyl}-amide;
4-(4-Chloro-benzoylamino)-N-{4-[4-(2-methoxy-4-methyl-phenyl)-piperazin-1-yl]-butyl}-benzamide;
4'-Trifluoromethyl-biphenyl-4-sulfonic acid{4-[4-(2-ethoxy-4-methyl-phenyl)-piperidin-1-yl]-butyl}-amide;
5-[4-(2-Ethoxy-4-methyl-phenyl)piperidin-1-yl]-pentanoic acid (4'-trifluoromethyl-biphenyl-4-yl)-amide;
4'-{5-[4-(1-Methoxy-naphtalen-2-yl)-piperidin-1-yl]-pentyloxy}-biphenyl-4-carbonitrile;
4'-{4-[4-(1-Methoxy-naphtalen-2-yl)-piperidin-1-yl]-butoxy}-biphenyl-4-carbonitrile;
4-Methyl-2-(4-trifluoromethyl-phenyl)-thiazole-5-carboxylic acid{-4-[4-(4-isopropyl-2-methoxyl-phenyl)-piperidin-1-yl]-butyl-amide;
2-(4-Chloro-phenyl)-1-methyl-1H-indole-5-carboxylic acid{4-[4-(2-ethoxy-4-methyl-phenyl)-piperidin-1-yl]-butyl}-amide;
2-(4-Trifluoromethyl-phenyl)-benzofuran-5-carboxylic acid{4-[4-(2-ethoxyl-4-methyl-phenyl)-piperidin-1-yl]-butyl}-amide;
2-(4-Chloro-phenyl)-benzofuran-5-carboxylic acid {4-[4-(2-ethoxyl-4-methyl-phenyl)-piperidin-1-yl]-butyl}-amide;
2-(3,4-Dichloro-phenyl)-benzofuran-5-carboxylic acid{4-[4-(1-cyclopropylmethoxy-5,6,7,8-tetrahydro-naphthalen-2-yl)-piperidin-1-yl]-butyl}-amide;
2-(6-Trifluoromethyl-pyridin-3-yl))-benzofuran-5-carboxylic acid{-4-[4-(1-cyclopropylmethoxy-5,6,7,8-tetrahydro-naphthalen-2-yl)-piperidin-1-yl]-butyl}-amide;
N-{4-[4-(2-Ethoxy-4-methyl-phenyl)-piperidin-1-yl]-butyl}-4-(4-trifluoromethyl-phenyl)-vinyl]-benzamide;
N-{-4-[4-(2-Ethoxy-4-methyl-phenyl)-piperidin-1-yl]-butyl}-4-(4-trifluoromethyl-benzyloxy)-benzamide;
4-[2-(3,5-dichloro-phenyl)-ethenyl]-N-{-4-[4-(2,4-dimethoxy-phenyl)-piperazin-1-yl]-butyl}-benzamide;
4-[2-(3,5-dichloro-phenyl)-ethyl]-N-{4-[4-(2,4-dimethoxy-phenyl)-piperazin-1-yl]-butyl}-benzamide;
4-(4-Benzoyl)-N-{4-[4-(4-propyl-2-methoxyl-phenyl)-piperidin-1-yl]-butyl}-benzamide;
4'-trifluoromethyl-biphenyl-4-carboxylic acid{4-[4-(2,4-diethoxy-benzyl)-piperidin-1-yl]-butyl}-amide;
4-(4-chloro-benzoylamino)-N-{4-[4-(2,4-dimethoxy-benzoyl)-piperidin-1-yl]-butyl}-benzamide;
4'-Cyano-biphenyl-4-carboxylic acid {4-[4-(1-methyl-1H-indol-3-yl)-piperidin-1-yl]-butyl}-amide
4-(4-chloro-benzoylamino)-N-{4-[4-(5-methyl-2-piperidin-4-yl-phenol)]-butyl}-benzamide;
4-(4-chloro-benzoylamino)-N-{4-[4-(5-ethyl-2-piperidin-4-yl-phenol)]-butyl}-benzamide;
4-(4-chloro-benzoylamino)-N-{4-[4-(1-hydroxy-5,6,7,8-tetrahydro-naphtalen-2-yl)-piperidin-1-yl]-butyl}-benzamide; or
4-(4-chloro-benzoylamino)-N-{4-[4-(1-hydroxy-naphtalen-2-yl)-piperidin-1-yl]-butyl}-benzamide;
or a physiologically acceptable salt, solvate or derivative thereof.

In the above formulae and compounds, where a 'lower' group is mentioned, the term lower means a number of carbon atoms which would be considered as a lower number by a skilled person for the particular groups in question. Preferably the terms means from $C_1$-$C_6$.

In a second aspect the invention provides a reactive mass label for labelling and detecting a biological molecule by mass spectrometry, comprising a reactive functionality for attaching the mass label to a biological molecule and a mass label as defined above. The reactive functionality may be attached to the mass normalization moiety of the mass label or attached to the mass marker moiety of the mass label.

The present inventors have discovered that the mass labels defined above can be easily identified in a mass spectrometer and also allow sensitive quantification.

In a preferred embodiment the aggregate molecular weight of the mass label is 600 Daltons or less, more preferably 500 Daltons or less, still more preferably 400 Daltons or less, most preferably from 300 to 400 Daltons. Particularly preferred molecular weights of the mass labels are 324, 338, 339 and 380 Daltons. These preferred embodiments are particularly advantageous because the small size of the mass labels means that the size of the biological molecule to be detected is minimally increased when labelled with the mass label of the present invention. Therefore, the biological molecule labelled with the mass label of the present invention may be viewed in the same mass spectrum window as the unlabelled biological molecule when analysed by mass spectrometry. This facilitates identification of peaks from the mass label itself.

In a preferred embodiment the molecular weight of the mass marker moiety is 300 Daltons or less, preferably 250 Daltons or less, more preferably 100 to 250 Daltons, most preferably 100-200 Daltons. These preferred embodiments are particularly advantageous because the small size of the mass marker moiety means that it produces a peak in the silent region of a mass spectrum, which allows the mass marker to be easily identified from the mass spectrum and also allows sensitive quantification.

The term silent region of a mass spectrum (such as an MS/MS spectrum) used in the present context is intended to refer to the region of a mass spectrum with low background "noise" caused by peaks relating to the presence of fragments generated by fragmentation of the labelled peptides. An MS/MS spectrum is obtained by the fragmentation of one peak in MS-mode, such that no contaminants, such as buffering reagents, denaturants and detergent should appear in the MS/MS spectrum. In this way, quantification in MS/MS mode is advantageous. Thus, the term silent region is intended to refer to the region of the mass spectrum with low "noise" caused by peaks relating to the biological molecule to be detected. When the biological molecule to be detected is a peptide or protein, the silent region of the mass spectrum is less than 200 Daltons. When the biological molecule to be detected is DNA, RNA, an oligonucleotide or a nucleic acid base, the silent region of the mass spectrum is less than 500 Daltons.

It has also been discovered by the present inventors that the mass labels and reactive mass labels defined above when not attached to the biological molecule to be detected can be easily separated from the biological molecule labelled with the mass label of the present invention prior to analysis in a mass spectrometer.

The present inventors have also discovered that the reactive mass labels defined above are easily and quickly reacted with the biological molecule to form a labelled biological molecule.

The present invention also provides a method of analysis, which method comprises detecting biological molecule or mixture of biological molecules by identifying by mass spectrometry a mass label relatable to the analyte, wherein the mass label is a mass label as defined above.

In a third aspect the invention provides set of two or more mass labels or reactive mass labels, wherein each label in the set is as defined above and wherein each mass normalisation moiety ensures that a mass label has a desired aggregate mass, and wherein the set comprises:

a group of labels having a mass marker moiety of common mass, each label in the group having a unique aggregate mass; or a group of labels having a mass marker moiety, each mass marker moiety having a mass different from that of all other mass marker moieties in that group, and each label in the group having a common aggregate mass;

and wherein all the mass labels in the set are distinguishable from each other by mass spectrometry.

The number of labels in the set is not especially limited, provided that the set comprises a plurality of labels. However, it is preferred if the set comprises two or more, three or more, four or more, or five or more labels, more preferably six or more labels, most preferably eight or more labels.

The term aggregate mass in the present context refers to the total mass of the mass label, i.e. the sum of the masses of the mass marker moiety, the cleavable linker, the mass normalisation moiety and any other components of the mass label.

The mass normalisation moiety is only limited by its mass, which may vary between different mass labels in a set. For instance, where a set comprises a group of labels having mass marker moieties of different masses but a common aggregate mass, the mass of the mass normalisation moiety will be different in each mass label in the set. In this case, the mass of the mass normalisation moiety in each individual mass label will be equal to the common aggregate mass minus the mass of the particular mass marker moiety in that mass label and minus the mass of the cleavable linker. Where the set comprises a group of labels having a mass marker moiety of common mass but different aggregate masses, it is clear that the mass of the mass normalisation moiety will need to vary such that the aggregate mass of all labels in the group is different.

All mass labels in the set are distinguishable from each other by mass spectrometry. Therefore, a mass spectrometer can discriminate between the mass labels, i.e. the peaks derived from individual mass labels can be clearly separated from one another. The difference in mass between the mass marker moieties or the mass labels means that a mass spectrometer can discriminate between ions derived from different mass labels or mass marker moieties.

The present invention also provides an array of mass labels, comprising two or more sets of mass labels as defined above, wherein the aggregate mass of each of the mass labels in any one set is different from the aggregate mass of each of the mass labels in every other set in the array.

In preferred embodiments of the invention, the array of mass labels are preferably all chemically identical and the masses of the mass normalisation and mass marker moieties are altered by isotope substitutions.

In further preferred embodiments of this invention, the mass labels may comprise a sensitivity enhancing group. The mass labels are preferably of the form:

sensitivity enhancing group —X-L-M- reactive functionality

In this example the sensitivity enhancing group is usually attached to the mass marker moiety, since it is intended to increase the sensitivity of the detection of this moiety in the mass spectrometer. The reactive functionality is shown as being present and attached to a different moiety than the sensitivity enhancing group. However, the mass labels need not be limited in this way and in some cases comprise the sensitivity enhancing group without the reactive functionality. In other embodiments the sensitivity enhancing group may be attached to the same moiety as the reactive functionality.

In certain embodiments of the invention the mass labels comprise an affinity capture reagent. Preferably, the affinity capture ligand is biotin. The affinity capture ligand allows labelled analytes to be separated from unlabelled analytes by capturing them, e.g. on an avidinated solid phase.

In a fourth aspect, the present invention also provides a method of analysing an analyte or analyte mixture, preferably biomolecule or a mixture of biomolecules, by identifying by mass spectrometry a mass label or a combination of mass labels relatable to the biological molecule or mixture of biological molecules, wherein the mass label is a mass label from a set or an array of mass labels as defined above.

This method preferably comprises the steps of:
1. Reacting the biomolecule or mixture of biomolecules with a mass label according to this invention;
2. Optionally separating the labelled biomolecule electrophoretically or chromatographically;
3. Ionising the labelled biomolecule;
4. Selecting ions of a predetermined mass to charge ratio corresponding to the mass to charge ratio of the preferred ions of the labelled biomolecule in a mass analyser;
5. Inducing dissociation of these selected ions by collision;
6. Detecting the collision products to identify collision product ions that are indicative of the mass labels.

In this embodiment, where the mass labels comprise an affinity tag, the affinity tagged biomolecules may be captured by a counter-ligand to allow labelled biomolecules to be separated from unlabelled biomolecules. This step preferably takes place prior to the optional second step above.

In certain embodiments the step of selecting the ions of a predetermined mass to charge ratio is performed in the first mass analyser of a serial instrument. The selected ions are then channeled into a separate collision cell where they are collided with a gas or a solid surface according to the fourth step. The collision products are then channeled into a further mass analyser of a serial instrument to detect collision products according to the fifth step. Typical serial instruments include triple quadrupole mass spectrometers, tandem sector instruments and quadrupole time of flight mass spectrometers.

In other embodiments, the step of selecting the ions of a predetermined mass to charge ratio, the step of colliding the selected ions with a gas and the step of detecting the collision products are performed in the same zone of the mass spectrometer. This may effected in ion trap mass analysers and Fourier Transform Ion Cyclotron Resonance mass spectrometers, for example.

In the present invention, matrix assisted laser desorption/ionisation (MALDI) techniques may be employed. MALDI requires that the biomolecule solution be embedded in a large molar excess of a photo-excitable 'matrix'. The application of laser light of the appropriate frequency results in the excitation of the matrix which in turn leads to rapid evaporation of the matrix along with its entrapped biomolecule. Proton transfer from the acidic matrix to the biomolecule gives rise to protonated forms of the biomolecule which can be detected by positive ion mass spectrometry, particularly by Time-Of-Flight (TOF) mass spectrometry. Negative ion mass spectrometry is also possible by MALDI TOF. This technique imparts a significant quantity of translational energy to ions, but tends not to induce excessive fragmentation despite this. The laser energy and the timing of the application of the potential difference used to accelerate the ions from the source can be used to control fragmentation with this technique. This technique is highly favoured due to its large mass range, due to the prevalence of singly charged ions in its spectra and due to the ability to analyse multiple peptides simultaneously. The TOF/TOF technique may be employed in the present invention.

The photo-excitable matrix comprises a 'dye', i.e. a compound that strongly absorbs light of a particular frequency, and which preferably does not radiate that energy by fluorescence or phosphorescence but rather dissipates the energy thermally, i.e. through vibrational modes. It is the vibration of the matrix caused by laser excitation that results in rapid sublimation of the dye, which simultaneously takes the embedded analyte into the gas phase.

Although MALDI techniques are useful in the context of the present invention, the invention is not limited to this type of technique, and other techniques common to the art can be employed by the skilled person in the present invention, if desired.

In another aspect, the present invention provides a labelled biological molecule comprising a mass label as defined above. The biological molecule may be any biological molecule of interest such as DNA, RNA, an oligonucleotide, a nucleic acid base, a protein, a peptide and/or an amino acid, or an analogue of any of the above. The biological molecule may be attached to the mass marker moiety of the mass label or the mass normalization moiety of the mass label.

This invention also provides sets or arrays of mass labelled biological molecules of the form:
biological molecule-linker-label
wherein the label is a mass label from a set or array according to this invention, the linker is a linker as described below and biological molecule may be any biological molecule of interest such as DNA, RNA, an oligonucleotide, a nucleic acid base, a protein, a peptide and/or an amino acid, or an analogue of any of the above.

One preferred aspect of this embodiment is where the biological molecules (one, more than one or even all the biological molecules) in the set or array are standard biological molecules with a known mass or with predetermined chromatographic properties. Such standards can be employed in the methods of the present invention for comparison with unknown biological molecules, for example when analysing the results of a chromatographic separation step.

The term 'MS/MS' in the context of mass spectrometers refers to mass spectrometers capable of selecting ions, subjecting selected ions to Collision Induced Dissociation (CID) and subjecting the fragment ions to further analysis.

The term 'serial instrument' refers to mass spectrometers capable of MS/MS in which mass analysers are organised in series and each step of the MS/MS process is performed one after the other in linked mass analysers. Typical serial instruments include triple quadrupole mass spectrometers, tandem sector instruments, quadrupole time of flight mass spectrometers and TOF/TOF mass spectrometers.

The invention will now be described in further detail by way of example only, with reference to the accompanying drawings, in which:

FIGS. 1a-e show five reactive mass labels according to the present invention, FIG. 1a is 3-[2-(2,6-Dimethyl-piperidin-1-yl)-acetylamino]-propanoic acid-(2,5-dioxo-pyrrolidine-1-yl)-ester (DMPip-βAla-OSu); FIG. 1b is 3-[2-(Pyrimidin-2-ylsulfanyl)-acetylamino]-propanoic acid-(2,5-dioxo-pyrrolidine-1-yl)-ester (Pyrm-βAla-OSu); FIG. 1c is 6-[(Pyrimidin-2-ylsulfanyl)-acetylamino]-hexanoic acid-(2,5-dioxo-pyrrolidine-1-yl)-ester (Pyrm-C6-OSu); FIG. 1d is 2-[2-(2,6-Dimethyl-piperidin-1-yl)-acetylamino]-propanoic acid-(2,5-dioxo-pyrrolidine-1-yl)-ester (DMPip-Ala-OSu);

and FIG. 1e is [2-(2,6-Dimethyl-piperidin-1-yl)-acetylamino]-acetic acid-(2,5-dioxo-pyrrolidin-1-yl)-ester (Pyrm-Gly-OSu);

FIG. 12 shows MS/SM analysis of Pyrm-C6-VATVSLPR;

FIGS. 29a and 29b show the distribution of the ratios of the different identified proteins from a strong cation exchange chromatography yeast fraction without the artificial mix;

FIG. 32 shows the relative protein measurement of three peptides labelled with 6-plex mass labels according to the present invention;

FIG. 34 shows the relative quantification of peptides labelled with 6-plex mass labels according to the present invention;

FIG. 36 shows the relative quantification of peptides labelled with 6-plex mass labels according to the present invention after applying a threshold filter; and FIG. 37 shows the relative quantification of peptides labelled with 6-plex mass labels according to the present invention after applying a threshold filter.

Figure 1A:
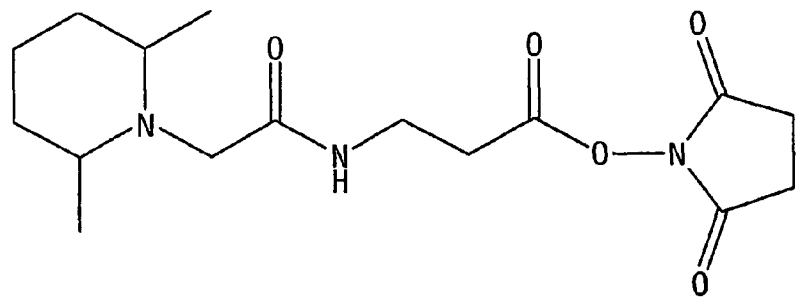
Figure 1B:
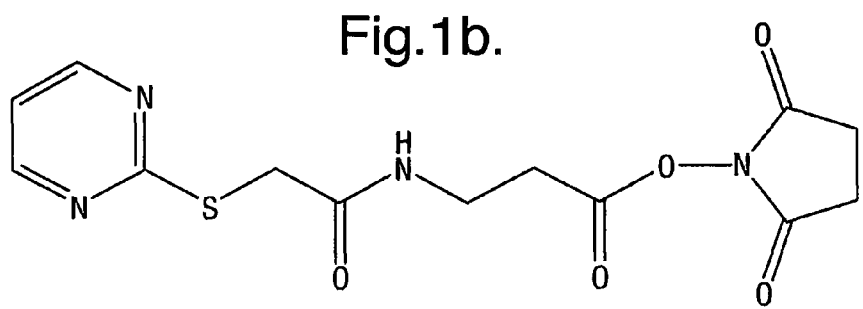
Figure 1C:
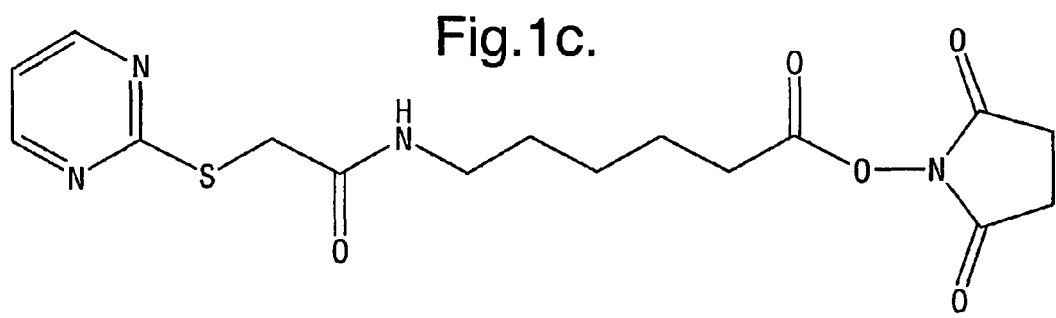
Figure 1D:
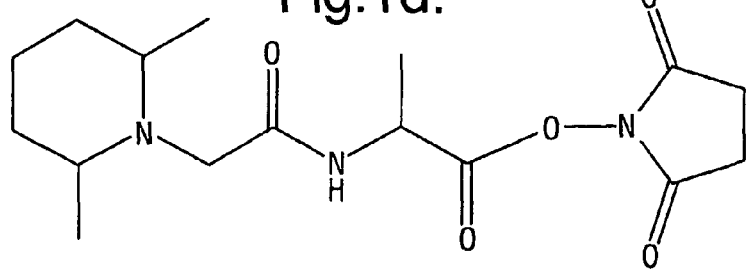
Figure 1E:
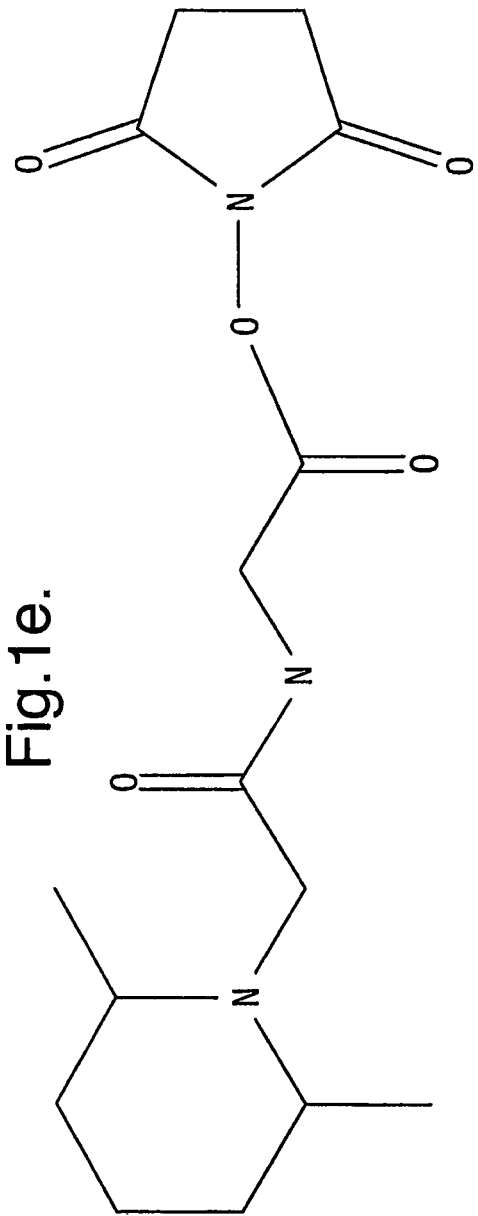

The present invention will now be described in more detail.

Mass Marker Moiety

In a preferred embodiment, the present invention provides a mass label as defined above wherein the molecular weight of the mass marker moiety is 300 Daltons or less, preferably 250 Daltons or less, more preferably 100 to 250 Daltons, most preferably 100-200 Daltons. Particularly preferred molecular weights of the mass marker moiety are 125, 126, 153 and 154 Daltons, or weights in which one or more or all of the 12C atoms are replaced by 13C atoms, e.g. for a non-substituted mass marker moiety having a weight of 125, masses for its substituted counterparts would be 126, 127, 128, 129, 130 and 131 Daltons for substitution with 1, 2, 3, 4, 5 and 6 13C atoms respectively and/or one or more or all of the 14N atoms are replaced by 15N atoms.

The components of the mass marker moiety of this invention are preferably fragmentation resistant so that the site of fragmentation of the markers can be controlled by the introduction of a linkage that is easily broken by Collision Induced Dissociation (CM).

The mass marker moiety of the present invention comprises the following group:

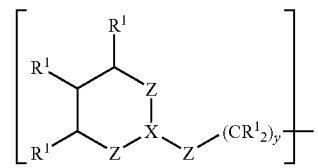

wherein the cyclic unit is aromatic or aliphatic and comprises from 0-3 double bonds independently between any two adjacent atoms; each Z is independently N, N(R$^1$), C(R$^1$), CO, CO(R$^1$) (i.e. —O—C(R$^1$)— or —C(R$^1$)—O—), C(R$^1$)$_2$, O or S; X is N, C or C(R$^1$); each R$^1$ is independently H, a substituted or unsubstituted straight or branched $C_1$-$C_6$ alkyl group, a substituted or unsubstituted aliphatic cyclic group, a substituted or unsubstituted aromatic group or a substituted or unsubstituted heterocyclic group; and M is an integer from 0-10, L is a cleavable linker comprising an amide bond and M is a mass normalization moiety.

The substituents of the mass marker moiety are not particularly limited and may comprise any organic group and/or one or more atoms from any of groups IIIA, IVA, VA, VIA or VIIA of the Periodic Table, such as a B, Si, N, P, O, or S atom or a halogen atom (e.g. F, Cl, Br or I).

When the substituent comprises an organic group, the organic group preferably comprises a hydrocarbon group. The hydrocarbon group may comprise a straight chain, a branched chain or a cyclic group. Independently, the hydrocarbon group may comprise an aliphatic or an aromatic group. Also independently, the hydrocarbon group may comprise a saturated or unsaturated group.

When the hydrocarbon comprises an unsaturated group, it may comprise one or more alkene functionalities and/or one or more alkyne functionalities. When the hydrocarbon comprises a straight or branched chain group, it may comprise one or more primary, secondary and/or tertiary alkyl groups. When the hydrocarbon comprises a cyclic group it may comprise an aromatic ring, an aliphatic ring, a heterocyclic group, and/or fused ring derivatives of these groups. The cyclic group may thus comprise a benzene, naphthalene, anthracene, indene, fluorene, pyridine, quinoline, thiophene, benzothiophene, furan, benzofuran, pyrrole, indole, imidazole, thiazole, and/or an oxazole group, as well as regioisomers of the above groups.

The number of carbon atoms in the hydrocarbon group is not especially limited, but preferably the hydrocarbon group comprises from 1-40 C atoms. The hydrocarbon group may thus be a lower hydrocarbon (1-6 C atoms) or a higher hydrocarbon (7 C atoms or more, e.g. 7-40 C atoms). The number of atoms in the ring of the cyclic group is not especially limited, but preferably the ring of the cyclic group comprises from 3-10 atoms, such as 3, 4, 5, 6 or 7 atoms.

The groups comprising heteroatoms described above, as well as any of the other groups defined above, may comprise one or more heteroatoms from any of groups WA, IVA, VA, VIA or VIIA of the Periodic Table, such as a B, Si, N, P, O, or S atom or a halogen atom (e.g. F, Cl, Br or I). Thus the substituent may comprise one or more of any of the common functional groups in organic chemistry, such as hydroxy groups, carboxylic acid groups, ester groups, ether groups, aldehyde groups, ketone groups, amine groups, amide groups, imine groups, thiol groups, thioether groups, sulphate groups, sulphonic acid groups, and phosphate groups etc. The substituent may also comprise derivatives of these groups, such as carboxylic acid anhydrydes and carboxylic acid halides.

In addition, any substituent may comprise a combination of two or more of the substituents and/or functional groups defined above.

In the present invention reference to the mass marker moiety comprising the group as defined above, means that the mass marker moiety may also comprise other groups depending upon where cleavage of the mass label occurs. In one embodiment where cleavage of the linker occurs at the amide bond between the CO and NH of the amide bond, the mass marker moiety may further comprise the CO group as shown below:

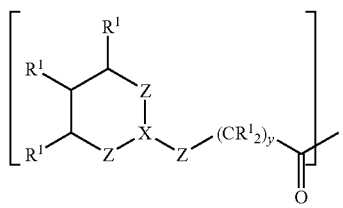

In an alternative embodiment, where the cleavage of the linker occurs at the bond after the NH group, the mass marker moiety may further comprise the CO and NH groups as shown below:

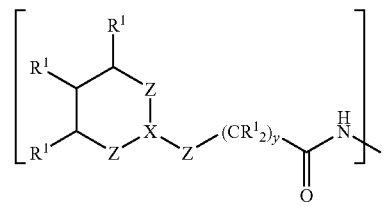

In a further alternative embodiment, where the linker cleaves before the CO group, the mass marker moiety only comprises the following group:

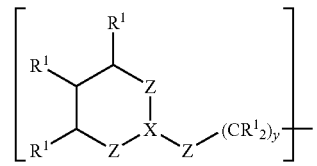

In a preferred embodiment, y is 0, 1 or 2, more preferably y is 0 or 1.

In one preferred embodiment the cyclic unit is aromatic and each Z in the cyclic unit is N. It is also preferred that X is C. It is also preferred that the Z not in the cyclic unit is S.

In an alternative preferred embodiment the cyclic unit is aliphatic and each Z in the cyclic unit is $C(R^1)_2$. It is also preferred that X is N. It is also preferred that the Z not in the cyclic unit is $C(R^1)_2$.

In a preferred embodiment the mass marker moiety comprises a group selected from the following groups:

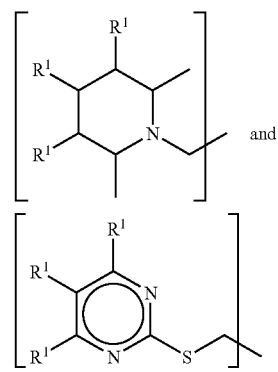

The above groups may also comprise other groups depending upon where cleavage of the mass label occurs. In one embodiment where cleavage of the linker occurs at the amide bond between the CO and NH of the amide bond, the above mass marker moiety groups may further comprise the CO group as shown below:

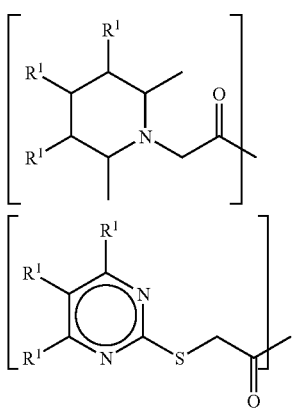

In an alternative embodiment, where the cleavage of the linker occurs at the bond after the NH group, the above mass marker moiety groups may further comprise the CO and NH groups as shown below:

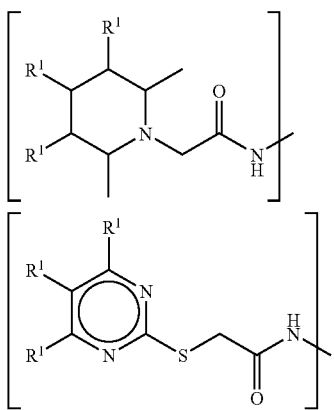

In a further alternative embodiment, where the linker cleaves before the CO group, the mass marker moiety only comprises the following group:

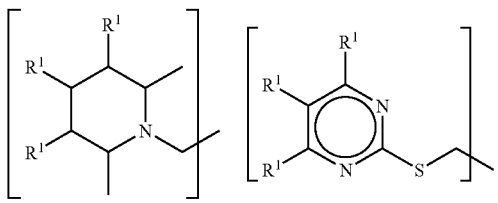

In a more preferred embodiment the mass marker moiety comprises a group selected from the following groups:

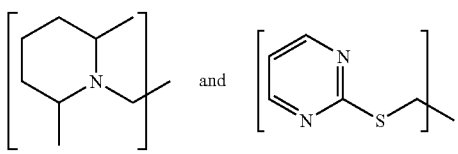

The above groups may also comprise other groups depending upon where cleavage of the mass label occurs. In one embodiment where cleavage of the linker occurs at the amide bond between the CO and NH of the amide bond, the above mass marker moiety groups may further comprise the CO group as shown below:

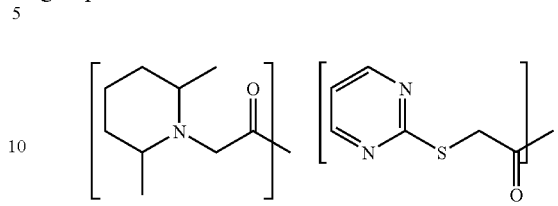

In an alternative embodiment, where the cleavage of the linker occurs at the bond after the NH group, the above mass marker moiety groups may further comprise the CO and NH groups as shown below:

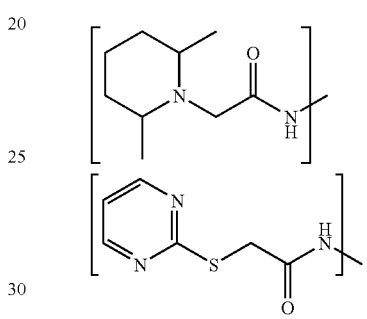

In a further alternative embodiment, where the linker cleaves before the CO group, the mass marker moiety only comprises the following group:

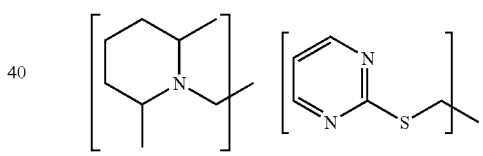

Linker

The cleavable linker of the mass label of the present invention comprises an amide bond. Preferably, the cleavable linker is a linker cleavable by collision. The structure of the linker is not particularly limited provided that it comprises an amide bond. However, preferably the linker consists of an amide bond.

In the discussion above and below reference is made to linker groups which may be used to connect molecules of interest to the mass label compounds of this invention. A variety of linkers is known in the art which may be introduced between the mass labels of this invention and their covalently attached biological molecule. Some of these linkers may be cleavable. Oligo- or poly-ethylene glycols or their derivatives may be used as linkers, such as those disclosed in Maskos, U. & Southern, E. M. Nucleic Acids Research 20: 1679-1684, 1992. Succinic acid based linkers are also widely used, although these are less preferred for applications involving the labelling of oligonucleotides as they are generally base labile and are thus incompatible with the base mediated deprotection steps used in a number of oligonucleotide synthesisers.

Propargylic alcohol is a bifunctional linker that provides a linkage that is stable under the conditions of oligonucleotide synthesis and is a preferred linker for use with this invention in relation to oligonucleotide applications. Similarly 6-aminohexanol is a useful bifunctional reagent to link appropriately functionalised molecules and is also a preferred linker.

A variety of known cleavable linker groups may be used in conjunction with the compounds of this invention, such as photocleavable linkers. Ortho-nitrobenzyl groups are known as photocleavable linkers, particularly 2-nitrobenzyl esters and 2-nitrobenzylamines, which cleave at the benzylamine bond. For a review on cleavable linkers see Lloyd-Williams et al., Tetrahedron 49, 11065-11133, 1993, which covers a variety of photocleavable and chemically cleavable linkers.

WO 00/02895 discloses the vinyl sulphone compounds as cleavable linkers, which are also applicable for use with this invention, particularly in applications involving the labelling of polypeptides, peptides and amino acids. The content of this application is incorporated by reference.

WO 00/02895 discloses the use of silicon compounds as linkers that are cleavable by base in the gas phase. These linkers are also applicable for use with this invention, particularly in applications involving the labelling of oligonucleotides. The content of this application is incorporated by reference.

Mass Normalisation Moiety

The structure of the mass normalization moiety of the mass label of the present invention is not particularly limited provided that it is suitable for ensuring that the mass label has a desired aggregate mass. However, the mass normalization moiety preferably comprises a straight or branched $C_1$-$C_{20}$ substituted or unsubstituted aliphatic group and/or one or more substituted or unsubstituted amino acids.

Preferably, the mass normalization moiety comprises a $C_1$-$C_6$ substituted or unsubstituted aliphatic group, more preferably a $C_1$, $C_2$, $C_3$, $C_4$, $C_5$ substituted or unsubstituted aliphatic group, still more preferably a $C_1$, $C_2$, or $C_5$ substituted or unsubstituted aliphatic group or a $C_1$ methyl substituted group.

The one or more substituted or unsubstituted amino acids may be any essential or non-essential naturally occurring amino acids or non-naturally occurring amino acids. Preferred amino acids are alanine, β-alanine and glycine.

The substituents of the mass normalisation moiety are not particularly limited and may comprise any organic group and/or one or more atoms from any of groups IIIA, IVA, VA, VIA or VIIA of the Periodic Table, such as a B, Si, N, P, O, or S atom or a halogen atom (e.g. F, Cl, Br or I).

When the substituent comprises an organic group, the organic group preferably comprises a hydrocarbon group. The hydrocarbon group may comprise a straight chain, a branched chain or a cyclic group. Independently, the hydrocarbon group may comprise an aliphatic or an aromatic group. Also independently, the hydrocarbon group may comprise a saturated or unsaturated group.

When the hydrocarbon comprises an unsaturated group, it may comprise one or more alkene functionalities and/or one or more alkyne functionalities. When the hydrocarbon comprises a straight or branched chain group, it may comprise one or more primary, secondary and/or tertiary alkyl groups. When the hydrocarbon comprises a cyclic group it may comprise an aromatic ring, an aliphatic ring, a heterocyclic group, and/or fused ring derivatives of these groups. The cyclic group may thus comprise a benzene, naphthalene, anthracene, indene, fluorene, pyridine, quinoline, thiophene, benzothiophene, furan, benzofuran, pyrrole, indole, imidazole, thiazole, and/or an oxazole group, as well as regioisomers of the above groups.

The number of carbon atoms in the hydrocarbon group is not especially limited, but preferably the hydrocarbon group comprises from 1-40 C atoms. The hydrocarbon group may thus be a lower hydrocarbon (1-6 C atoms) or a higher hydrocarbon (7 C atoms or more, e.g. 7-40 C atoms). The number of atoms in the ring of the cyclic group is not especially limited, but preferably the ring of the cyclic group comprises from 3-10 atoms, such as 3, 4, 5, 6 or 7 atoms.

The groups comprising heteroatoms described above, as well as any of the other groups defined above, may comprise one or more heteroatoms from any of groups IIIA, IVA, VA, VIA or VIIA of the Periodic Table, such as a B, Si, N, P, O, or S atom or a halogen atom (e.g. F, Cl, Br or I). Thus the substituent may comprise one or more of any of the common functional groups in organic chemistry, such as hydroxy groups, carboxylic acid groups, ester groups, ether groups, aldehyde groups, ketone groups, amine groups, amide groups, imine groups, thiol groups, thioether groups, sulphate groups, sulphonic acid groups, and phosphate groups etc. The substituent may also comprise derivatives of these groups, such as carboxylic acid anhydrydes and carboxylic acid halides.

In addition, any substituent may comprise a combination of two or more of the substituents and/or functional groups defined above.

Reactive Mass Label

The reactive mass label of the present invention for labelling and detecting a biological molecule by mass spectrometry comprises a reactive functionality for facilitating attachment of or for attaching the mass label to a biological molecule and a mass label as defined above. In preferred embodiments of the present invention, the reactive functionality allows the mass label to be reacted covalently to an appropriate functional group in the biological molecule, such as, but not limited to, a nucleotide oligonucleotide, polynucleotide, amino acid, peptide or polypeptide. The reactive functionality may be attached to the mass labels via a linker which may or may not be cleavable. The reactive functionality may be attached to the mass marker moiety of the mass label or the mass normalization moiety of the mass label.

A variety of reactive functionalities may be introduced into the mass labels of this invention. The structure of the reactive functionality is not particularly limited provided that it is capable of reacting with one or more reactive sites on the biological molecule to be labelled. The reactive functionality is preferably a nucleophile or an electrophile.

In the simplest embodiments this may be an N-hydroxysuccinimide ester. An N-hydroxysuccinimide activated mass label could also be reacted with hydrazine to give a hydrazide reactive functionality, which can be used to label periodate oxidised sugar moieties, for example. Aminogroups or thiols can be used as reactive functionalities in some applications. Lysine can be used to couple mass labels to free carboxyl functionalities using a carbodiimide as a coupling reagent. Lysine can also be used as the starting point for the introduction of other reactive functionalities into the mass labels of this invention. The thiol-reactive maleimide functionality can be introduced by reaction of the lysine epsilon amino group with maleic anhydride. The cysteine thiol group can be used as the starting point for the synthesis of a variety of alkenyl sulphone compounds, which are useful protein labelling reagents that react with thiols and amines. Compounds such as aminohexanoic acid can be used to provide a spacer between the mass modified mass marker moiety or mass normalization moiety and the reactive functionality.

Table 1 below lists some reactive functionalities that may be reacted with nucleophilic functionalities which are found in biomolecules to generate a covalent linkage between the two entities. For applications involving synthetic oligonucleotides, primary amines or thiols are often introduced at the termini of the molecules to permit labelling. Any of the functionalities listed below could be introduced into the compounds of this invention to permit the mass markers to be attached to a biological molecule of interest. A reactive functionality can be used to introduce a further linker groups with a further reactive functionality if that is desired. Table 1 is not intended to be exhaustive and the present invention is not limited to the use of only the listed functionalities.

TABLE 1

| Nucleophilic Functionality | Reactive Functionality | Resultant Linking Group |
|---|---|---|
| —SH | —SO$_2$—CH=CR$_2$ | —S—CR$_2$—CH$_2$—SO$_2$— |
| —NH$_2$ | —SO$_2$—CH=CR$_2$ | —N(CR$_2$—CH$_2$—SO$_2$—)$_2$ or —NH—CR$_2$—CH$_2$—SO$_2$— |
| —NH$_2$ | 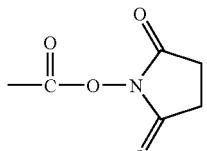 | —CO—NH— |
| —NH$_2$ | 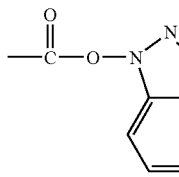 | —CO—NH— |
| —NH$_2$ | —NCO | —NH—CO—NH— |
| —NH$_2$ | —NCS | —NH—CS—NH— |
| —NH$_2$ | —CHO | —CH$_2$—NH— |
| —NH$_2$ | —SO$_2$Cl | —SO$_2$—NH— |
| —NH$_2$ | —CH=CH— | —NH—CH$_2$—CH$_2$— |
| —OH | —OP(NCH(CH$_3$)$_2$)$_2$ | —OP(=O)(O)O— |

In a preferred embodiment of the present invention the reactive functionality comprises the following group:

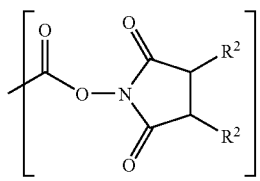

wherein each R$^2$ is independently H, a substituted or unsubstituted straight or branched C$_1$-C$_6$ alkyl group, a substituted or unsubstituted aliphatic cyclic group, a substituted or unsubstituted aromatic group or a substituted or unsubstituted heterocyclic group.

The substituents of the reactive functionality are not particularly limited and may comprise any organic group and/or one or more atoms from any of groups IIIA, IVA, VA, VIA or VITA of the Periodic Table, such as a B, Si, N, P, O, or S atom or a halogen atom (e.g. F, Cl, Br or I).

When the substituent comprises an organic group, the organic group preferably comprises a hydrocarbon group. The hydrocarbon group may comprise a straight chain, a branched chain or a cyclic group. Independently, the hydrocarbon group may comprise an aliphatic or an aromatic group. Also independently, the hydrocarbon group may comprise a saturated or unsaturated group.

When the hydrocarbon comprises an unsaturated group, it may comprise one or more alkene functionalities and/or one or more alkyne functionalities. When the hydrocarbon comprises a straight or branched chain group, it may comprise one or more primary, secondary and/or tertiary alkyl groups. When the hydrocarbon comprises a cyclic group it may comprise an aromatic ring, an aliphatic ring, a heterocyclic group, and/or fused ring derivatives of these groups. The cyclic group may thus comprise a benzene, naphthalene, anthracene, indene, fluorene, pyridine, quinoline, thiophene, benzothiophene, furan, benzofuran, pyrrole, indole, imidazole, thiazole, and/or an oxazole group, as well as regioisomers of the above groups.

The number of carbon atoms in the hydrocarbon group is not especially limited, but preferably the hydrocarbon group comprises from 1-40 C atoms. The hydrocarbon group may thus be a lower hydrocarbon (1-6 C atoms) or a higher hydrocarbon (7 C atoms or more, e.g. 7-40 C atoms). The number of atoms in the ring of the cyclic group is not especially limited, but preferably the ring of the cyclic group comprises from 3-10 atoms, such as 3, 4, 5, 6 or 7 atoms.

The groups comprising heteroatoms described above, as well as any of the other groups defined above, may comprise one or more heteroatoms from any of groups IIIA, WA, VA, VIA or VIIA of the Periodic Table, such as a B, Si, N, P, O, or S atom or a halogen atom (e.g. F, Cl, Br or I). Thus the substituent may comprise one or more of any of the common functional groups in organic chemistry, such as hydroxy groups, carboxylic acid groups, ester groups, ether groups, aldehyde groups, ketone groups, amine groups, amide groups, imine groups, thiol groups, thioether groups, sulphate groups, sulphonic acid groups, and phosphate groups etc. The substituent may also comprise derivatives of these groups, such as carboxylic acid anhydrydes and carboxylic acid halides.

In addition, any substituent may comprise a combination of two or more of the substituents and/or functional groups defined above.

In a more preferred embodiment the reactive functionality comprises the following group:

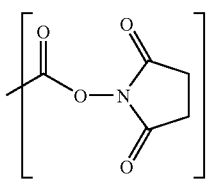

In a preferred embodiment of the present invention the reactive mass label has one of the following structures:

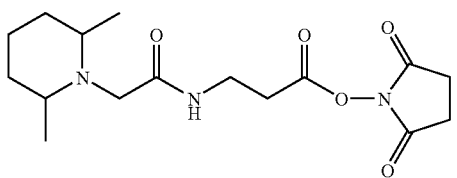 [SMILES: CC1CCCC(C)N1CC(=O)NCCC(=O)ON1C(=O)CCC1=O]

3-[2-(2,6-Dimethyl-piperidin-1-yl)-acetylamino]-propanoic acid-(2,5-dioxo-pyrrolidine-1-yl)-ester (DMPip-βAla-OSu)

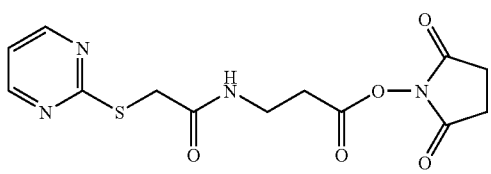 [SMILES: O=C(CSc1ncccn1)NCCC(=O)ON1C(=O)CCC1=O]

3-[2-(Pyrimidin-2-ylsulfanyl)-acetylamino]-propanoic acid-(2,5-dioxo-pyrrolidine-1-yl)-ester (Pyrm-βAla-OSu)

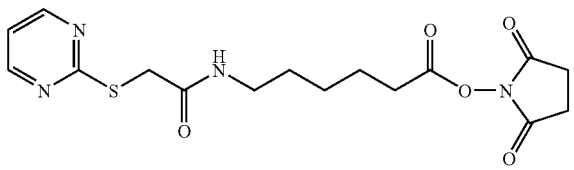 [SMILES: O=C(CSc1ncccn1)NCCCCCC(=O)ON1C(=O)CCC1=O]

6-[(Pyrimidin-2-ylsulfanyl)-acetylamino]-hexanoic acid-(2,5-dioxo-pyrrolidine-1-yl)-ester (Pyrm-C6-OSu)

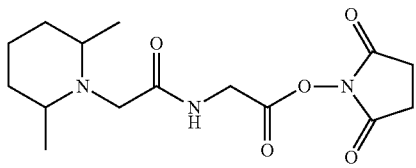 [SMILES: CC1CCCC(C)N1CC(=O)NCC(=O)ON1C(=O)CCC1=O]

[2-(2,6-Dimethyl-piperidin-1-yl)-acetylamino]-acetic acid-(2,5-dioxo-pyrrolidine-1-yl)-ester (Pyrm-Gly-OSu)

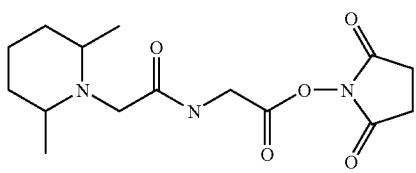 [SMILES: CC1CCCC(C)N1CC(=O)NCC(=O)ON1C(=O)CCC1=O]

[2-(2,6-Dimethyl-piperidin-1-yl)-acetylamino]-acetic acid-(2,5-dioxo-pyrrolidine-1-yl)-ester (Pyrm-Gly-OSu).

According to a preferred embodiment of the third aspect of the present invention, each label in the set has a mass marker moiety having a common mass and each label in the set has a unique aggregate mass, (the first label type).

In an alternative, more preferred embodiment, each label in the set has a common aggregate mass and each label in the set has a mass marker moiety of a unique mass, (second label type).

The set of labels need not be limited to the two preferred embodiments described above, and may for example comprise labels of both types, provided that all labels are distinguishable by mass spectrometry, as outlined above.

It is preferred that, in a set of labels of the second type, each mass marker moiety in the set has a common basic structure and each mass normalisation moiety in the set has a common basic structure, and each mass label in the set comprises one or more mass adjuster moieties, the mass adjuster moieties being attached to or situated within the basic structure of the mass marker moiety and/or the basic structure of the mass normalisation moiety. In this embodiment, every mass marker moiety in the set comprises a different number of mass adjuster moieties and every mass label in the set has the same number of mass adjuster moieties.

Throughout this description, by common basic structure, it is meant that two or more moieties share a structure which has substantially the same structural skeleton, backbone or core. The skeleton comprises the mass marker moiety of the formula given above or the mass normalisation moiety as defined above, but may additionally comprise a number of amino acids linked by amide bonds. However, other units such as aryl ether units may also be present. The skeleton or backbone may comprise substituents pendent from it, or atomic or isotopic replacements within it, without changing the common basic structure.

In a preferred embodiment the set of mass labels or reactive mass labels according to the first and/or second type defined above comprises mass labels having the following structure:

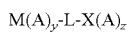

wherein M is a mass normalisation moiety, X is a mass marker moiety, A is a mass adjuster moiety, L is a cleavable linker, y and z are integers of 0 or greater, and y+z is an integer of 1 or greater. Preferably M is a fragmentation resistant group, L is a linker that is susceptible to fragmentation on collision with another molecule or atom and X is preferably a pre-ionised, fragmentation resistant group.

If the set of mass labels is of the second type referred to above the sum of the masses of M and X is the same for all members of the set. Preferably M and X have the same basic structure or core structure, this structure being modified by the mass adjuster moieties. The mass adjuster moiety ensures that the sum of the masses of M and X in is the same for all mass labels in a set, but ensures that each X has a distinct (unique) mass.

The mass adjuster moiety (A) is preferably selected from:
(a) an isotopic substituent situated within the mass marker moiety and/or within the mass normalisation moiety, and
(b) substituent atoms or groups attached to the mass marker moiety and/or attached to the mass normalisation moiety.

Preferably the mass adjuster moiety is selected from a halogen atom substituent, a methyl group substituent, and $^{2}H$, $^{15}N$, $^{18}O$, or $^{13}C$ isotopic substituents.

In one preferred embodiment of the third aspect of the present invention, each mass label in the set of mass labels as defined above has the following structure:

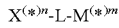

wherein X is the mass marker moiety, L is the cleavable linker, M is the mass normalisation moiety, * is an isotopic mass adjuster moiety, and n and m are integers of 0 or greater such that either:

each label in the set comprises a mass marker moiety having a common mass and each label in the set has a unique aggregate mass; or each label in the set comprises a mass marker moiety having a unique mass and each label in the set has a common aggregate mass.

It is preferred that X comprises the following group:

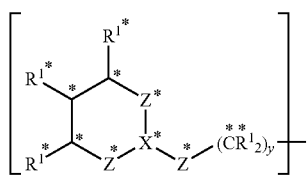

wherein $R^1$, Z, X and y are as defined above and each label in the set comprises 0, 1 or more * such that either:

each label in the set comprises a mass marker moiety having a common mass and each label in the set has a unique aggregate mass; or each label in the set comprises a mass marker moiety having a unique mass and each label in the set has a common aggregate mass.

In a preferred embodiment the mass marker moiety comprises a group selected from the following groups:

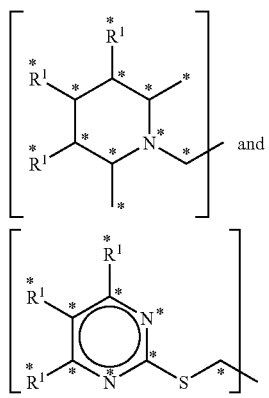

wherein the set comprises 0, 1 or more * such that either:

each label in the set comprises a mass marker moiety having a common mass and each label in the set has a unique aggregate mass; or each label in the set comprises a mass marker moiety having a unique mass and each label in the set has a common aggregate mass.

In a further preferred embodiment the mass marker moiety comprises a group selected from the following groups:

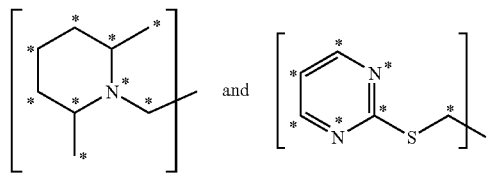

wherein the set comprises 0, 1 or more * such that either:

each label in the set comprises a mass marker moiety having a common mass and each label in the set has a unique aggregate mass; or each label in the set comprises a mass marker moiety having a unique mass and each label in the set has a common aggregate mass.

In a further preferred embodiment, the reactive mass labels of the present invention comprise the following reactive functionality group:

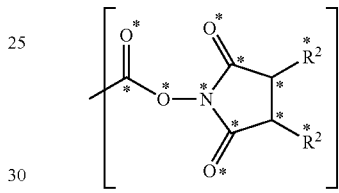

wherein $R^2$ is as defined above and the set comprises 0, 1 or more * such that either:

each label in the set comprises a mass marker moiety having a common mass and each label in the set has a unique aggregate mass; or each label in the set comprises a mass marker moiety having a unique mass and each label in the set has a common aggregate mass.

Preferably the reactive functionality comprises the following group:

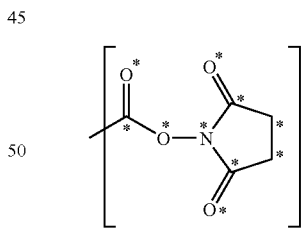

wherein the set comprises 0, 1 or more * such that either:

each label in the set comprises a mass marker Moiety having a common mass and each label in the set has a unique aggregate mass; or each label in the set comprises a mass marker moiety having a unique mass and each label in the set has a common aggregate mass.

In a preferred embodiment the set of reactive mass labels comprises two or more mass labels of any of the following structures:

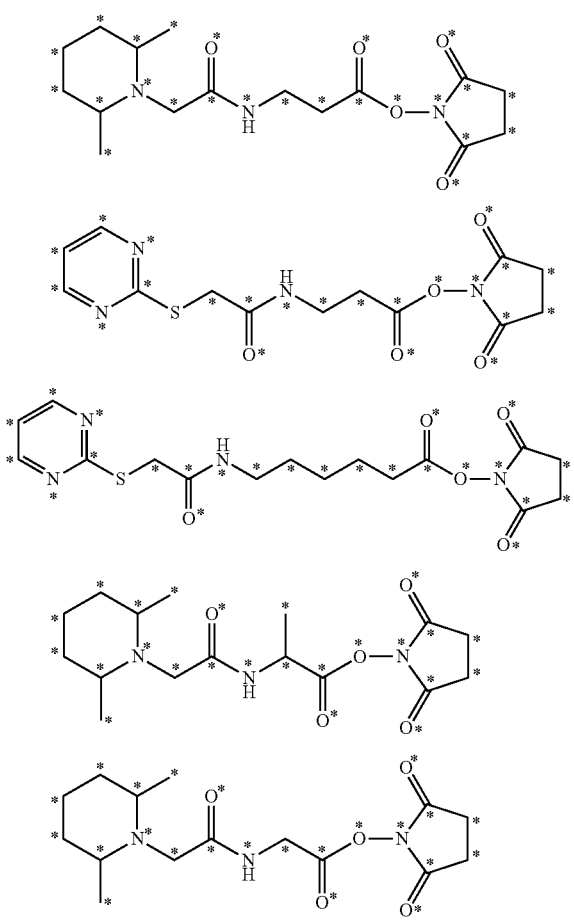

wherein * represents that the oxygen is $^{18}O$, carbon is $^{13}C$ or the nitrogen is $^{15}N$, and wherein the each label in the set comprises one or more * such that either:

each label in the set comprises a mass marker moiety having a common mass and each label in the set has a unique aggregate mass; or each label in the set comprises a mass marker moiety having a unique mass and each label in the set has a common aggregate mass.

In a preferred embodiment the set of reactive mass labels comprises two or more mass labels of any of the following structures:

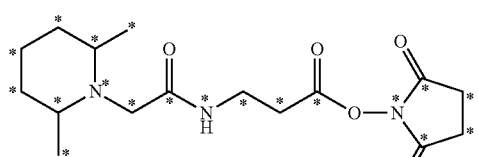

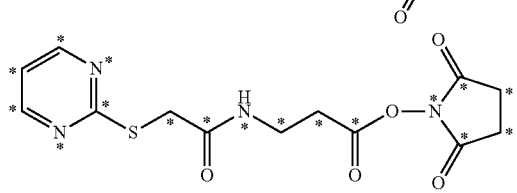

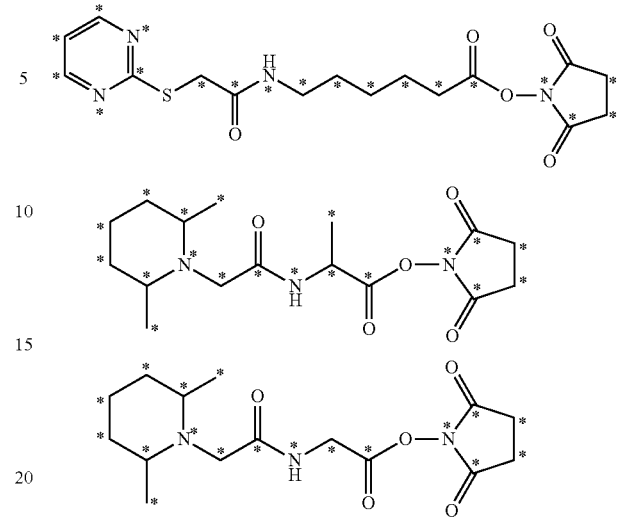

wherein * represents that the carbon is $^{13}C$ or the nitrogen is $^{15}N$, and wherein the each label in the set comprises one or more * such that either:

each label in the set comprises a mass marker moiety having a common mass and each label in the set has a unique aggregate mass; or each label in the set comprises a mass marker moiety having a unique mass and each label in the set has a common aggregate mass.

More preferably, the set of reactive mass labels as defined above comprises two or more mass labels of any of the following structures:

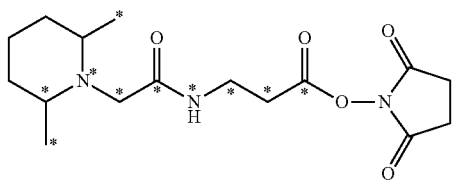

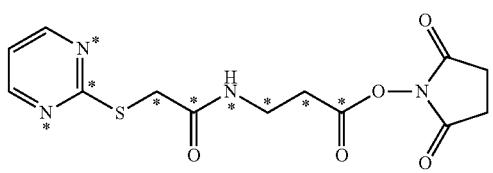

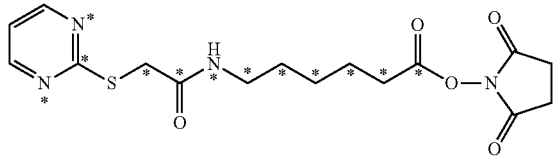

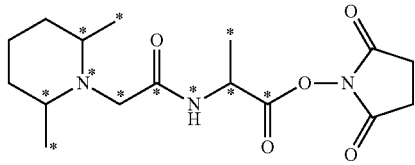

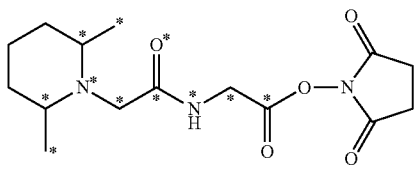

wherein * represents that the carbon is $^{13}$C or the nitrogen is $^{15}$N, and wherein the each label in the set comprises one or more * such that either:

each label in the set comprises a mass marker moiety having a common mass and each label in the set has a unique aggregate mass; or each label in the set comprises a mass marker moiety having a unique mass and each label in the set has a common aggregate mass.

In all of the above preferred compounds and formulae, it is particularly preferred that the isotopic species * is situated within the mass marker moiety and/or the linker and/or the mass adjuster moiety, rather than on any reactive moiety that is present to facilitate attaching the label to an analyte. It is most preferred that * is present within the mass marker moiety, X. The number of isotopic substituents is not especially limited and can be determined depending on the number of labels in the set. Typically, the number of * species is from 0-20, more preferably from 0-15 and most preferably from 1-10, e.g. 1, 2, 3, 4, 5, 6, 7 or 8. In a set of two labels, it is preferred that the number of species * is 1, whilst in a set of 5 labels, it is preferred that the number is 4, whilst in a set of 6 labels it is preferred that the number is 5. However, the number may be varied depending upon the chemical structure of the label.

If desired, isotopic variants of S may also be employed as mass adjuster moieties, if the labels contain one or more sulphur atoms.

In a particularly preferred embodiment wherein the mass adjuster moiety is $^{15}$N or $^{13}$C the set of reactive mass labels comprises two mass labels having the following structures:

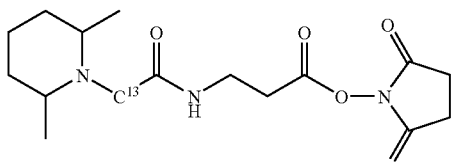

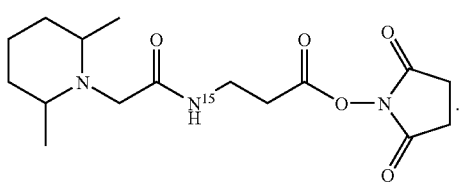

In an alternative particularly preferred embodiment wherein the mass adjuster moiety is $^{15}$N or $^{13}$C the set of reactive mass labels comprises the set comprises five mass labels having the following structures:

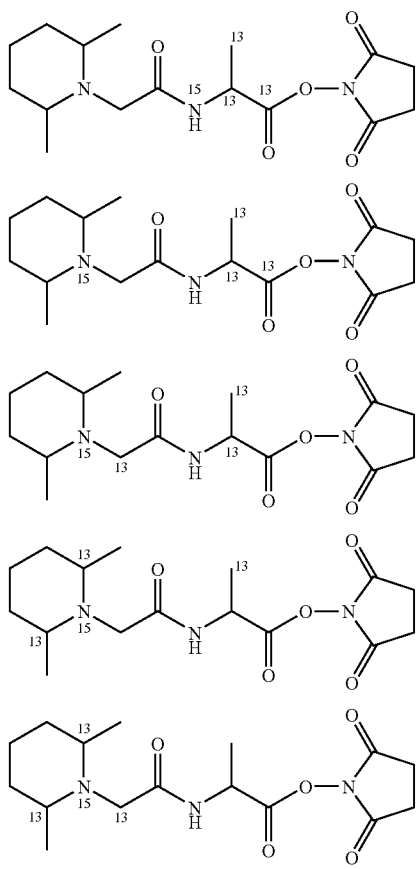

In an alternative particularly preferred embodiment wherein the mass adjuster moiety is $^{15}$N or $^{13}$C the set of reactive mass labels comprises six mass labels I-VI having the following structures, or stereoisomers of these structures:

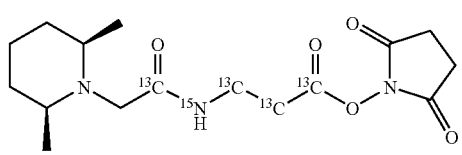

I

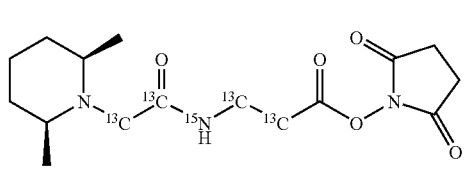

II

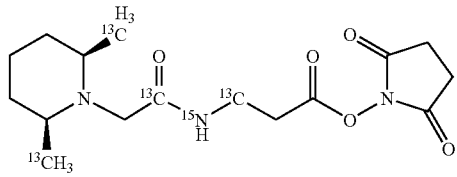

III

-continued

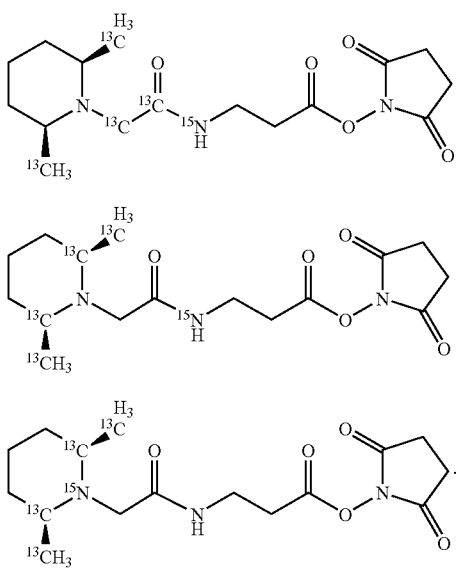

The present invention also encompasses arrays of a plurality of sets of mass labels as defined above. The arrays of mass labels of the present invention are not particularly limited, provided that they contain a plurality of sets of mass labels according to the present invention. It is preferred that the arrays comprise two or more, three or more, four or more, or five or more sets of mass labels. Preferably each mass label in the array has either of the following structures:

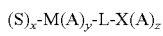

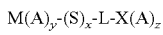

wherein S is a mass series modifying group, M, X and L are as defined above, A is the mass adjuster moiety, x is an integer of 0 or greater, y and z are integers of 0 or greater, and y+z is an integer of 1 or greater. The mass series modifying group separates the masses of the sets from each other. This group may be any type of group, but is preferably an amino acid, or aryl ether group. Sets may be separated in mass by comprising a different number of amino acids in their moieties than other tags from different sets.

In the discussion below reference is made to "charge carrying functionalities" and solubilising groups. These groups may be introduced into the mass labels such as in the mass markers of the invention to promote ionisation and solubility. The choice of markers is dependent on whether positive or negative ion detection is to be used. Table 2 below lists some functionalities that may be introduced into mass markers to promote either positive or negative ionisation. The table is not intended as an exhaustive list, and the present invention is not limited to the use of only the listed functionalities.

TABLE 2

| Positive Ion Mode | Negative Ion Mode |
| --- | --- |
| —$NH_2$ | —$SO_3^-$ |
| —$NR_2$ | —$PO_4^-$ |
| —$NR_3^+$ | —$PO_3^-$ |

TABLE 2-continued

| Positive Ion Mode | Negative Ion Mode |
| --- | --- |
| (guanidinium structure) | —$CO_2^-$ |
| (pyridinium structure) | |
| —$SR_2^+$ | |

WO 00/02893 discloses the use of metal-ion binding moieties such as crown-ethers or porphyrins for the purpose of improving the ionisation of mass markers. These moieties are also be applicable for use with the mass markers of this invention.

The present invention also provides a set of two or more probes, each probe in the set being different and being attached to a unique mass label or a unique combination of mass labels, from a set or an array of mass labels as defined above.

Further provided is an array of probes comprising two or more sets of probes, wherein each probe in any one set is attached to a unique mass label, or a unique combination of mass labels, from a set of mass labels as defined above, and wherein the probes in any one set are attached to mass labels from the same set of mass labels, and each set of probes is attached to mass labels from unique sets of mass labels from an array of mass labels as defined above.

In one embodiment, each probe is preferably attached to a unique combination of mass labels, each combination being distinguished by the presence or absence of each mass label in the set of mass labels and/or the quantity of each mass label attached to the probe. This is termed the "mixing mode" of the present invention, since the probes may be attached to a mixture of mass labels.

In the above aspects, the nature of the probe is not particularly limited. However, preferably each probe comprises a biomolecule. Any biomolecule can be employed, but the biomolecule is preferably selected from a DNA, an RNA, an oligonucleotide, a nucleic acid base, a peptide, a polypeptide, a protein and an amino acid.

In one preferred embodiment, this invention provides sets and arrays of mass labelled biological molecules, such as nucleotides, oligonucleotides and polynucleotides, of the form:

biological molecule-linker-label

Wherein the linker is a linker as defined above, and label is a mass label from any of the sets and arrays defined above.

Any biological molecule can be employed, but the biomolecule is preferably selected from a DNA, an RNA, an oligonucleotide, a nucleic acid base, a peptide, a polypeptide, a protein and an amino acid.

In one embodiment, each biological molecule is preferably attached to a unique combination of mass labels, each combination being distinguished by the presence or absence of each mass label in the set of mass labels and/or the quantity of each mass label attached to the probe. As mentioned above, this is termed the "mixing mode" of the present invention, since the probes may be attached to a mixture of mass labels.

As mentioned above, the present invention provides a method of analysis, which method comprises detecting a biological molecule by identifying by mass spectrometry a mass label or a combination of mass labels unique to the biological molecule, wherein the mass label is a mass label from a set or an array of mass labels as defined above. The type of method is not particularly limited, provided that the method benefits from the use of the mass labels of the present invention to identify a biological molecule. The method may be, for example, a method of sequencing nucleic acid or a method of profiling the expression of one or more genes by detecting quantities of protein in a sample. The method is especially advantageous, since it can be used to readily analyse a plurality of biological molecules simultaneously. However, the method also has advantages for analysing single biological molecules individually, since using the present mass labels, mass spectra which are cleaner than conventional spectra are produced, making the method accurate and sensitive.

In a further preferred embodiment, the present invention provides a method which method comprises:
(a) contacting one or more biological molecules with a set of probes, or an array of probes, each probe in the set or array being specific to at least one biological molecule, wherein the probes are as defined above,
(b) identifying a biological molecule, by detecting the probe specific to that biological molecule.

In this embodiment it is preferred that the mass label is cleaved from the probe prior to detecting the mass label by mass spectrometry.

The nature of the methods of this particular embodiment is not especially limited. However, it is preferred that the method comprises contacting one or more nucleic acids with a set of hybridisation probes. The set of hybridisation probes typically comprises a set of up to 256 4-mers, each probe in the set having a different combination of nucleic acid bases. This method may be suitable for identifying the presence of target nucleic acids, or alternatively can be used in a stepwise method of primer extension sequencing of one or more nucleic acid templates.

The mass labels of the present invention are particularly suitable for use in methods of 2-dimensional analysis, primarily due to the large number of labels that can be simultaneously distinguished. The labels may thus be used in a method of 2-dimensional gel electrophoresis, or in a method of 2-dimensional mass spectrometry.

Mass Modified Mass Marker Moiety and Mass Normalization Moiety

Figure 2:
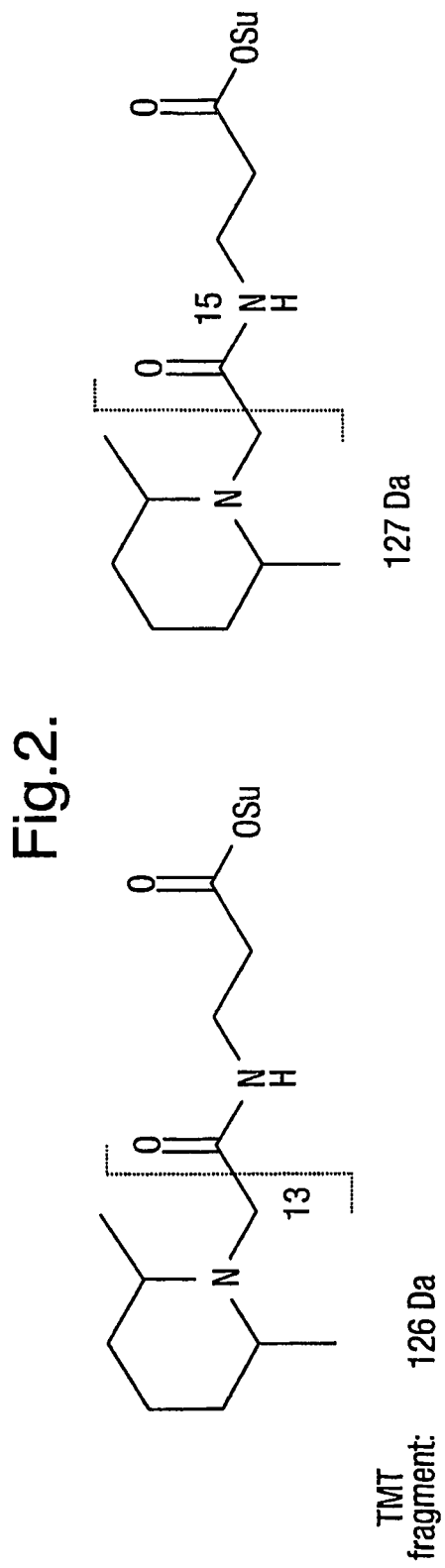
FIG. 2 shows two isotopic forms of a mass label according to the present invention.
Figure 3:
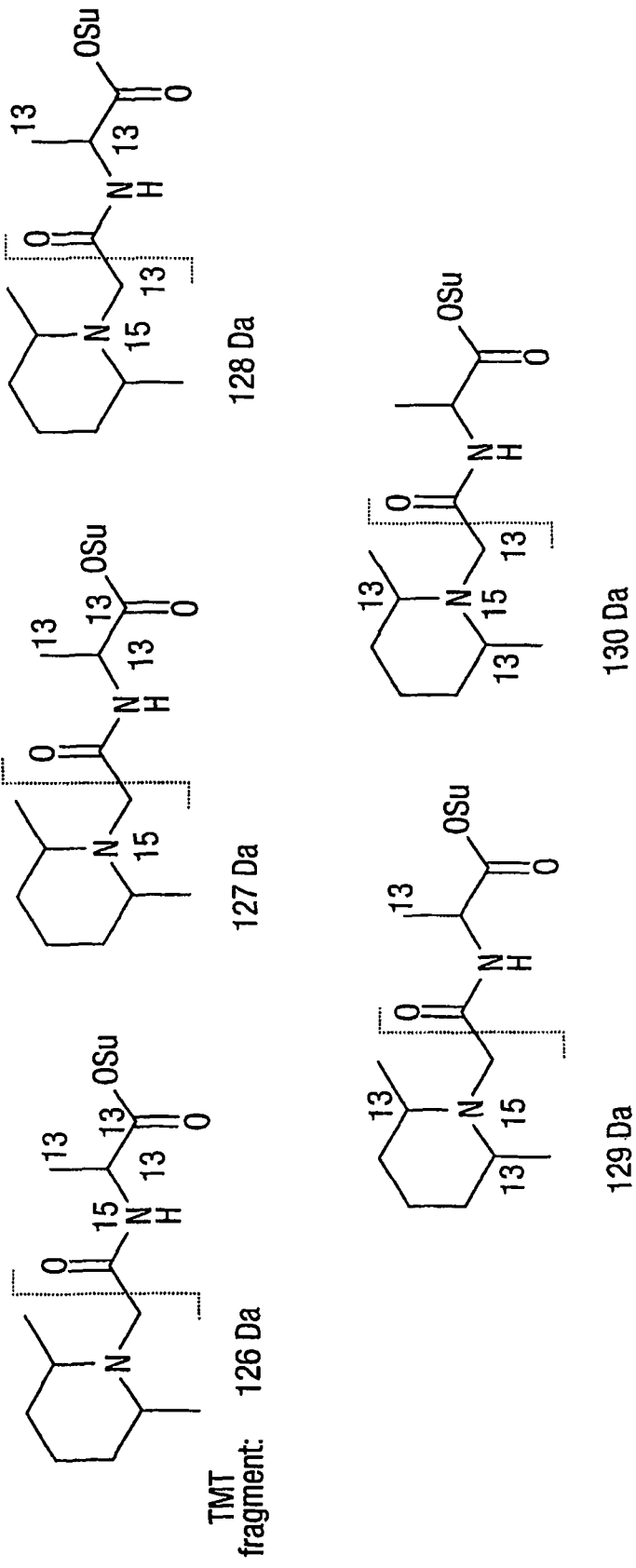
FIG. 3 shows five isotopic forms of a mass label according to the present invention.
Figure 22:
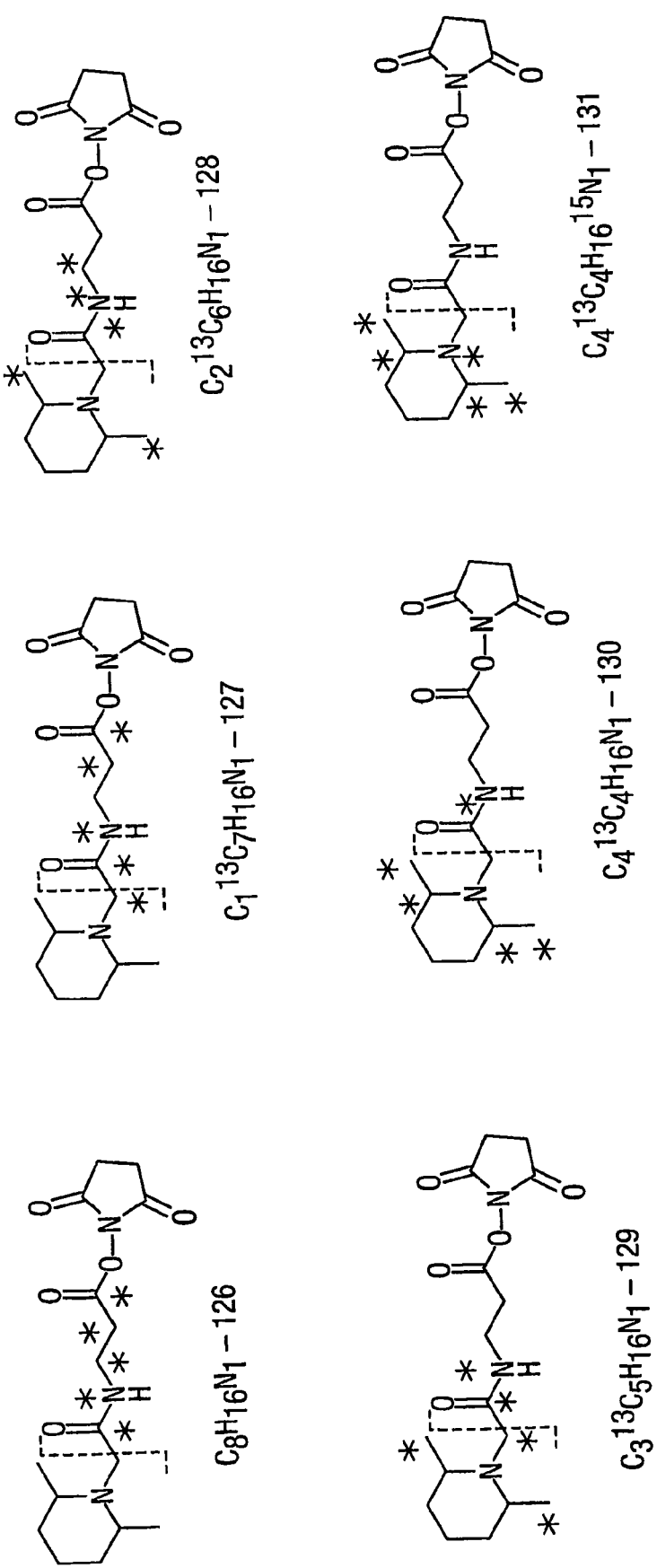
FIG. 22 shows six isotopic forms of a mass label according to the present invention including the molecular weight of the mass marker moiety fragment (X)

As discussed above, the mass of the mass marker moiety and the mass normalization moiety may be modified by including one or more isotopes as mass adjuster moieties during synthesis of the mass label. Suitable isotopes include deuterium ($^2$H), $^{13}$C, $^{14}$C, $^{15}$N, $^{18}$O. A set of mass labels is shown in FIGS. 2 and 3. FIG. 2 shows a set of two mass labels where both mass labels have the same aggregate mass but each mass label has a mass marker moiety (TMT fragment) with a different mass due to the inclusion of isotopes in the mass marker moiety or the mass normalization moiety. FIG. 3 shows a set of five mass labels where all five mass labels have the same aggregate mass but each mass label has a mass marker moiety with a different mass to every other mass marker moiety due to the inclusion of isotopes in the mass marker moiety and/or the mass normalization moiety. FIG. 22 (Carbon 13 or a Nitrogen 15 when labelled with an asterisk) shows a set of six mass labels where all six mass labels have the same aggregate mass but each mass label has a mass marker moiety with a different mass to every other mass marker moiety due to the inclusion of isotopes in the mass marker moiety and/or the mass normalization moiety.

Figure 14:
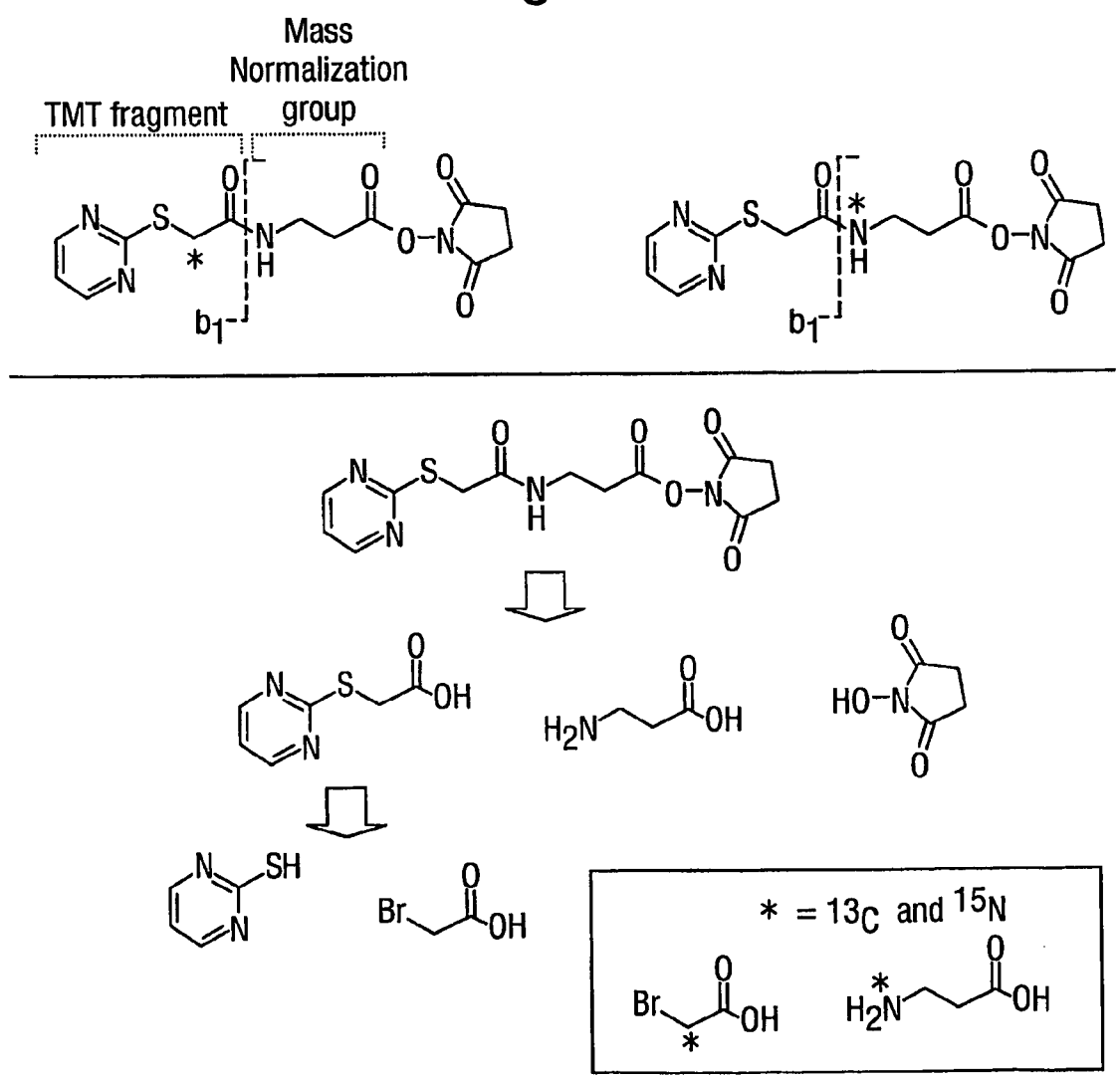
FIG. 14 shows retro-synthesis of duplex reagents for Pyrm-βAla-OSu.
Figure 15:
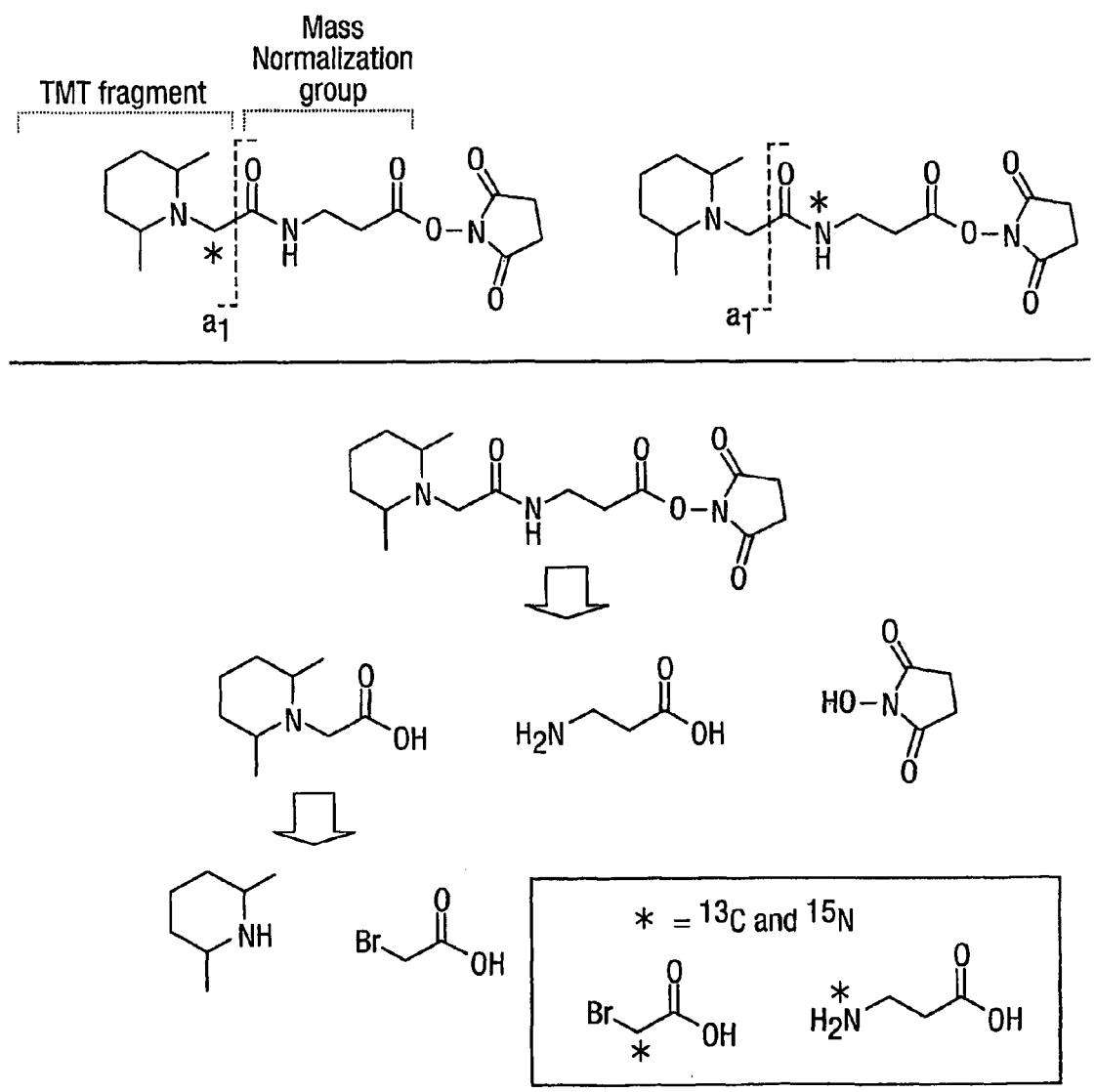
FIG. 15 shows retro-synthesis of duplex reagents for DMPip-βAla-OSu.

The synthesis of mass labels of the present invention comprising isotopes is set out in Examples 4 and 5. FIG. 14 shows the reaction scheme for retro-synthesis of duplex reagents for 3-[2-(Pyrimidin-2-ylsulfanyl)-acetylamino]-propanoic acid-(2,5-dioxo-pyrrolidine-1-yl)-ester (Pyrm-βAla-OSu). FIG. 15 shows the reaction scheme for retro-synthesis of duplex reagents for 3-[2-(2,6-Dimethyl-piperidin-1-yl)-acetylamino]-propanoic acid-(2,5-dioxo-pyrrolidine-1-yl)-ester (DMPip-βAla-OSu).

Mass Modified Amino Acids in the Mass Marker or Mass Normalization Moiety

In a preferred embodiment when the mass marker or mass normalisation moiety further comprises one or more amino acids a variety of amino acids can be used. Neutral amino acids are preferred in the mass normalisation moiety. A number of commercially available isotopically mass modified amino acids are shown in Table 5 below. Any combination of 1, 2, 3, or 4 or more amino acids from this list may be present in the mass marker moiety or the mass normalization moieties according to the present invention.

TABLE 5

| Amino acid | Isotope Forms |
| --- | --- |
| Alanine | $CH_3CH(NH_2)^{13}CO_2H$, |
| | $CH_3CD(NH_2)CO_2H$, |
| | $CH_3^{13}CH(^{15}NH_2)CO_2H$, |
| | $CD_3CH(NH_2)CO_2H$, |
| | $CD_3CD(NH_2)CO_2H$, |
| | $CD_3CH(NH_2)^{13}CO_2H$, |
| | $CD_3^{13}CH(NH_2)CO_2H$, |
| | $^{13}CH_3^{13}CH(^{15}NH_2)^{13}CO_2H$ |
| Arginine | $[(^{15}NH_2)_2CNHCH_2CH_2CH(NH_2)CO_2H]^+$ |
| Asparagine | $H_2N^{13}COCH_2CH(NH_2)CO_2H$, |
| | $H_2N^{13}CO^{13}CH_2^{13}CH(NH_2)^{13}CO_2H$, |
| | $H_2^{15}NCOCH_2CH(NH_2)CO_2H$, |
| | $H_2^{15}NCOCH_2CH(^{15}NH_2)CO_2H$, |
| Aspartic Acid | $HO_2^{13}CCH_2CH(NH_2)CO_2H$, |
| | $HO_2C^{13}CH_2CH(NH_2)CO_2H$, |
| | $HO_2CCH_2CH(NH_2)^{13}CO_2H$, |
| | $HO_2^{13}CCH_2CH(NH_2)CO_2H$, |
| | $HO_2CCH_2^{13}CH(NH_2)CO_2H$, |
| | $HO_2^{13}C^{13}CH_2CH(NH_2)CO_2H$, |
| | $HO_2^{13}C^{13}CH_2^{13}CH(NH_2)^{13}CO_2H$, |
| | $HO_2CCD_2CD(NH_2)CO_2H$, |
| | $HO_2CCH_2CH(^{15}NH_2)CO_2H$, |
| | $HO_2CCH_2CH(^{15}NH_2)^{13}CO_2H$ |
| Cysteine | Not available |
| Glutamic Acid | $HO_2CCH_2CH_2CH(NH_2)^{13}CO_2H$, |
| | $HO_2CCH_2CH_2^{13}CH(NH_2)CO_2H$, |
| | $HO_2CCH_2^{13}CH_2CH(NH_2)CO_2H$, |
| | $HO_2C^{13}CH_2CH_2CH(NH_2)CO_2H$, |
| | $HO_2^{13}CCH_2CH_2CH(NH_2)CO_2H$, |
| | $HO_2^{13}C^{13}CH_2^{13}CH_2^{13}CH(NH_2)^{13}CO_2H$, |
| | $HO_2CCD_2CH_2CH(NH_2)CO_2H$, |
| | $HO_2CCD_2CD_2CD(NH_2)CO_2H$, |
| | $HO_2^{13}C^{13}CH_2^{13}CH_2^{13}CH(^{15}NH_2)^{13}CO_2H$ |
| Glutamine | $H_2NCOCH_2CH_2CH(NH_2)^{13}CO_2H$, |
| | $H_2N^{13}COCH_2CH_2CH(NH_2)CO_2H$, |
| | $H_2NCOCD_2CD_2CD(NH_2)CO_2H$, |
| | $H_2^{15}NCOCH_2CH_2CH(NH_2)CO_2H$, |
| | $H_2NCOCH_2CH_2CH(^{15}NH_2)CO_2H$, |
| | $H_2^{15}NCOCH_2CH_2CH(^{15}NH_2)CO_2H$, |
| | $H_2^{15}N^{13}CO^{13}CH_2^{13}CH_2^{13}CH(^{15}NH_2)^{13}CO_2H$ |
| Glycine | $H_2NCH_2^{13}CO_2H$, |
| | $H_2N^{13}CH_2CO_2H$, |
| | $H_2N^{13}CH_2^{13}CO_2H$, |
| | $H_2NCD_2CO_2H$, |
| | $H_2^{15}NCH_2CO_2H$, |
| | $H_2^{15}N^{13}CH_2CO_2H$, |
| | $H_2^{15}NCH_2^{13}CO_2H$, |
| | $H_2^{15}CH_2^{13}CO_2H$ |
| Histidine | $(CH)_2N_2CCH_2CH(NH_2)^{13}CO_2H$, |
| | $(CH)_2N_2CCH_2CH(^{15}NH_2)CO_2H$, |
| | $(CH)_2^{15}N_2CCH_2CH(NH_2)CO_2H$ |
| Isoleucine | Not available |

TABLE 5-continued

| Amino acid | Isotope Forms |
|---|---|
| Leucine | $(CH_3)_2CHCH_2CH(NH_2)^{13}CO_2H$, $(CH_3)_2CHCH_2^{13}CH(NH_2)CO_2H$, $(CH_3)_2CHCH_2^{13}CH(NH_2)^{13}CO_2H$, $(CH_3)_2CHCH_2CD(NH_2)CO_2H$, $(CH_3)_2CHCD_2CD(NH_2)CO_2H$, $(CD_3)(CH_3)CHCH_2CH(NH_2)CO_2H$, $(CD_3)_2CHCH_2CH(NH_2)CO_2H$, $(CD_3)_2CDCD_2CD(NH_2)CO_2H$, $(CH_3)_2CHCH_2CH(^{15}NH_2)CO_2H$, $(CH_3)_2CHCH_2CH(^{15}NH_2)^{13}CO_2H$ |
| Lysine | $H_2NCH_2CH_2CH_2CH_2CH(NH_2)^{13}CO_2H$, $H_2NCH_2CH_2CH_2CH_2^{13}CH(NH_2)CO_2H$, $H_2N^{13}CH_2CH_2CH_2CH_2CH(NH_2)CO_2H$, $H_2NCH_2CH_2CH_2CH_2^{13}CH(NH_2)^{13}CO_2H$, $H_2NCH_2CD_2CD_2CH_2CH(NH_2)CO_2H$, $H_2NCD_2CD_2CD_2CD_2CH(NH_2)CO_2H$, $H_2NCH_2CH_2CH_2CH_2CH(^{15}NH_2)CO_2H$, $H_2^{15}NCH_2CH_2CH_2CH_2CH(NH_2)CO_2H$, $H_2^{15}N^{13}CH_2CH_2CH_2CH_2CH(NH_2)CO_2H$ |
| Methionine | $CH_3SCH_2CH_2CH(NH_2)^{13}CO_2H$, $CH_3SCH_2CH_2^{13}CH(NH_2)CO_2H$, $^{13}CH_3SCH_2CH_2CH(NH_2)CO_2H$, $CH_3SCH_2CH_2CD(NH_2)CO_2H$, $CD_3SCH_2CH_2CH(NH_2)CO_2H$, $CH_3SCH_2CH_2CH(^{15}NH_2)CO_2H$, $^{13}CD_3SCH_2CH_2CH(NH_2)CO_2H$, $CH_3SCH_2CH_2^{13}CH(^{15}NH_2)CO_2H$ |
| Phenylalanine | $C_6H_5CH_2CH(NH_2)^{13}CO_2H$, $C_6H_5CH_2^{13}CH(NH_2)CO_2H$, $^{13}C_6H_5CH_2CH(NH_2)CO_2H$, $C_6H_5CH_2CD(NH_2)CO_2H$, $C_6H_5CD_2CH(NH_2)CO_2H$, $C_6D_5CH_2CH(NH_2)CO_2H$, $C_6D_5CD_2CD(NH_2)CO_2H$, $C_6H_5CH_2CH(^{15}NH_2)CO_2H$ |
| Proline | 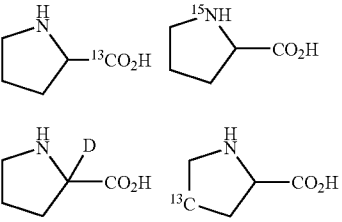 |
| Serine | $HOCH_2CH(NH_2)^{13}CO_2H$, $HOCH_2^{13}CH(NH_2)CO_2H$, $HO^{13}CH_2CH(NH_2)CO_2H$, $HOCH_2CH(^{15}NH_2)CO_2H$, $HOCH_2^{13}CH(^{15}NH_2)CO_2H$ |
| Threonine | $CH_3CH(OH)CH(NH_2)^{13}CO_2H$ |
| Tryptophan | 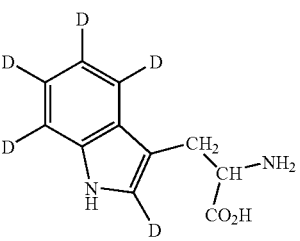 [SMILES: [2H]c1[nH]c2c([2H])c([2H])c([2H])c([2H])c2c1CC(N)C(=O)O] |
| Tyrosine | $HO(C_6H_4)CH_2CH(NH_2)^{13}CO_2H$, $HO(C_6H_4)CH_2^{13}CH(NH_2)CO_2H$, $HO(C_6H_4)^{13}CH_2CH(NH_2)CO_2H$, $HO(C_6H_4)^{13}CH_2^{13}CH(NH_2)^{13}CO_2H$, $HO(^{13}C_6H_4)CH_2CH(NH_2)CO_2H$, $HO(^{13}C_6H_4)^{13}CH_2^{13}CH(NH_2)^{13}CO_2H$, $HO(C_6H_4)CD_2CH(NH_2)CO_2H$, $HO(C_6D_2H_2)CH_2CH(NH_2)CO_2H$, $HO(C_6D_4)CH_2CH(NH_2)CO_2H$, $HO(C_6H_4)CH_2CH(^{15}NH_2)CO_2H$, $H^{17}O(C_6H_4)CH_2CH(NH_2)CO_2H$, |

TABLE 5-continued

| Amino acid | Isotope Forms |
|---|---|
| | $H^{18}O(C_6H_4)CH_2CH(NH_2)CO_2H$, $HO(C_6H_4)CH_2^{13}CH(^{15}NH_2)CO_2H$, $HO(^{13}C_6H_4)^{13}CH_2^{13}CH(^{15}NH_2)^{13}CO_2H$ |
| Valine | $(CH_3)_2CHCH(NH_2)^{13}CO_2H$, $(CH_3)_2CH^{13}CH(NH_2)CO_2H$, $(CH_3)_2CHCD(NH_2)CO_2H$, $(CD_3)_2CDCD(NH_2)CO_2H$, $(CH_3)_2CHCH(^{15}NH_2)CO_2H$ |

For many of the above amino acids, both the D- and L-forms are available (from ISOTEC Inc., Miamisburg, Ohio for example), either of which may be used in the preparation of the mass normalization moieties of this invention. Mixtures of D and L forms are also available but are less preferred if the tags of this invention are to be used in chromatographic separations. For some, FMOC or t-BOC protected derivatives are also available. Mass modified amino acids based on substitution of deuterium for hydrogen and on substitution of $^{13}C$ and $^{15}N$ isotopes for $^{12}C$ and $^{13}N$ isotopes are also available and are equally applicable for the synthesis of the mass normalization moieties of this invention. Various amino acids that are not typically found in peptides may also be used in the mass normalization moieties of this invention, for example deuterated forms of amino-butyric acid are commercially available. For the purposes of this invention non-radioactive, stable isotopes are preferred for safety reasons but there is no necessary limitation to stable isotopes.

Fluorinated derivatives of a number of amino acids are also available. Some of the commercially available fluorinated amino acids are shown in Table 6 below.

TABLE 6

| Amino acid | Fluorinated Forms |
|---|---|
| Glutamic Acid | $HO_2CCFHCH_2CH(NH_2)CO_2H$ |
| Leucine | $(CH_3)(CF_3)CHCH_2CH(NH_2)CO_2H$ |
| Phenylalanine | $C_6FH_4CH_2CH(NH_2)CO_2H$, $C_6F_2H_3CH_2CH(NH_2)CO_2H$, $C_6F_3H_2CH_2CH(NH_2)CO_2H$ |
| Phenylglycine | $C_6FH_4CH(NH_2)CO_2H$, $C_6F_2H_3CH(NH_2)CO_2H$, $C_6F_3H_2CH(NH_2)CO_2H$ |
| Valine | $(CH_3)_2CFCH(NH_2)CO_2H$ |

For most of the above fluorinated amino acids, the reagents are available as mixtures of D and L forms. In general, fluorinated variants of amino acids are less preferred than isotope substituted variants. The fluorinated compounds can be used to generate a range of mass labels with the same mass but each mass label will be chemically different, which means that their behaviour in the mass spectrometer will vary more than isotope substituted mass labels. Moreover, the mass labels will not have identical chromatographic properties if the mass labels are to be used in chromatographic separations.

Affinity Capture Ligands

In certain embodiments of the invention the mass markers comprise an affinity capture ligand. Affinity capture ligands are ligands, which have highly specific binding partners. These binding partners allow molecules tagged with the ligand to be selectively captured by the binding partner. Preferably a solid support is derivatised with the binding partner so that affinity ligand tagged molecules can be selectively captured onto the solid phase support. A preferred affinity capture ligand is biotin, which can be introduced into the mass labels of this invention by standard methods known in the art. In particular a lysine residue may be incorporated after the mass marker moiety or mass normalization moiety through which an amine-reactive biotin can be linked to the mass labels (see for example Geahlen R. L. et al., Anal Biochem 202(1): 68-67, "A general method for preparation of peptides biotinylated at the carboxy terminus." 1992; Sawutz D. G. et al., Peptides 12(5): 1019-1012, "Synthesis and molecular characterization of a biotinylated analogue of [Lys]bradykinin." 1991; Natarajan S. et al., Int J Pept Protein Res 40(6): 567-567, "Site-specific biotinylation. A novel approach and its application to endothelin-1 analogues and PTH-analogue.", 1992). Iminobiotin is also applicable. A variety of avidin counter-ligands for biotin are available, which include monomeric and tetrameric avidin and streptavidin, all of which are available on a number of solid supports.

Other affinity capture ligands include digoxigenin, fluorescein, nitrophenyl moieties and a number of peptide epitopes, such as the c-myc epitope, for which selective monoclonal antibodies exist as counter-ligands. Metal ion binding ligands such as hexahistidine, which readily binds $Ni^{2+}$ ions, are also applicable. Chromatographic resins, which present iminodiacetic acid chelated $Ni^{2+}$ ions are commercially available, for example. These immobilised nickel columns may be used to capture mass labels. As a further alternative, an affinity capture functionality may, be selectively reactive with an appropriately derivatised solid phase support. Boronic acid, for example, is known to selectively react with vicinal cis-diols and chemically similar ligands, such as salicylhydroxamic acid.

Mass Spec Sensitivity Enhancing Groups and Mass Differentiation

In preferred embodiments of the invention the peptide mass tags comprise Sensitivity Enhancing Groups. Methylation and guanidination may be used as methods of improving sensitivity. The guanidino group and the tertiary amino group are both useful Sensitivity Enhancing Groups for electrospray mass spectrometry.

Various other methods for derivatising peptides have been also been developed. These include the use of quaternary ammonium derivatives, quaternary phosphonium derivatives and pyridyl derivatives for positive ion mass spectrometry. Halogenated compounds, particularly halogenated aromatic compounds are well known electrophores, i.e. they pick up thermal electrons very easily. A variety of derivatisation reagents based on fluorinated aromatic compounds (Bian N. et al., Rapid Commun Mass Spectrom 11(16): 1781-1784, "Detection via laser desorption and mass spectrometry of multiplex electrophore-labelled albumin." 1997) have been developed for electron capture detection, which is a highly sensitive ionisation and detection process that can be used with negative ion mass spectrometry (Abdel-Baky S. & Giese R. W., Anal Chem 63(24):2986-2989, "Gas chromatography/electron capture negative-ion mass spectrometry at the zeptomole level." 1991). A fluorinated aromatic group could also be used as a sensitivity enhancing group. Aromatic sulphonic acids have also been used for improving sensitivity in negative ion mass spectrometry.

Each type of Sensitivity Enhancing Group has different benefits, which depend on the method of ionisation used and on the methods of mass analysis used. The mechanism by which sensitivity is enhanced may also be different for each type of group. Some derivatisation methods increase basicity and thus promote protonation and charge localisation, while other methods increase surface activity of the tagged peptides, which improves sensitivity in surface desorption techniques like Matrix Assisted Laser Desorption Ionisation (MALDI) and Fast Atom Bombardment (FAB). Negative ion mass spectrometry is often more sensitive because there is less background noise. Charge derivatisation can also change the fragmentation products of derivatised peptides, when collision induced dissociation is used. In particular some derivatisation techniques simplify fragmentation patterns, which is highly advantageous. The choice of Sensitivity Enhancing Group is determined by the mass spectrometric techniques that will be employed (for a review see Roth et al., Mass Spectrometry Reviews 17:255-274, "Charge derivatisation of peptides for analysis by mass spectrometry", 1998). For the purposes of this invention all of the known derivatisation techniques could be used with the peptide mass tags of this invention. The published protocols could be used without modification to derivatise the peptide mass tags of this invention after solid phase peptide synthesis or the protocols could be readily adapted for use during solid phase synthesis if desired.

Analysis of Peptides by Mass Spectrometry

The essential features of a mass spectrometer are as follows:

Inlet System→Ion Source→Mass Analyser→Ion Detector→Data Capture System

There are preferred inlet systems, ion sources and mass analysers for the purposes of analysing peptides.

Inlet Systems

In some aspects of this invention a chromatographic or electrophoretic separation is preferred to reduce the complexity of the sample prior to analysis by mass spectrometry. A variety of mass spectrometry techniques are compatible with separation technologies particularly capillary zone electrophoresis and High Performance Liquid Chromatography (HPLC). The choice of ionisation source is limited to some extent if a separation is required as ionisation techniques such as MALDI and FAB (discussed below) which ablate material from a solid surface are less suited to chromatographic separations. For most purposes, it has been very costly to link a chromatographic separation in-line with mass spectrometric analysis by one of these techniques. Dynamic FAB and ionisation techniques based on spraying such as electrospray, thermospray and APCI are all readily compatible with in-line chromatographic separations and equipment to perform such liquid chromatography mass spectrometry analysis is commercially available.

Ionisation Techniques

For many biological mass spectrometry applications so called 'soft' ionisation techniques are used. These allow large molecules such as proteins and nucleic acids to be ionised essentially intact. The liquid phase techniques allow large biological molecules to enter the mass spectrometer in solutions with mild pH and at low concentrations. A number of techniques are appropriate for use with this invention including but not limited to Electrospray Ionisation Mass Spectrometry (ESI-MS), Fast Atom Bombardment (FAB), Matrix Assisted Laser Desorption Ionisation Mass Spectrometry (MALDI MS) and Atmospheric Pressure Chemical Ionisation Mass Spectrometry (APCI-MS).

Electrospray Ionisation

Electrospray ionisation requires that the dilute solution of the analyte biological molecule is 'atomised' into the spectrometer, i.e. injected as a fine spray. The solution is, for example, sprayed from the tip of a charged needle in a stream of dry nitrogen and an electrostatic field. The mechanism of ionisation is not fully understood but is thought to work broadly as follows. In a stream of nitrogen the solvent is evaporated. With a small droplet, this results in concentration of the analyte molecule. Given that most biological molecules have a net charge this increases the electrostatic repulsion of the dissolved molecule. As evaporation continues this repulsion ultimately becomes greater than the surface tension of the droplet and the droplet disintegrates into smaller droplets. This process is sometimes referred to as a 'Coulombic explosion'. The electrostatic field helps to further overcome the surface tension of the droplets and assists in the spraying process. The evaporation continues from the smaller droplets which, in turn, explode iteratively until essentially the biological molecules are in the vapour phase, as is all the solvent. This technique is of particular importance in the use of mass labels in that the technique imparts a relatively small amount of energy to ions in the ionisation process and the energy distribution within a population tends to fall in a narrower range when compared with other techniques. The ions are accelerated out of the ionisation chamber by the use of electric fields that are set up by appropriately positioned electrodes. The polarity of the fields may be altered to extract either negative or positive ions. The potential difference between these electrodes determines whether positive or negative ions pass into the mass analyser and also the kinetic energy with which these ions enter the mass spectrometer. This is of significance when considering fragmentation of ions in the mass spectrometer. The more energy imparted to a population of ions the more likely it is that fragmentation will occur through collision of analyte molecules with the bath gas present in the source. By adjusting the electric field used to accelerate ions from the ionisation chamber it is possible to control the fragmentation of ions. This is advantageous when fragmentation of ions is to be used as a means of removing tags from a labelled biological molecule. Electrospray ionisation is particularly advantageous as it can be used in-line with liquid chromatography, referred to as Liquid Chromatography Mass Spectrometry (LC-MS).

Matrix Assisted Laser Desorption Ionisation (MALDI)

MALDI requires that the biological molecule solution be embedded in a large molar excess of a photo-excitable 'matrix'. The application of laser light of the appropriate frequency results in the excitation of the matrix which in turn leads to rapid evaporation of the matrix along with its entrapped biological molecule. Proton transfer from the acidic matrix to the biological molecule gives rise to protonated forms of the biological molecule which can be detected by positive ion mass spectrometry, particularly by Time-Of-Flight (TOF) mass spectrometry. Negative ion mass spectrometry is also possible by MALDI TOF. This technique imparts a significant quantity of translational energy to ions, but tends not to induce excessive fragmentation despite this. Accelerating voltages can again be used to control fragmentation with this technique though.

Fast Atom Bombardment

Fast Atom Bombardment (FAB) has come to describe a number of techniques for vaporising and ionising relatively involatile molecules. In these techniques a sample is desorbed from a surface by collision of the sample with a high energy beam of xenon atoms or caesium ions. The sample is coated onto a surface with a simple matrix, typically a non volatile material, e.g. m-nitrobenzyl alcohol (NBA) or glycerol. FAB techniques are also compatible with liquid phase inlet systems—the liquid eluting from a capillary electrophoresis inlet or a high pressure liquid chromatography system pass through a frit, essentially coating the surface of the frit with analyte solution which can be ionised from the frit surface by atom bombardment.

Mass Analysers

Fragmentation of peptides by collision induced dissociation is used in this invention to identify tags on proteins. Various mass analyser geometries may be used to fragment peptides and to determine the mass of the fragments.

MS/MS and MS" Analysis of Peptides

Tandem mass spectrometers allow ions with a pre-determined mass-to-charge ratio to be selected and fragmented by collision induced dissociation (CID). The fragments can then be detected providing structural information about the selected ion. When peptides are analysed by CID in a tandem mass spectrometer, characteristic cleavage patterns are observed, which allow the sequence of the peptide to be determined. Natural peptides typically fragment randomly at the amide bonds of the peptide backbone to give series of ions that are characteristic of the peptide. CID fragment series are denoted $a_n$, $b_n$, $c_n$, etc. for cleavage at the $n^{th}$ peptide bond where the charge of the ion is retained on the N-terminal fragment of the ion. Similarly, fragment series are denoted $x_n$, $y_n$, $z_n$, etc. where the charge is retained on the C-terminal fragment of the ion.

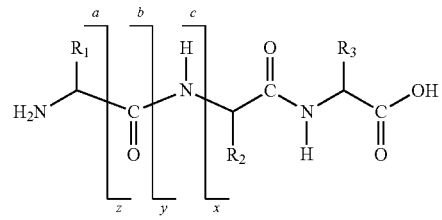

Trypsin and thrombin are favoured cleavage agents for tandem mass spectrometry as they produce peptides with basic groups at both ends of the molecule, i.e. the alpha-amino group at the N-terminus and lysine or arginine side-chains at the C-terminus. This favours the formation of doubly charged ions, in which the charged centres are at opposite termini of the molecule. These doubly charged ions produce both C-terminal and N-terminal ion series after CID. This assists in determining the sequence of the peptide. Generally speaking only one or two of the possible ion series are observed in the CID spectra of a given peptide. In low-energy collisions typical of quadrupole based instruments the b-series of N-terminal fragments or the y-series of C-terminal fragments predominate. If doubly charged ions are analysed then both series are often detected. In general, the y-series ions predominate over the b-series.

In general peptides fragment via a mechanism that involves protonation of the amide backbone follow by intramolecular nucleophilic attack leading to the formation of a 5-membered oxazolone structure and cleavage of the amide linkage that was protonated (Schlosser A. and Lehmann W. D. J. Mass Spectrom. 35: 1382-1390, "Five-membered ring formation in unimolecular reactions of peptides: a key structural element controlling low-energy collision induced dissociation", 2000). FIG. 16a shows one proposed mechanism by which this sort of fragmentation takes place. This mechanism requires a carbonyl group from an amide bond adjacent to a protonated amide on the N-terminal side of the protonated amide to carry out the nucleophilic attack. A charged oxazolonium ion gives rise to b-series ions, while proton transfer from the N-terminal fragment to the C-terminal fragment gives rise to y-series ions as shown in FIG. 16a. This requirement for an appropriately located carbonyl group does not account for cleavage at amide bonds adjacent to the N-terminal amino acid, when the N-terminus is not protected and, in general, b-series ions are not seen for the amide between the N-terminal and second amino acid in a peptide. However, peptides with acetylated N-termini do meet the structural requirements of this mechanism and fragmentation can take place at the amide bond immediately after the first amino acid by this mechanism. Peptides with thioacetylated N-termini, as shown in FIG. 16c, will cleave particularly easily by the oxazolone mechanism as the sulphur atom is more nucleophilic than an oxygen atom in the same position. Fragmentation of the amide backbone of a peptide can also be modulated by methylation of the backbone. Methylation of an amide nitrogen in a peptide can promote fragmentation of the next amide bond C-terminal to the methylated amide and also favours the formation of b-ions. The enhanced fragmentation may be partly due to the electron donating effect of the methyl group increasing the nucleophilicity of the carbonyl group of the methylated amide, while the enhanced formation of b-ions may be a result of the inability of the oxazolonium ion that forms to transfer protons to the C-terminal fragment as shown in FIG. 16b. In the context of this invention thioacetylation of the N-terminus of a tag dipeptide can be used to enhance cleavage of the tag peptide at the next amide bond. Similarly, methylation of the nitrogen atom of an N-terminal acetyl or thioacetyl group will also enhance cleavage of the adjacent amide bond.

The ease of fragmentation of the amide backbone of a polypeptide or peptide is also significantly modulated by the side chain functionalities of the peptide. Thus the sequence of a peptide determines where it will fragment most easily. In general it is difficult to predict which amide bonds will fragment easily in a peptide sequence. This has important consequences for the design of the peptide mass tags of this invention. However, certain observations have been made that allow peptide mass tags that fragment at the desired amide bond to be designed. Proline, for example, is known to promote fragmentation at its N-terminal amide bond (Schwartz B. L., Bursey M. M., Biol. Mass Spectrom. 21:92, 1997) as fragmentation at the C-terminal amide gives rise to an energetically unfavourable strained bicyclic oxazolone structure. Aspartic acid also promotes fragmentation at its N-terminal amide bond. Asp-Pro linkages, however, are particularly labile in low energy CID analysis (Wysocki V. H. et al., J Mass Spectrom. 35(12): 1399-1406, "Mobile and localized protons: a framework for understanding peptide dissociation." 2000) and in this situation aspartic acid seems to promote the cleavage of the amide bond on its C-terminal side. Thus proline, and asp-pro linkages can also be used in the tag peptides of this invention to promote fragmentation at specified locations within a peptide.

A typical tandem mass spectrometer geometry is a triple quadrupole which comprises two quadrupole mass analysers separated by a collision chamber, also a quadrupole. This collision quadrupole acts as an ion guide between the two mass analyser quadrupoles. A gas can be introduced into the collision quadrupole to allow collision with the ion stream from the first mass analyser. The first mass analyser selects ions on the basis of their mass/charge ration which pass through the collision cell where they fragment. The fragment ions are separated and detected in the third quadrupole. Induced cleavage can be performed in geometries other than tandem analysers. Ion trap mass spectrometers can promote fragmentation through introduction of a gas into the trap itself with which trapped ions will collide. Ion traps generally contain a bath gas, such as helium but addition of neon for example, promotes fragmentation. Similarly photon induced fragmentation could be applied to trapped ions. Another favourable geometry is a Quadrupole/Orthogonal Time of Flight tandem instrument where the high scanning rate of a quadrupole is coupled to the greater sensitivity of a reflectron TOF mass analyser to identify the products of fragmentation.

Conventional 'sector' instruments are another common geometry used in tandem mass spectrometry. A sector mass analyser comprises two separate 'sectors', an electric sector which focuses an ion beam leaving a source into a stream of ions with the same kinetic energy using electric fields. The magnetic sector separates the ions on the basis of their mass to generate a spectrum at a detector. For tandem mass spectrometry a two sector mass analyser of this kind can be used where the electric sector provide the first mass analyser stage, the magnetic sector provides the second mass analyser, with a collision cell placed between the two sectors. Two complete sector mass analysers separated by a collision cell can also be used for analysis of mass tagged peptides.

Ion Traps

Ion Trap mass analysers are related to the quadrupole mass analysers. The ion trap generally has a 3 electrode construction—a cylindrical electrode with 'cap' electrodes at each end forming a cavity. A sinusoidal radio frequency potential is applied to the cylindrical electrode while the cap electrodes are biased with DC or AC potentials. Ions injected into the cavity are constrained to a stable circular trajectory by the oscillating electric field of the cylindrical electrode. However, for a given amplitude of the oscillating potential, certain ions will have an unstable trajectory and will be ejected from the trap. A sample of ions injected into the trap can be sequentially ejected from the trap according to their mass/charge ratio by altering the oscillating radio frequency potential. The ejected ions can then be detected allowing a mass spectrum to be produced.

Ion traps are generally operated with a small quantity of a 'bath gas', such as helium, present in the ion trap cavity. This increases both the resolution and the sensitivity of the device as the ions entering the trap are essentially cooled to the ambient temperature of the bath gas through collision with the bath gas. Collisions both increase ionisation when a sample is introduced into the trap and dampen the amplitude and velocity of ion trajectories keeping them nearer the centre of the trap. This means that when the oscillating potential is changed, ions whose trajectories become unstable gain energy more rapidly, relative to the damped circulating ions and exit the trap in a tighter bunch giving a narrower larger peaks.

Ion traps can mimic tandem mass spectrometer geometries, in fact they can mimic multiple mass spectrometer geometries allowing complex analyses of trapped ions. A single mass species from a sample can be retained in a trap, i.e. all other species can be ejected and then the retained species can be carefully excited by super-imposing a second oscillating frequency on the first. The excited ions will then collide with the bath gas and will fragment if sufficiently excited. The fragments can then be analysed further. It is possible to retain a fragment ion for further analysis by ejecting other ions and then exciting the fragment ion to fragment. This process can be repeated for as long as sufficient sample exists to permit further analysis. It should be noted that these instruments generally retain a high proportion of fragment ions after induced fragmentation. These instruments and FTICR mass spectrometers (discussed below) represent a form of temporally resolved tandem mass spectrometry rather than spatially resolved tandem mass spectrometry which is found in linear mass spectrometers.

Fourier Transform Ion Cyclotron Resonance Mass Spectrometry (FTICR MS)

FTICR mass spectrometry has similar features to ion traps in that a sample of ions is retained within a cavity but in FTICR MS the ions are trapped in a high vacuum chamber by crossed electric and magnetic fields. The electric field is generated by a pair of plate electrodes that form two sides of a box. The box is contained in the field of a superconducting magnet which in conjunction with the two plates, the trapping plates, constrain injected ions to a circular trajectory between the trapping plates, perpendicular to the applied magnetic field. The ions are excited to larger orbits by applying a radio-frequency pulse to two 'transmitter plates' which form two further opposing sides of the box. The cycloidal motion of the ions generate corresponding electric fields in the remaining two opposing sides of the box which comprise the 'receiver plates'. The excitation pulses excite ions to larger orbits which decay as the coherent motions of the ions is lost through collisions. The corresponding signals detected by the receiver plates are converted to a mass spectrum by Fourier Transform (FT) analysis.

For induced fragmentation experiments these instruments can perform in a similar manner to an ion trap—all ions except a single species of interest can be ejected from the trap. A collision gas can be introduced into the trap and fragmentation can be induced. The fragment ions can be subsequently analysed. Generally fragmentation products and bath gas combine to give poor resolution if analysed by FT analysis of signals detected by the 'receiver plates', however the fragment ions can be ejected from the cavity and analysed in a tandem configuration with a quadrupole, for example.

Separation of Labelled Peptides by Chromatography or Electrophoresis.

In the optional second step of the fourth aspect of this invention, labelled biomolecules are subjected to a chromatographic separation prior to analysis by mass spectrometry. This is preferably High Performance Liquid Chromatography (HPLC) which can be coupled directly to a mass spectrometer for in-line analysis of the peptides as they elute from the chromatographic column. A variety of separation techniques may be performed by HPLC but reverse phase chromatography is a popular method for the separation of peptides prior to mass spectrometry. Capillary zone electrophoresis is another separation method that may be coupled directly to a mass spectrometer for automatic analysis of eluting samples. These and other fractionation techniques may be applied to reduce the complexity of a mixture of biological molecules prior to analysis by mass spectrometry. A combination of separation techniques may also be used, including orthogonal separation.

Applications of the Invention

Labelling Peptides and Polypeptides and Analysis by LC-MS-MS

In preferred embodiments of the invention, the mass labels are used for the analysis of mixtures of peptides by liquid chromatography tandem mass spectrometry (LC-MS-MS). The use of the mass labels of this invention according to the these aspects will now be discussed in the context of the analysis of peptides. Reactive mass labels such as those in FIGS. 1 *a* to *e* may be used to label peptides.

After attachment of the mass labels, the labelled peptides will have a mass that is shifted by the mass of the label. The mass of the peptide may be sufficient to identify the source protein. In this case only the mass label needs to be detected which can be achieved by selected reaction monitoring with a triple quadrupole, discussed in more detail below. Briefly, the first quadrupole of the triple quadrupole is set to let through ions whose mass-to-charge ratio corresponds to that of the peptide of interest, adjusted for the mass of the mass marker moiety. The selected ions are then subjected to collision induced dissociation (CID) in the second quadrupole. Under the sort of conditions used in the analysis of peptides the ions will fragment mostly at the amide bonds in the molecule. Although the mass labels all have the same mass, the terminal portion is different because of differences in the substituents. Thus the mass marker moieties can be distinguished from each other. The presence of the marker fragment associated with an ion of a specific mass should confirm that the ion was a peptide and the relative peak heights of the tags from different samples will give information about the relative quantities of the peptides in their samples. If the mass is not sufficient to identify a peptide, either because a number of terminal peptides in the sample have the same terminal mass or because the peptide is not known, then sequence information may be determined by analysis of the complete CID spectrum. The peptide fragmentation peaks can be used to identify the peptides while the mass label peaks give information about the relative quantities of the peptides.

The analysis of proteins by tandem mass spectrometry, particularly mixtures of peptides, is complicated by the 'noisiness' of the spectra obtained. Peptides isolated from biological samples are often contaminated with buffering reagents, denaturants and detergents, all of which introduce peaks into the mass spectrum. As a result, there are often more contamination peaks in the spectrum than peptide peaks and identifying peaks that correspond to peptides is major problem, especially with small samples of proteins that are difficult to isolate. As a result various methods are used to determine which peaks correspond to peptides before detailed CID analysis is performed. Triple quadrupole based instruments permit 'precursor ion scanning' (see Wilm M. et al., Anal Chem 68(3):527-33, "Parent ion scans of unseparated peptide mixtures." (1996)). The triple quadrupole is operated in 'single reaction monitoring' mode, in which the first quadrupole scans over the full mass range and each gated ion is subjected to CID in the second quadrupole. The third quadrupole is set to detect only one specific fragment ion, which is usually a characteristic fragment ion from a peptide such as immonium ions. The presence of phosphate groups can also be detected using this sort of technique. An alternative method used with quadrupole/time-of-flight mass spectrometers scans for doubly charged ions by identifying ions which when subjected to CID produce daughter ions with higher mass-to-charge ratios than the parent ion. A further method of identifying doubly charged ions is to look for sets of peaks in the spectrum which are only 0.5 Daltons apart with appropriate intensity ratios which would indicate that the ions are the same differing only by the proportion of $^{13}C$ present in the molecule.

By labelling peptides with the mass labels of this invention, a novel form of precursor ion scanning may be envisaged in which peptide peaks are identified by the presence of fragments corresponding to the mass labels of this invention after subjecting the labelled peptides to CID. In particular, the peptides isolated from each sample by the methods of this invention may be labelled with more than one mass label. An equimolar mixture of a 'precursor ion scanning' mass label which is used in all samples and a sample specific mass label may be used to label the peptides in each sample. In this way changes in the level of peptides in different samples will not have an adverse effect on the identification of peptide peaks in a precursor ion scan.

Having identified and selected a peptide ion, it is subjected to CID. The CID spectra are often quite complex and determining which peaks in the CID spectrum correspond to meaningful peptide fragment series is a further problem in determining the sequence of a peptide by mass spectrometry. Shevchenko et al., Rapid Commun. Mass Spec. 11: 1015-1024 (1997) describe a further method, which involves treating proteins for analysis with trypsin in 1:1 $^{16}O/^{18}O$ water.

The hydrolysis reaction results in two populations of peptides, the first whose terminal carboxyl contains $^{16}O$ and the second whose terminal carboxyl contains $^{18}O$. Thus for each peptide in the sample there should be a double peak of equal intensity for each peptide where the double peak is 2 Daltons apart. This is complicated slightly by intrinsic peptide isotope peaks but allows for automated scanning of the CID spectrum for doublets. The differences in mass between doublets can be determined to identify the amino acid by the two fragments differ. This method may be applicable with the methods of this invention if N-terminal peptides are isolated.

Protein Expression Profiling

To understand the changes in a cancerous tissue, for example, requires an understanding of all of the molecular changes in that tissue, ideally relating these changes to normal tissue. To determine all of the molecular changes requires the ability to measure changes in gene expression, protein expression and ultimately metabolite changes. It is possible to compare the expression, between different tissue samples, of large numbers of genes simultaneously at the level of messenger RNA (mRNA) using microarray technology (see for example Iyer V. R. et al., Science 283(5398):83-87, "The transcriptional program in the response of human fibroblasts to serum." 1999), however mRNA levels do not correlate directly to the levels of protein in a tissue. To determine a protein expression profile for a tissue, 2-dimensional gel electrophoresis is widely used. Unfortunately, this technique is extremely laborious and it is difficult to compare two or more samples simultaneously on a 2-D gel due to the difficulty of achieving reproducibility. As discussed above peptides may be analysed effectively using the methods of this invention. The mass labels of this invention allow the same peptide from different samples to be identified using LC-MS-MS. In addition, the relative quantities of the same peptide in different samples may be determined. The ability to rapidly and sensitively determine the identity and relative quantities of peptides in a number of samples allows for expression profiling. Therefore it is an object of this invention to provide improved methods for comparative analysis of complex protein samples based on the selective isolation and labelling of peptides. Two published approaches for the global analysis of protein expression are discussed and various methods for the analysis of particular protein states, such as phosphorylation and carbohydrate modification are also described below.

Terminal Peptide Isolation for Global Protein Expression Profiling

Isolation of N- or C-terminal peptides has been described as a method to determine a global expression profile of a protein sample. Isolation of terminal peptides ensures that at least one and only one peptide per protein is isolated thus ensuring that the complexity of the sample that is analysed does not have more components than the original sample. Reducing large polypeptides to shorter peptides makes the sample more amenable to analysis by mass spectrometry. Methods for isolating peptides from the termini of polypeptides are discussed in PCT/GB98/00201, PCT/GB99/03258.

Isolation of Carbohydrate Modified Proteins

Carbohydrates are often present as a post-translational modification of proteins. Various affinity chromatography techniques for the isolation of these sorts of proteins are known (For a review see Gerard C., Methods Enzymol. 182: 529-539, "Purification of glycoproteins." 1990). A variety of natural protein receptors for carbohydrates are known. The members of this class of receptors, known as lectins, are highly selective for particular carbohydrate functionalities. Affinity columns derivatised with specific lectins can be used to isolate proteins with particular carbohydrate modifications, whilst affinity columns comprising a variety of different lectins could be used to isolate populations of proteins with a variety of different carbohydrate modifications. In one embodiment of the invention, a protocol for the analysis of a sample of proteins, which contains carbohydrate modified proteins, comprises the steps of:

1. Treating the sample with a sequence specific cleavage reagent such as Trypsin or Lys-C;
2. Passing the protein sample through affinity columns containing lectins or boronic acid derivatives to isolate only carbohydrate modified peptides;
3. Labelling the captured sugar modified peptides at the free alpha amino group generated by the sequence specific cleavage, using the mass labels of this invention; and
4. Analysing the labelled peptides by LC-MS-MS.

An N-hydroxysuccinimide activated mass label could be used to label the free alpha-amino groups. If Lys-C is used then each carbohydrate modified peptide will have a free epsilon-amino group as well as a free alpha amino group, both of which can be labelled.

Many carbohydrates have vicinal-diol groups present, i.e. hydroxyl groups present on adjacent carbon atoms. Diol containing carbohydrates that contain vicinal diols in a 1,2-cis-diol configuration will react with boronic acid derivatives to form cyclic esters. This reaction is favoured at basic pH but is easily reversed at acid pH. Resin immobilised derivatives of phenyl boronic acid have been used as ligands for affinity capture of proteins with cis-diol containing carbohydrates. In one embodiment of the sixth aspect of this invention a set of affinity ligand peptide mass labels comprising biotin linked to a phenylboronic acid entity could be synthesised. These boronic acid tags could used to label two separate samples comprising peptides or proteins with carbohydrate modifications that contain vicinal cis-diols. In another embodiment of the invention, a protocol for the analysis of a protein sample containing carbohydrate modified polypeptides comprises the steps of:

1. Reacting at least one protein sample at basic pH with a boronic acid affinity ligand mass label,
2. Cleaving the polypeptides with a sequence specific endoprotease,
3. Capturing labelled peptides onto an avidin derivatised solid support; and
4. Analysing the captured labelled peptides by LC-MS-MS.

The sample may be digested with the sequence specific endoprotease before or after reaction of the sample with the affinity ligand mass label.

Vicinal-diols, in sialic acids for example, can also be converted into carbonyl groups by oxidative cleavage with periodate. Enzymatic oxidation of sugars containing terminal galactose or galactosamine with galactose oxidase can also convert hydroxyl groups in these sugars to carbonyl groups. Complex carbohydrates can also be treated with carbohydrate cleavage enzymes, such as neuramidase, which selectively remove specific sugar modifications leaving behind sugars, which can be oxidised. These carbonyl groups can be labelled allowing proteins bearing such modifications to be detected or isolated. Hydrazide reagents, such as Biocytin hydrazide (Pierce & Warriner Ltd, Chester, UK) will react with carbonyl groups in carbonyl-containing carbohydrate species (E. A. Bayer et al., Anal. Biochem. 170: 271-281, "Biocytin hydrazide—a selective label for sialic acids, galactose, and other sugars in glycoconjugates using avidin biotin technology", 1988). Alternatively a carbonyl group can be labelled with an amine modified biotin, such as Biocytin and EZ-Link™ PEO-Biotin (Pierce & Warriner Ltd, Chester, UK), using reductive alkylation (Means G. E., Methods Enzymol 47: 469-478, "Reductive alkylation of amino groups." 1977; Rayment I., Methods Enzymol 276: 171-179, "Reductive alkylation of lysine residues to alter crystallization properties of proteins." 1997). Proteins bearing vicinal-diol containing carbohydrate modifications in a complex mixture can thus be biotinylated. Biotinylated, hence carbohydrate modified, proteins may then be isolated using an avidinated solid support.

A set of peptide mass labels according to this invention can be synthesised for the analysis of carbohydrate modified peptides that have been oxidised with periodate A further embodiment of the invention comprises the steps of
1. Treating a sample of polypeptides with periodate, so that carbohydrates with vicinal cis-diols on glycopeptides will gain a carbonyl functionality;
2. Labelling this carbonyl functionality with a hydrazide activated mass label linked to biotin;
3. Digesting the protein sample with a sequence specific endoprotease;
4. Capturing labelled peptides onto an avidin derivatised solid support; and
5. Analysing the biotinylated peptides by LC-MS-MS.

The protein sample may be digested with the sequence specific endoprotease before or after reaction of the sample with the affinity ligand mass label.

Isolation of Phosphopeptides

Phosphorylation is a ubiquitous reversible post-translational modification that appears in the majority of signalling pathways of almost all organisms as phosphorylation is widely used as a transient signal to mediate changes in the state of individual proteins. It is an important area of research and tools which allow the analysis of the dynamics of phosphorylation are essential to a full understanding of how cells responds to stimuli, which includes the responses of cells to drugs.

Figure 8:
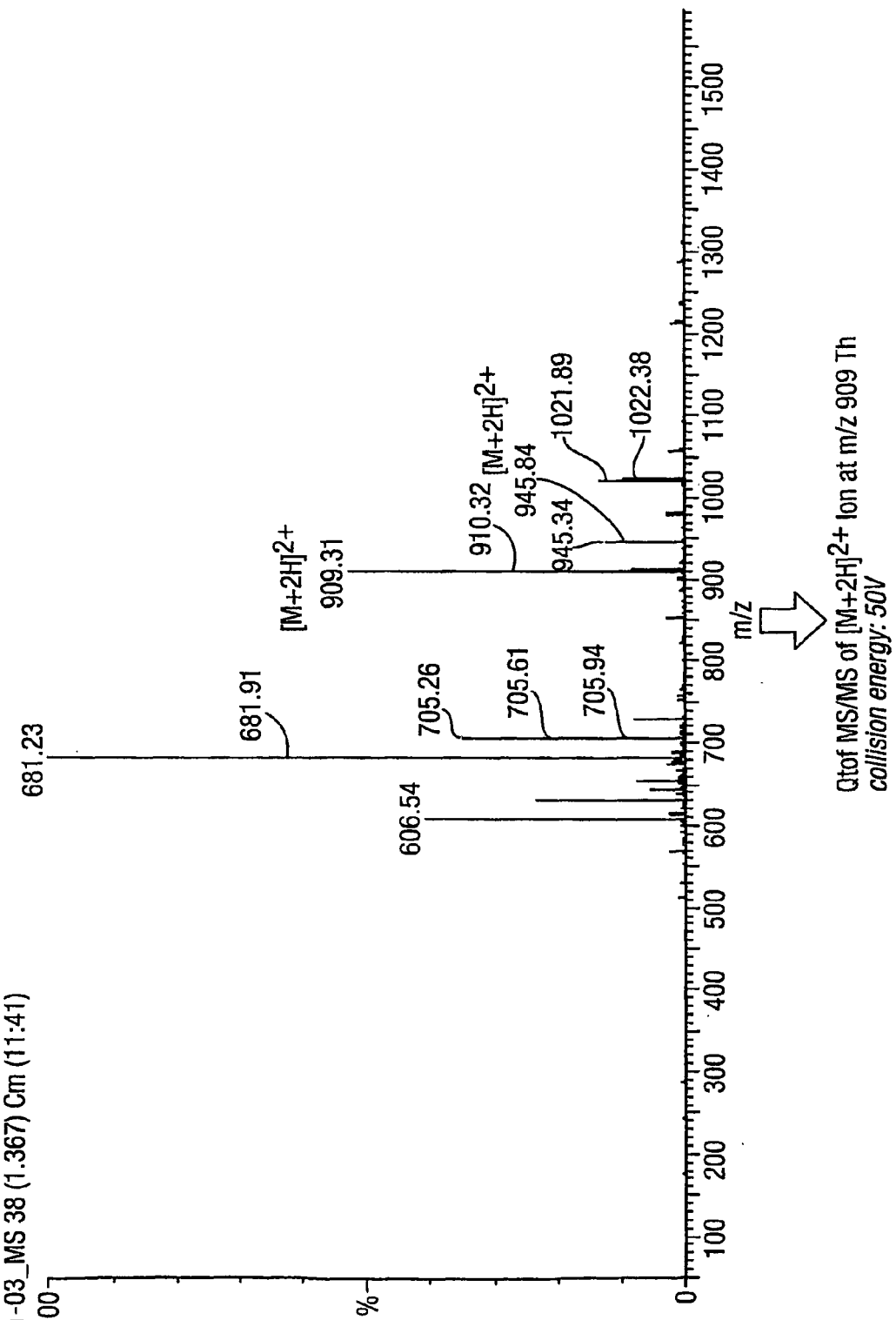
FIG. 8 shows MS/MS analysis of DMPip-βAla-DYEGATLSDIGALIR.
Figure 8:
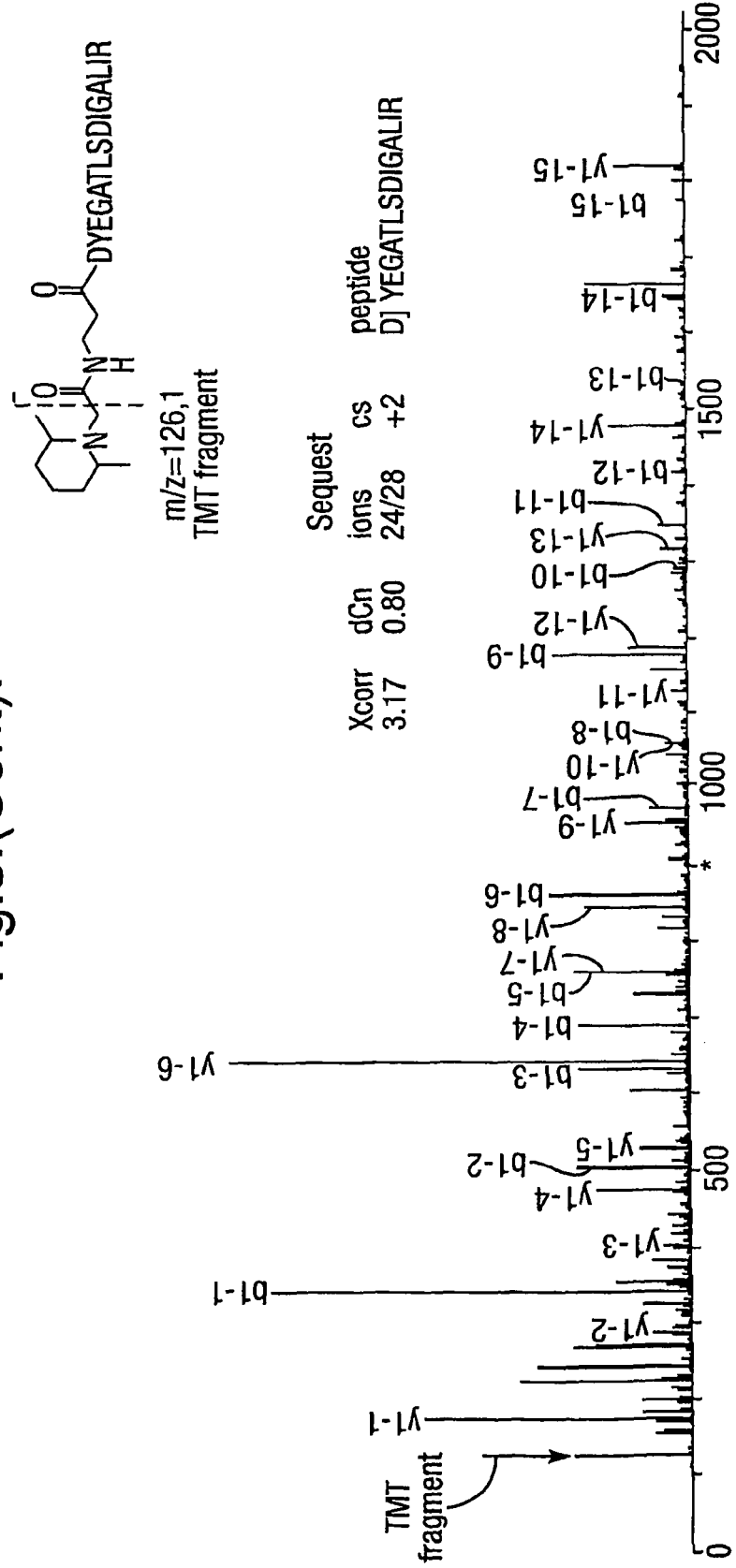
Figure 9:
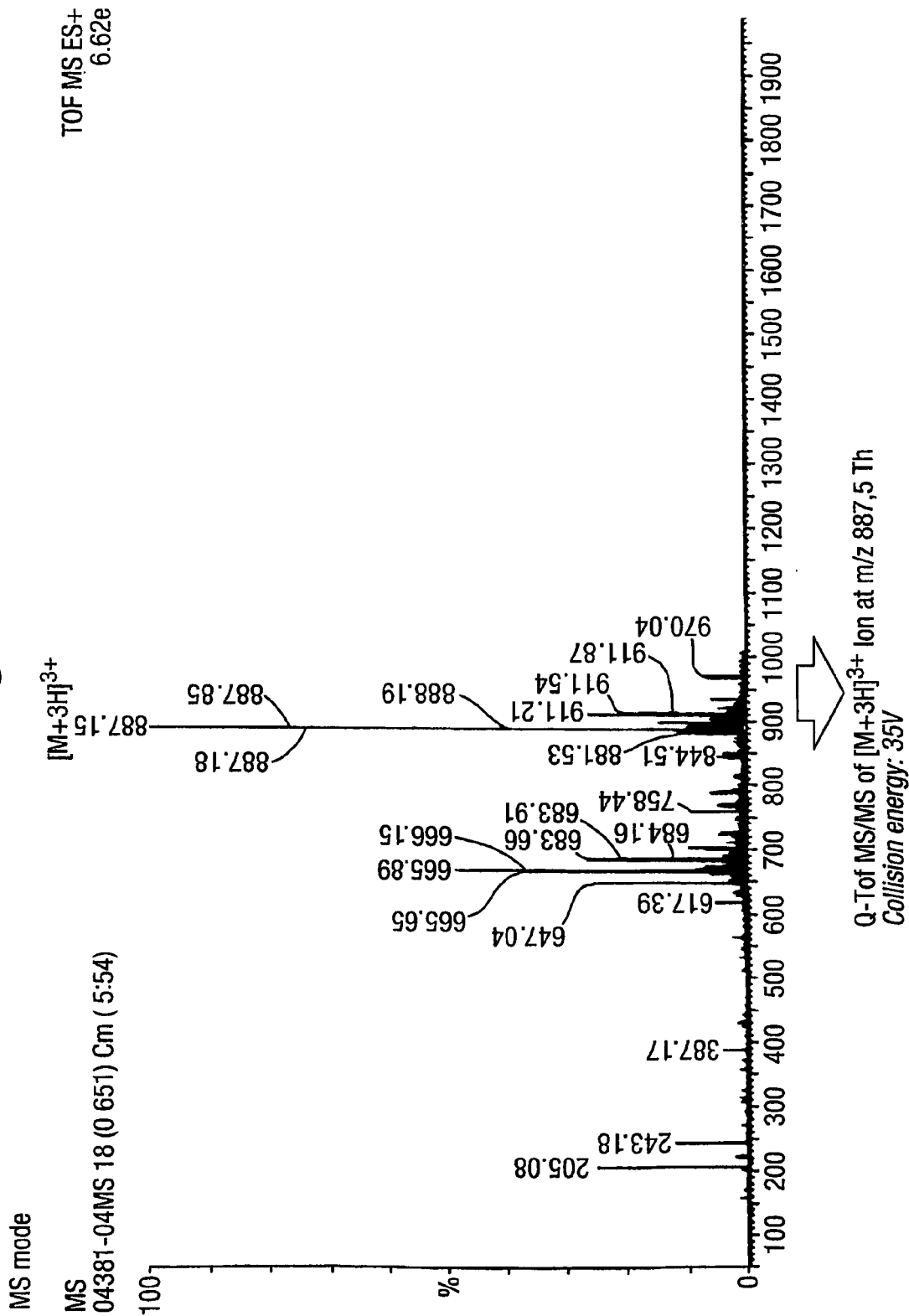
FIG. 9 shows MS/MS analysis of DMPip-βAla-LGEHNIDVLEGNEQFINAA (DMPip-βAla-) K.
Figure 10:
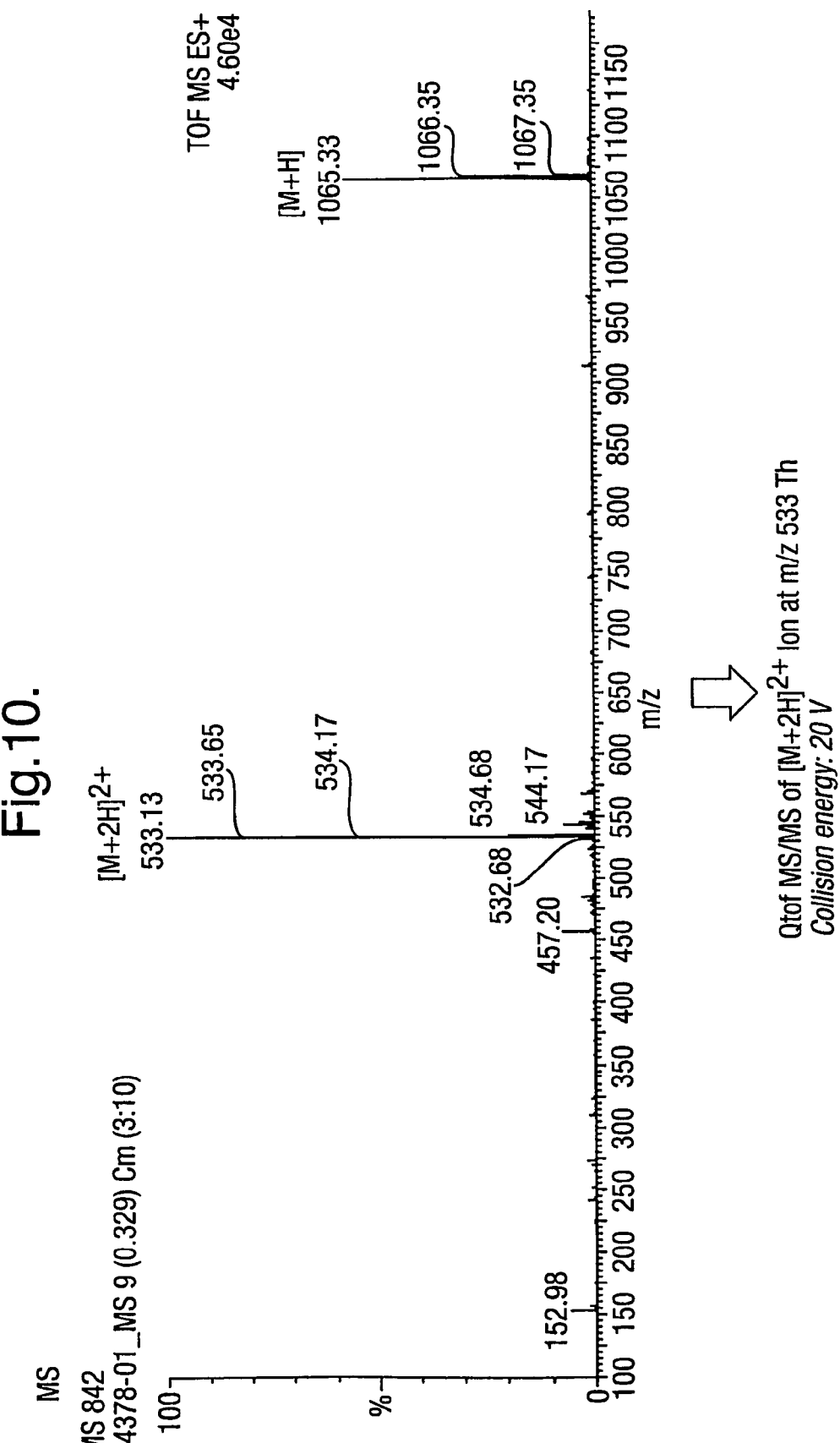
FIG. 10 shows MS/MS analysis of Pyrm-βAla-VATVSLPR.
Figure 10:
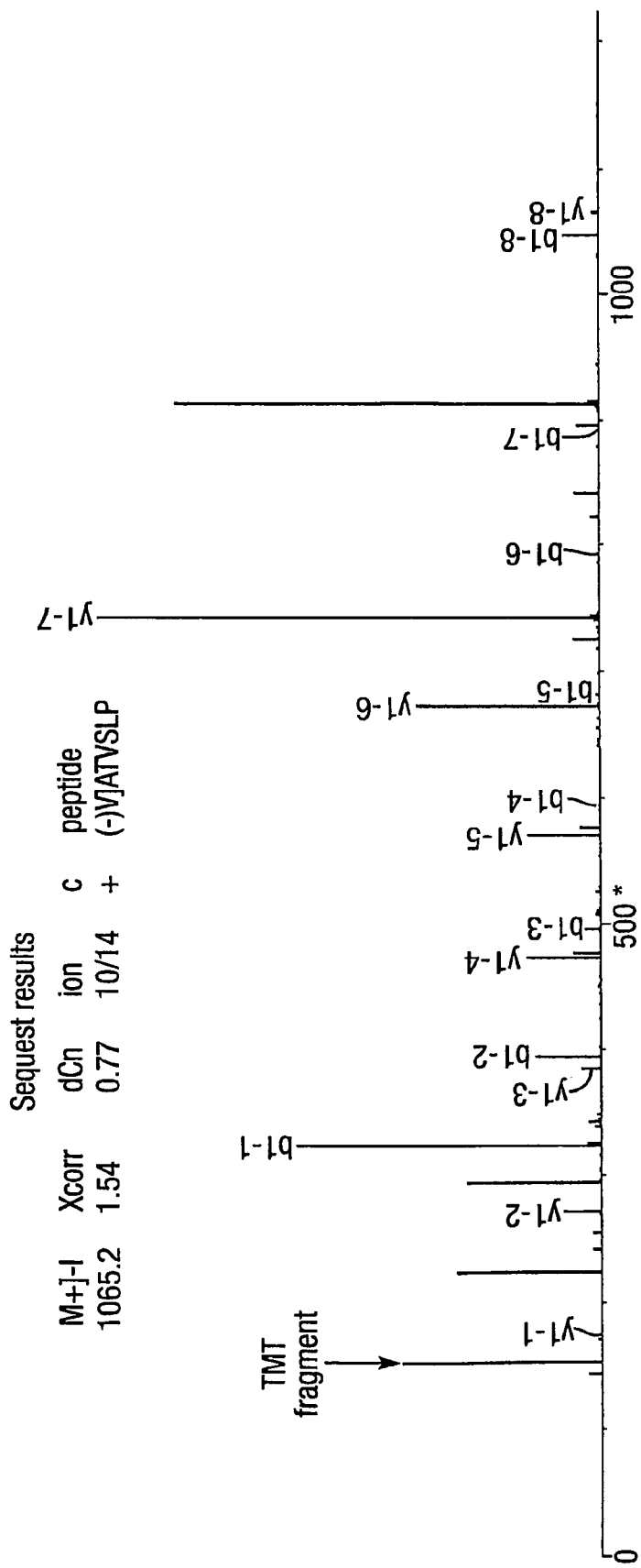
Figure 11:
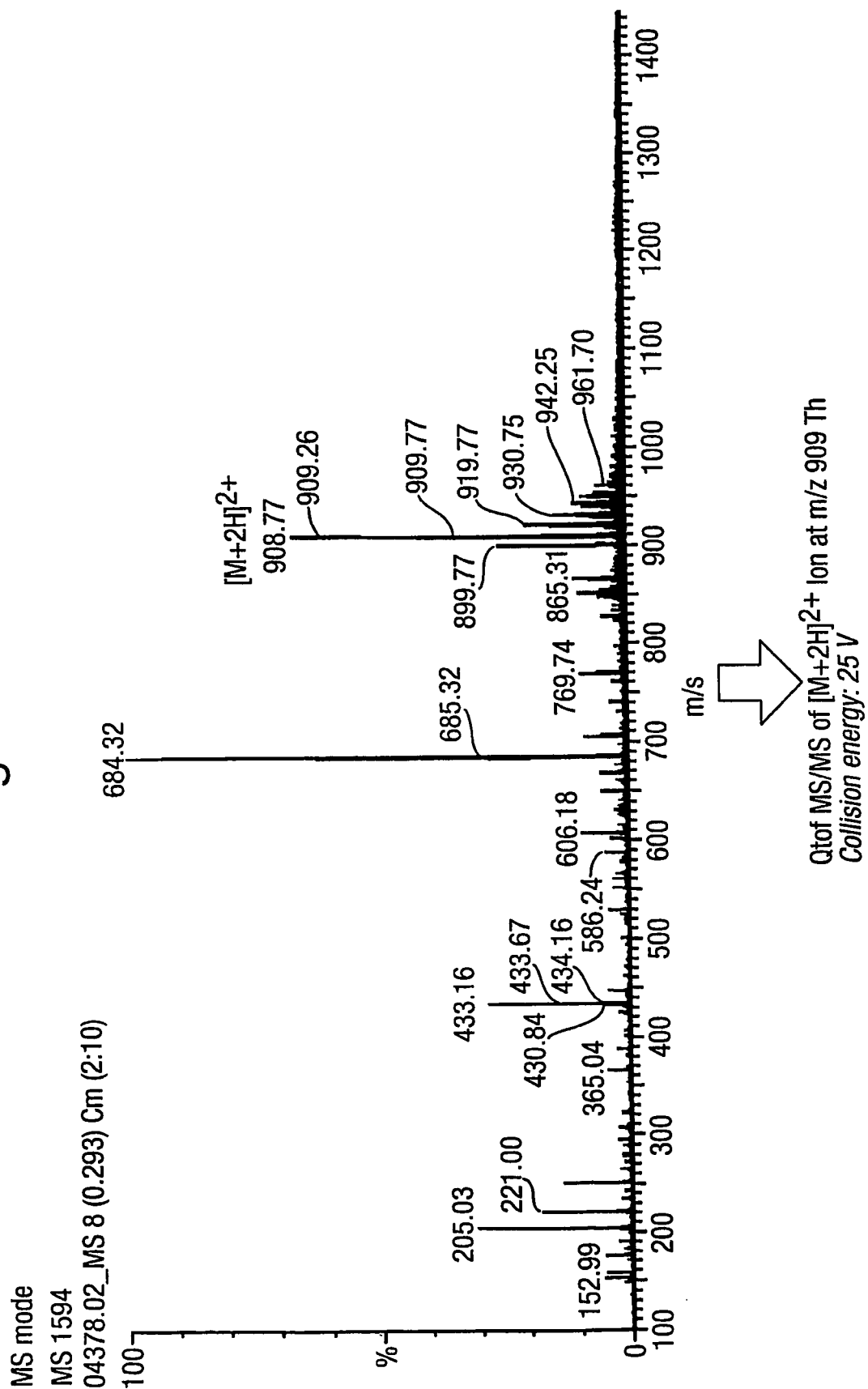
FIG. 11 shows MS/MS analysis of Pyrm-βAla-DYEGATLSDIGALIR.
Figure 13:
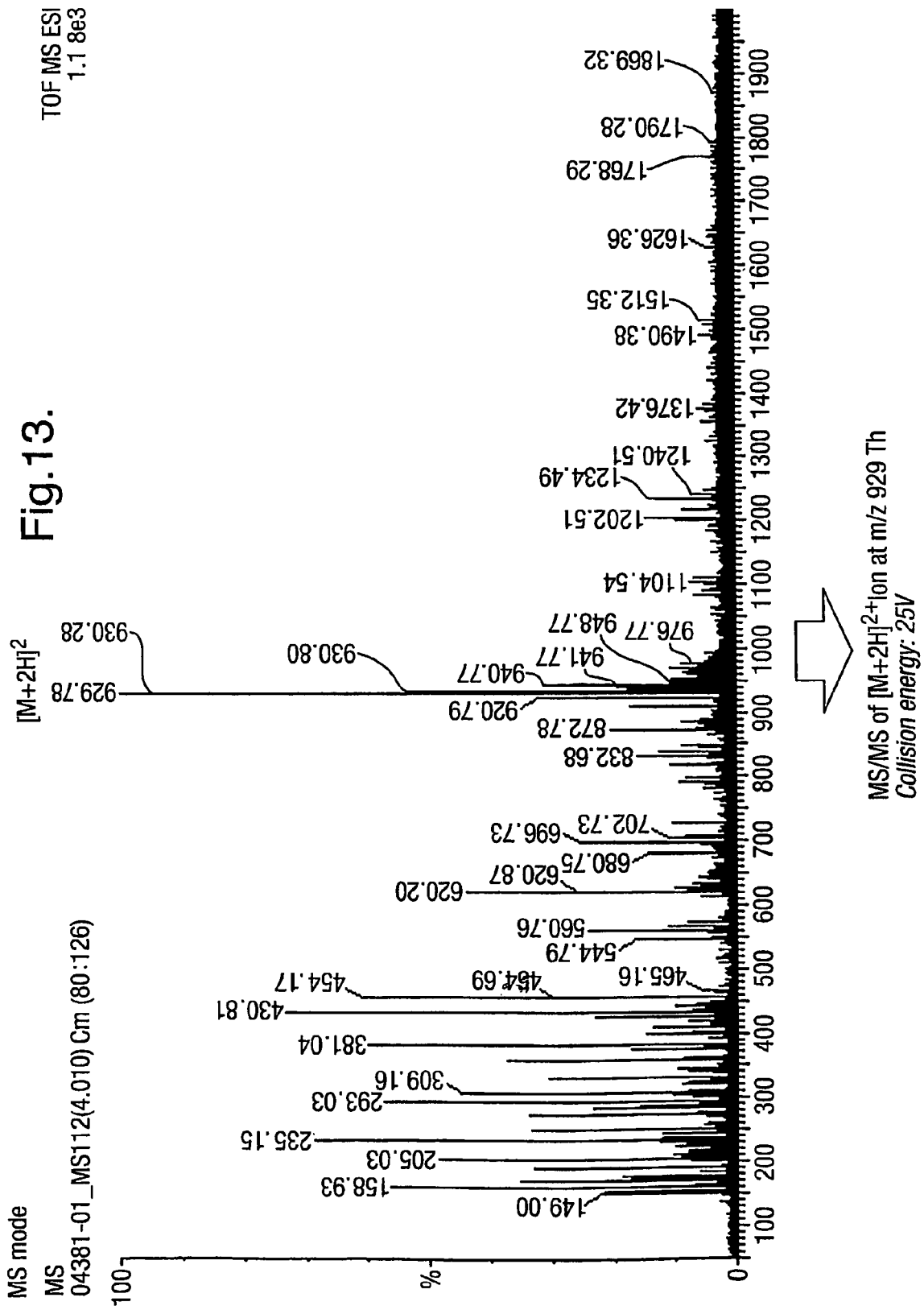
FIG. 13 shows MS/MS analysis of Pyrm-C6-DYEGATLSDIGALIR
Figure 13:
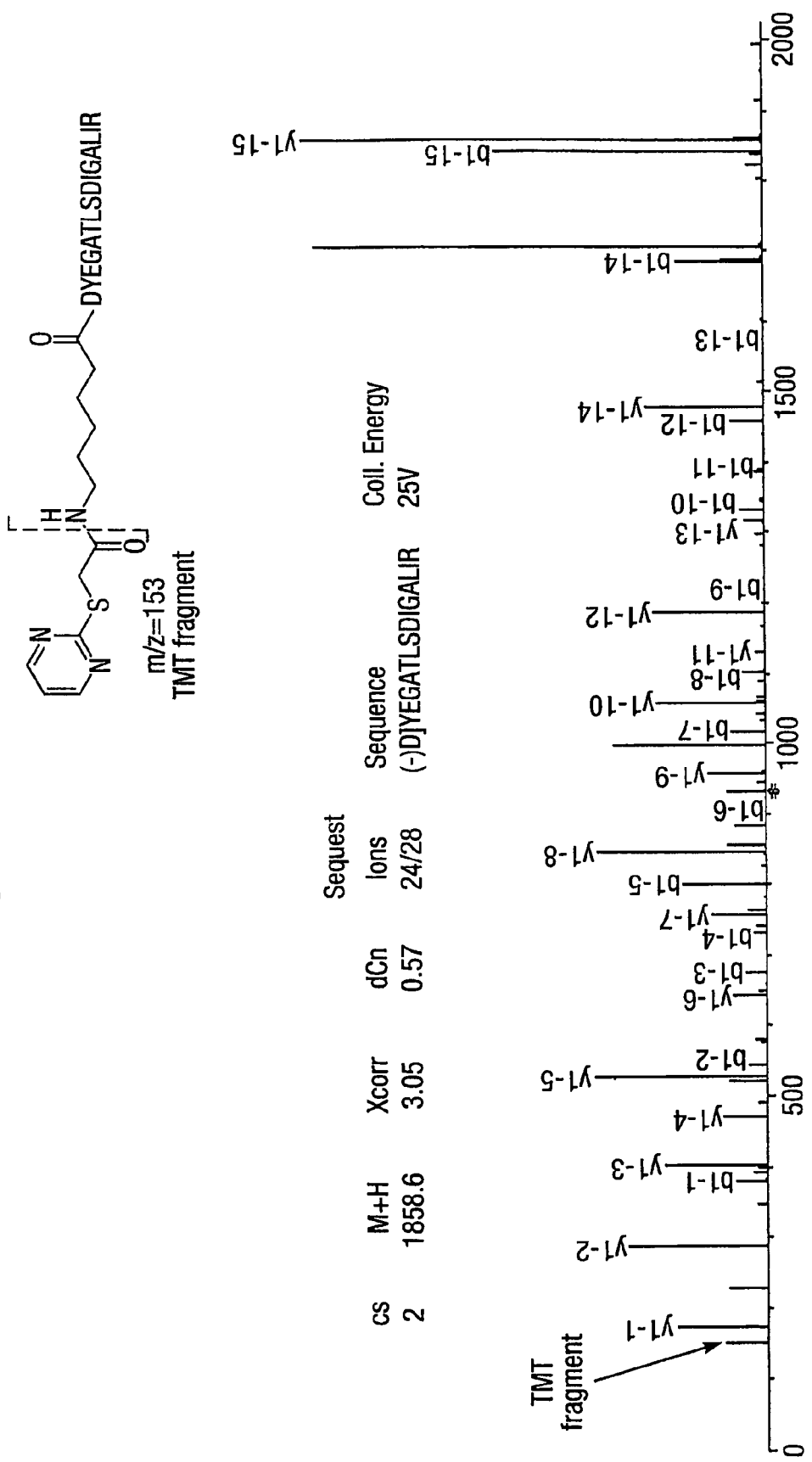

Techniques for the analysis of phosphoserine and phosphothreonine containing peptides are well known. One class of such methods is based on a well known reaction for beta-elimination of phosphates. This reaction results in phosphoserine and phosphothreonine forming dehydroalanine and methyldehydroalanine, both of which are Michael acceptors and will react with thiols. This has been used to introduce hydrophobic groups for affinity chromatography (See for example. Holmes C. F., FEBS Lett 215(1): 21-24, "A new method for the selective isolation of phosphoserine-containing peptides:" 1987). Dithiol linkers have also been used to introduce fluorescein and biotin into phosphoserine and phosphothreonine containing peptides (Fadden P, Haystead T A, Anal Biochem 225(1): 81-8, "Quantitative and selective fluorophore labelling of phosphoserine on peptides and proteins: characterization at the attomole level by capillary electrophoresis and laser-induced fluorescence." 1995; Yoshida O. et al., Nature Biotech 19: 379-382, "Enrichment analysis of phosphorylated proteins as a tool for probing the phosphoproteome", 2001). The method of Yoshida et al. for affinity enrichment of proteins phosphorylated at serine and threonine could be improved by using the maleimide tag shown in FIG. 8 to allow the comparison of multiple samples. This would be particularly useful for the analysis of the dynamics of phosphorylation cascades.

A number of research groups have reported on the production of antibodies, which bind to phosphotyrosine residues in a wide variety of proteins. (see for example A. R. Frackelton et al., Methods Enzymol 201: 79-92, "Generation of monoclonal antibodies against phosphotyrosine and their use for affinity purification of phosphotyrosine-containing proteins.", 1991 and other articles in this issue of Methods Enzymol.). This means that a significant proportion of proteins that have been post-translationally modified by tyrosine phosphorylation may be isolated by affinity chromatography using these antibodies as the affinity column ligand.

These phosphotyrosine binding antibodies can be used in the context of this invention to isolate peptides from proteins containing phosphotyrosine residues. The tyrosine-phosphorylated proteins in a complex mixture may be isolated using anti-phosphotyrosine antibody affinity columns. In a further embodiment of the invention, a protocol for the analysis of a sample of proteins, which contains proteins phosphorylated at tyrosine, comprises the steps of:
1. Treating the sample with a sequence specific cleavage reagent such as Trypsin or Lys-C;
2. Passing the protein sample through affinity columns contain anti-phosphotyrosine antibodies to isolate only phosphotyrosine modified peptides;
3. Labelling the captured phosphopeptides at the free alpha amino group generated by the sequence specific cleavage, using the mass labels of this invention; and
4. Analysing the labelled peptides by LC-MS-MS.

An N-hydroxysuccinimide activated tag could be used to label the free alpha-amino groups.

Immobilised Metal Affinity Chromatography (IMAC) represents a further technique for the isolation of phosphoproteins and phosphopeptides. Phosphates adhere to resins comprising trivalent metal ions particularly to Gallium(III) ions (Posewitch, M. C. and Tempst, P., Anal. Chem., 71: 2883-2892, "Immobilized Gallium (III) Affinity Chromatography of Phosphopeptides"; 1999). This technique is advantageous as it can isolate both serine/threonine phosphorylated and tyrosine phosphorylated peptides and proteins simultaneously.

IMAC can therefore also be used in the context of this invention for the analysis of samples of phosphorylated proteins. In a further embodiment of the invention, a protocol for the analysis of a sample of proteins, which contains phosphorylated proteins, comprises the steps of:
1. Treating the sample with a sequence specific cleavage reagent such as Trypsin or Lys-C;
2. Passing the protein sample through an affinity column comprising immobilised metal ions to isolate only phosphorylated peptides;
3. Labelling the captured phosphopeptides at the free alpha amino group generated by the sequence specific cleavage, using the mass labels of this invention; and
4. Analysing the labelled peptides by LC-MS-MS.

An N-hydroxysuccinimide activated label could be used to label the free alpha-amino groups.

In an alternative embodiment of the invention, a sample of phosphorylated proteins may be analysed by isolating phosphorylated proteins followed by analysis of the N or C terminal peptides of the phosphoproteins. Techniques for the isolation of terminal peptides are disclosed in a number of patent applications, e.g. WO98/32876, WO 00/20870 and EP 01304975.4. A protocol for the analysis of a sample of proteins, which contains phosphorylated proteins, would comprise the steps of:
1. Passing the protein sample through an affinity column comprising immobilised metal ions to isolate only phosphorylated proteins;
2. Isolating C and/or N terminal peptides from the captured phosphorylated proteins;
3. Labelling the captured terminal peptides, using the mass labels of this invention; and
4. Analysing the labelled peptides by LC-MS-MS.

In the following, the invention will be described in further detail, by way of example only, with reference to the following specific embodiments.

EXAMPLES

Examples 1 to 7 describe the syntheses of preferred mass labels of the present invention. All reagents were obtained from Sigma-Aldrich (Sigma-Aldrich Chemie GmbH, Eschenstrasse 5, 82024 Tauflcirchen, Germany) except the following ones:

The isotope reagents bromo-2-$^{13}$C-acetic acid and 3-$^{15}$N-aminopropanoic acid were purchased by Campro Scientific (Campro Scientific GmbH, 10414 Berlin, Germany). The products 3-aminopropanoic acid benzyl ester, 2-aminopropanoic and amino acetic acid were obtained from Merck Biosciences (Merck Biosciences GmbH, 65824 Schwalbach, Germany).

Amberlite XAD-16 is a nonionic polymeric adsorbent used for purification. Florisil is a synthetic activated magnesia-silica gel used for chromatography.

The tandem mass tags were synthesised by activation of the corresponding carboxylic acids to give the N-hydroxysuccinimide esters by standard methods. The reagents (pyrimidin-2-ylsulfanyl)-acetic acid (a), bromoacetic acid (c), 3-amino-propanoic acid (e), 6-aminohexanoic acid (d) and 2,6-dimethylpiperidine (b) are commercially available.

Commercially available compounds described in the different synthetic protocols are labelled with a letter.

Example 1

Synthesis of 6-[(pyrimidin-2-ylsulfanyl)-acetylamino]-hexanoic acid-(2,5-dioxo-pyrrolidine-1-yl)-ester (3)

Synthesis of 6-[(pyrimidin-2-ylsulfanyl)-acetylamino]-hexanoic acid-(2,5-dioxo-pyrrolidine-1-yl)-ester (3) was carried out in three steps.

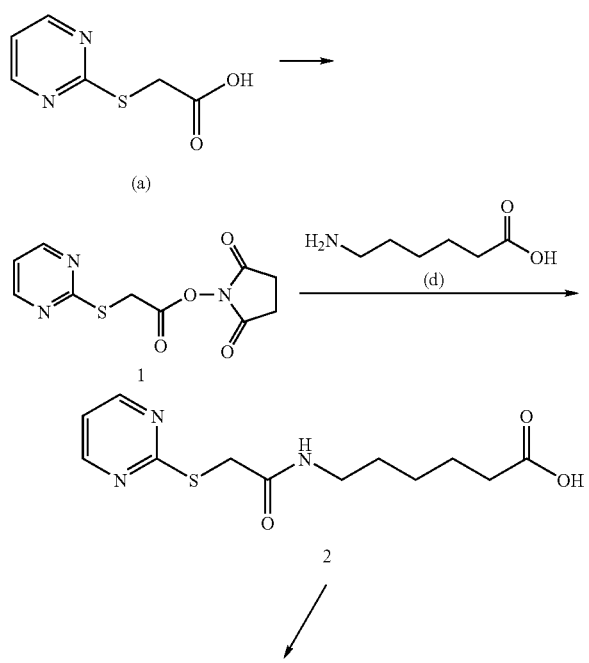

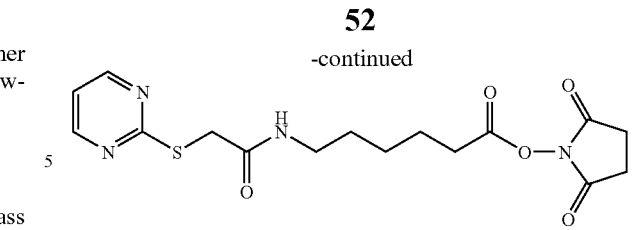

1. Synthesis of (Pyrimidin-2-ylsulfanyl-acetic acid-(2,5-dioxo-pyrrolidine-1-yl)-ester (1)

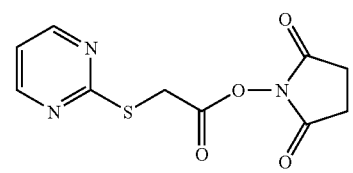

2.30 g (20 mMol) N-hydroxysuccinimide and 4.50 g (22 mMol) N,N'-dicyclohexylcarbodiimide were added at 0° C. to a solution of 3.40 g (20 mMol) (pyrimidin-2-ylsulfanyl)-acetic acid dissolved in 50 ml DMF. The reaction mixture was stirred for 16 h at RT. The residue was filtered and the black-coloured filtrate was evaporated in vacuo to dryness. The remaining product was dissolved under reflux in 100 ml ethyl acetate, the hot solution was filtered and evaporated. After dissolving the residue in CH$_2$Cl$_2$, the solution was washed with NaHCO$_3$, dried over sodium sulphate, and purified with activated charcoal. After filtration of the solution, the solvent was evaporated. The compound was then recrystallised from ethyl acetate.

Yield: 1.7 g (26%)
Retention factor (R$_F$)=0.26 (ethyl acetate/methanol 5:1)
$^1$H-NMR (d$_6$-DMSO) δ 2.80 (s, 4H, O-Su), 4.41 (s, 2H, S—CH$_2$), 7.28 (t, 1H, pyr5-CH), 8.65 (d, 2H, pyr4,6-CH)

2. Synthesis of 6-[2-(Pyrimidin-2-ylsulfanyl)-acetylamino]-hexanoic acid 2

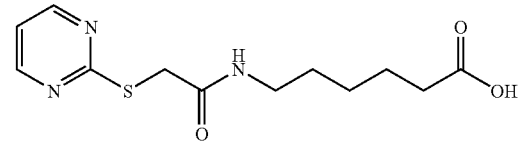

1 g (3.74 mMol) (pyrimidin-2-sulfanyl)-acetic acid-(2,5-dioxo-pyrrolidine-1-yl)-ester was dissolved in 50 ml DMF. After adding 0.5 g (3.75 mM) 6-aminohexanoic acid and 1.05 ml (7.5 mMol) triethylamine to the solution, the reaction mixture was stirred overnight. After removing the solvents, the product was dissolved in 50 ml water and the pH of the solution was adjusted to pH 9.5 with 2N NaOH. The aqueous solution was then washed 5 times with CH$_2$Cl$_2$ and the basicity of the solution was adjusted to pH 8 with 2N HCl. The mixture was then treated with activated charcoal, filtered and the pH of the filtrate was adjusted to pH 2 with 2N HCl before evaporating the solution. The residue was treated with a small amount of cold water allowing a pasting. The pasting was filtered and washed with water and acetone.

Yield: 0.17 g (16%)

$R_F$=0.40 (acetone/methanol/water/dichloromethane/ethyl acetate/acetic acid 9:2:2:6:2:1)

$^1$H-NMR (d$_6$-DMSO) δ 1.20-1.45 (m, 6H, CH$_2$), 2.18 (t, 2H, CH$_2$—CO), 3.06 (m, 2H, N—CH$_2$), 3.81 (s, 2H, S—CH$_2$), 7.22 (t, 1H, pyr5-CH), 8.10 (s, 1H, NH), 8.64 (d, 2H, pyr4,6-CH)

3. Synthesis of 6-[2-(Pyrimidin-2-ylsulfanyl)-acetylamino]-hexanoic acid-(2,5-dioxo-pyrrolidine-1-yl)-ester 3

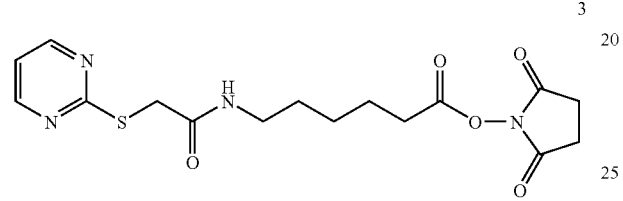

0.17 g (0.6 mMol) 6-[2-(Pyrimidin-2-ylsulfanyl-acetylamino]-hexanoic acid 2 was added to 69 mg (0.6 mMol) N-hydroxysuccinimide and 124 mg (0.6 mMol) N,N'-dicylohexylcarbodiimide in 5 ml dichloromethane. The reaction mixture was stirred for 16 h at RT. The solution was filtered and the filtrate was evaporated in vacuo to dryness. After dissolving the residue in 25 ml dichloromethane, the product was subjected to a chromatographic purification (Florisil) using ethyl acetate. The compound was then recrystallised from diisopropylether.

Yield: 0.19 g (82%)

$R_F$=0.23 (ethyl acetate)

Mp: 103-105° C.

$^1$H-NMR (d$_6$-DMSO) δ 1.20-1.45 (m, 6H, CH$_2$), 2.66 (t, 2H, CH$_2$—CO), 2.83 (s, 4H, O-Su), 3.06 (m, 2H, N—CH$_2$), 3.86 (s, 2H, S—CH$_2$), 7.22 (t, 1H, pyr5-CH), 8.08 (s, 1H, NH), 8.61 (d, 2H, pyr4,6-CH)

Example 2

Synthesis of 3-[2-(2,6-Dimethyl-piperidin-1-yl)-acetylamino]-propanoic acid-(2,5-dioxo-pyrrolidine-1-yl)-ester (8)

Synthesis of 3-[2-(2,6-Dimethyl-piperidin-1-yl)-acetylamino]propanoic acid-(2,5-dioxo-pyrrolidine-1-yl)-ester (8) was carried out in 5 steps.

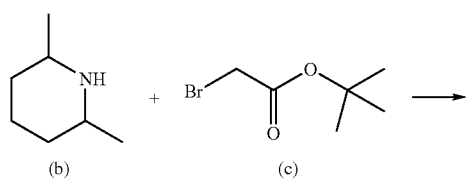

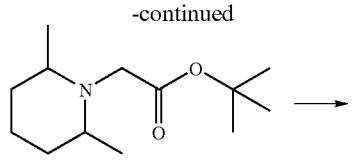

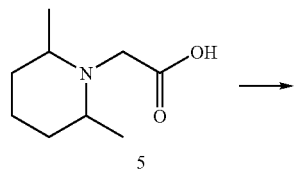

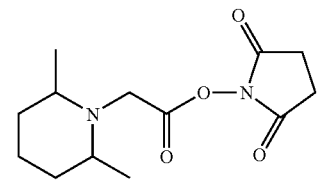

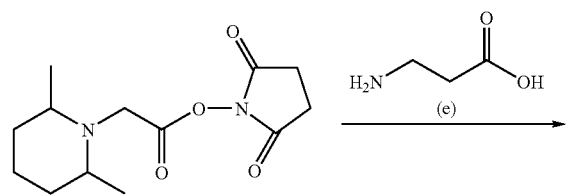

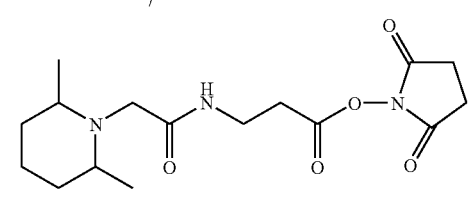

1. Synthesis of (2,6-Dimethyl-piperidine-1-yl)-acetic acid-tert.butylester (4)

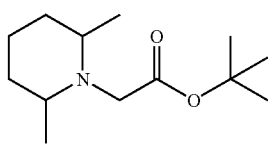

15.1 ml (102 mMol) bromoacetic acid-tert.butylester (c) and 30 ml (234 mMol) 2,6-dimethyl-piperidine (b) were stirred for 5 h at reflux in 150 ml THF. After removing the solvents, the product was dissolved in water and the pH of the solution was adjusted to pH 11.5 with 2N NaOH. The heterogeneous reaction mixture was extracted with ethyl acetate, washed with water and dried over sodium sulphate. The residue, after evaporation of the solvent, was eluted from a silica gel column with diisopropylether.

Yield: 23 g (>99%)

$R_F$=0.58 (diisopropylether)

$^1$H-NMR (CDCl$_3$) δ 1.09 (d, 6H, N—C—CH$_3$), 1.16-1.67 (m, 6H, pip3,4,5-CH$_2$); 1.43 (s, 9H, tert-Bu); 2.81 (m, 2H, N—CH); 3.45 (s, 2H, N—CH$_2$)

2. Synthesis of (2,6-Dimethyl-piperidine-1-yl)-acetic acid hydrochloride (5)

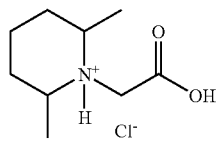

5

23 g (0.1 Mol) (2,6-dimethyl-piperidine-1-yl)-acetic acid-tert.butylester (4) was stirred with 25 ml (300 mMol) 12 N HCl in 100 ml water for 2 h at 60° C. After distillation of water and excess HCl in vacuo, the residue was azeotropically dried with toluene.

Yield: 21.03 g (>99%)

$R_F$=0.18 (CH$_2$Cl$_2$/CH$_3$OH=5:1)

$^1$H-NMR (d$_6$-DMSO) δ 1.1-1.38 (m, 6H, N—C—CH$_3$); 1.4-1.9 (m, 6H, pip3,4,5-CH$_2$); 3.35-3.65 (m, 2H, N—CH); 4.05 (s, 2H, N—CH$_2$); 9.05 (br.s, 1H, N—H); 10.85 (s, 1H, COOH)

3. Synthesis of (2,6-Dimethyl-piperidine-1-yl)-acetic acid-(2,5-dioxo-pyrrolidine-1-yl)-ester (6)

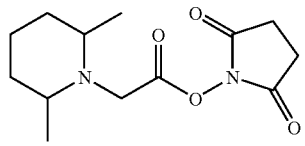

6

12.60 g (60 mMol) (2,6-Dimethyl-piperidine-1-yl)-acetic acid hydrochloride (5), in 100 ml DMF, was added to 7.02 g (60 mMol) N-hydroxysuccinimide and 12.58 g (60 mMol) N,N-dicyclohexylcarbodiimide. The reaction mixture was stirred for 16 h at RT. The residue was filtered and the filtrate was evaporated in vacuo to dryness. After dissolving the residue in 300 ml CH$_2$Cl$_2$, the solution was washed with NaHCO$_3$, dried over sodium sulphate and the solvent was evaporated. The compound was then recrystallised from diisopropylether (activated charcoal).

Yield: 12.61 g (77%)

Mp 73° C.

$^1$H-NMR (CDCl$_3$) δ 1.14 (d, 6H, N—C—CH$_3$), 1.18-1.7 (m, 6H, pip-3,4,5-CH$_2$); 2.75-2.85 (m, 2H, N—CH); 2.82 (s, 4H, O-Su); 3.9 (s, 2H, N—CH$_2$)

4. Synthesis of 3-[2-(2,6-Dimethyl-piperidin-1-yl)-acetylamino]-propanoic acid (7)

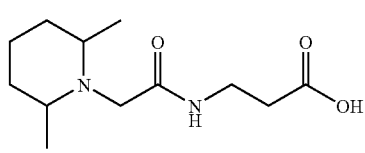

7

2.68 g (10 mMol) (2,6-dimethyl-piperidine-1-yl)-acetic acid-(2,5-dioxo-pyrrolidine-1-yl)-ester (6), in 50 ml DMF, was added to 0.9 g (10 mMol) 3-aminopropanoic acid and 2.02 g (20 mMol) triethylamine. The reaction mixture was stirred for 16 h at RT. The solution was evaporated and the residue was dissolved in water and the pH of the solution was adjusted to pH 3 with 2N HCl. The heterogeneous reaction mixture was purified over XAD-16. The residue, after evaporation of the solvent, was dried with toluene using a water separator.

Yield: 4.98 g (>99%)

$R_F$=at starting point (methanol/dichloromethane 1:1)

$^1$H-NMR (CDCl$_3$) δ 1.14 (d, 6H, N—C—CH$_3$), 1.18-1.7 (m, 6H, pip3,4,5-CH$_2$); 2.18 (t, 2H, CH$_2$—CO); 2.75-2.85 (m, 2H, N—CH); 3.90 (s, 2H, N—CH$_2$)

5. Synthesis of 3-[2-(2,6-Dimethyl-piperidin-1-yl)-acetylamino]-propanoic acid-(2,5-dioxo-pyrrolidine-1-yl)-ester (8)

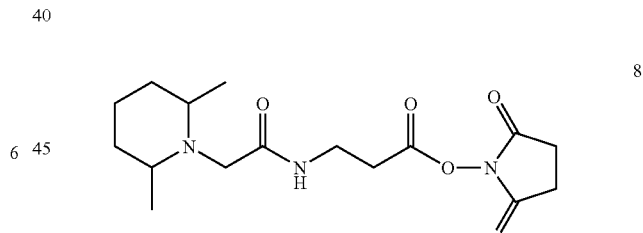

8

4.98 g (10 mMol) 3-[2-(2,6-Dimethyl-piperidin-1-yl)-acetylamino]-propanoic acid (7), in 50 ml DMF, was added to 1.15 g (60 mMol) N-hydroxysuccinimide and 4.12 g (60 mMol) N,N'-dicyclohexylcarbodiimide. The reaction mixture was stirred for 16 h at RT. After diluting the mixture with 100 ml CH$_2$Cl$_2$, the solution was filtered and the filtrate was evaporated in vacuo to dryness. After dissolving the residue in 30 ml ethyl acetate, the solution was washed, filtered and the solvent evaporated. The product was purified by chromatography (Florisil, 27 mm×320 mm) using ethyl acetate.

Yield: 3 g (88%)

$R_F$=0.3 (ethyl acetate)

$^1$H-NMR (CDCl$_3$) δ 0.98 (d, 6H, N—C—CH$_3$), 1.15-1.63 (m, 6H, pip-3,4,5-CH$_2$); 2.42 (br.s, 2H, CH$_2$—CO); 2.85 (m, 2H, N—CH); 2.81 (s, 4H, O-Su); 2.99 (m, 2H, NH—CH$_2$); 3.44 (s, 2H, N—CH$_2$); 7.94 (t, 1H, N—H)

Example 3

Synthesis of 3-[2-(Pyrimidin-2-ylsulfanyl)-acetylamino]-propanoic acid-(2,5-dioxo-pyrrolidine-1-yl)-ester Synthesis of 3-[2-(Pyrimidin-2-ylsulfanyl)-acetylamino]-propanoic acid-(2,5-dioxo-pyrrolidine-1-yl)-ester was carried out in three steps.

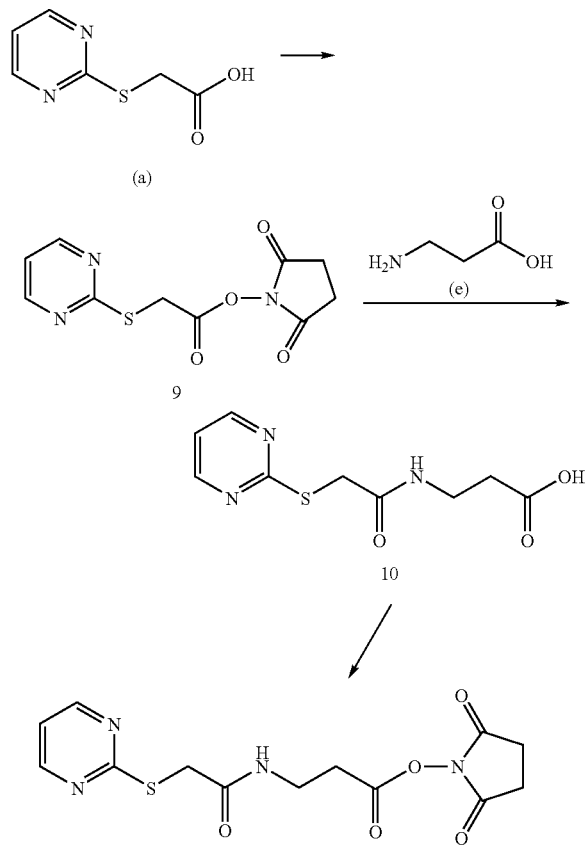

1. Synthesis of (Pyrimidin-2-ylsulfanyl)-acetic acid-(2,5-dioxo-pyrrolidine-1-yl)-ester (9)

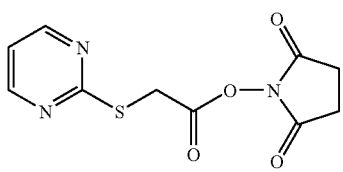

12.31 g (107 mMol) N-hydroxysuccinimide and 22.70 g (110 mMol) dicyclohexylcarbodiimide were added at −35° C. to a solution of 18.27 g (107 mMol) (Pyrimidin-2-ylsulfanyl)-acetic acid (a) dissolved in 200 ml DMF. The reaction mixture was stirred for 16 h under argon. The residue was filtered and the filtrate was evaporated in vacuo to dryness. The remaining product was dissolved under reflux in 400 ml ethyl acetate, the hot solution was filtered and the mixture was subjected to a chromatographic purification (Florisil) using ethyl acetate. The compound was then recrystallised from ethyl acetate.

Yield: 4.90 g (17%)

$^1$H-NMR (d$_6$-DMSO) δ 2.80 (s, 4H, O-Su), 4.41 (s, 2H, S—CH$_2$), 7.28 (t, 1H, pyr5-CH), 8.65 (d, 2H, pyr4,6-CH)

2. Synthesis of 3-[2-(Pyrimidin-2-ylsulfanyl)-acetylamino]-propanoic acid (10)

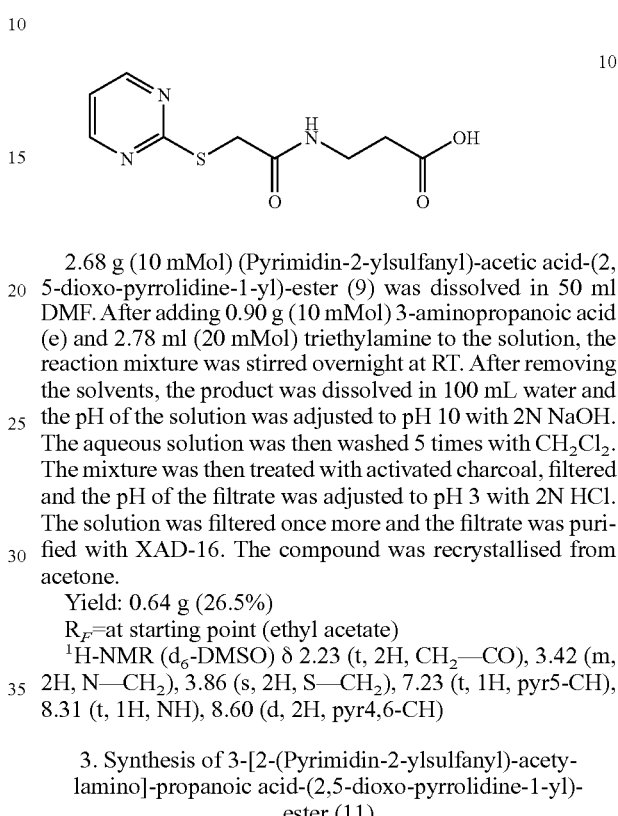

2.68 g (10 mMol) (Pyrimidin-2-ylsulfanyl)-acetic acid-(2,5-dioxo-pyrrolidine-1-yl)-ester (9) was dissolved in 50 ml DMF. After adding 0.90 g (10 mMol) 3-aminopropanoic acid (e) and 2.78 ml (20 mMol) triethylamine to the solution, the reaction mixture was stirred overnight at RT. After removing the solvents, the product was dissolved in 100 mL water and the pH of the solution was adjusted to pH 10 with 2N NaOH. The aqueous solution was then washed 5 times with CH$_2$Cl$_2$. The mixture was then treated with activated charcoal, filtered and the pH of the filtrate was adjusted to pH 3 with 2N HCl. The solution was filtered once more and the filtrate was purified with XAD-16. The compound was recrystallised from acetone.

Yield: 0.64 g (26.5%)

$R_F$=at starting point (ethyl acetate)

$^1$H-NMR (d$_6$-DMSO) δ 2.23 (t, 2H, CH$_2$—CO), 3.42 (m, 2H, N—CH$_2$), 3.86 (s, 2H, S—CH$_2$), 7.23 (t, 1H, pyr5-CH), 8.31 (t, 1H, NH), 8.60 (d, 2H, pyr4,6-CH)

3. Synthesis of 3-[2-(Pyrimidin-2-ylsulfanyl)-acetylamino]-propanoic acid-(2,5-dioxo-pyrrolidine-1-yl)-ester (11)

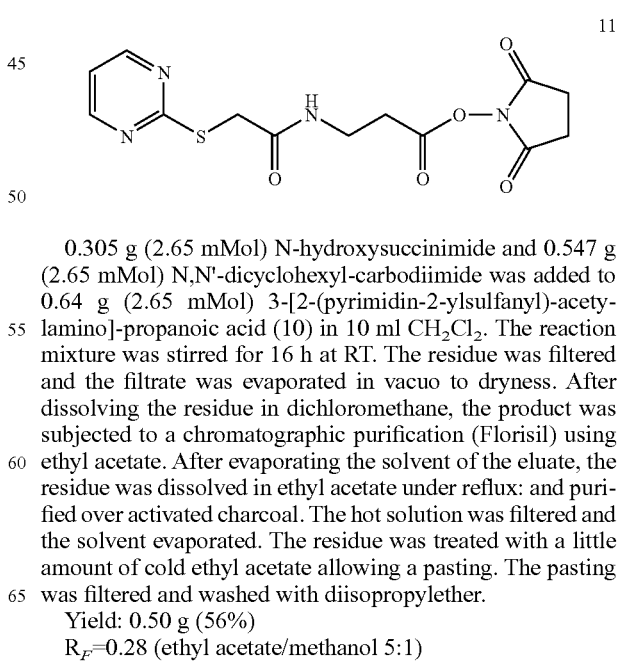

0.305 g (2.65 mMol) N-hydroxysuccinimide and 0.547 g (2.65 mMol) N,N'-dicyclohexyl-carbodiimide was added to 0.64 g (2.65 mMol) 3-[2-(pyrimidin-2-ylsulfanyl)-acetylamino]-propanoic acid (10) in 10 ml CH$_2$Cl$_2$. The reaction mixture was stirred for 16 h at RT. The residue was filtered and the filtrate was evaporated in vacuo to dryness. After dissolving the residue in dichloromethane, the product was subjected to a chromatographic purification (Florisil) using ethyl acetate. After evaporating the solvent of the eluate, the residue was dissolved in ethyl acetate under reflux: and purified over activated charcoal. The hot solution was filtered and the solvent evaporated. The residue was treated with a little amount of cold ethyl acetate allowing a pasting. The pasting was filtered and washed with diisopropylether.

Yield: 0.50 g (56%)

$R_F$=0.28 (ethyl acetate/methanol 5:1)

¹H-NMR (d₆-DMSO) δ 2.84 (m, 6H, CH₂—CO, O-Su), 3.39 (m, 2H, N—CH₂), 3.88 (s, 2H, S—CH₂), 7.22 (t, 1H, pyr5-CH), 8.31 (t, 1H, NH), 8.62 (d, 2H, pyr4,6-CH)

Example 4

Synthesis of 3-[2-(2,6-Dimethyl-piperidin-1-yl)-2-¹³C-acetylamino]-propanoic acid-(2,5-dioxo-pyrrolidine-1-yl)-ester Synthesis of 3-[2-(2,6-Dimethyl-piperidin-1-yl)-2-¹³C-acetylamino]-propanoic acid-(2,5-dioxo-pyrrolidine-1-yl)-ester was carried out in six steps.

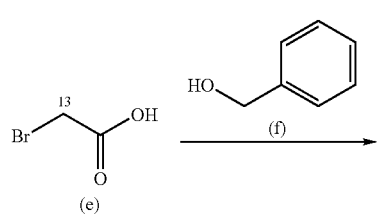

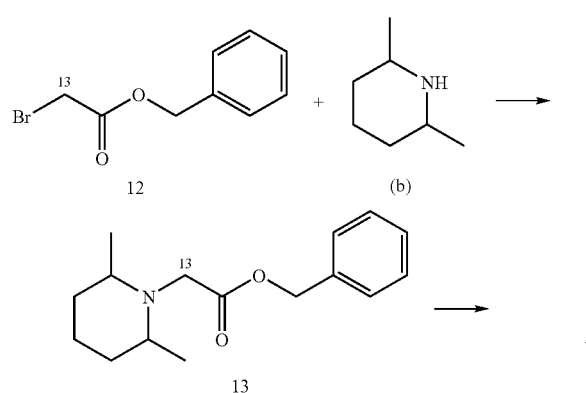

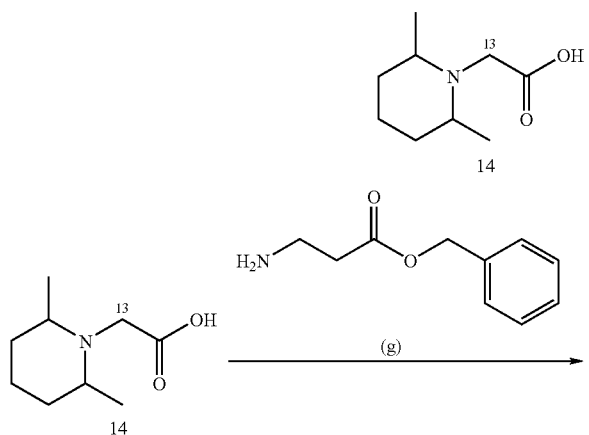

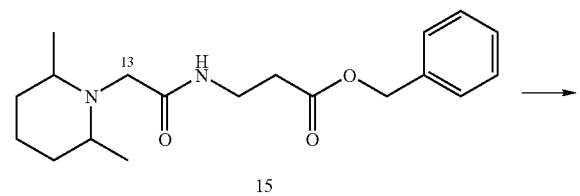

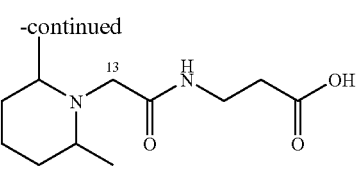

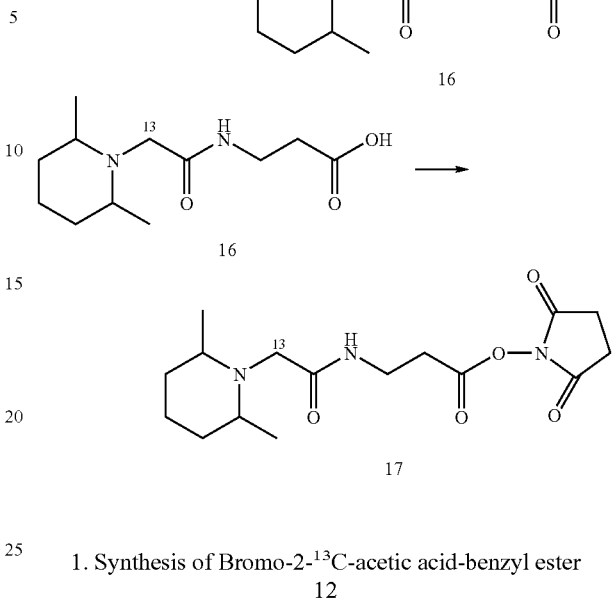

1. Synthesis of Bromo-2-¹³C-acetic acid-benzyl ester 12

5 g (34.47 mMol) Bromo-2-¹³C-acetic acid (e) were added to 4.22 g (39 mMol) Benzyl alcohol (g), 8.50 g (39 mMol) N,N'-Dicyclohexylcarbodiimide and 0.40 g 4-N,N-Dimethylaminopyridine dissolved in 150 ml dichloromethane. The reaction mixture was stirred overnight at room temperature. The residue was filtered and the filtrate was washed with saturated NaHCO₃. The aqueous layer was extracted three times with dichloromethane, the combined organic phases were dried over Na₂SO₄ and the solvent was evaporated in vacuo. The product was purified by flash chromatography using dichloromethane as eluent.

Yield: 7.37 g (91%)
$R_F$=0.5 (CH₂Cl₂)

2. Synthesis of (2,6-Dimethyl-piperidin-1-yl)-2-¹³C-acetic acid-benzylester 13

7.37 g (32 mMol) Bromo-2-¹³C-acetic acid-benzylester (12) and 9 ml (70 mMol) 2,6-Dimethyl-piperidine (b) were stirred for 5 h at refluxing in 150 ml THF. After evaporating the solvent, the product was dissolved in a emulsion of 150 ml water and 150 ml ethyl acetate and the pH of the aqueous layer was adjusted to pH 11.6 with 2N NaOH. After separation of the layers, the aqueous phase was extracted three times with ethyl acetate, the organic layers were combined, washed with saturated NaCl solution and dried over $Na_2SO_4$. After evaporation of the solvent, the residue was purified by flash chromatography with diisopropylether as eluent.

Yield: 8.32 g (>99%)

$R_F$=0.3 $(iPr)_2$)

3. Synthesis of (2,6-Dimethyl-piperidin-1-yl)-2-$^{13}$C-acetic acid 14

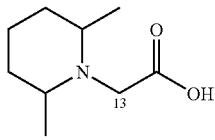

14

8.32 g (32 mMol) (2,6-Dimethyl-piperidin-1-yl)-2-$^{13}$C-acetic acid-benzylester (13) were dissolved in 100 ml methanol. 0.5 g Pd/C (5%) were added to the solution and the hydrogenation was carried out with 730 ml hydrogen at normal pressure and room temperature for 30 minutes. The reaction mixture was filtered, the solvent evaporated and the residue was treated with a small amount of cold diisopropylether to allow a pasting. The solvent was filtered off and the product was dried in vacuo.

Yield: 5.28 g (96%)

$R_F$=0.1 $(CH_2Cl_2/CH_3OH$ 5:1)

4. Synthesis of 3-[2-(2,6-Dimethyl-piperidin-1-yl)-2-$^{13}$C-acetylamino]-propanoic acid benzylester 15

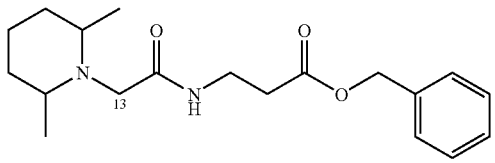

15

5.28 g (30.6 mMol) (2,6-Dimethyl-piperidin-1-yl)-acetic acid (14) were added to a mixture of 9.40 g (61.2 mMol) 1-Hydroxybenzotriazole and 12.62 g (61.2 mMol) N,N'-Dicyclohexylcarbodiimide dissolved in 50 ml DMF. After 30 minutes stirring at room temperature, 10.75 g (30.6 mMol) 3-Amino propanoic acid benzyl ester and 6.18 g (61.2 mMol) triethylamine were added to the reaction mixture and stirred overnight at room temperature. The solvent was evaporated and the residue was dissolved in 200 ml ethyl acetate, the solution filtered and the filtrate was washed 3 times with 80 ml 1N NaOH solution and 1 time with saturated NaCl solution. The organic phase was dried over $MgSO_4$ and the solvent was evaporated. The residue was purified from a first flash chromatography using ethyl acetate and the product was eluted from a second flash chromatography using $CH_2Cl_2$: $CH_3OH$ 50:1 as eluent.

Yield: 9.07 g (89%)

$R_F$=0.47 $(CH_2Cl_2/CH_3OH$ 10:1)

5. Synthesis of 3-[2-(2,6-Dimethyl-piperidin-1-yl)-2-$^{13}$C-acetylamino]-propanoic acid 16

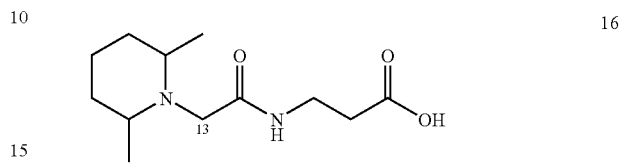

16

9.07 g (27.20 mMol) 3-[2-(2,6-Dimethyl-piperidin-1-yl)-2-$^{13}$C-acetylamino]-propanoic acid benzylester (15) were dissolved in 200 ml methanol. 0.5 g Pd/C (5%) was added to the solution and the hydrogenation was carried out with 640 ml hydrogen at normal pressure and room temperature for 30 minutes. The reaction mixture was filtered and the solvent evaporated.

Yield: 6.80 g (>99%)

$R_F$=0.1 $(CH_2Cl_2/CH_3OH$ 5:1)

6. Synthesis of 3-[2-(2,6-Dimethyl-piperidin-1-yl)-2-$^{13}$C-acetylamino]-propanoic acid-(2,5-dioxo-pyrrolidine-1-yl)-ester 17

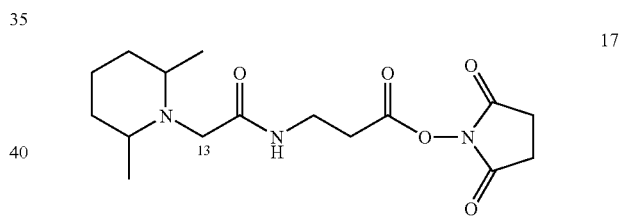

17

4.98 g (10 mMol) 3-[2-(2,6-Dimethyl-piperidin-1-yl)-2-$^{13}$C-acetylamino]-propanoic acid (16), were added to 3.22 g (28 mMol) N-Hydroxysuccinimide and 5.78 g (28 mMol) N,N'-Dicyclohexylcarbodiimide dissolved in 200 ml dichloromethane. The reaction mixture was stirred for 16 h at room temperature. The solution was filtered and the filtrate was evaporated in vacuo to dryness. The product was washed with diisopropylether.

Yield: 8 g (84%)

$M_p$=108-109° C.

Example 5

Synthesis of 3-[2-(2,6-Dimethyl-piperidin-1-yl) acetyl-$^{15}$N-amino]propanoic acid-(2,5-dioxo-pyrrolidine-1-yl)-ester 7

Synthesis of 3-[2-(2,6-Dimethyl-piperidin-1-yl) acetyl-$^{15}$N-amino]-propanoic acid-(2,5-dioxo-pyrrolidine-1-yl)-ester 7 was carried out in seven steps.

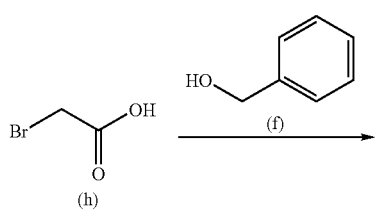

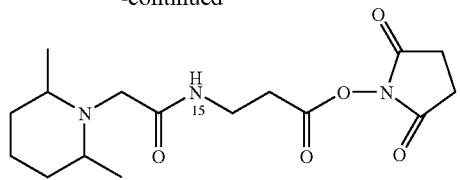

24

1. Synthesis of Bromoacetic acid-benzyl ester 18

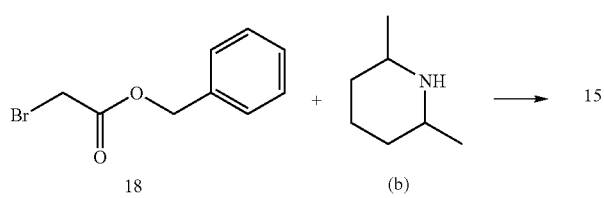

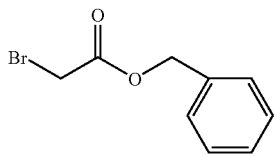

18

5 g (34.47 mMol) Bromoacetic acid (h) were added to 4.22 g (39 mMol) Benzyl alcohol (f), 8.50 g (39 mMol) N,N'-Dicyclohexylcarbodiimide and 0.40 g 4-Dimethylaminopyridine dissolved in 150 ml dichloromethane. The reaction mixture was stirred overnight at room temperature. The residue was filtered and the filtrate was washed with saturated NaHCO$_3$. The aqueous layer was extracted 3 times with dichloromethane, the combined organic phases were dried over Na$_2$SO$_4$ and the solvent was evaporated in vacuo to dryness. The product was purified by flash chromatography using dichloromethane as eluent.

Yield: 7.45 g (92%)

R$_F$=0.5 (CH$_2$Cl$_2$)

2. Synthesis of (2,6-Dimethyl-piperidin-1-yl)-acetic acid-benzylester 19

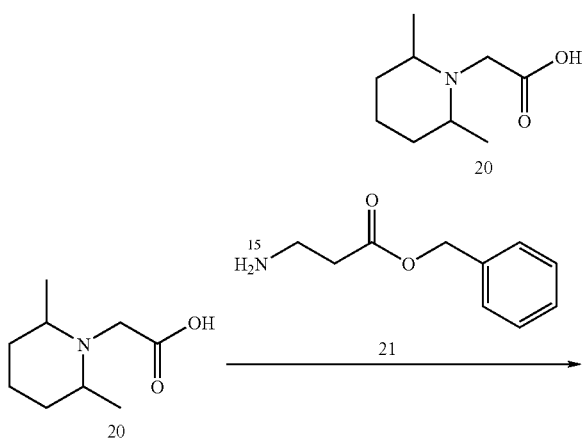

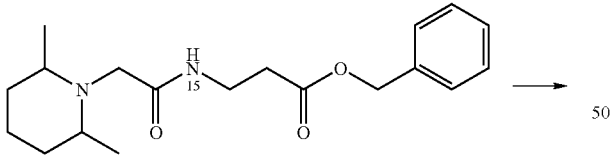

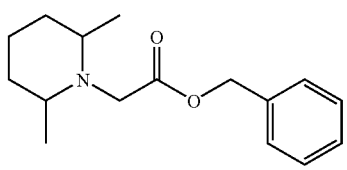

19

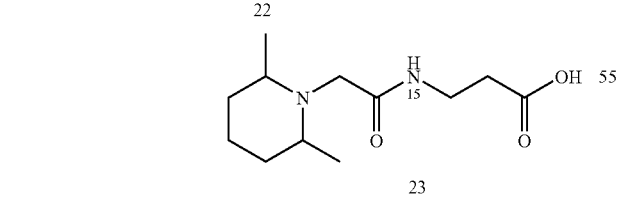

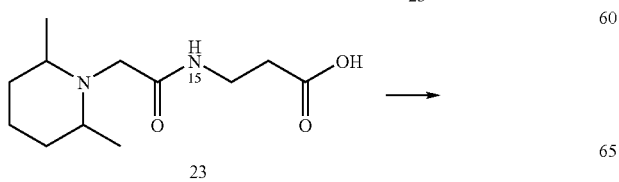

7.39 g (32 mMol) Bromoacetic acid-benzylester (18) and 9 ml (70 mMol) 2,6-Dimethyl-piperidine (b) were stirred for 5 h at refluxing in 150 ml THF. After evaporating the solvent, the product was dissolved in an emulsion of 150 ml water and 150 ml ethyl acetate and the pH of the aqueous layer was adjusted to pH 11.6 with 16.5 ml 2N NaOH. After separation of the layers, the aqueous phase was extracted 3 times with ethyl acetate, the organic layers were combined, washed with saturated NaCl solution and dried over Na$_2$SO$_4$. After evaporation of the solvent, the residue was purified by a flash chromatography using diisopropylether as eluent.

Yield: 8 g (95%)

R$_F$=0.3 ((iPr)$_2$O)

3. Synthesis of (2,6-Dimethyl-piperidin-1-yl)-acetic acid 20

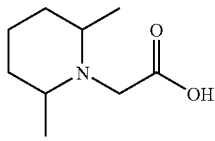

20

8 g (31 mMol) (2,6-Dimethyl-piperidin-1-yl)-acetic acid-benzylester (19) were dissolved in 100 ml methanol. 0.5 g Pd/C (5%) was added to the solution and the hydrogenation was carried out with 725 ml hydrogen at normal pressure and room temperature for 30 minutes. The reaction mixture was filtered, the solvent evaporated and the residue was washed with a small amount of cold diisopropylether to allow a pasting. The solvent was filtered off and the product was dried in vacuo.

Yield: 5 g (94%)
$R_F$=0.1 ($CH_2Cl_2$:$CH_3OH$ 5:1)
$F_p$=179-180° C.

4. Synthesis of 3-$^{15}$N-amino propanoic acid benzyl ester hydro-p-tosylate 21

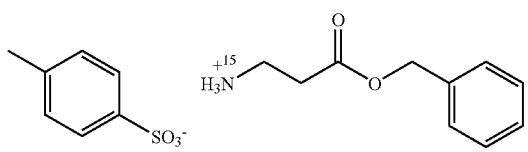

21

3.13 g (16.5 mMol) p-toluenesulphonic acid were heated under reflux for 1 h in 20 ml toluene using a water separator. 6.6 ml (63.4 mMol) Benzyl alcohol and 1.5 g (16.5 mMol) 3-$^{15}$N-amino propanoic acid were added to the cooled mixture. The reaction mixture was heated under reflux one more hour. 90 mL diisopropylether were added to the cooled solution. After keeping overnight the solution at −20° C., the precipitate was filtered and washed with diisopropylether.

Yield: 4.68 g (81%)
$M_p$=122-125° C.

5. Synthesis of 3-[2-(2,6-Dimethyl-piperidin-1-yl)-acetyl-$^{15}$N-amino]-propanoic acid benzylester 22

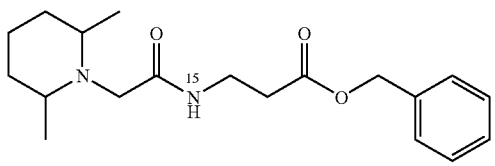

22

2.28 g (13.33 mMol) (2,6-Dimethyl-piperidin-1-yl)-acetic acid (21) were added to a mixture of 4.08 g (26.66 mMol) 1-Hydroxybenzotriazole and 5.50 g (61.2 mMol) N,N'-Dicyclohexylcarbodiimide dissolved in 100 ml DMF. After 30 minutes stirring at room temperature, 4.68 g (13.33 mMol) 3-$^{15}$N-amino propanoic acid benzyl ester and 3.69 ml (66.66 mMol) triethylamine were added to the reaction mixture and stirred overnight at room temperature. The mixture was evaporated and the residue was dissolved in 200 ml ethyl acetate, the solution filtered and the filtrate was washed three times with 80 ml 1N NaOH solution and one time with saturated NaCl solution. The organic phase was dried over $MgSO_4$ and the solvent was evaporated. The residue was purified from a first flash chromatography using ethyl acetate and the product was eluted from a flash chromatography using $CH_2Cl_2$:$CH_3OH$ 50:1 as eluent.

Yield: 0.87 g (20%)
$R_F$=0.47 ($CH_2Cl_2$/$CH_3OH$ 10:1)

6. Synthesis of 3-[2-(2,6-Dimethyl-piperidin-1-yl) acetyl-$^{15}$N-amino]propanoic acid 23

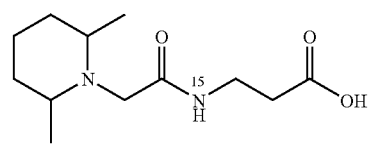

23

0.87 g (2.60 mMol) 3-[2-(2,6-Dimethyl-piperidin-1-yl) acetyl-$^{15}$N-amino]-propanoic acid benzylester (22) were dissolved in 50 ml methanol. 0.15 g Pd/C (5%) was added to the solution and the hydrogenation was carried out with 58 ml hydrogen at normal pressure and room temperature for 30 minutes. The reaction mixture was filtered and the solvent evaporated.

Yield: 0.59 g (>93%)
$R_F$=0.1 ($CH_2Cl_2$/$CH_3OH$ 5:1)

7. Synthesis of 3-[2-(2,6-Dimethyl-piperidin-1-yl) acetyl-$^{15}$N-amino]-propanoic acid-(2,5-dioxo-pyrrolidine-1-yl)-ester 24

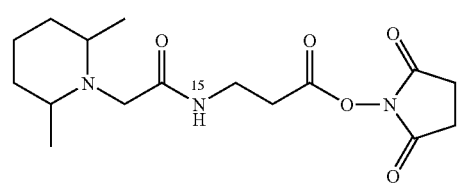

24

0.59 g (2.42 mMol) 3-[2-(2,6-Dimethyl-piperidin-1-yl) acetyl-$^{15}$N-amino]-propanoic acid (23), were added to 0.28 g (2.42 mMol) N-Hydroxysuccinimide and 0.5 g (2.42 mMol) N,N'-Dicyclohexylcarbodiimide in 20 ml dichloromethane. The reaction mixture was stirred for 16 h at room temperature. The solution was filtered and the filtrate was evaporated in vacuo to dryness. The product was recrystallised from diisopropylether.

Yield: 0.7 g (85%)
$M_p$=109-110° C.

Example 6

Synthesis of 3-[2-(2,6-Dimethyl-piperidin-1-yl)acetyl-$^{15}$N-amino]propanoic acid-(2,5-dioxo-pyrrolidine-1-yl)-ester 5

Synthesis of 3-[2-(2,6-Dimethyl-piperidin-1-yl) acetyl-$^{15}$N-amino]-propanoic acid-(2,5-dioxo-pyrrolidine-1-yl)-ester 5 was carried out in four steps.

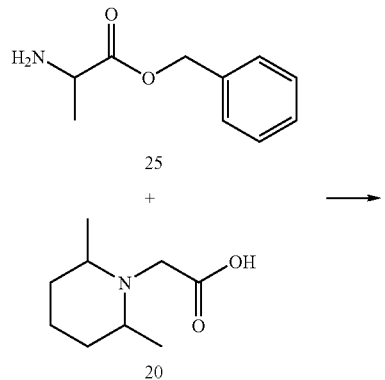

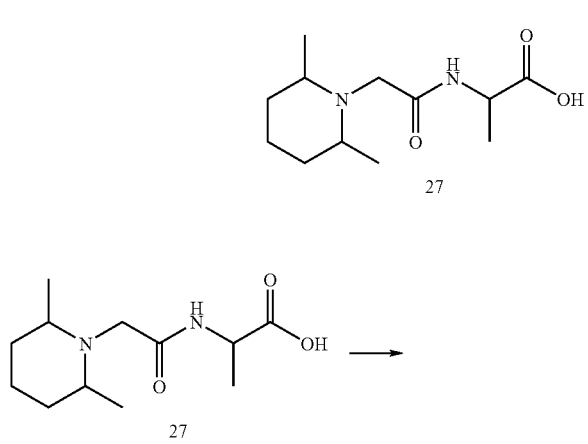

1. Synthesis of 2-amino propanoic acid benzyl ester hydro p-tosylate 25

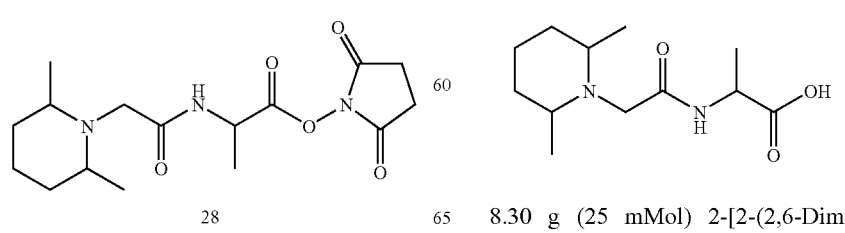

4.45 g (50 mMol) 2-Amino propanoic acid were added to 9.7 (51 mMol) p-toluenesulphonic acid and 20 ml (193 mMol) Benzyl alcohol in 10 ml toluene. The reaction mixture was heated under reflux for 2 h using a water separator. 30 ml dichloromethane was added to the cooled reaction mixture. The product was purified by flash chromatography using $CH_2Cl_2:CH_3OH$ 50:1.

Yield: 8.5 g (49%)

2. Synthesis of 2-[2-(2,6-Dimethyl-piperidin-1-yl)-acetylamino]-propanoic acid benzylester 26

3.11 g (15 mMol) (2,6-Dimethyl-piperidin-1-yl)-acetic acid (20) were added to a mixture of 4.59 g (30 mMol) 1-Hydroxybenzotriazole, 6.19 g (30 mMol) N,N'-Dicyclohexylcarbodiimide dissolved in 50 ml DMF. After 30 minutes stirring at room temperature, 3.11 g (15 mMol) 2-Amino propanoic acid benzyl ester (1) and 4.15 ml (30 mMol) triethylamine were added to the reaction mixture and stirred overnight at room temperature. The mixture was filtered and the solution was evaporated. The residue was dissolved in 250 ml ethyl acetate and the solution was washed three times with 200 ml 0.5N NaOH solution and one time with saturated NaCl solution. The organic phase was dried over $MgSO_4$ and the solvent was evaporated. The residue was purified by flash chromatography using $CH_2Cl_2:CH_3OH$ 95:5 as eluent.

Yield: 3.92 g (80%)
$R_F$=0.75 ($CH_2Cl_2/CH_3OH$ 5:1)

3. Synthesis of 2-[2-(2,6-Dimethyl-piperidin-1-yl)acetylamino]-propanoic acid 27

8.30 g (25 mMol) 2-[2-(2,6-Dimethyl-piperidin-1-yl)acetylamino]-propanoic acid benzylester (26) were dissolved in 150 ml methanol. 0.5 g Pd/C (5%) was added to the solution and the hydrogenation was carried out with 560 ml hydrogen at normal pressure and room temperature for 30 minutes. The reaction mixture was filtered and the solvent evaporated.

Yield: 6.3 g (>99%)

$R_F$=0.1 (CH$_2$Cl$_2$/CH$_3$OH 5:1)

4. Synthesis of 2-[2-(2,6-Dimethyl-piperidin-1-yl) acetylamino]-propanoic acid-(2,5-dioxo-pyrrolidine-1-yl)-ester 28

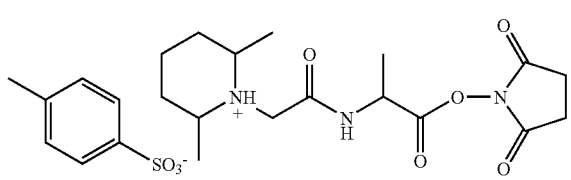

28

4.75 g (25 mMol) p-toluenesulphonic acid were heated under reflux for 1 h in 20 ml toluene using a water separator. After having evaporating the solvent, 6.30 g (25 mMol) 2-[2-(2,6-Dimethyl-piperidin-1-yl) acetylamino]-propanoic acid (27), 2.88 g (25 mMol) N-Hydroxysuccinimide and 5.15 g (25 mMol) N,N'-Dicyclohexylcarbodiimide were added to the residue dissolved in 100 ml dichloromethane. The reaction mixture was stirred for 16 h at room temperature. The solution was filtered and the filtrate was evaporated in vacuo to dryness. The product was recrystallised from diisopropylether.

Yield: 12 g (93%)

$M_p$=109-110° C.

Example 7

Synthesis of [2-(2,6-Dimethyl-piperidin-1-yl)acetylamino]-acetic acid-(2,5-dioxo-pyrrolidine-1-yl)-ester 5

Synthesis of [2-(2,6-Dimethyl-piperidin-1-yl) acetylamino]-acetic acid-(2,5-dioxo-pyrrolidine-1-yl)-ester 5 was carried out in three steps.

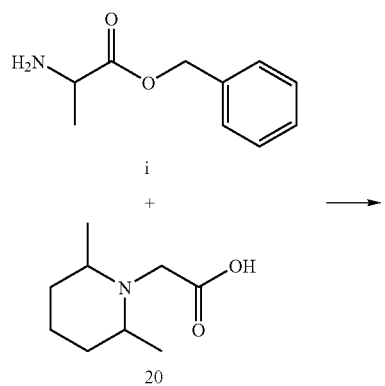

1. Synthesis of [2-(2,6-Dimethyl-piperidin-1-yl)-acetylamino]-acetic acid benzylester 29

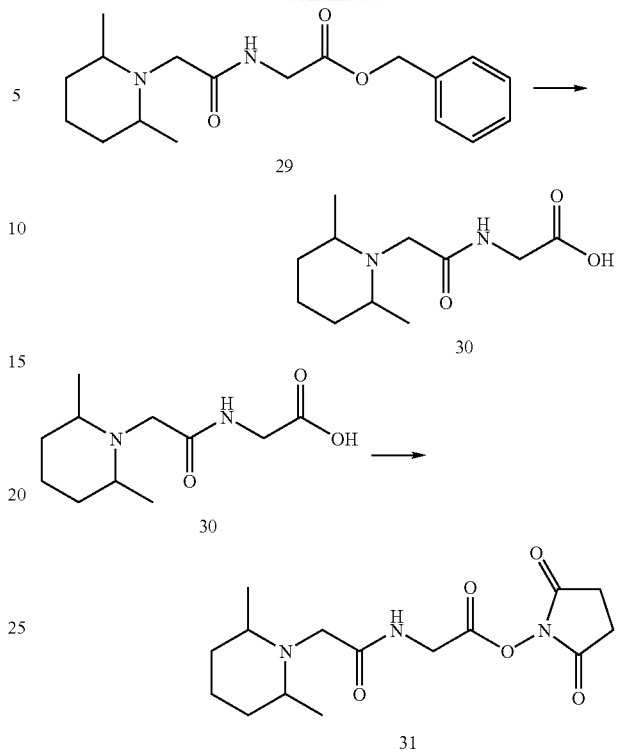

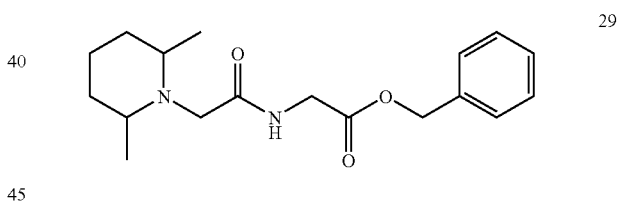

7.69 g (37 mMol) (2,6-Dimethyl-piperidin-1-yl)-acetic acid (20) were added to a mixture of 11.34 g (74 mMol) 1-Hydroxybenzotriazole and 15.27 g (74 mMol) N,N'-Dicyclohexyl-carbodiimide dissolved in 100 ml DMF. After 30 minutes stirring at room temperature, 12.5 g (37 mMol) amino acetic acid benzyl ester (1) dissolved in 100 ml DMF and 10.25 ml (74 mMol) triethylamine were added to the reaction mixture and stirred overnight at room temperature. The mixture was filtered and the solution was evaporated. The residue was dissolved in 250 ml dichloromethane, the solution was filtered once again and then evaporated. After having dissolved the residue in 100 ml ethyl acetate, the solution was washed 3 times with 200 ml 0.5N NaOH solution and 1 time with saturated NaCl solution. The organic phase was dried over MgSO$_4$ and the solvent was evaporated. The residue was purified by a first flash chromatography using ethyl acetate as eluent and the product was eluted from a second silica gel column with CH$_2$Cl$_2$:CH$_3$OH 10:1.

Yield: 6.54 g (56%)

$R_F$=0.77 (CH$_2$Cl$_2$/CH$_3$OH 5:1)

2. Synthesis of [2-(2,6-Dimethyl-piperidin-1-yl)acetylamino]-acetic acid 30

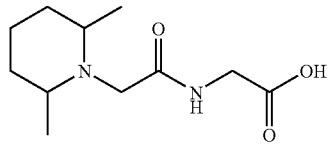

30

6.54 g (20 mMol) [2-(2,6-Dimethyl-piperidin-1-yl) acetylamino]-acetic acid benzylester (29) were dissolved in 150 ml methanol. 0.5 g Pd/C (5%) was added to the solution and the hydrogenation was carried out with 470 ml hydrogen at normal pressure and room temperature for 30 minutes. The reaction mixture was filtered and the solvent evaporated.

Yield: 4.54 g (>99%)
$R_F$=0.1 ($CH_2Cl_2/CH_3OH$ 5:1)

3. Synthesis of [2-(2,6-Dimethyl-piperidin-1-yl)acetylamino]-acetic acid-(2,5-dioxo-pyrrolidine-1-yl)-ester 31

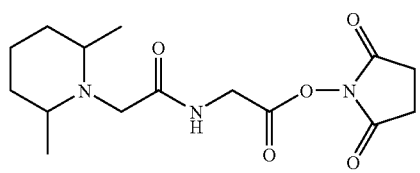

31

4.54 g (20 mMol) [2-(2,6-Dimethyl-piperidin-1-yl)acetylamino]-acetic acid (30) were added to 2.30 g (20 mMol) N-Hydroxysuccinimide and 4.12 g (20 mMol) N,N'-Dicyclohexyl-carbodiimide dissolved in 150 ml dichloromethane. The reaction mixture was stirred for 16 h at room temperature. The solution was filtered and the filtrate was evaporated in vacuo to dryness. The residue was dissolved in 50 mL dichloromethane and treated with charcoal. After filtration, the solution was evaporated in vacuo to dryness and the product was recrystallised from ethyl acetate.

Yield: 4.03 g (62%)
K=150-151° C.

Example 8

Coupling of Tandem Mass Labels to model tryptic peptides

Model Tryptic Peptides Used:

```
VATVSLPR              MW: 842.01

DYEGATLSDIGALIR       MW: 1593.75

LGEHNIDVLEGNEQFINAAK  MW: 2211.42
```

Reactive Mass Labels Tested:
6-[(Pyrimidin-2-ylsulfanyl)-acetylamino]-hexanoic acid-(2,5-dioxo-pyrrolidine-1-yl)-ester (Pyrm-C6-OSu)
3-[2-(Pyrimidin-2-ylsulfanyl)-acetylamino]-propanoic acid-(2,5-dioxo-pyrrolidine-1-yl)-ester (Pyrm-βAla-OSu),
3-[2-(2,6-Dimethyl-piperidin-1-yl)-acetylamino]-propanoic acid-(2,5-dioxo-pyrrolidine-1-yl)-ester (DMPip-βAla-OSu)
2-[2-(2,6-Dimethyl-piperidin-1-yl)-acetylamino]-propanoic acid-(2,5-dioxo-pyrrolidine-1-yl)-ester (DMPip-Ala-OSu)

General Coupling Reaction Protocol to the Model Peptides:

35 μL water and 37.54, (400 mM) Borat-Puffer at pH 7.5-7.8 was mixed with 37.5 μl (750 nMol) peptide dissolved in water/ACN (ratio 3:1). The TMT reagent (reactive mass label) (40 mM) dissolved in 40 μL DMF was then added to the peptide solution. After stirring for 3' h at RT, the reaction mixture was then purified using HPLC (Phenomenex Luna—250 mm/4.6 mm-5μ C18) and the labelled peptide was analysed in MS.

Figure 4:
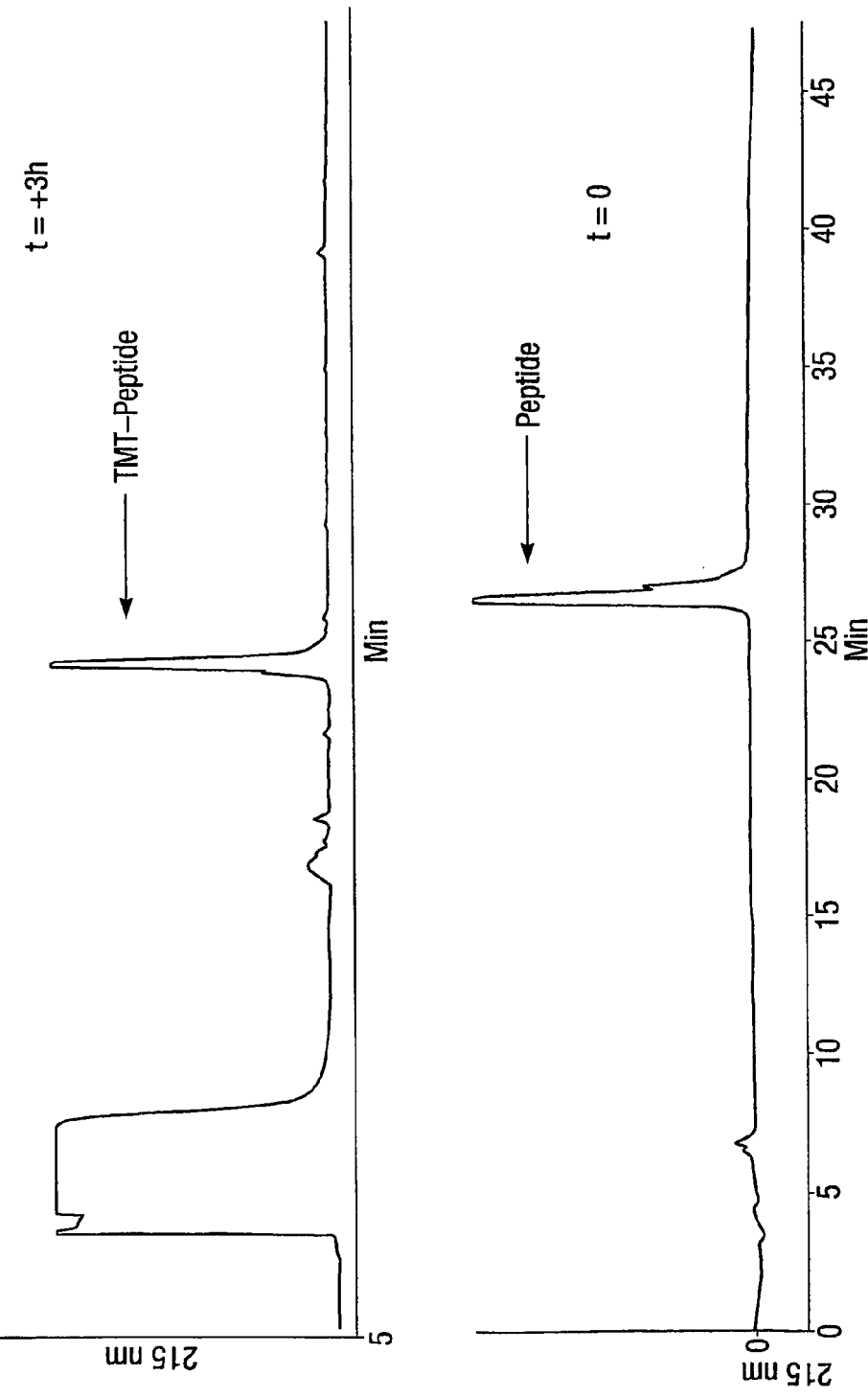
FIG. 4 shows formation of DMPip-βAla-LGEHNIDVLEGNEQFINAA (DMPip-βAla-) K.

FIG. 4 shows that the reaction between the model peptide LGEHNIDVLEGNEQFINAAK and the reactive mass label 3-[2-(2,6-Dimethyl-piperidin-1-yl)-acetylamino]-propanoic acid-(2,5-dioxo-pyrrolidine-1-yl)-ester to form the labelled peptide DMPip-βAla-LGEHNEDVLEGNEQFINAA (DMPip-βAla-)K was complete after three hours.

Figure 5:
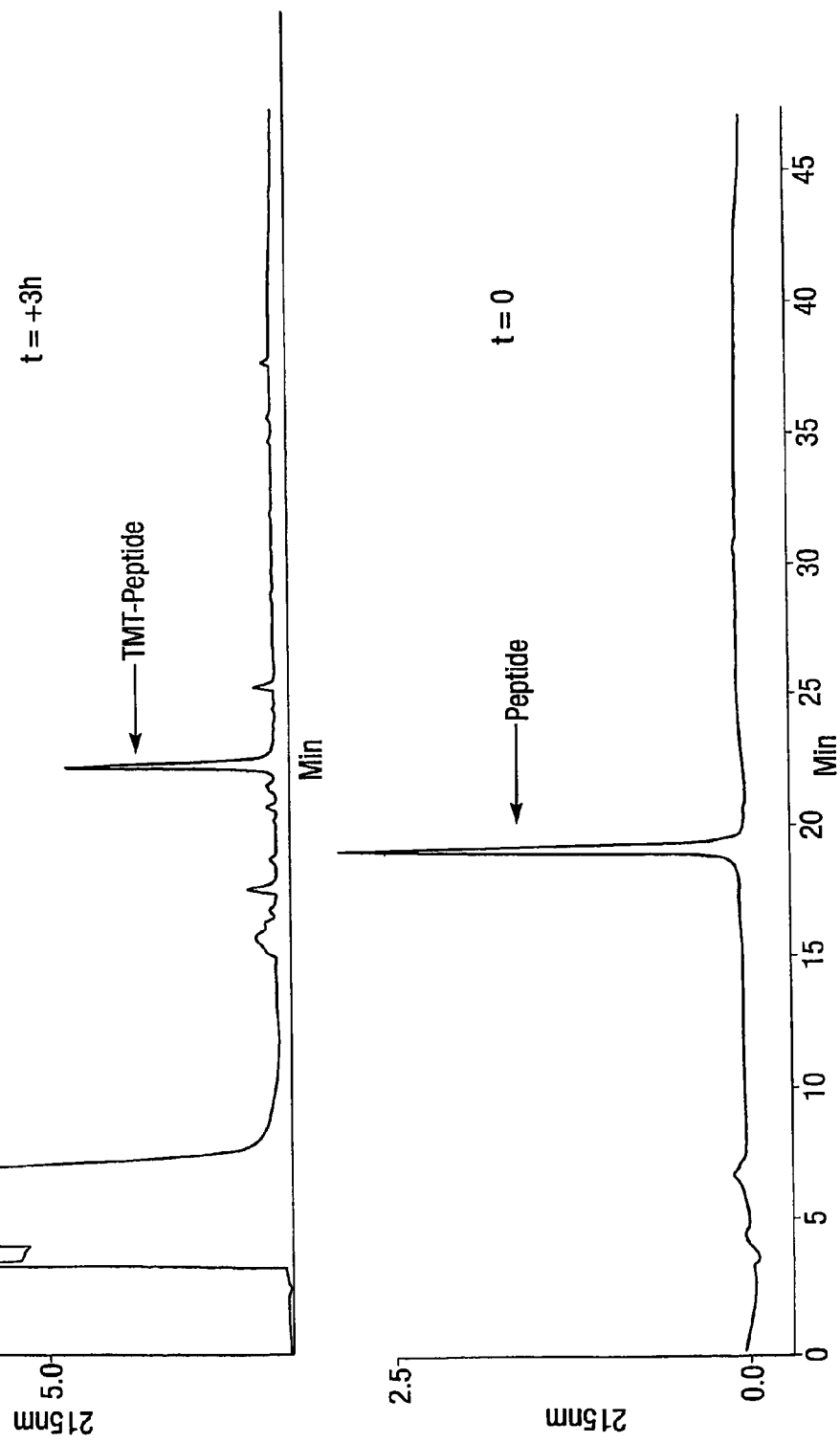
FIG. 5 shows formation of DMPip-βAla-VATVSLPR.

FIG. 5 shows that the reaction between the model peptide VATVSLPR and the reactive mass label 3-[2-(2,6-Dimethyl-piperidin-1-yl)-acetylamino]-propanoic acid-(2,5-dioxo-pyrrolidine-1-yl)-ester to form the labelled peptide DMPip-βAla-VATVSLPR was complete after three hours.

Figure 6:
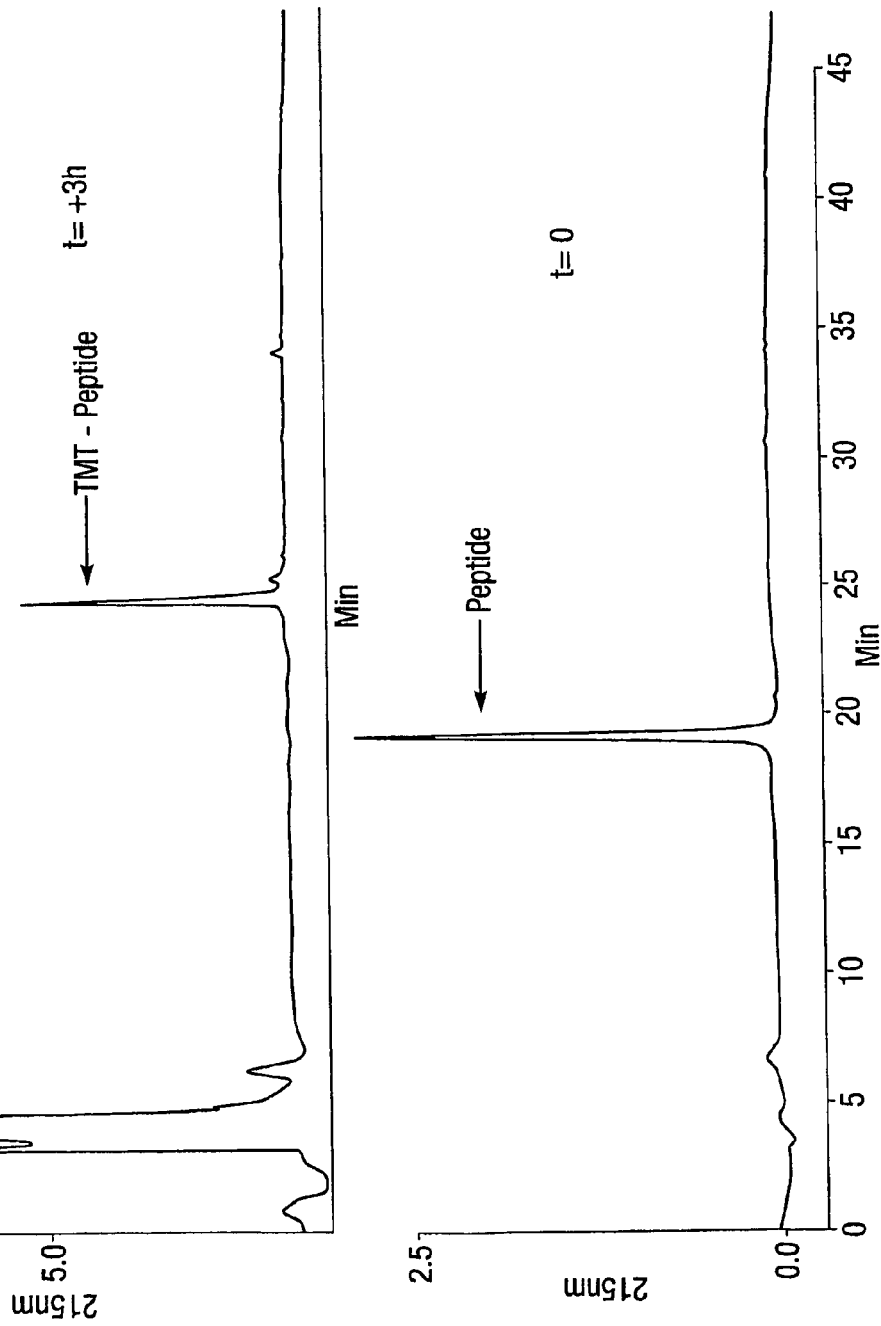
FIG. 6 shows formation of Pyrm-βAla-VATVSLPR.
Figure 7:
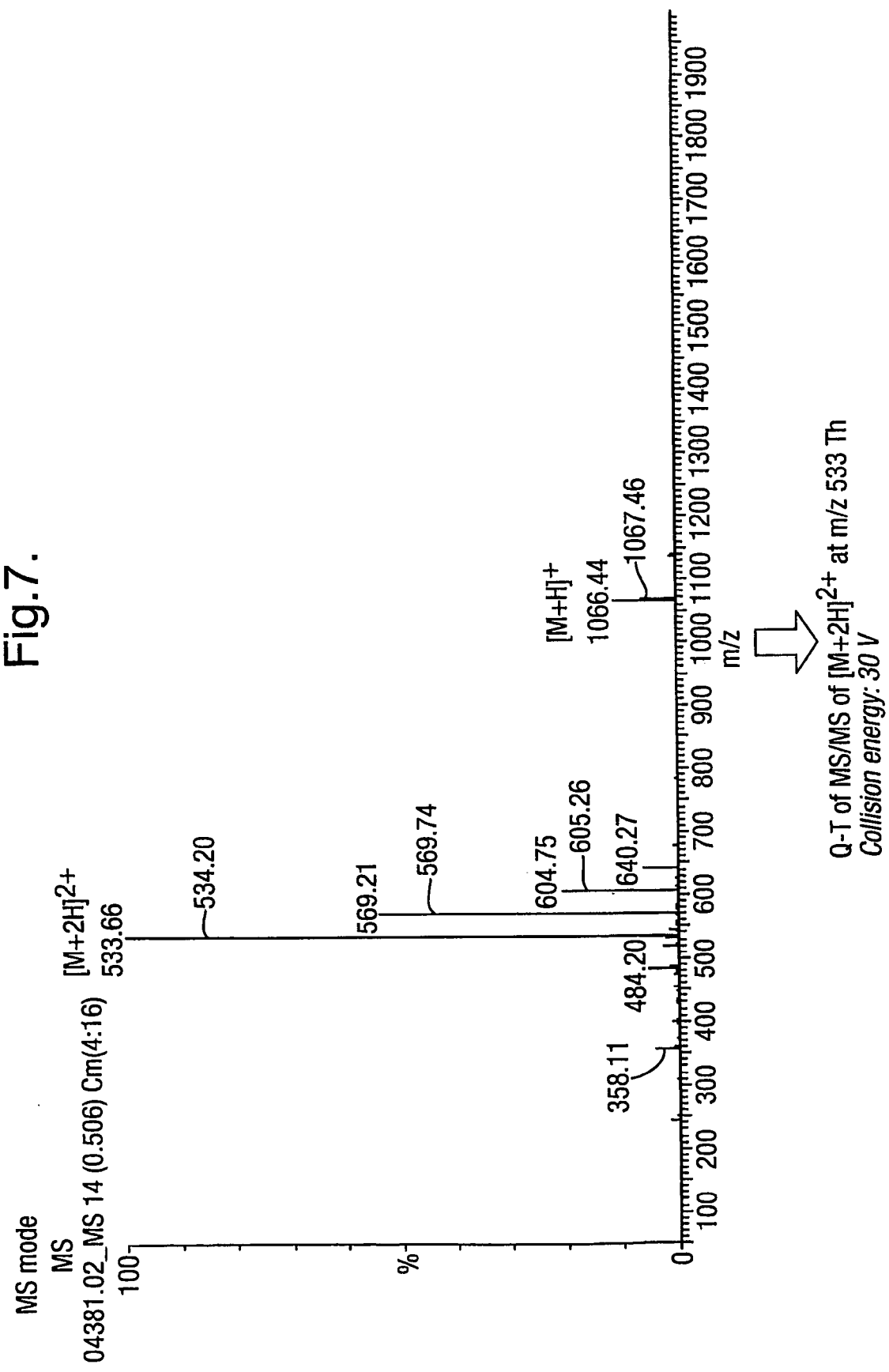
FIG. 7 shows MS/MS analysis of DMPip-βAla-VATVSLPR.
Figure 7:
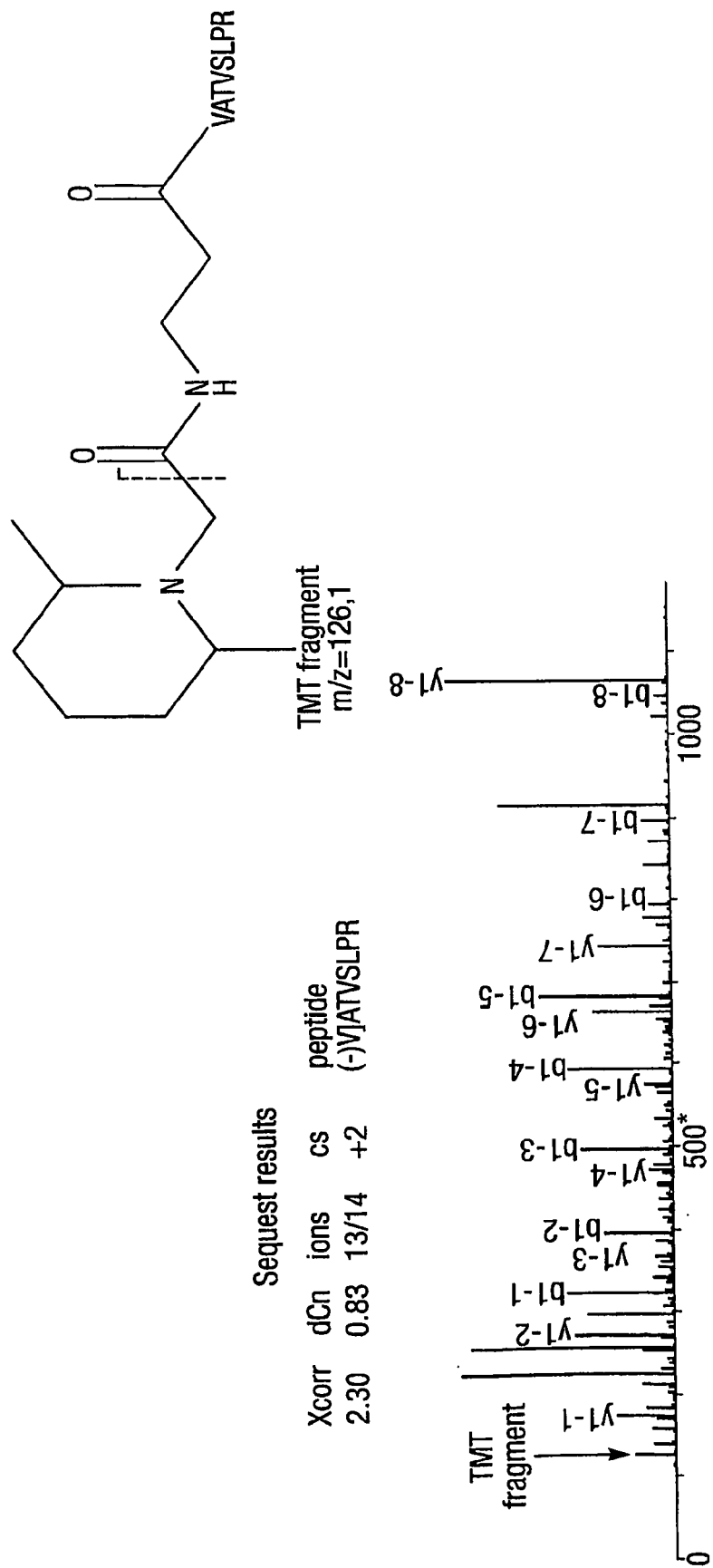

FIG. 6 shows that the reaction between the model peptide VATVSLPR and the reactive mass label 3-[2-(Pyrimidin-2-ylsulfanyl)-acetylamino]-propanoic acid-(2,5-dioxo-pyrrolidine-1-yl)-ester to form the labelled peptide Pyrm-βAla-VATVSLPR was complete after three hours.

Figure 16:
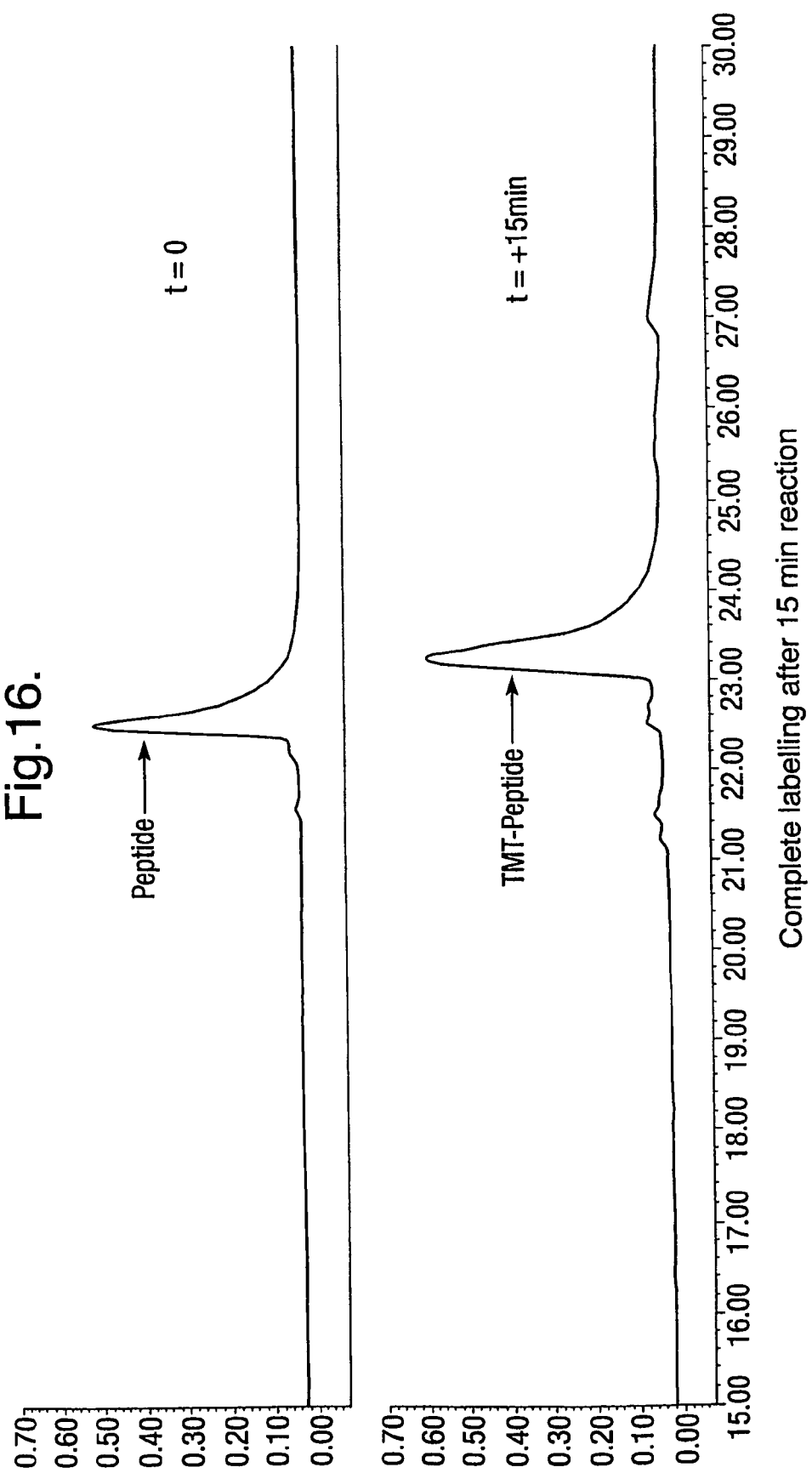
FIG. 16 shows the formation of DMPip-Ala-VATVSLPR.
Figure 17:
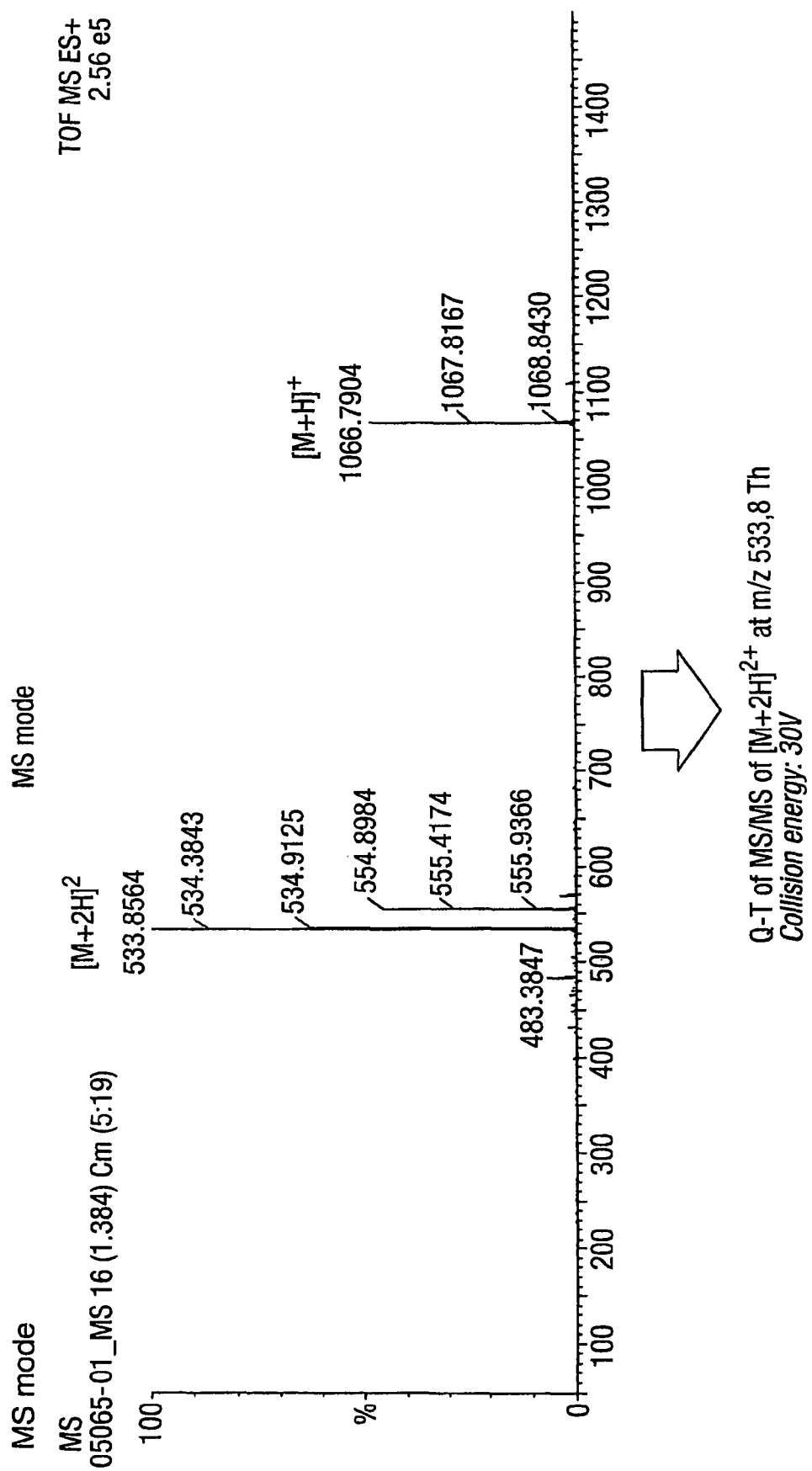
FIG. 17 shows the MS/MS analysis of DMPip-Ala-VATVSLPR.
Figure 17:
Figure 18:
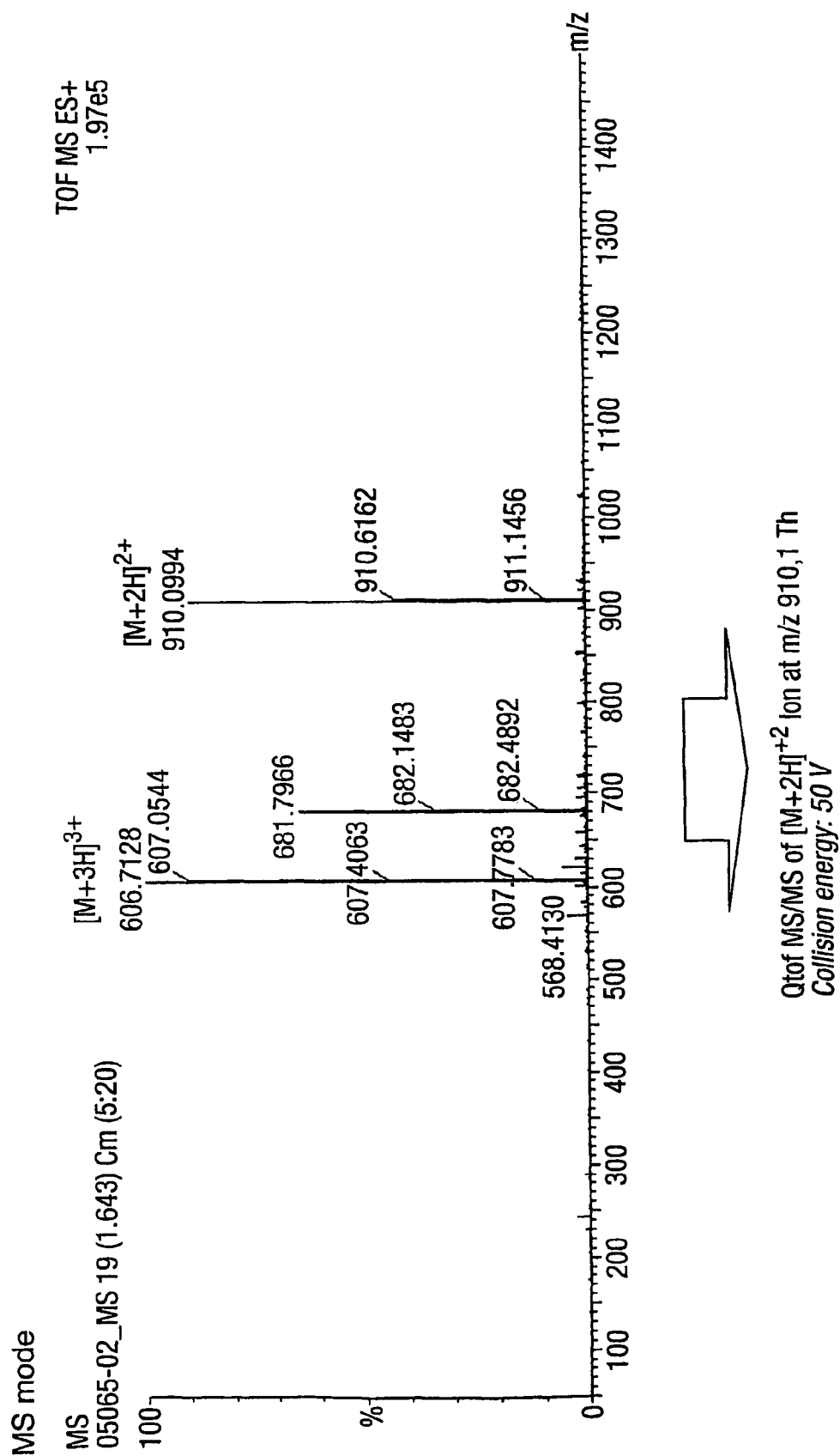
FIG. 18 shows the MS/MS analysis of DMPip-Ala-DYEGATLSDIGALIR.
Figure 18:
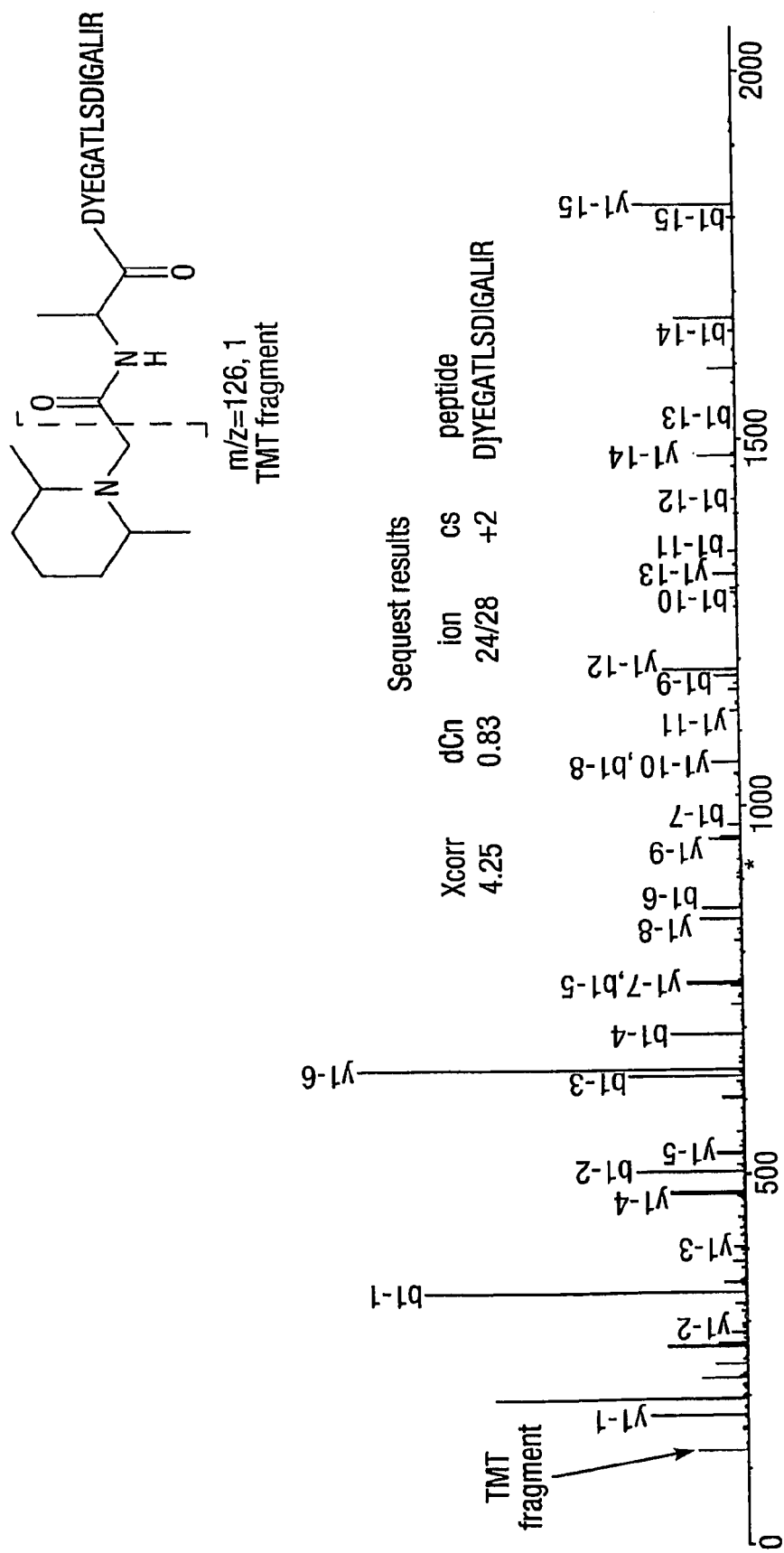
Figure 19:
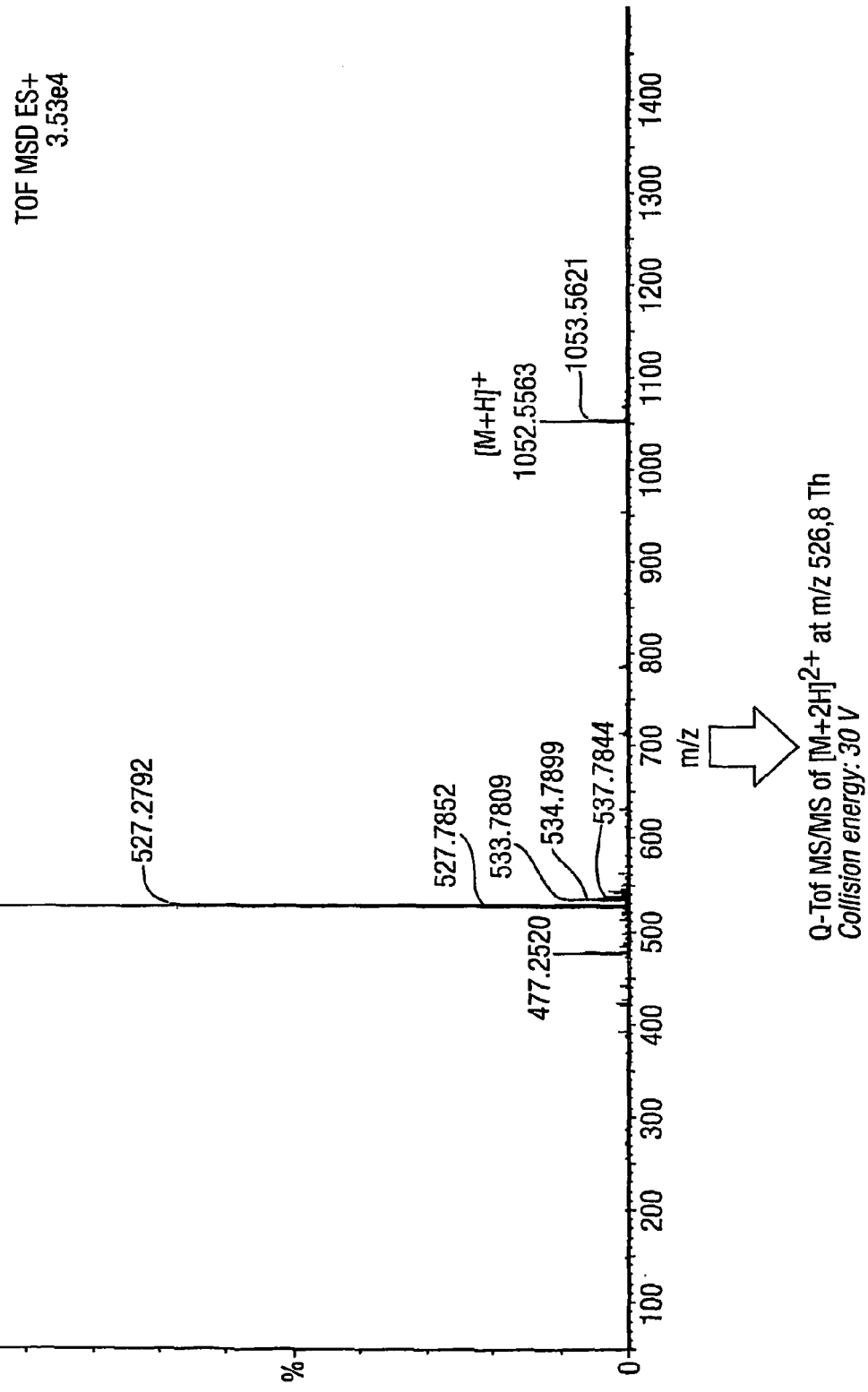
FIG. 19 shows the MS/MS analysis of DMPip-Gly-VATVSLPR.
Figure 19:
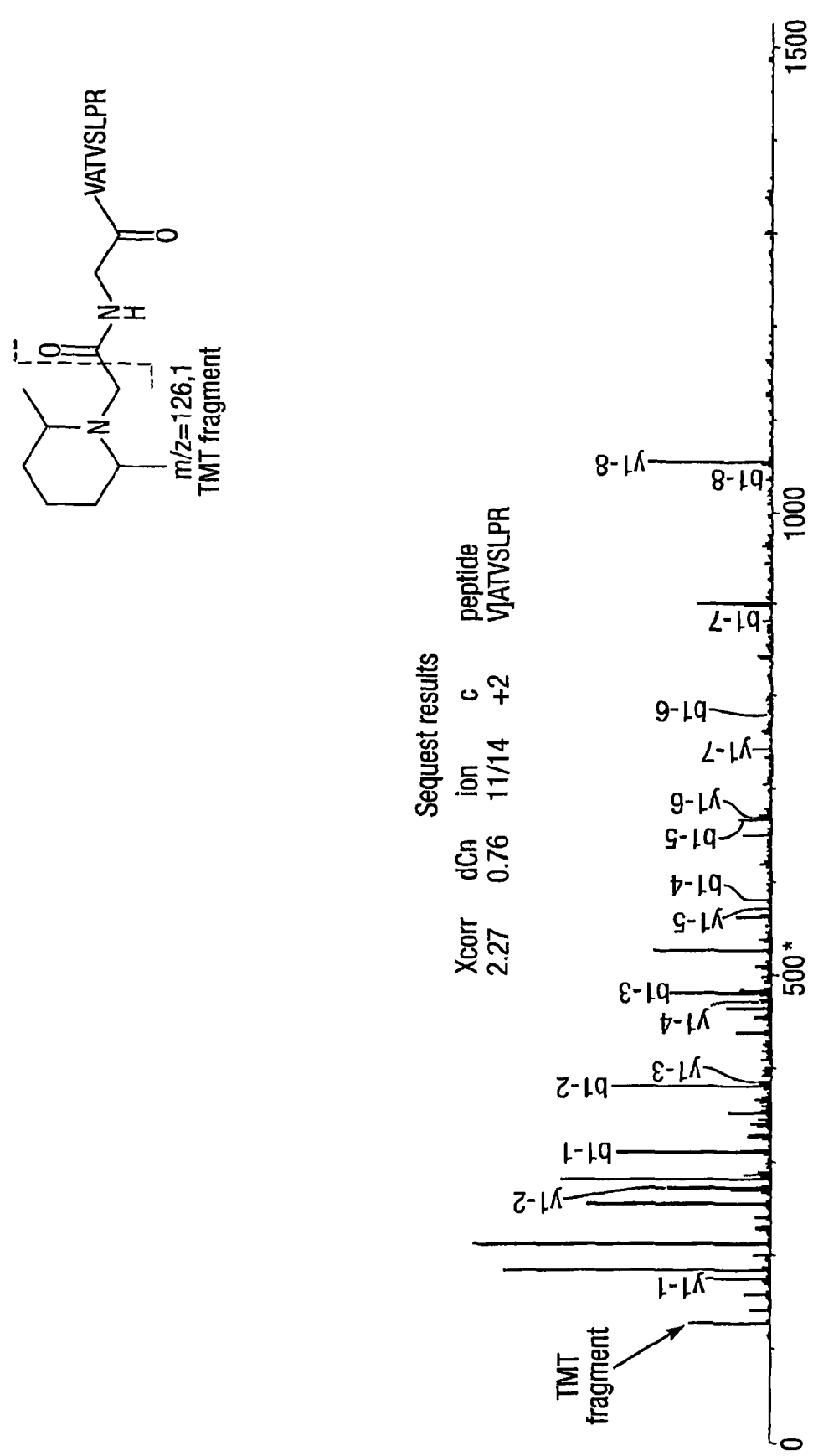
Figure 20:
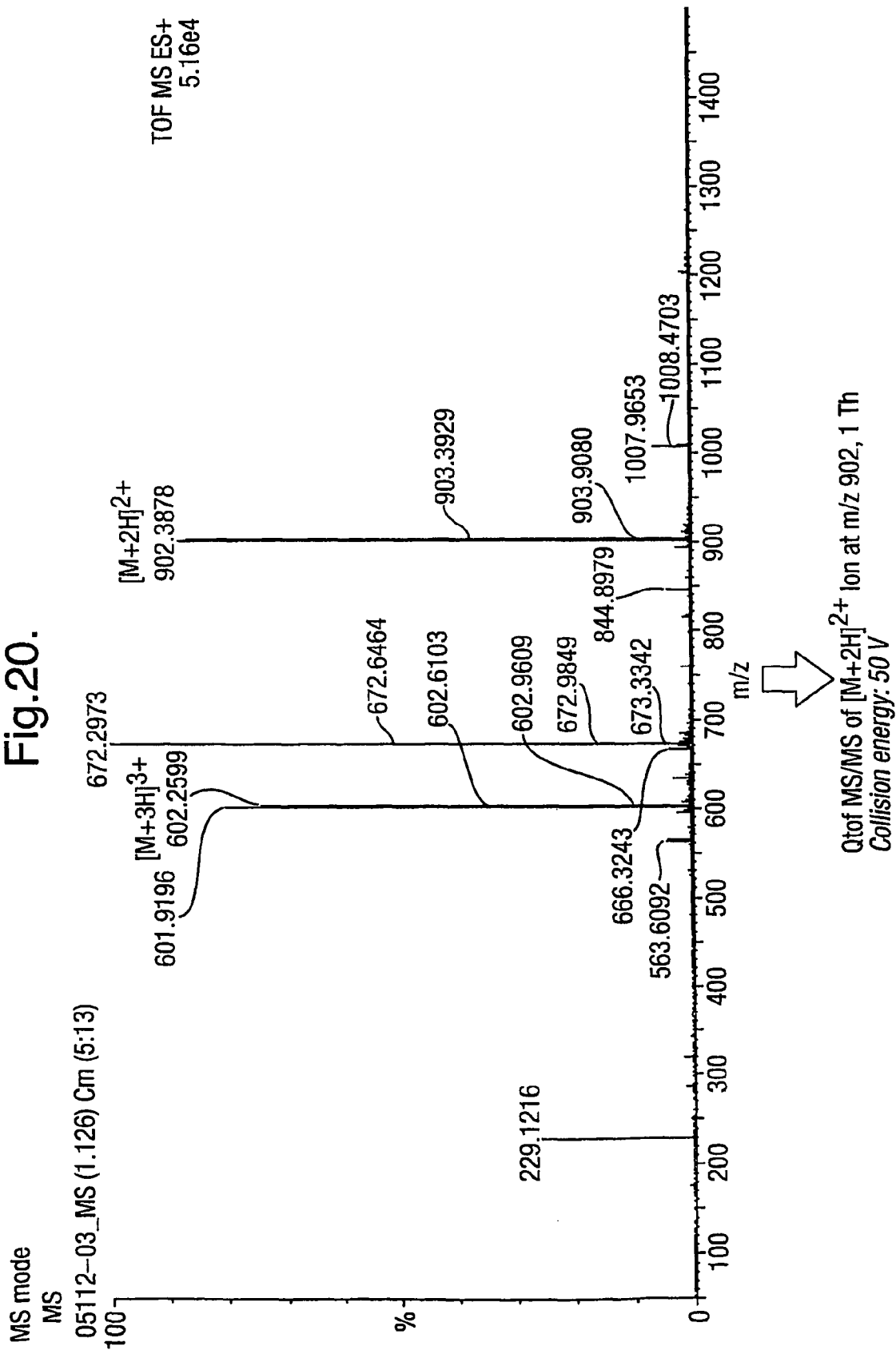
FIG. 20 shows the MS/MS analysis of DMPip-Gly-DYEGATLSDIGALIR.
Figure 21:
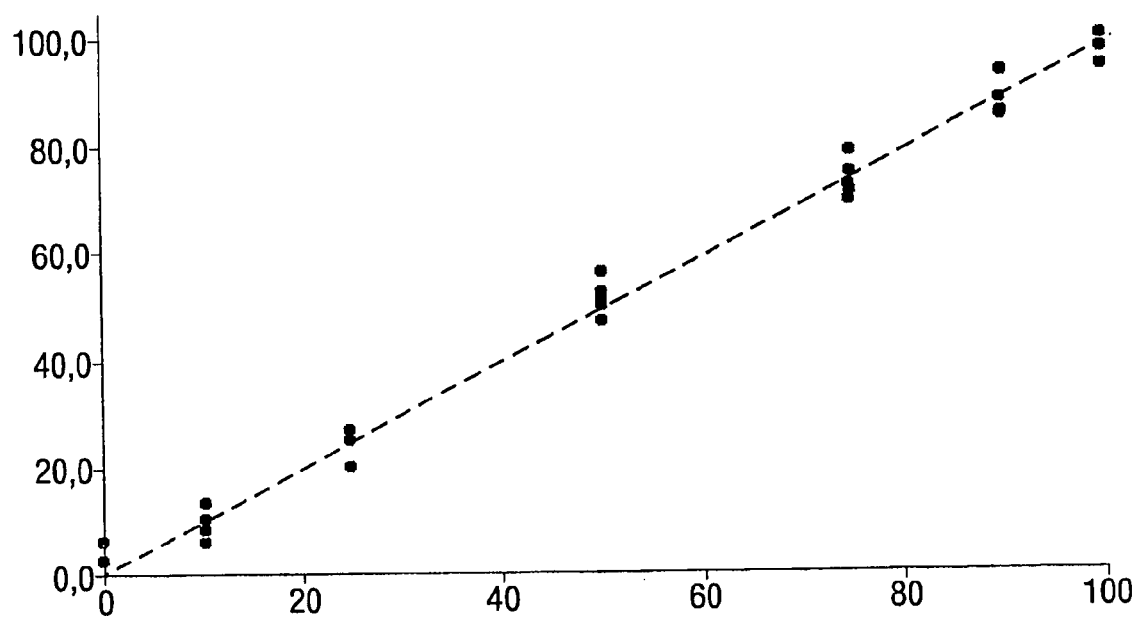
FIG. 21 shows measured peptide ratios (H:L+H)×100 plotted against expected peptide ratios (H:L+H)×100.

FIG. 16 shows that the reaction between the model peptide VATVSLPR and the reactive mass label 2-[2-(2,6-Dimethyl-piperidin-1-yl)-acetylamino]-propanoic acid-(2,5-dioxo-pyrrolidine-1-yl)-ester to form the labelled peptide DMPip-Ala-VATVSLPR was complete after 15 minutes.

Example 9

MS/MS Analysis of Mass Labelled-Peptides

Protocol for MS/MS Experiments:

MS and MS/MS analyses were performed on a QTOF2 mass spectrometer (Micromass, Manchester, UK). HPLC analysis was performed with a CAP-LC HPLC system (Waters Corporation, Milford, Mass., USA) (Column: PepMap™ C18 HPLC column from Dionex with a 75 μm inner diameter and a length of 150 mm; Solvents: 95% Water to 95% Acetonitrile both with 0.2% Formic Acid).

Ion abundance ratios were determined by summation and smoothing of spectra for each peptide as it is ionised in the electrospray source followed by determination of peak intensities of the TMT fragments.

FIGS. 7-13 and 17-20 show MS and MS/MS spectra for doubly or triply charged ions of peptide sequences labelled with TMTs, respectively DMPip-βAla-VATVSLPR, DMPip-βAla-DYEGATLSDIGALIR, DMPip-βAla-LGEHNIDV-LEGNEQFINAA (DMPip-βAla)-K, Pyrm-βAla-VATVS-LPR, Pyrm-βAla-DYEGATLSDIGALIR, Pyrm-C6-VATVSLPR, Pyrm-C6-DYEGATLSDIGALIR, DMPip-Ala-VATVSLPR, DMPip-Ala-DYEGATLSDIGALIR, DMPip-Gly-VATVSLPR, DMPip-Gly-DYEGATLSDIGALIR. In each figure, the first figure shows the MS-mode TOF spectrum of the corresponding labeled peptide. The second one shows the CID spectra at a defining collision's energy of the labeled peptides. The presence of the expected tag fragment (TMT fragment) at m/z of 126 for DMPip-Gly, DMPip-Ala, DMPip-βAla or m/z of 153 for Pyrm-βAla and Pyrm-C6 is indicated by an arrow. Results of the SEQUEST analysis of the MS/MS spectrum are shown for each labeled peptide.

Example 10

Relative Quantitation Using Duplex Strategy

Relative quantification of confected ratios was carried out, using 5 different tryptic model peptides. The peptides and ratios tested were as follows:

| | |
|---|---|
| 5 different peptides | FSWGAEGER |
| | VATVSLPR |
| | LGEHNIDVLEGNEQFINAAK |
| | EIQAEGNR |
| | DIAIHHPWIR |
| 7 different ratios: | 0:100 |
| | 10:90 |
| | 25:75 |
| | 50:50 |
| | 75:25 |
| | 90:10 |
| | 100:0 |

The TMT tag employed was DMPip-βAla-Osu, as a light and heavy fragment, as follows:

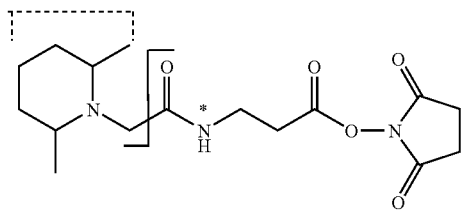

Light fragment

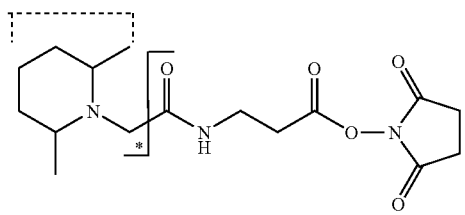

Heavy fragment

The TMT tag fragment ESI-MS/MS data fitted with a regression line for 7 different expected and observed ratios of the 5 described peptides. The corresponding TMT labelled peptides were analyzed. Abundance ratios were determined by analyzing the peak maxima at the C13 (Heavy tag (=H) m/z of 127) and C12 (Light tag (=L) m/z of 126) of the tag fragment ion peaks.

Example 11

Synthesis of isotopically labelled 3-[2-((2S,6R)-2,6-Dimethyl-piperidin-1-yl)-acetylamino]-propanoic acid 2,5-dioxo-pyrrolidine-1-yl ester; general reaction scheme

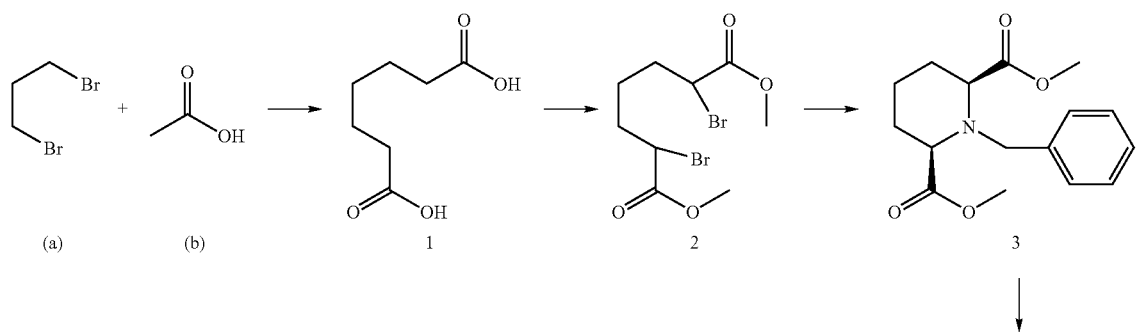

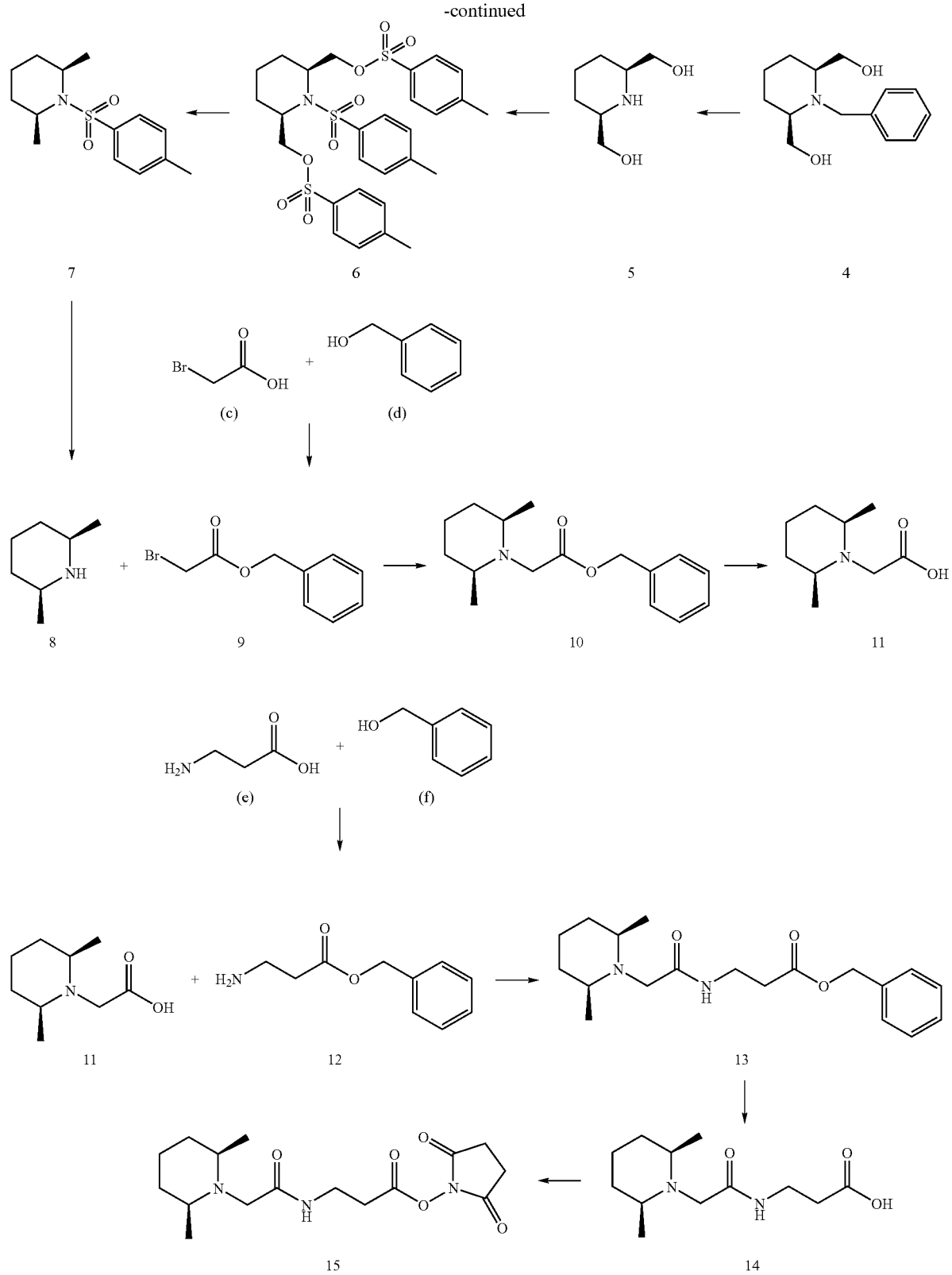
Synthesis of six isotopically labelled mass labels (TMT compounds) I-VI was carried out using part or all of the above reaction scheme using isotopically labelled starting materials shown in the table below:

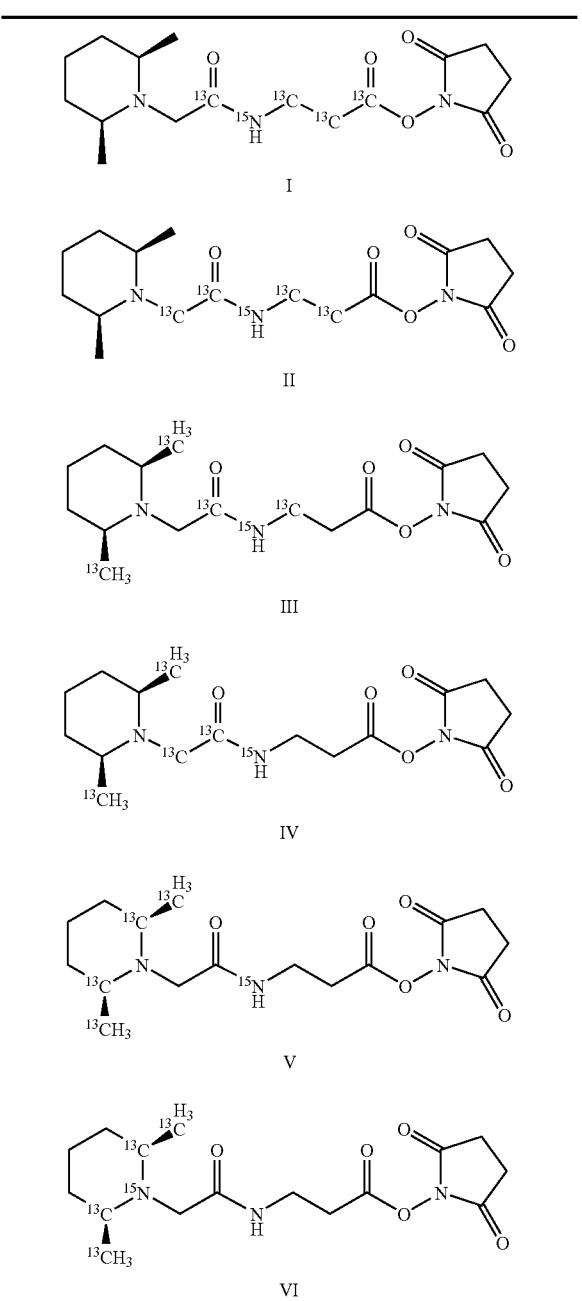

| compound | Acetic acid (b) | Bromoacetic acid c) | β-Alanine (e) | Benzylamine | X Mass marker moiety mass (TMT fragment mass) |
|---|---|---|---|---|---|
| I | — | 1-$^{13}$C | $^{13}$C$_3$, $^{15}$N | — | 126 |
| II | — | $^{13}$C$_2$ | 2,3-$^{13}$C$_2$, $^{15}$N | — | 127 |
| III | 1-$^{13}$C | 1-$^{13}$C | 3-$^{13}$C, $^{15}$N | — | 128 |
| IV | 1-$^{13}$C | $^{13}$C$_2$ | $^{15}$N | — | 129 |
| V | $^{13}$C$_2$ | — | $^{15}$N | — | 130 |
| VI | $^{13}$C$_2$ | — | — | $^{15}$N | 131 |

Synthesis of compounds I and II started directly from unlabelled, commercially available cis-2,6-dimethylpiperidine 8 (see reaction scheme above).

Synthesis of compound IV is set out in detail below:

(i) Synthesis of 1,7-$^{13}$C$_2$-heptanedioic acid 1

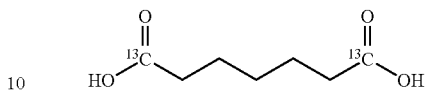

124 ml (0.885 mmol) diisopropylamine were added to 590 ml dry tetrahydrofuran under a nitrogen atmosphere. After cooling to −20° C., 560 ml 1.6 molar n-butyllithium (BuLi) in hexane were added dropwise. The temperature was raised to 0° C. and 70 ml hexamethylphosphoramide (HMPA) were added. After stirring for 10 minutes at 0° C., first 23 ml (0.396 mol) acetic acid-1-$^{13}$C (b) were added dropwise and then 140 ml HMPA were added, both at 0° C. The solution was stirred for 1 hour at 0° C. and for 2 hours at room temperature. After cooling to 0° C., 20.4 ml (0.2 mol) 1,3-dibromopropane (a) were added. The solution was stirred overnight at room temperature. After dilution with 800 ml water, the organic phase was separated and extracted with diethyl ether/water (2:1) and water. The aqueous extracts were pooled, washed with diethyl ether, acidified to pH 3 with concentrated hydrochloric acid, saturated with sodium chloride and extracted with diethyl ether. The ether extracts were combined and dried over sodium sulphate. The solvent was removed in vacuo and the resulting oil was purified by flash chromatography using diisopropyl ether as eluent. The reaction was repeated 2 times with 0.2 mol and 0.174 mol acetic acid-1-$^{13}$C (b), respectively.

Yield: 34.5 g (37%)

$R_F$=0.63 (ethyl acetate/methanol 5:1)

(ii) Synthesis of (2R,6S)-2,6-dibromo-1,7-$^{13}$C$_2$-heptanedioic acid-dimethyl ester 2

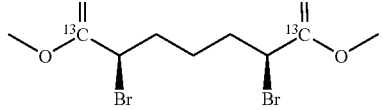

To a suspension of 32.4 g (0.2 mol) 1,7-$^{13}$C$_2$-heptanedioic acid 1 in 400 ml 1,2-dichloroethane were added 34.82 ml (0.477 mol) thionylchloride in 150 ml 1,2-dichloroethane. After refluxing for 1.5 hours, 150 ml 1,2-dichloroethane were removed by distillation and 29.35 ml (0.576 mol) bromine in 150 ml 1,2-dichloromethane were added dropwise. After refluxing for an additional 10 hours, the hot solution is added dropwise to boiling methanol. The mixture is refluxed for 0.5 hours and the solvent removed in vacuo. The residue was dissolved in 1500 ml diisopropyl ether, washed with sodium bisulphite solution, sodium bicarbonate solution, saturated sodium chloride solution and water. The solution was dried over sodium sulphate, filtered and the solvent removed in vacuo.

Yield: 70 g (>99%)

$R_F$=0.63 (dichloromethane)

(iii) Synthesis of (2R,6S)-1-benzyl-piperidine-2,6-di-(1-$^{13}$C-carboxylic acid) dimethyl ester 3

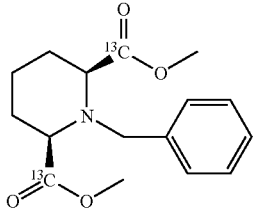 [SMILES: CO[13C](=O)[C@H]1CCC[C@@H]([13C](=O)OC)N1Cc1ccccc1]

A solution of 76.5 ml (0.722 mol) benzylamine in 250 ml toluene was heated to reflux and 70 g (0.2 mol) (2R,6S)-2,6-dibromo-1,7-$^{13}$C$_2$-heptanedioic acid dimethyl ester 2 in 150 ml toluene were added dropwise. After refluxing for 5 hours, the solvent was removed in vacuo. The residue was dissolved in 2000 ml diisopropyl ether/saturated sodium bicarbonate solution (1:1) and the ether phase was separated. The aqueous phase was extracted with diisopropyl ether and the combined ether extracts were washed with sodium chloride solution, dried over sodium sulphate, filtrated and the solvent removed in vacuo. The residue was purified by flash chromatography using diisopropyl ether/hexane (1:3).

Yield: 25.5 g (43.5%)

$R_F$=0.53 (diisopropyl ether)

(iv) Synthesis of ((2R,6S)-1-benzyl-6-hydroxy-$^{13}$C-methyl-piperidin-2-yl)-$^{13}$C-methanol 4

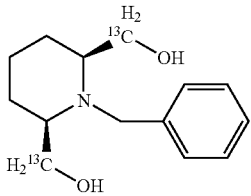

To a solution of 5.6 g (0.148 mol) lithium aluminium hydride in 600 ml dry diethyl ether under nitrogen were added 25.5 g (87 mmol) (2R,6S)-1-benzyl-piperidine-2,6-di-(1-$^{13}$C-carboxylic acid) dimethyl ester 3 in 200 ml dry diethyl ether. After refluxing for 1 hour, 5.6 ml water, 5.6 ml 15% sodium hydroxide solution and 16.8 ml water were added successively and the mixture stirred for 2 hours at room temperature. The suspension was filtered, washed with diethyl ether and the solvent removed in vacuo. The residue was purified by flash chromatography using ethyl acetate/methanol (5:1) as eluent.

Yield: 20 g (99%)

$R_F$=0.38 (ethyl acetate/methanol 5:1)

(v) Synthesis of ((2S,6R)-6-Hydroxy-$^{13}$C-methyl-piperidin-2-yl)-$^{13}$C-methanol 5

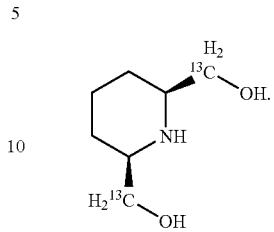

To a solution of 20 g (87 mmol) ((2R,6S)-1-benzyl-6-hydroxy-$^{13}$C-methyl-piperidin-2-yl)-$^{13}$C-methanol 4 in 250 ml methanol 1 g palladium-on-charcoal catalyst (Pd/C) (5%) is added. The hydrogenation was carried out with 1800 ml hydrogen at normal pressure and room temperature. The solution was filtered and the solvent removed in vacuo. The residue was dissolved in dichloromethane, cleared by means of filter aid and the solvent removed in vacuo.

Yield: 11.14 g (87%)

$R_F$=0.06 (ethyl acetate/methanol 5:1)

(vi) Synthesis of (2R,6R)-2,6-di-((toluene-4-sulfonyl)-oxy-$^{13}$C-methyl)-piperidin-1-yl-toluenesulfonamide 6

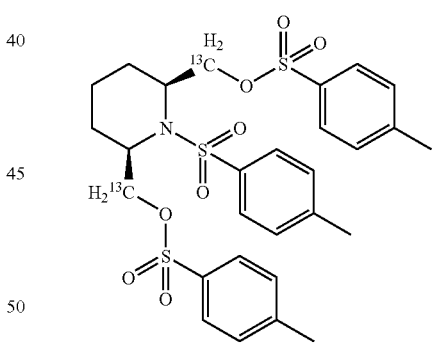

To a solution of 11.14 g (76.72 mmol) ((2S,6R)-6-Hydroxy-$^{13}$C-methyl-piperidin-2-yl)-$^{13}$C-methanol 5 in 300 ml dichloromethane were added dropwise at 0° C. 32 ml (231.6 mmol) triethylamine in 250 ml dichloromethane and 44.16 g (231.6 mmol) 4-toluenesulfonyl chloride in 250 ml dichloromethane. The solution was stirred for 3 hours at 0° C. and for additional 5 days at room temperature. The reaction mixture was washed with water, dried over sodium sulphate and the solvent removed in vacuo. The residue was purified by flash chromatography using ethyl acetate/hexane (1:1) as eluent.

Yield: 11.5 g (25%)

$R_F$=0.41 (hexane/ethyl acetate 6:4)

(vii) Synthesis of (2R,6S)-2,6-Di-$^{13}$C-methyl-1-(toluene-4-sulfonyl)-piperidine 7

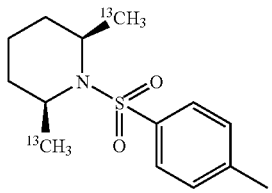 [SMILES: Cc1ccc(S(=O)(=O)N2[C@H]([13CH3])CCC[C@@H]2[13CH3])cc1]

To a solution of 7 g (0:184) lithium aluminium hydride in 50 ml tetrahydrofuran were added dropwise 11.5 g (18.9 mmol) (2R,6R)-2,6-di-((toluene-4-sulfonyl)-oxy-$^{13}$C-methyl)-piperidin-1-yl-toluenesulfonamide 6 in 50 ml tetrahydrofuran and the solution was refluxed for 4 hours. The reaction mixture was diluted with 300 ml diethyl ether and 7 ml water, 7 ml 15% sodium hydroxide solution and 21 ml water were added successively. The suspension was stirred on ice for 1 hour, filtered, washed with ethyl acetate and dichloromethane and the solvent removed in vacuo. The residue was purified by flash chromatography using diisopropyl ether/hexane (1:1) as eluent.

Yield: 3.4 g (67%)

$R_F$=0.83 (diisopropyl ether)

(viii) Synthesis of (2R,6S)-2,6-di-$^{13}$C-methyl-piperidine 8

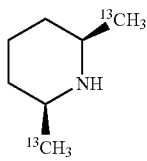

A solution of 10.54 g (72 mmol) naphthalene and 1.87 g (72 mmol) sodium in 170 ml 1,2-dimethoxyethane was stirred under nitrogen over night and 3.4 g (12.6 mmol) (2R,6S)-2,6-di-$^{13}$C-methyl-1-(toluene-4-sulfonyl)-piperidine 7 were added. After stirring for additional 2 hours, 100 ml 1 molar hydrochloric acid in diethyl ether were added and the solvent was removed in vacuo. The residue was suspended in 50 ml water, washed with diisopropyl ether and the solvent removed in vacuo. The residue was dissolved in 30 ml 2 molar sodium hydroxide solution, saturated with sodium chloride and extracted with ethyl acetate. The ethyl acetate extracts were combined, dried over sodium sulphate, diluted with 30 ml 1 molar hydrochloric acid in diethylether and the solvent removed in vacuo.

Yield: 1.75 g (91.6%) (as chloride salt)

(ix) Synthesis of Bromo-$^{13}$C$_2$-acetic acid-benzyl ester 9

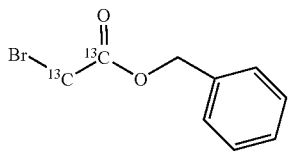 [SMILES: O=[13C]([13CH2]Br)OCc1ccccc1]

To a solution of 20 g (0.14 mmol) Bromo-$^{13}$C$_2$-acetic acid (c) in 500 ml dichloromethane were added 16.2 ml (0.157 mol) benzyl alcohol (d), 1 g 4-N,N-dimethylaminopyridine and 32.2 g (0.156 mol) N,N'-dicyclohexylcarbodiimide. The reaction mixture was stirred overnight at room temperature. The residue was filtered and the filtrate was washed with saturated sodium bicarbonate solution. The aqueous layer was extracted three times with dichloromethane, the combined organic phases were washed with sodium chloride solution, dried over sodium sulphate and the solvent was evaporated in vacuo. The product was purified by flash chromatography using dichloromethane/hexane (1:1) as eluent.

Yield: 28.2 g (87%)

$R_F$=0.67 (dichloromethane)

(X) Synthesis of ((2S,6R)-2,6-Di-$^{13}$C-methyl-piperidin-1-yl)-$^{13}$C$_2$-acetic acid benzyl ester 10

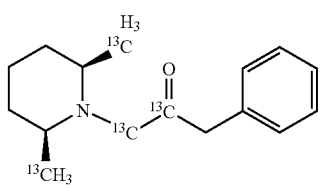

0.85 g (5.6 mmol) (2R,6S)-2,6-Di-$^{13}$C-methyl-piperidine 8 (as chloride salt) were stirred in a solution of 0.222 g (5.55 mmol) sodium hydroxide in 2 ml water for 5 minutes and 50 ml tetrahydrofuran and 0.8 g (3.5 mmol) bromo-$^{13}$C$_2$-acetic acid-benzylester 9 were added. After refluxing for 5 hours, the solvent was removed in vacuo. The residue was dissolved in diisopropyl ether, washed with sodium bicarbonate solution, dried over sodium sulphate and the solvent removed in vacuo. The residue was purified by flash chromatography with diisopropyl ether/hexane (1:1) as eluent.

Yield: 0.61 g (82%)

$R_F$=0.5 (diisopropyl ether)

(xi) Synthesis of ((2S,6R)-2,6-Di-$^{13}$C-methyl-piperidin-1-yl)-$^{13}$C$_2$-acetic acid 11

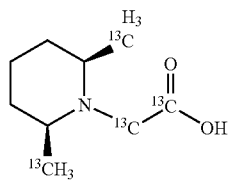

0.61 g (2.3 mmol) ((2S,6R)-2,6-Di-$^{13}$C-methyl-piperidin-1-yl)-$^{13}$C$_2$-acetic acid benzyl ester 10 were dissolved in 25 ml methanol. 0.1 g palladium on charcoal (5%) were added to the solution and the hydrogenation was carried out with 55 ml hydrogen at normal pressure and room temperature for 30 minutes. The reaction mixture was filtered and the solvent removed in vacuo.
Yield: 0.37 g (92.5%)
$R_F$=0.05 (diisopropyl ether)

(xii) Synthesis of 3-$^{15}$N-Amino-propionic acid benzyl ester 12

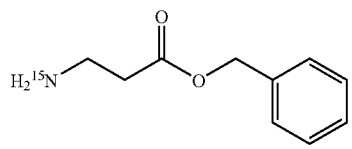 [SMILES: [15NH2]CCC(=O)OCc1ccccc1]

A solution of 1.4 g (15.55 mmol) β-alanine-$^{15}$N, 3.18 g 4-toluenesulfonic acid and 13.14 ml (127 mmol) benzylalcohol in 120 ml toluene was refluxed for 4 hours. After cooling to room temperature, the solution was diluted with 75 ml diisopropyl ether, kept at 4° C. overnight and the precipitate filtrated, washed with diisopropyl ether and dried in vacuo.
Yield: 5.32 g (97.5%) (as tosylate salt)

(xiii) Synthesis of 3-[2-((2S,6R)-2,6-Di-$^{13}$C-methyl-piperidin-1-yl)-$^{13}$C$_2$-acetyl-$^{15}$N-amino]-propionic acid benzyl ester 13

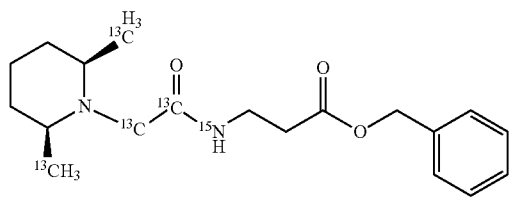

0.37 g (2.1 mmol) ((2S,6R)-2,6-Di-$^{13}$C-methyl-piperidin-1-yl)-$^{13}$C$_2$-acetic acid 11, 0.64 g (4.18 mmol) 1-hydroxybenzotriazole, 0.87 g (4.2 mmol) N,N'-dicyclohexylcarbodiimide and 0.58 ml (4.2 mmol) triethylamine were dissolved in 25 ml dimethylformamide. After 30 minutes stirring at room temperature, 0.78 g (2.21 mmol) 3-$^{15}$N-amino-propanoic acid benzyl ester 12 (as tosylate salt) and 0.58 ml (4.2 mmol) triethylamine were added to the reaction mixture and stirred overnight at room temperature. The solvent was evaporated and the residue was dissolved in 200 ml ethyl acetate, the solution filtered and the filtrate was washed with 1 molar sodium hydroxide solution and saturated sodium chloride solution. The organic phase was dried over magnesium sulphate and the solvent was evaporated. The residue was purified from a first flash chromatography using ethyl acetate and the product was eluted from a second flash chromatography using dichloromethane/methanol 50:1 as eluent.
Yield: 0.69 g (97%)
$R_F$=0.56 (dichloromethane/methanol 10:1)

(xiv) Synthesis of 3-[2-((2S,6R)-2,6-Di-$^{13}$C-methyl-piperidin-1-yl)-$^{13}$C$_2$-acetyl-$^{15}$N-amino]-propanoic acid 14

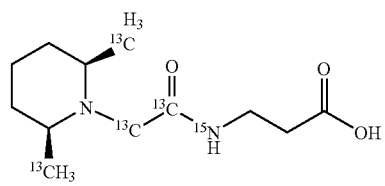

0.69 g (2 mMol) 3-[2-((2S,6R)-2,6-Di-$^{13}$C-methyl-piperidin-1-yl)-$^{13}$C$_2$-acetyl-$^{15}$N-amino]-propanoic acid benzyl ester 12 were dissolved in 20 ml methanol. 0.5 g palladium on charcoal (5%) were added to the solution and the hydrogenation was carried out with 50 ml hydrogen at normal pressure and room temperature for 30 minutes. The reaction mixture was filtered and the solvent evaporated.
Yield: 0.4 g (81%)
$R_F$=0.05 (ethyl acetate/methanol 5:1)

(xv) Synthesis of 3-[2-((2S,6R)-2,6-Di-$^{13}$C-methyl-piperidin-1-yl)-$^{13}$C$_2$-acetyl-$^{15}$N-amino]-propanoic acid 2,5-dioxo-pyrrolidin-1-yl ester 15

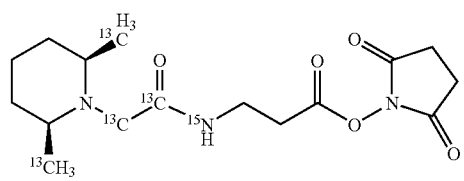 [SMILES: C[C@@H]1CCC[C@H]([13CH3])N1[13CH2][13C](=O)[15NH]CCC(=O)ON1C(=O)CCC1=O]

0.39 g (1.55 mmol) 3-[2-((2S,6R)-2,6-Di-$^{13}$C-methyl-piperidin-1-yl)-$^{13}$C$_2$-acetyl-$^{15}$N-amino]-propanoic acid 13 were added to 170.5 mg (1.48 mmol) N-hydroxysuccinimide and 305.4 mg (1.48 mmol) N,N'-dicyclohexylcarbodiimide dissolved in 10 ml dichloromethane. The reaction mixture was stirred for 16 h at room temperature. The solution was filtered and the filtrate was evaporated in vacuo to dryness. The product was washed with diisopropyl ether.
Yield: 450 mg (84%)
$M_p$=108-109° C.

Example 12

Estimation of the Quantitative Performance of the Duplex Mass Label (TMT) Strategy Applied to a Complex Biological Sample was Performed by the Following Spiking Experiment Mass labelled (TMT) peptides gained from a 8 protein mixture represented the starting material to be spiked into a complex biological sample, a SCX fraction of a protein digest coming from an yeast total lysate sample.

The protein mix consists of equimolar amount (1 nmol) of glyceraldehydes-3-phosphate dehydrogenase (G3P_RABIT), lysozyme (LYC_CHICK), myoglobin (MYG_HORSE), β-galactosidase (BGAL_ECOLI), lactate dehydrogenase (LDHA_RABIT), phosphorylase b (PHS2_RABIT), pyruvate kinase (KPYM_RABIT) and BSA (ALBU_BOVIN), all were purchased from Sigma, Tauficirchen, Germany. The protein mixture was labelled in a duplex strategy with well defined ratios: G3P_RABIT, ratio 1:1; MYG_HORSE, ratio 1:1; PHS2_RABIT, ratio 1:3; LYC_CHICK 1:1; BGAL_ECOLI, ratio 3:1; KPYM_RABIT, ratio 2:1; ALBU_BOVIN ratio 1:2; LDHA_RABIT ratio 1:1. The mass (TMT) labelling procedure was carried out as follows: Briefly, the obtained 2 confected protein samples were dissolved in 50 mM Borate buffer and 1% SDS pH7.5, subjected to reduction and allylation of Cys residue with 1 mM tris[2-Carboxyethylphosphine] (TCEP) and 7.5 mM iodoacetamide (IAA). The 2 protein mixtures were then subjected to tryptic digestion (pH 7.8, 37° C., 20 h, SDS<0.1%), pooled and subjected to the mass (TMT) labelling (20 mM, 3 h, pH7.5) with the dimethyl piperidine (DMP) duplex tags according to the present invention.

The sample was then treated with N-Hydroxylamine (0.25% $NH_2OH$, 30 min).

The mass label (TMT) duplex strategy was also applied to a total lysate fraction of yeast in a 1:1 ratio. Two equivalent portions of the yeast fraction (500 µg for each one) were applied to the mass (TMT) labelling procedure in the same manner as the artificial protein mixture.

After applying the mass (TMT) labelling procedure to the 2 samples, the resulted 2 mass (TMT) labelled peptide mixtures were first purified on a C18 guard column and then fractionated using a SCX chromatography. The purification and desalting step of the 2 peptide fractions were performed on a SunFire C18 guard column (4.6×20 mm, 5 µm, Waters, Eschborn, Germany) using a stepwise gradient (8 mL/min) from 100% buffer A ($H_2O$/ACN/TFA:99.8/0.1/0.1) for 3 min to 50% buffer A and 50% buffer B (ACN/$H_2O$/TFA:99.8/0.1/0.1) for 6 min and 100% buffer B for 8 min. The mass (TMT) labelled peptide mixtures derived from the yeast sample and the peptide mix were then fractionated by Strong Cation Exchange (SCX) chromatography using a PolySulfoethyl A column (4.6×100 mm, 5 µm, 200A, PolyLC Inc, Columbia, Md., USA). Peptides were eluted with 2 successive linear gradients, one starting from 0-250 mM KCl (25% v/v ACN, 5 mM $KH_2PO_4$, pH3) over 20 minutes and continuing from 250 to 500 mM KCl (25% v/v ACN, 5 mM KH2PO4, pH3) over 10 min, both at a flow rate of 2 ml/min with fractions collected at 1 minute intervals.

LC-MS/MS analyses of the collected fractions of the mass (TMT) labelled peptide mixture from the artificial protein mix and from a SCX fraction of the yeast sample were separately carried out in QT of II in order to estimate their concentration by using the base peak trace. The ratio of artificial mix to yeast lysate ranged from 1:1 to 1:10 w/w. (1:1; 1:1.5; 1:2; 1:3; 1:4; 1:5; 1:8; 1:10). The different spiked samples were analyzed in LC-MS/MS using the QToF II. The relative ratios of the parent proteins from the 8 artificial protein mix were then quantified in this complex proteome background. In addition, for one SCX fraction we evaluated all MS/MS profiles to identify as many yeast proteins and determine the relative concentration reported by the mass label (TMT) duplex reagents.

Data analysis and interpretation: Peptide and protein identification were performed using the SEQUEST and Protein-Prophet search engine. Yeast database was used to identify proteins from the yeast fraction and a small in-house developed database was employed to identify the peptides coming from the 8 protein mix. The SEQUEST search was applied to the identification of the 8 protein mix. Signature-ion peak area from the mass label (TMT) fragments (mass marker moiety, X) were extracted from the SEQUEST data files to perform the relative quantification. The quantitative data were then matched to the list of identified peptide sequences using our prototype software tool. The relative abundance ratio calculations were based on the value of the integration of the mass label (TMT) reporter ions (mass marker moiety) extracted from the data files. The quantitative results are presented first without and then with a threshold filter to remove peptides where the mass label (TMT) reporter intensity was relatively low (>90 counts in the MS/MS spectrum).

Results

Relative Abundance of Proteins from the Artificial Mix in Yeast Lysate:

The CV's for the relative abundance across all peptides from the same parent protein ranged from 1-10%. When the data was re-analysed to remove peptides where the TMT reporter intensity was relatively low the CV's improved with a maximum level of 6.8%.

Precision of the reported ratio compared to the expected ratio was in the range of −0.7 to +9.8%. In all cases the reported ratios were essentially unaffected by the ratio of Artificial Mix to Yeast Lysate.

Figure 23A:
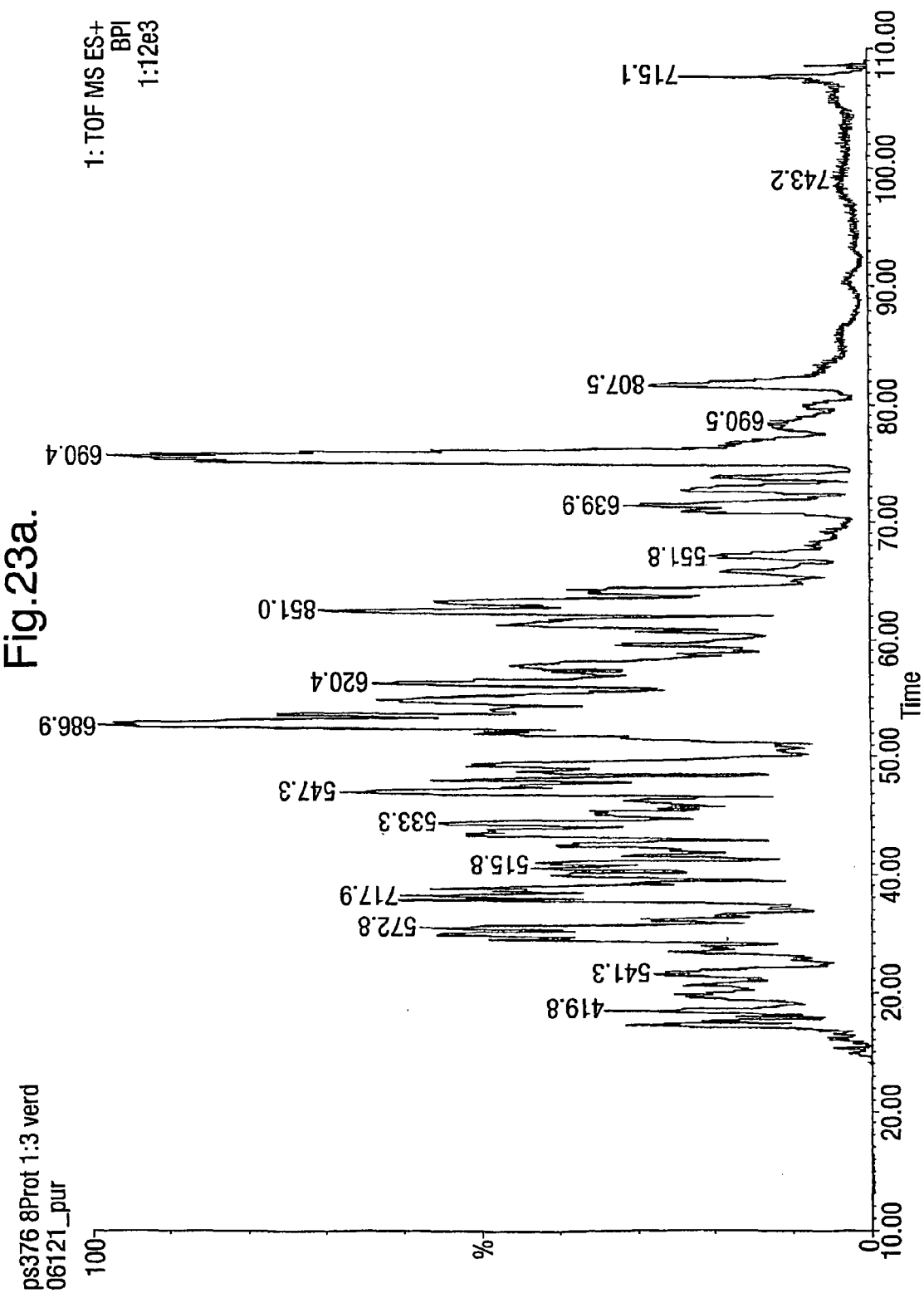
FIGS. 23a and 23b show base peak chromoatograms of proteins labelled with mass labels of the present invention.
Figure 23B:
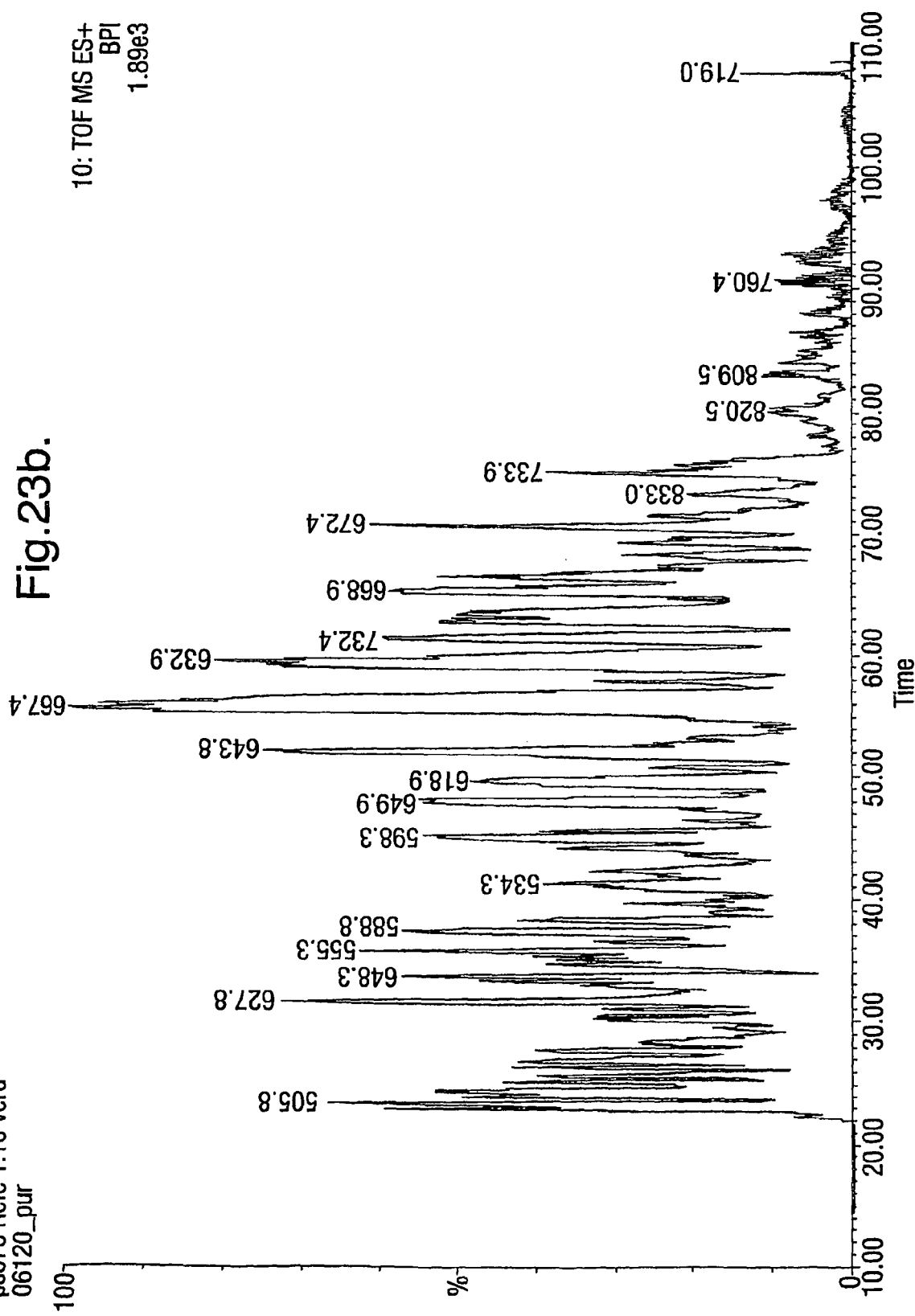

FIGS. 23a and 23b show Base Peak Chromatograms of the stock solutions of the TMT labelled peptide mixtures (a) from the 8 protein mix and (b) from a yeast protein fraction.

Figure 24A:
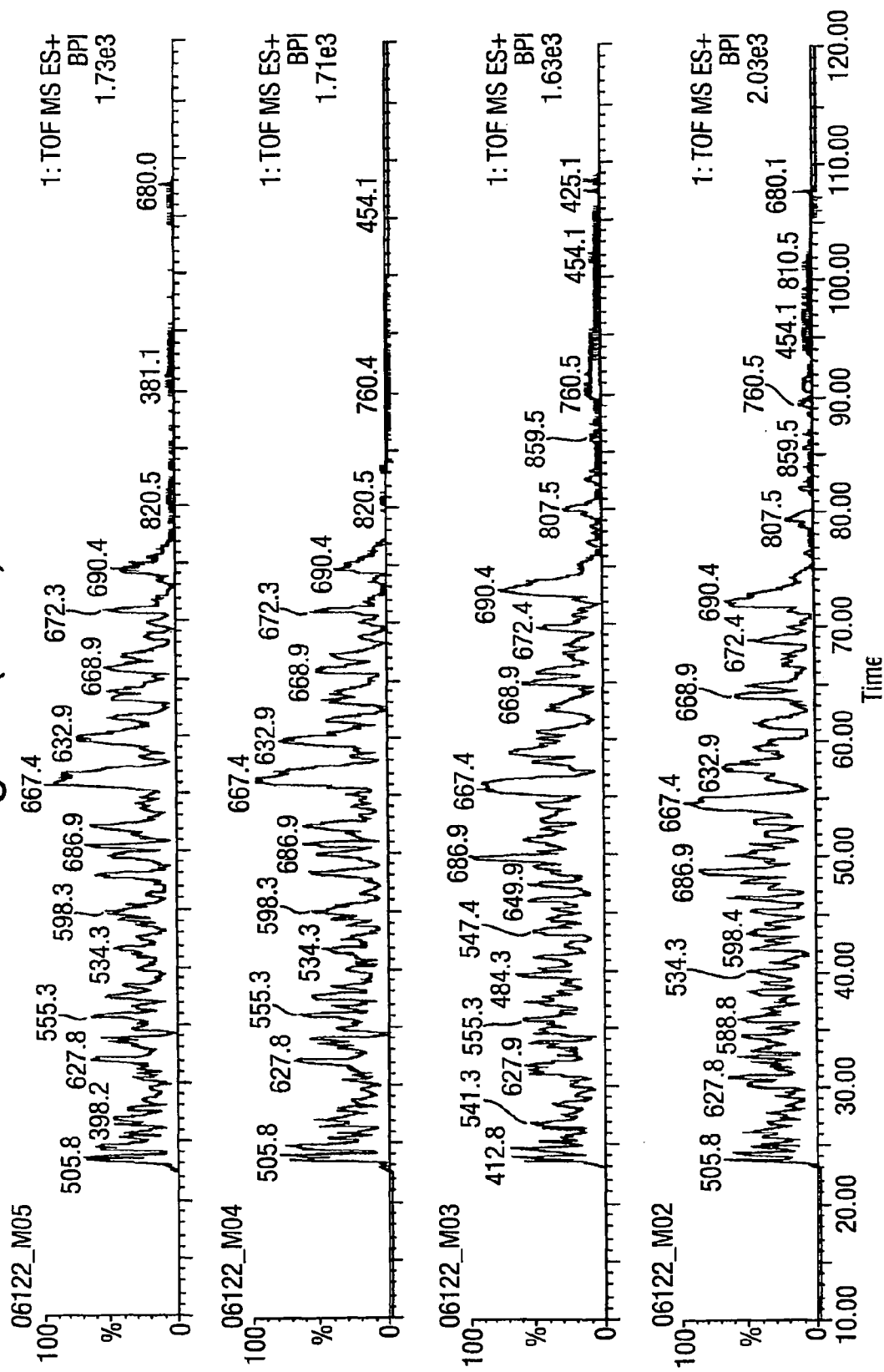
FIGS. 24a and 24b show base peak chromoatograms of proteins labelled with mass labels of the present invention.

FIG. 24a. Base Peak Chromatograms of the different dilution of the TMT labelled peptide mixture from the 8 protein mix when spiked in the complex TMT labelled peptide mixture from a yeast protein fraction.

Figure 24B:
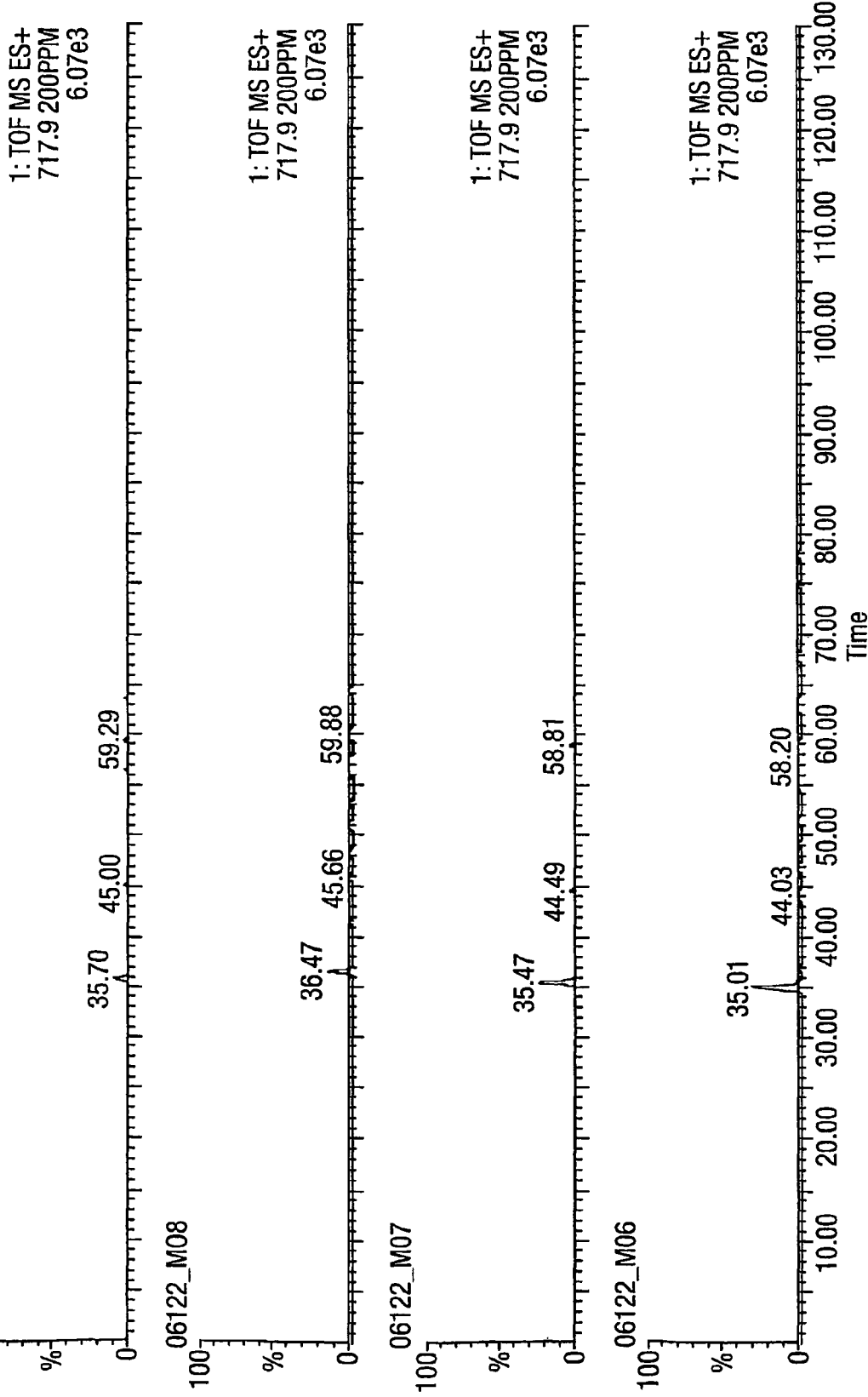
Figure 24B:
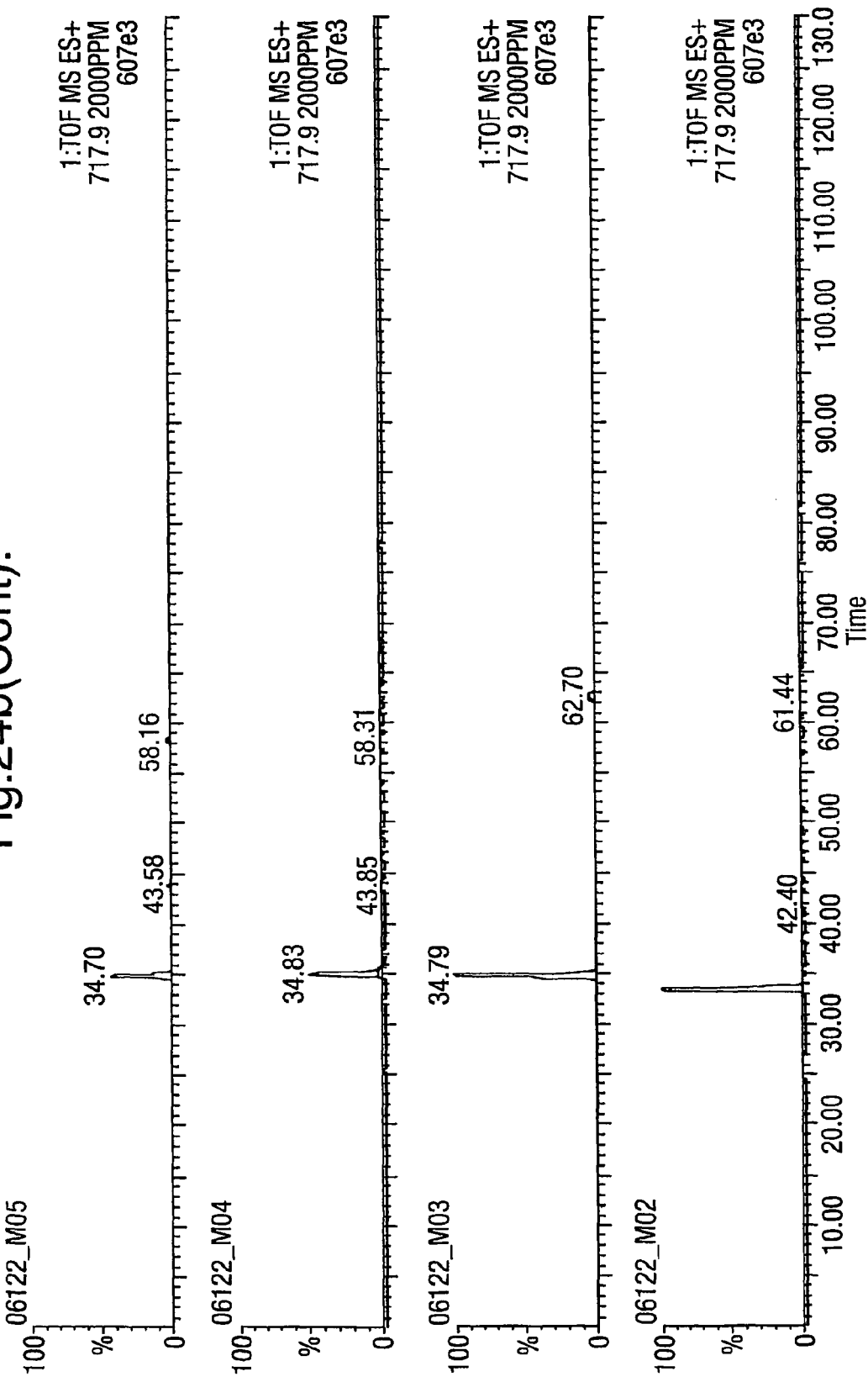

FIG. 24b. Base Peak Chromatograms of the identified peptide D*YSVTANSK* from the protein LDHA_RABIT (P13491). The depicted Base Peak Chromatograms show the mass intensity of the peptide within the spiking experiments using 8 different concentrations of the TMT mass labelled peptide mixture from the 8 protein mix spiked into the TMT mass labelled peptide mixture from the yeast fraction, i.e. 1:1, 1:1.5, 1:2, 1:3, 1:4, 1:5, 1:8, 1:10, which is illustrated from the bottom to the top, respectively.

Figure 25:
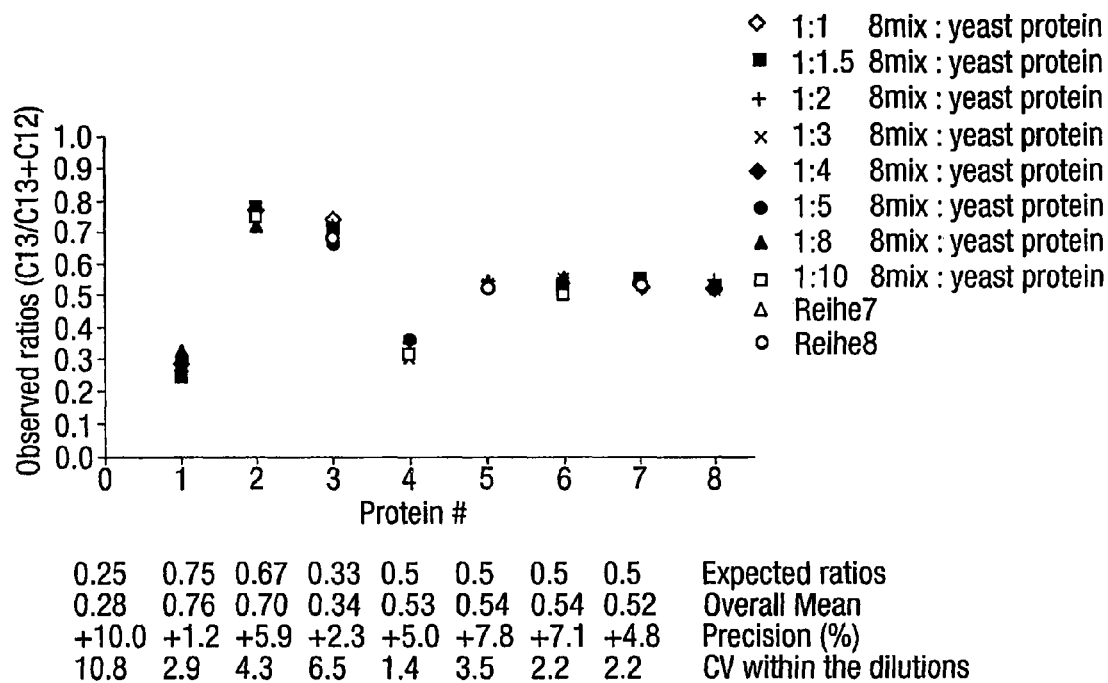
FIG. 25 shows relative quantification data from a mix of proteins (artificial mix) labelled with mass labels according to the present invention.

FIG. 25. Relative quantitative data from the Artificial Mix: Protein ratios for each dilution experiment and protein. Protein 1 represents βGAL_ECOLI, protein 2 PHS2_RABIT, protein 3 ALBU_BOVIN, protein 4 KPYM_RABIT, protein 5 G3P_RABIT, protein 6 LDHA_RABIT, protein 7 MYG_HORSE and protein 8 LYS_CHECK. Each protein displays 8 different dot points corresponding to the dilution of the artificial mix spiked in the yeast digest fraction.

Figure 26:
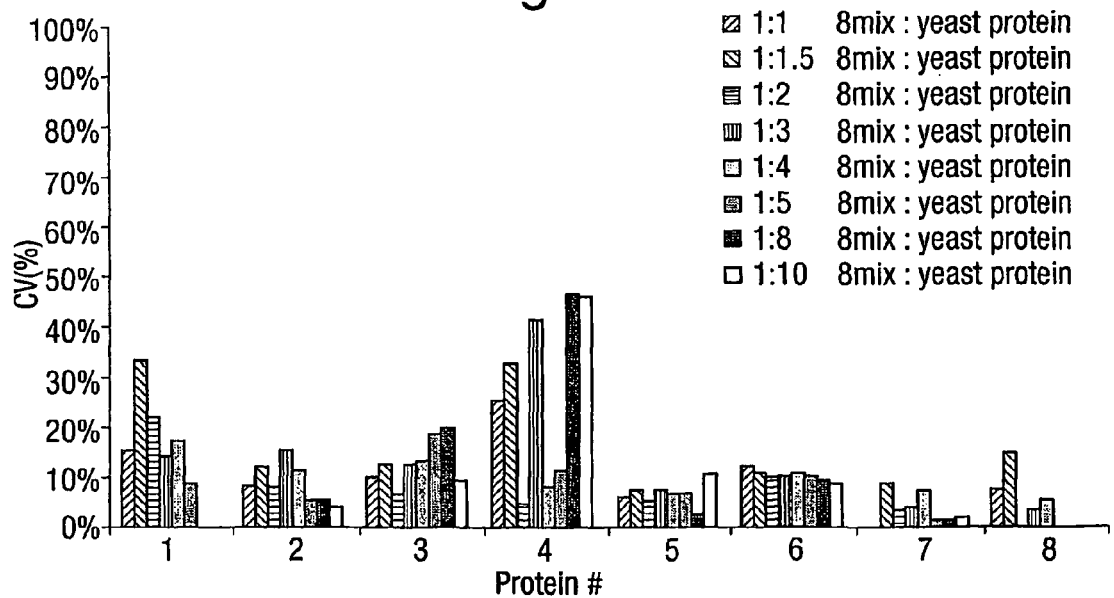
FIG. 26 shows the corresponding CVs of each protein from the mix of proteins labelled with mass labels according to the present invention from FIG. 25.

FIG. 26. Corresponding CVs of each protein for each dilution. Data are linked to the ratios from the FIG. 25.

Figure 27:
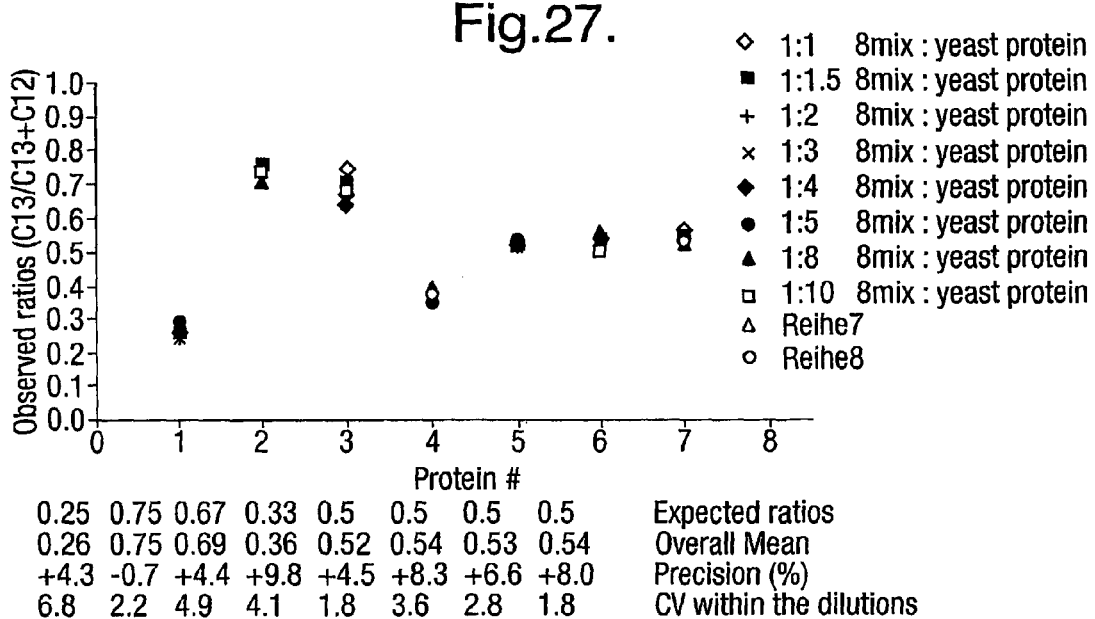
FIG. 27 shows relative quantification data from a mix of proteins (artificial mix) labelled with mass labels according to the present invention after applying a threshold filter to remove peptides which low intense mass marker moiety fragments in MS/MS spectrum.

FIG. 27. Relative quantitative data from the Artificial Mix: Protein ratios for each dilution experiment and protein after applying a threshold filter to remove peptides with low intensity TMT reporter ions (mass marker moieties) in the MS/MS spectrum.

Figure 28:
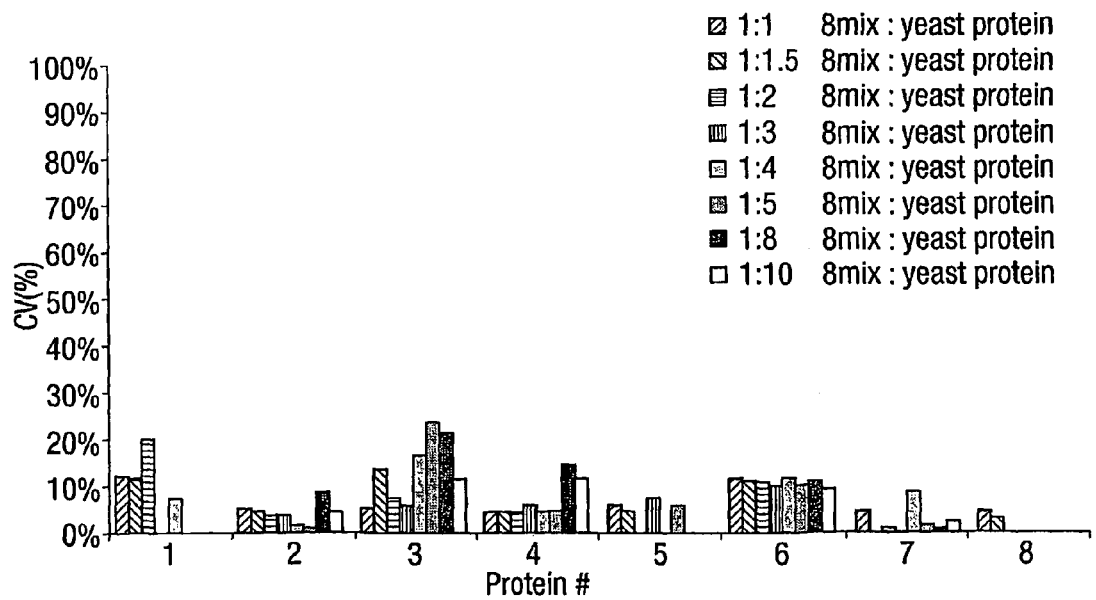
FIG. 28 shows the corresponding CVs of each protein from the mix of proteins labelled with mass labels according to the present invention from FIG. 27.

FIG. 28. Corresponding CVs of each protein for each dilution. Data are linked to the ratios from the FIG. 27.

Relative Abundance of Yeast Proteins in the Yeast Lysate

The standard MS/MS parameters run in this experiment permitted identification and quantification of 94-126 different yeast protein depending on the protein mix and MS filtering algorithms employed. The expected ratio of yeast proteins for all experiments was 0.5 though the TMT mass label duplex reagents consistently reported a ratio of 0.42-0.43. CV's were typically in the range of 15-25% for unfiltered data with significant improvement to 5-6% when the low-intensity filter was applied.

FIGS. 29 a and b. Distribution of the ratios of the different identified proteins from a SCX yeast fraction w/o the artificial mix.

FIG. 29a. By considering all the peptides, the average mean of the 129 identified proteins with 509 peptides is 0.43 with an average CV of 24.3%. 74.5% of the peptides show a CV between 0-10%, 6.1% between 10-20% and 19.4% above 20%.

FIG. 29b. By applying a threshold filter to remove the peptides having their TMT reporters (mass marker moieties) below 90 counts in MS/MS, the average mean of the 116 identified proteins with 393 peptides is 0.42 with an average CV of 5%. Now, 94.3% of the peptides show a CV between 0-10%, 2.3% between 10-20% and only 3.4% above 20%.

Figure 30A:
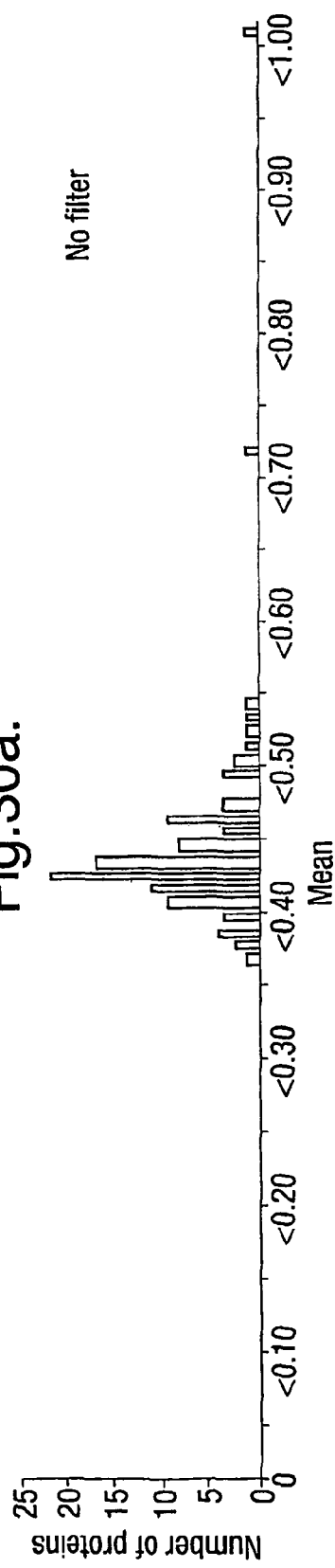
FIGS. 30a and 30b show the distribution of the ratios of the different identified proteins from a strong cation exchange chromatography yeast fraction spiked with the artificial mix in a 1:1 proportion.

FIGS. 30a and b. Distribution of the ratios of the different identified proteins, from a SCX yeast fraction spiked with the artificial mix in a 1:1 proportion.

FIG. 30a. By considering all the peptides, the average mean of the 103 identified proteins with 363 peptides is 0.43 and these proteins show an average CV of 16.5%.

Precisely, 69.9% of the proteins show a CV between 0-10%, 12.3% between 10-20% and 17.8% above 20%.

Figure 30B:
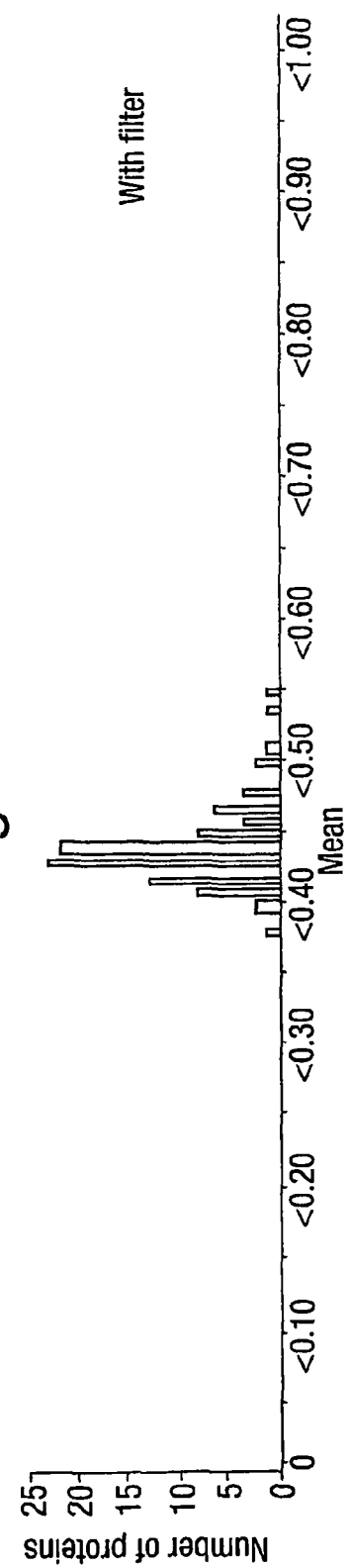

FIG. 30b. By applying a threshold filter to remove the peptides having their TMT reporters (mass marker moieties) below 90 counts in MS/MS, the average mean of the 94 identified proteins with 276 peptides is 0.42 and the average CV is 6.4%. Now, 88.5% of the proteins show a CV between 0-10%, 8.2% between 10-20% and only 3.3% above 20%.

FIGS. 31 a and b. Distribution of the ratios of the different identified proteins from a SCX yeast fraction spiked with the artificial mix in a 1:0.1 proportion, respectively.

Figure 31A:
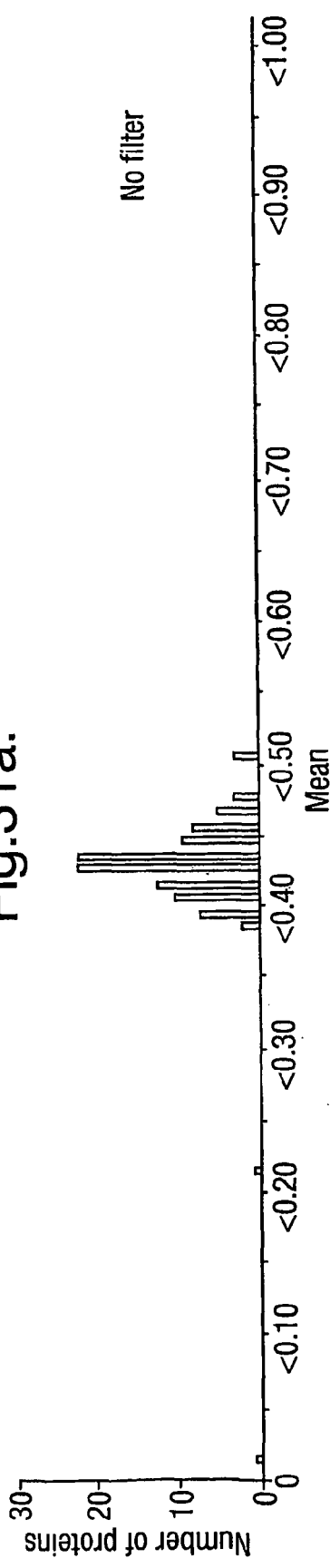
FIGS. 31a and 31b show the distribution of the ratios of the different identified proteins from a strong cation exchange chromatography yeast fraction spiked with the artificial mix in a 1:0.1 proportion.

FIG. 31a. By considering all the peptides, the average mean of the 107 identified proteins with 401 peptides is 0.42 and these proteins show an average CV of 14.6%. Precisely, 76.7% of the proteins show a CV between 0-10%, 12.8% between 10-20% and 10.5% above 20%.

Figure 31B:
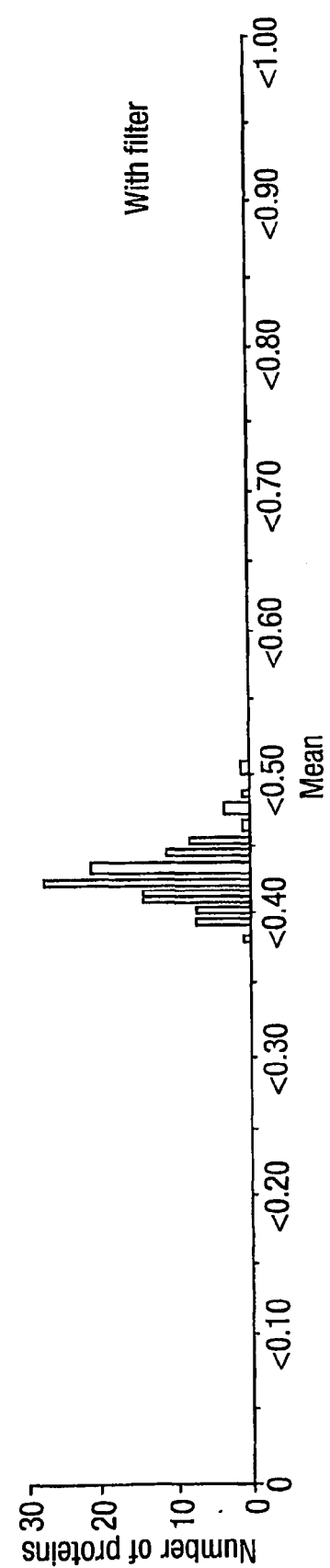

FIG. 31b. By applying a threshold filter to remove the peptides having their TMT reporters (mass marker moieties) below 90 counts in MS/MS, the average mean of the 103 identified proteins with 303 peptides is 0.42 and the average CV is 5.1%. Now, 89% of the proteins show a CV between 0-10%, 9% between 10-20% and less than 1% above 20%.

Example 13

Experiments to Estimate the Quantitative Performance of the 6-Plex Mass labels (TMT Reagents)

1—Peptide mixture: Model tryptic peptides used to estimate the quantitative performance of the 6-plex strategy:

| Peptide 1: | FSWGAEGQR | MW: 1037.11 |
| Peptide 2: | VATVSLHPR | MW: 979.16 |
| Peptide 3: | VATVSLPR | MW: 842.01 |

Reactive mass (TMT) labels from the 6-plex strategy: Carbon 13 or a Nitrogen 15 when labelled with an asterisk.

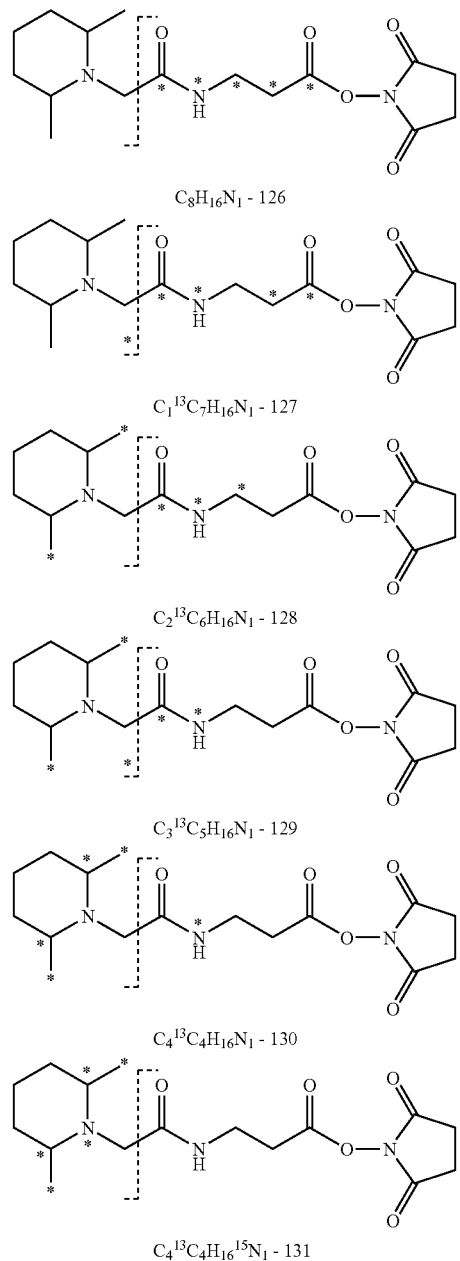

$C_8H_{16}N_1$ - 126

$C_1{}^{13}C_7H_{16}N_1$ - 127

$C_2{}^{13}C_6H_{16}N_1$ - 128

$C_3{}^{13}C_5H_{16}N_1$ - 129

$C_4{}^{13}C_4H_{16}N_1$ - 130

$C_4{}^{13}C_4H_{16}{}^{15}N_1$ - 131

General Coupling Reaction Protocol to the Model Peptides:

The peptide mixture (0.2 μmol for each peptide) dissolved in 83 μl water/ACN (ratio 1:9) were mixed to 82 μl Borate buffer (200 mM) and the pH of the solution was adjusted to 7.8. The TMT reagent (reactive mass label) (15 mM) dissolved in 23 μl DMF was then added to the peptide solution. After stirring for 2 h at RT, the respective peptide reaction mixtures were pooled together in the given proportion. The final mixture was then purified using HPLC (Phenomenex Luna—250 mm/4.6 mm—5μ C18) and the labelled peptide was analysed in LC-MS-MS/MS.

FIG. 32. FIG. 32 shows the relative protein measurement of 3 peptides labelled with the TMT reagents in a 6-plex strategy. Each peptides is labelled in an equimolar proportion (1:1:1:1:1:1 for 126:127:128:129:130:131) The ratios were measured as follows TMT/(TMT+control), where the control and the TMT (mass label) values are represented by their peak areas. The expected ratio for each peptide is 0.5.

Figure 33:
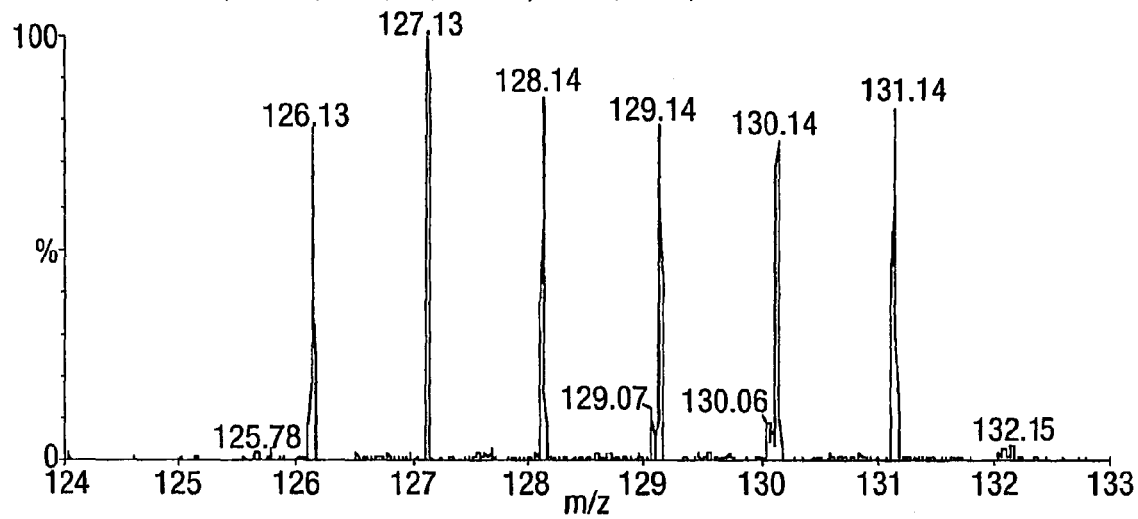
FIG. 33 shows the signature ion regions from, a peptide labelled with a mass label of the present invention.

FIG. 33. Example of the signature ion regions from the peptide TMT-VATVSLHPR TMT labelled in a 1:1:1:1:1:1 ratios reflected by the TMT reporter ion (mass marker moiety) series 126.1, 127.1, 128.1, 129.1, 130.1, and 131.1.

FIG. 34. Relative quantification of confected ratios was carried out from the 3 tryptic described tryptic model peptides. Aliquots of each peptide are labelled with the 6 TMT reagents (mass labels) in proportion 1:5:2:1:0.5:0.2. The TMT reporter fragment (mass marker moiety) ESI-MS/MS data was fitted with a regression line for 5 different expected and observed ratios for each 3 described peptides. Intensity of each reporter ions were determined by measuring their peak area at 126.1, 127.1, 128.1, 129.1, 130.1, and 131.1. TMT reporter ion (mass marker moiety) 126 is taken as the control to calculate the 5 ratios. The ratios were measured as follows TMT/(TMT+control), where the control and the TMT values are represented by their peak areas. The expected ratios for each protein are 0.83, 0.67, 0.50, 0.33 and 0.16.

Figure 35:
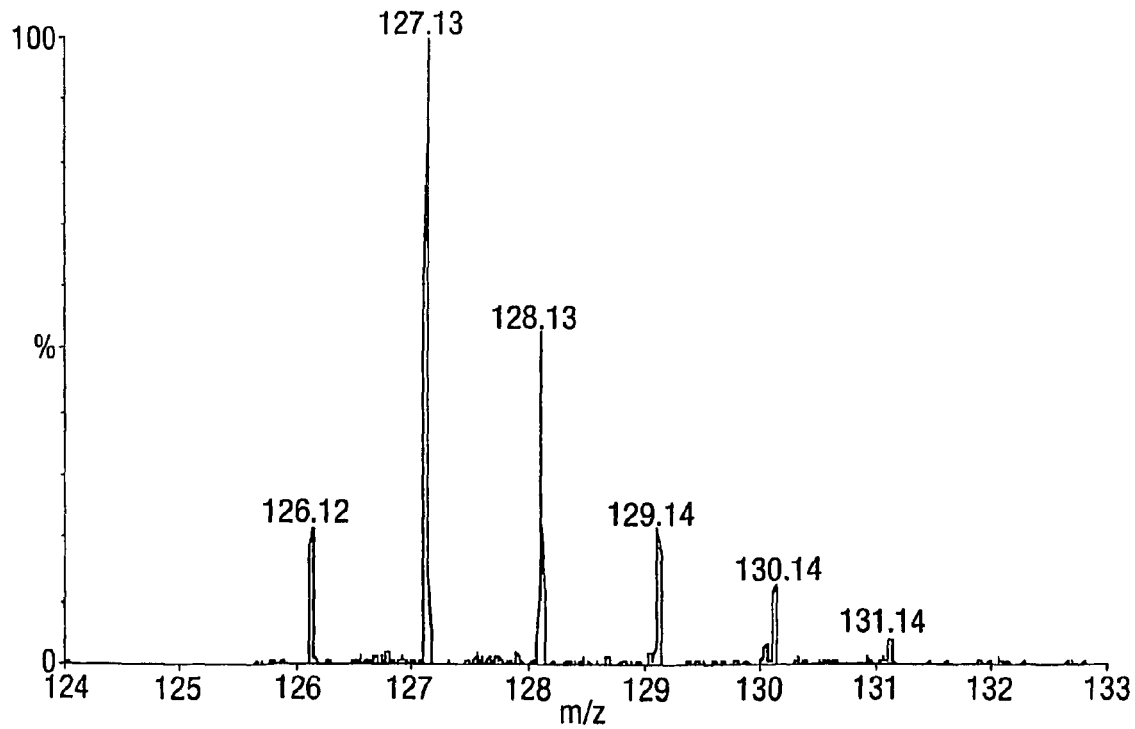
FIG. 35 shows the signature ion regions from a peptide labelled with a mass label of the present invention.

FIG. 35. Example of the signature ion regions from the peptide TMT-VATVSLHPR TMT labelled in a 1:5:2:1:0.5: 0.2 ratios reflected by the TMT reporter ion (mass mark moiety) series 126.1, 127.1, 128.1, 129.1, 130.1, and 131.1. 2—Protein mixture: Proteins used in the protein mixture to estimate the quantitative performance of the 6-plex strategy: protein 1, βGAL_ECOLI; protein 2, PHS2_RABIT; protein 3, ALBU_BOVIN; protein 4, KPYM_RABIT; protein 5; G3P_RABIT; protein 6, LDHA_RABIT The following examples show the precision and analytical variability of the tagging protocol based on analysis of a six protein mixture:

Example 14

FIG. 36. Six equivalent aliquots of each of six proteins was labelled with a different member of the TMT six-plex. All 36 protein-tag mixtures are then pooled and analysed in a single LC-MS/MS run. The relative quantitative data are shown for 5 ratios for each protein after applying a threshold filter to remove peptides with low intense TMT reporter ions in MS/MS spectrum. Each protein is labelled in an equimolar proportion (1:1:1:1:1:1 for 126:127:128:129:130:131) and TMT fragment 126 is taken as the control fragment to calculate the 5 ratios. The ratios were measured as follows TMT/ (TMT+control), where the control and the TMT values are represented by their peak areas. Expected ratios are in that case 0.5.

Example 15

FIG. 37. Six different amounts of each protein labelled with each TMT six-plex member to produce five ratios as shown. The relative quantitative data are depicted for each protein for 5 ratios after applying a threshold filter to remove peptides with low intense TMT reporter ions in MS/MS spectrum. Each protein is labelled with different proportion (1:5: 2:1:0.5:0.2 for 126:127:128:129:130:131). TMT fragment 126 is taken as the control fragment and the ratios was calculated as follows TMT/(TMT+control) e.g. 127/(127+126) where the control and the TMT values are represented by their peak areas. The expected ratios for each protein are 0.83, 0.67, 0.50, 0.33 and 0.16.

MS/MS Analysis of Mass Labelled-Peptides
Protocol for MS/MS Experiments:
MS and MS/MS analyses were performed on a QTOF2 mass spectrometer (Micromass, Manchester, UK). HPLC analysis was performed with a CAP-LC HPLC system (Waters Corporation, Milford, Mass., USA) (Column: PepMap™ C18 HPLC column from Dionex with a 75 μm inner diameter and a length of 150 mm; Solvents: 95% Water to 95% Acetonitrile both with 0.2% Formic Acid).

Ion abundance ratios were determined by summation and smoothing of spectra for each peptide as it is ionised in the electrospray source followed by determination of peak area of the corresponding TMT reporter ions.

The invention claimed is:

1. A reactive mass label for labelling and detecting a biological molecule by mass spectrometry, comprising a mass label X-L-M and a reactive functionality bonded to M of the mass label, wherein X is a mass marker moiety comprising a group selected from the following groups:

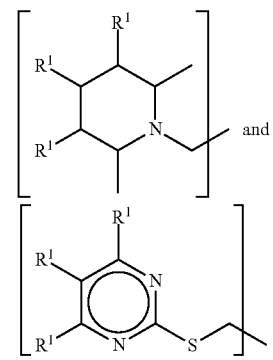

wherein each $R^1$ is independently H, a substituted or unsubstituted straight or branched $C_1$-$C_6$ alkyl group, a substituted or unsubstituted aliphatic cyclic group, a substituted or unsubstituted aromatic group or a substituted or unsubstituted heterocyclic group; L is a cleavable linker comprising an amide bond and M is a mass normalization moiety, and wherein when X is

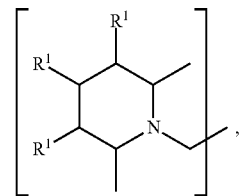

the reactive functionality is selected from a group consisting of: an N-hydroxysuccinimide ester group, —C(=O)NRNR$_2$, and a maleimide group, and wherein when X is

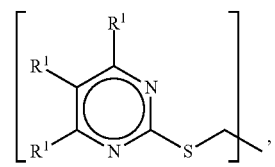

the reactive functionality is selected from a group consisting of: an N-hydroxysuccinimide ester group, —C(=O)NHNH$_2$, a thiol group, and a maleimide group.

2. A reactive mass label for labelling and detecting a biological molecule by mass spectrometry, comprising a mass label X-L-M and a reactive functionality bonded to M of the mass label, wherein X is a mass marker moiety comprising a group selected from the following groups:

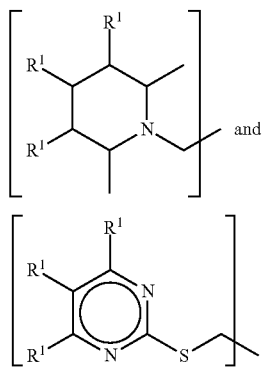

wherein each R$^1$ is independently H, a substituted or unsubstituted straight or branched C$_1$-C$_6$ alkyl group, a substituted or unsubstituted aliphatic cyclic group, a substituted or unsubstituted aromatic group or a substituted or unsubstituted heterocyclic group; L is a cleavable linker comprising an amide bond and M is a mass normalization moiety, and wherein the reactive functionality is selected from a group consisting of:

—SO$_2$—CH=CR$_2$, —NCO, —NCS, —SO$_2$Cl,

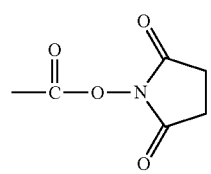

and

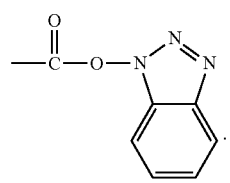

3. A reactive mass label for labelling and detecting a biological molecule by mass spectrometry, comprising a mass label X-L-M and a reactive functionality bonded to M of the mass label, wherein X is a mass marker moiety comprising a group selected from the following groups:

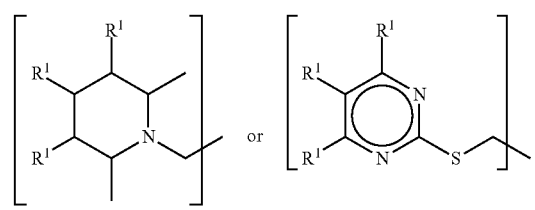

wherein each R$^1$ is independently H, a substituted or unsubstituted straight or branched C$_1$-C$_6$ alkyl group, a substituted or unsubstituted aliphatic cyclic group, a substituted or unsubstituted aromatic group or a substituted or unsubstituted heterocyclic group; L is a cleavable linker comprising an amide bond; and M is a mass normalization moiety, and wherein the reactive functionality comprises the following group:

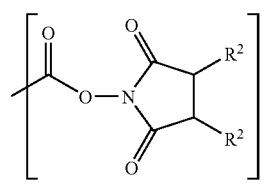

wherein each R$^2$ is independently H, a substituted or unsubstituted straight or branched C$_1$-C$_5$ alkyl group, a substituted or unsubstituted aliphatic cyclic group, a substituted or unsubstituted aromatic group or a substituted or unsubstituted heterocyclic group, wherein X, L, M and the reactive functionality comprise 0, 1 or more of an isotopic substituent.

4. The reactive mass label according to claim 3, wherein the aggregate molecular weight of the mass label X-L-M is 600 Daltons or less.

5. The reactive mass label according to claim 3, wherein the molecular weight of the mass marker moiety is 300 Daltons or less.

6. The reactive mass label according to claim 3, wherein the mass marker moiety comprises a group selected from the following groups:

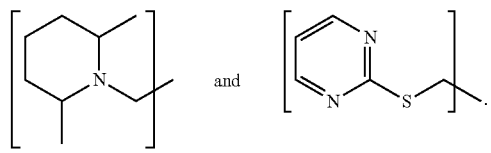

7. The reactive mass label according to claim 3, wherein the cleavable linker attaching the mass marker moiety to the mass normalization moiety is a linker cleavable by collision.

8. The reactive mass label according to claim 7, wherein the linker is cleavable by Collision Induced Dissociation (CID) or Surface Induced Dissociation (SID) using mass spectrometry.

9. The reactive mass label according to claim 3, wherein the mass normalization moiety comprises one or more of a substituted or unsubstituted straight chain C$_1$-C$_{20}$ alkyl group, a substituted or unsubstituted branched C$_1$-C$_{20}$ aliphatic group and an amino acid.

10. The reactive mass label according to claim 9, wherein the mass normalization group comprises a $C_1$-$C_6$ substituted or unsubstituted aliphatic group.

11. The reactive mass label according to claim 3, wherein the reactive functionality comprises the following group:

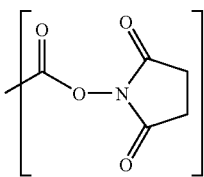

12. The reactive mass label according to claim 11, wherein the reactive mass label has one of the following structures:

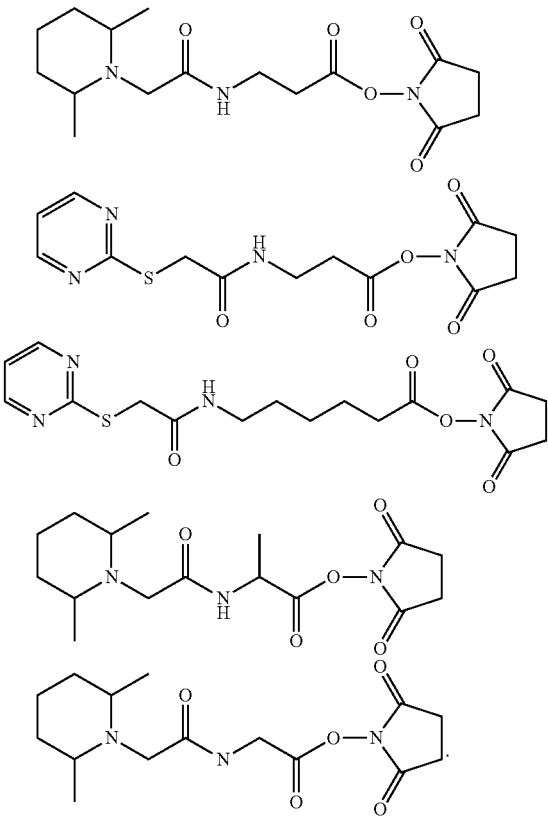

13. The reactive mass label according to claim 3, wherein $R^1$ comprises a sensitivity enhancing group.

14. The reactive mass label according to claim 13, wherein the sensitivity enhancing group is a pre-ionised group.

15. The reactive mass label according to claim 3, wherein $R^1$ comprises an affinity capture ligand.

16. The reactive mass label according to claim 3, wherein the reactive mass label is for labelling and detecting a biological molecule selected from a DNA, an RNA, an oligonucleotide, a nucleic acid base, a protein, a peptide, an amino acid and an analogue of any of the above.

17. A method of labeling a biological molecule, the method comprising reacting the biological molecule with the reactive mass label of claim 3.

18. The method of claim 17, wherein following the reacting of the biological molecule with the reactive mass label, the biological molecule is attached to the mass normalization moiety via a remaining portion of the reactive functionality.

19. The method of claim 18, wherein the biological molecule is selected from a DNA molecule, an RNA molecule, an oligonucleotide, a nucleic acid base, a protein, a peptide, an amino acid, and an analogue of any of the above.

20. A method of analysis, which method comprises reacting a biological molecule with the reactive mass label of claim 3 to form a labelled biological molecule, and detecting the biological molecule by identifying by mass spectrometry the mass label X-L-M.

21. The method according to claim 20, further comprising the step of separating the labelled biological molecule from an unlabeled analyte.

22. The method according to claim 20, wherein the mass spectrometry is tandem mass spectrometry.

23. The method according to claim 20, wherein the labelled biological molecule is separated from the unlabelled analyte by reverse phase high pressure liquid chromatography, cation exchange chromatography or size exclusion chromatography.

24. A set of reactive mass labels, wherein each reactive mass label in the set is as defined in claim 3 and wherein the mass normalization moiety M of the mass label X-L-M of each reactive mass label in the set ensures that the corresponding mass label has a desired aggregate mass, and wherein the set comprises:
    a group comprising a plurality of the reactive mass labels, wherein the mass marker moiety X of each reactive mass label in the group is of common mass, and each reactive mass label in the group has a unique aggregate mass; or
    a group comprising a plurality of the reactive mass labels, wherein the mass marker moiety X of each reactive mass label in the group has a mass different from each other mass marker moiety in the group, and each reactive mass label in the group has a common aggregate mass; and
    wherein when each of the reactive mass labels in the set is reacted with a biological molecule to form a labelled biological molecule, each labelled biological molecule is distinguishable from each other by mass spectrometry.

25. The set of reactive mass labels according to claim 24, wherein the mass marker moiety of each reactive mass label in the set has a common mass and each reactive mass label in the set has a unique aggregate mass.

26. The set of reactive mass labels according to claim 24, wherein the mass marker moiety of each reactive mass label in the set has a unique mass and wherein each reactive mass label in the set has a common aggregate mass.

27. The set of reactive mass labels according to claim 24, wherein the mass marker moiety comprises a group selected from the following groups:

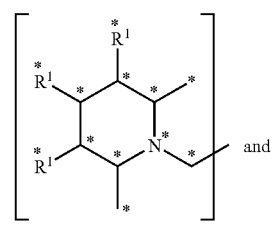

and

-continued

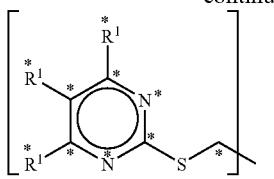

wherein the mass marker moiety comprises 0, 1 or more of the isotopic substituent * such that either:
  the mass marker moiety of each reactive mass label in the set has a common mass and each reactive mass label in the set has a unique aggregate mass; or
  the mass marker moiety of each reactive mass label in the set has a unique mass and each reactive mass label in the set has a common aggregate mass.

28. The set of reactive mass labels according to claim 27, wherein the mass marker moiety comprises a group selected from the following groups:

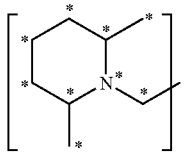 and 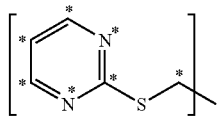

wherein the mass marker moiety comprises 0, 1 or more of the isotopic substituent * such that either:
  the mass marker moiety of each reactive mass label in the set has a common mass and each reactive mass label in the set has a unique aggregate mass; or
  the mass marker moiety of each reactive mass label in the set has a unique mass and each reactive mass label in the set has a common aggregate mass.

29. The set of reactive mass labels according to claim 24, wherein the reactive functionality comprises the following group:

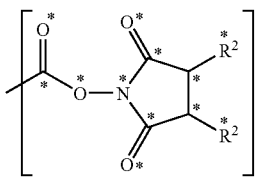

wherein $R^2$ is independently H, a substituted or unsubstituted straight or branched $C_1$-$C_6$ alkyl group, a substituted or unsubstituted aliphatic cyclic group, a substituted or unsubstituted aromatic group or a substituted or unsubstituted heterocyclic group, and the reactive functionality comprises 0, 1 or more of the isotopic substituent * such that either:
  the mass marker moiety of each reactive mass label in the set has a common mass and each reactive mass label in the set has a unique aggregate mass; or
  the mass marker moiety of each reactive mass label in the set has a unique mass and each reactive mass label in the set has a common aggregate mass.

30. The set of reactive mass labels according to claim 29, wherein the reactive functionality comprises the following group:

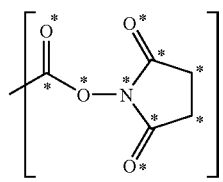

wherein the reactive functionality comprises 0, 1 or more of the isotopic substituent * such that either:
  the mass marker moiety of each reactive mass label in the set has a common mass and each reactive mass label in the set has a unique aggregate mass; or
  the mass marker moiety of each reactive mass label in the set has a unique mass and each reactive mass label in the set has a common aggregate mass.

31. The set of reactive mass labels according to claim 24, wherein the set comprises two or more of the reactive mass labels having the following structure:

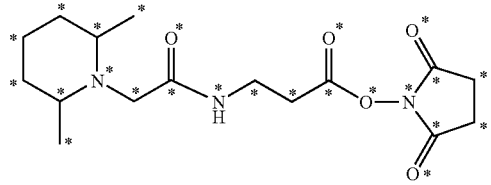 [SMILES: CC1CCCC(C)N1CC(=O)NCCC(=O)ON1C(=O)CCC1=O]

wherein the isotopic substituent * represents that the oxygen is $^{18}O$, the carbon is $^{13}C$ or the nitrogen is $^{15}N$, and wherein each reactive mass label in the set comprises one or more * such that either:
  the mass marker moiety of each reactive mass label in the set has a common mass and each reactive mass label in the set has a unique aggregate mass; or
  the mass marker moiety of each reactive mass label in the set has a unique mass and each reactive mass label in the set has a common aggregate mass.

32. The set of reactive mass labels according to claim 24, wherein the set comprises two or more of the reactive mass labels having the following structure:

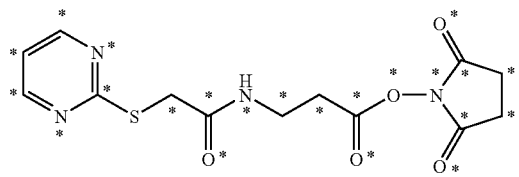 [SMILES: O=C(CSc1ncccn1)NCCC(=O)ON1C(=O)CCC1=O]

wherein the isotopic substituent * represents that the oxygen is $^{18}O$, carbon is $^{13}C$ or the nitrogen is $^{15}N$, and wherein each reactive mass label in the set comprises one or more * such that either:
  the mass marker moiety of each reactive mass label in the set has a common mass and each reactive mass label in the set has a unique aggregate mass; or
  the mass marker moiety of each reactive mass label in the set has a unique mass and each reactive mass label in the set has a common aggregate mass.

33. The set of reactive mass labels according to claim 24, wherein the set comprises two or more of the reactive mass labels having the following structure:

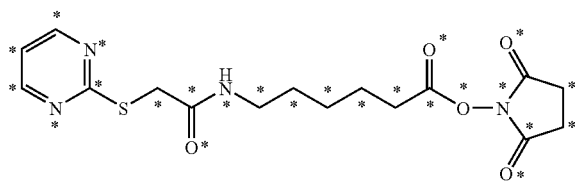 [SMILES: O=C(CSc1ncccn1)NCCCCCC(=O)ON1C(=O)CCC1=O]

wherein the isotopic substituent * represents that the oxygen is $^{18}O$, carbon is $^{13}C$ or the nitrogen is $^{13}N$, and wherein each reactive mass label in the set comprises one or more * such that either:
the mass marker moiety of each reactive mass label in the set has a common mass and each reactive mass label in the set has a unique aggregate mass; or
the mass marker moiety of each reactive mass label in the set has a unique mass and each reactive mass label in the set has a common aggregate mass.

34. The set of reactive mass labels according to claim 24, wherein the set comprises two or more of the reactive mass labels having the following structure:

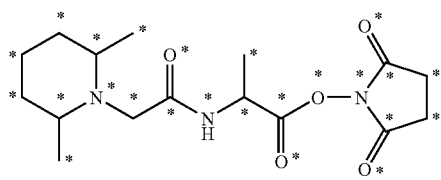 [SMILES: CC(NC(=O)CN1C(C)CCCC1C)C(=O)ON1C(=O)CCC1=O]

wherein the isotopic substituent * represents that the oxygen is $^{18}O$, carbon is $^{13}C$ or the nitrogen is $^{15}N$, and wherein each reactive mass label in the set comprises one or more * such that either:
the mass marker moiety of each reactive mass label in the set has a common mass and each reactive mass label in the set has a unique aggregate mass; or
the mass marker moiety of each reactive mass label in the set has a unique mass and each reactive mass label in the set has a common aggregate mass.

35. The set of reactive mass labels according to claim 24, wherein the set comprises two or more of the reactive mass labels having the following structure:

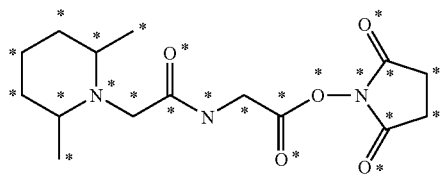 [SMILES: CC1CCCC(C)N1CC(=O)NCC(=O)ON1C(=O)CCC1=O]

wherein the isotopic substituent * represents that the oxygen is $^{18}O$, carbon is $^{13}C$ or the nitrogen is $^{15}N$, and wherein each reactive mass label in the set comprises one or more * such that either:
the mass marker moiety of each reactive mass label in the set has a common mass and each reactive label in the set has a unique aggregate mass; or
the mass marker moiety of each reactive mass label in the set has a unique mass and each reactive mass label in the set has a common aggregate mass.

36. The set of reactive mass labels according to claim 24, wherein the set comprises two or more of the reactive mass labels having the following structure:

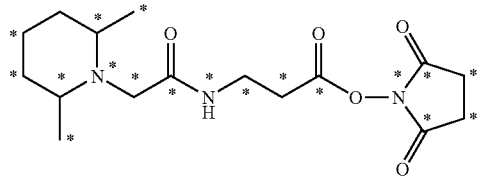

wherein the linker L comprises the isotopic substituent and wherein the isotopic substituent * represents that the carbon is $^{13}C$ or the nitrogen is $^{15}N$, and wherein each reactive mass label in the set comprises one or more * such that either:
the mass marker moiety of each reactive mass label in the set has a common mass and each reactive mass label in the set has a unique aggregate mass; or
the mass marker moiety of each reactive mass label in the set has a unique mass and each reactive mass label in the set has a common aggregate mass.

37. The set of reactive mass labels according to claim 24, wherein the set comprises two or more of the reactive mass labels having the following structure:

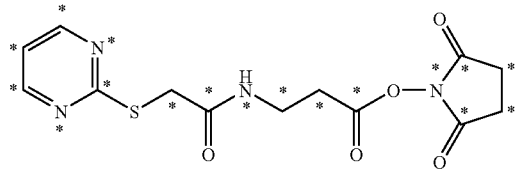 [SMILES: O=C(CSc1ncccn1)NCCC(=O)ON1C(=O)CCC1=O]

wherein the linker L comprises the isotopic substituent and wherein the isotopic substituent * represents that the carbon is $^{13}C$ or the nitrogen is $^{15}N$, and wherein each reactive mass label in the set comprises one or more * such that either:
the mass marker moiety of each reactive mass label in the set has a common mass and each reactive mass label in the set has a unique aggregate mass; or
the mass marker moiety of each reactive mass label in the set has a unique mass and each reactive mass label in the set has a common aggregate mass.

38. The set of reactive mass labels according to claim 24, wherein the set comprises two or more of the reactive mass labels having the following structure:

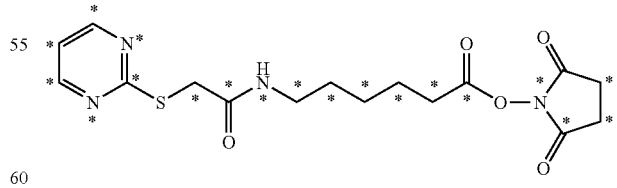

wherein the isotopic substituent * represents that the carbon is $^{13}C$ or the nitrogen is $^{15}N$, and wherein each reactive mass label in the set comprises one or more * such that either:
the mass marker moiety of each reactive mass label in the set has a common mass and each reactive mass label in the set has a unique aggregate mass; or the mass marker moiety of each reactive mass label in the set has a unique mass and each reactive mass label in the set has a common aggregate mass.

39. The set of reactive mass labels according to claim 24, wherein the set comprises two or more of the reactive mass labels having the following structure:

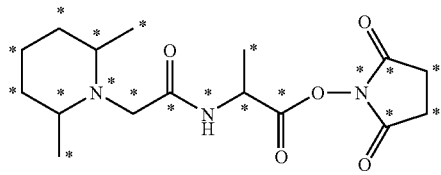 [SMILES: CC(NC(=O)CN1C(C)CCCC1C)C(=O)ON1C(=O)CCC1=O]

wherein the isotopic substituent * represents that the carbon is $^{13}$C or the nitrogen is $^{15}$N, and wherein each reactive mass label in the set comprises one or more * such that either:
  the mass marker moiety of each reactive mass label in the set has a common mass and each reactive mass label in the set has a unique aggregate mass; or
  the mass marker moiety of each reactive mass label in the set has a unique mass and each reactive mass label in the set has a common aggregate mass.

40. The set of reactive mass labels according to claim 24, wherein the set comprises two or more of the reactive mass labels having the following structure:

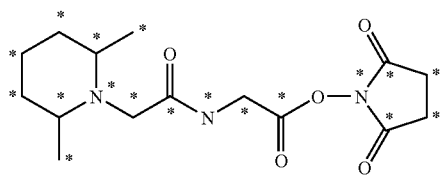 [SMILES: CC1CCCC(C)N1CC(=O)NCC(=O)ON1C(=O)CCC1=O]

wherein the isotopic substituent * represents that the carbon is $^{13}$C or the nitrogen is $^{15}$N, and wherein each reactive mass label in the set comprises one or more such that either:
  the mass marker moiety of each reactive mass label in the set has a common mass and each reactive mass label in the set has a unique aggregate mass; or
  the mass marker moiety of each reactive mass label in the set has a unique mass and each reactive mass label in the set has a common aggregate mass.

41. The set of reactive mass labels according to claim 24, wherein the set comprises two or more of the reactive mass labels having the following structure:

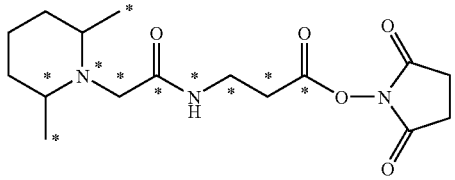 [SMILES: CC1CCCC(C)N1CC(=O)NCCC(=O)ON1C(=O)CCC1=O]

wherein the isotopic substituent * represents that the carbon is $^{13}$C or the nitrogen is $^{15}$N, and wherein each reactive mass label in the set comprises one or more * such that either:
  the mass marker moiety of each reactive mass label in the set has a common mass and each reactive mass label in the set has a unique aggregate mass; or
  the mass marker moiety of each reactive mass label in the set has a unique mass and each reactive mass label in the set has a common aggregate mass.

42. The set of reactive mass labels according to claim 41, wherein the isotopic substituent * is $^{15}$N or $^{13}$C and the set comprises two mass labels having the following structures:

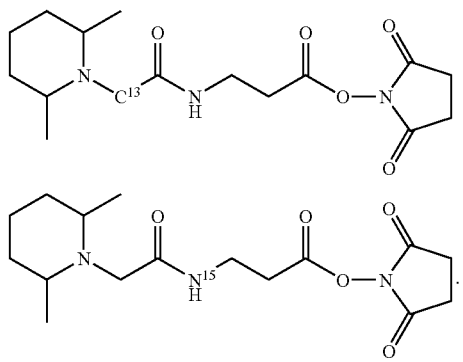

43. The set of reactive mass labels according to claim 41, wherein the isotopic substituent * is $^{15}$N and $^{13}$C and the set comprises six mass labels having the following structures:

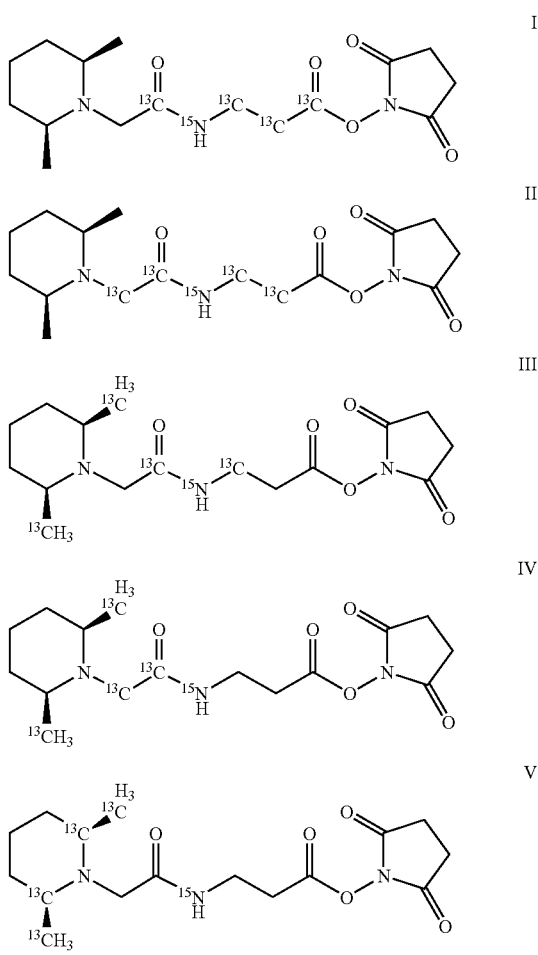

-continued

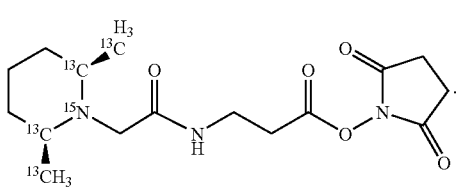

VI

44. The set of reactive mass labels according to claim 24, wherein the set comprises two or more of the reactive mass labels having the following structure:

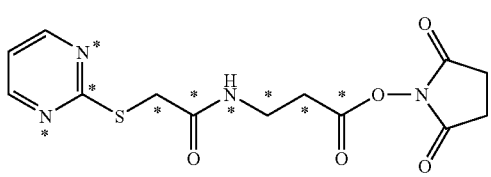 [SMILES: O=C(CSc1ncccn1)NCCC(=O)ON1C(=O)CCC1=O]

wherein the isotopic substituent * represents that the carbon is $^{13}$C or the nitrogen is $^{15}$N, and wherein each reactive mass label in the set comprises one or more * such that either:
  the mass marker moiety of each reactive mass label in the set has a common mass and each reactive mass label in the set has a unique aggregate mass; or
  the mass marker moiety of each reactive mass label in the set has a unique mass and each reactive mass label in the set has a common aggregate mass.

45. The set of reactive mass labels according to claim 24, wherein the set comprises two or more of the reactive mass labels having the following structure:

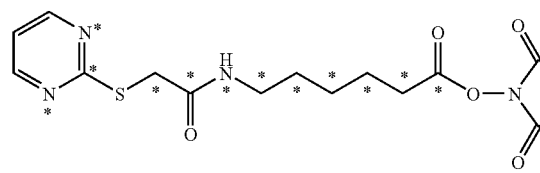

wherein the isotopic substituent * represents that the carbon is $^{13}$C or the nitrogen is $^{15}$N, and wherein each reactive mass label in the set comprises one or more * such that either:
  the mass marker moiety of each reactive mass label in the set has a common mass and each reactive mass label in the set has a unique aggregate mass; or the mass marker moiety of each reactive mass label in the set has a unique mass and each reactive mass label in the set has a common aggregate mass.

46. A set of reactive mass labels according to claim 24, wherein the set comprises two or more of the reactive mass labels having the following structure:

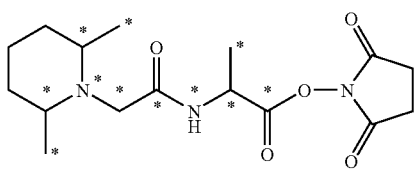 [SMILES: CC(NC(=O)CN1C(C)CCCC1C)C(=O)ON1C(=O)CCC1=O]

wherein the isotopic substituent * represents that the carbon is $^{13}$C or the nitrogen is $^{15}$N, and wherein each reactive mass label in the set comprises one or more * such that either:
  the mass marker moiety of each reactive mass label in the set has a common mass and each reactive mass label in the set has a unique aggregate mass; or
  the mass marker moiety of each reactive mass label in the set has a unique mass and each reactive mass label in the set has a common aggregate mass.

47. The set of reactive mass labels according to claim 24, wherein the set comprises two or more of the reactive mass labels having the following structure:

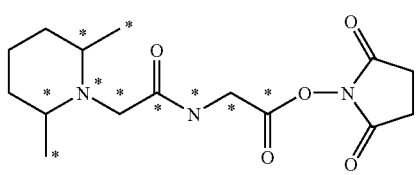 [SMILES: CC1CCCC(C)N1CC(=O)NCC(=O)ON1C(=O)CCC1=O]

wherein the isotopic substituent * represents that the carbon is $^{13}$C or the nitrogen is $^{15}$N, and wherein each reactive mass label in the set comprises one or more * such that either:
  the mass marker moiety of each reactive mass label in the set has a common mass and each reactive mass label in the set has a unique aggregate mass; or
  the mass marker moiety of each reactive mass label in the set has a unique mass and each reactive mass label in the set has a common aggregate mass.

48. The set of reactive mass labels according to claim 24, wherein the isotopic substituent * is $^{15}$N or $^{13}$C and the set comprises five mass labels having the following structures:

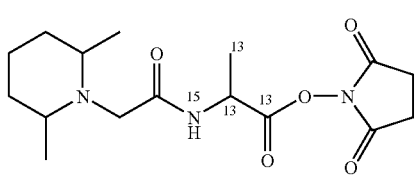

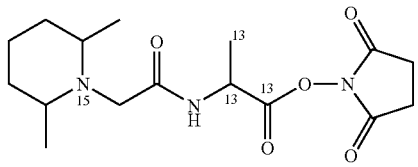

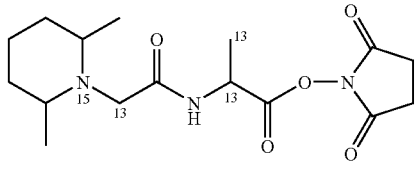

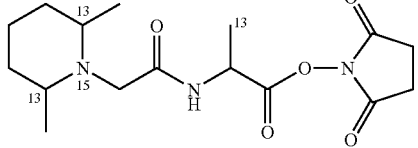

-continued
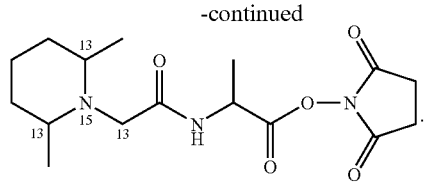
* * * * *

UNITED STATES PATENT AND TRADEMARK OFFICE
CERTIFICATE OF CORRECTION

PATENT NO.         : 9,023,656 B2
APPLICATION NO.    : 11/996910
DATED              : May 5, 2015
INVENTOR(S)        : Christian Hamon et al.

It is certified that error appears in the above-identified patent and that said Letters Patent is hereby corrected as shown below:

In the claims,
Column 92, line 32, Claim 3: Change the subscript "5" to "6" in the phrase "$C_1$-$C_5$ alkyl group".
Column 93, line 48, Claim 12: Add an "H" to the last chemical structure in the set.
Column 94, line 19, Claim 23: Change the dependency to reflect that this claim depends from claim 21 instead of claim 20.
Column 97, line 45, Claim 35: Add an "H" to the chemical structure.
Column 99, line 36, Claim 40: Add an "H" to the chemical structure.
Column 102, line 20, Claim 47: Add an "H" to the chemical structure.

Signed and Sealed this
Twenty-sixth Day of July, 2016

Michelle K. Lee
*Director of the United States Patent and Trademark Office*